US012534507B2

(12) United States Patent
Maher et al.

(10) Patent No.: US 12,534,507 B2
(45) Date of Patent: Jan. 27, 2026

(54) B CELL TARGETED PARALLEL CAR (pCAR) THERAPEUTIC AGENTS

(71) Applicant: KING'S COLLEGE LONDON, London (GB)

(72) Inventors: John Maher, London (GB); Leena Halim, London (GB)

(73) Assignee: KING'S COLLEGE LONDON, London (GB)

( * ) Notice: Subject to any disclaimer, the term of this patent is extended or adjusted under 35 U.S.C. 154(b) by 975 days.

(21) Appl. No.: 17/638,742

(22) PCT Filed: Aug. 28, 2020

(86) PCT No.: PCT/EP2020/074071
§ 371 (c)(1),
(2) Date: Feb. 25, 2022

(87) PCT Pub. No.: WO2021/038036
PCT Pub. Date: Mar. 4, 2021

(65) Prior Publication Data

US 2022/0298223 A1 Sep. 22, 2022

Related U.S. Application Data

(60) Provisional application No. 62/983,451, filed on Feb. 28, 2020, provisional application No. 62/892,936, filed on Aug. 28, 2019.

(51) Int. Cl.

| | |
|---|---|
| ***C07K 14/725*** | (2006.01) |
| ***A61K 40/11*** | (2025.01) |
| ***A61K 40/31*** | (2025.01) |
| ***A61K 40/42*** | (2025.01) |
| ***C07K 16/28*** | (2006.01) |

(52) U.S. Cl.
CPC .......... *C07K 14/7051* (2013.01); *A61K 40/11* (2025.01); *A61K 40/31* (2025.01); *A61K 40/4211* (2025.01); *A61K 40/4212* (2025.01); *A61K 40/4221* (2025.01); *C07K 16/2803* (2013.01); *C07K 16/2851* (2013.01); *C07K 16/2887* (2013.01); *A61K 2239/31* (2023.05); *A61K 2239/38* (2023.05); *A61K 2239/48* (2023.05); *C07K 2317/34* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 9,845,362 | B2 * | 12/2017 | Mukherjee | A61K 39/39558 |
| 10,221,245 | B2 * | 3/2019 | Brogdon | C07K 14/70503 |
| 11,021,694 | B2 * | 6/2021 | Lo | C07K 16/2827 |
| 2015/0239974 | A1 | 8/2015 | Chang et al. | |

FOREIGN PATENT DOCUMENTS

| | | | | |
|---|---|---|---|---|
| CN | 108220247 | A | 6/2018 | |
| CN | 109485732 | A | 3/2019 | |
| JP | 2012-517806 | A | 8/2012 | |
| JP | 2018-508215 | A | 3/2018 | |
| WO | WO-0034309 | A1 * | 6/2000 | C07K 14/4702 |
| WO | WO-03002607 | A1 * | 1/2003 | A61P 19/02 |
| WO | WO-2007147901 | A1 * | 12/2007 | C07K 16/2803 |
| WO | 2010/093480 | A2 | 8/2010 | |
| WO | WO-2012079000 | A1 * | 6/2012 | A61K 35/17 |
| WO | 2014/055668 | A1 | 4/2014 | |
| WO | 2016/139487 | A1 | 9/2016 | |
| WO | WO-2017021701 | A1 * | 2/2017 | A61K 35/14 |
| WO | WO-2017172981 | A2 * | 10/2017 | A61K 31/18 |
| WO | 2018/200496 | A1 | 11/2018 | |
| WO | 2021/038036 | A1 | 3/2021 | |

OTHER PUBLICATIONS

BD Biosciences. CD Marker Handbook Human CD Markers. 2016 (Year: 2016).*
Mirzaei et al. Prospects for chimeric antigen receptor (CAR) γδ T cells: A potential game changer for adoptive T cell cancer immunotherapy. Cancer Letters 380 (2016) 413-423. (Year: 2016).*
Albanza et al. Function of Novel Anti-CD19 Chimeric Antigen Receptors with Human Variable Regions Is Affected by Hinge and Transmembrane Domains. Molecular Therapy vol. 25 No. 11 Nov. 2017. (Year: 2017).*
Strausberg et al.Generation and initial analysis of more than 15,000 full-length human and mouse cDNA sequences. Proc. Natl. Acad. Sci. U.S.A. 99 (26), 16899-16903. (Year: 2008).*
De la Calle-Martin et al. Familial CD8 deficiency due to a mutation in the CD8 alpha gene. J. Clin. Invest. 108 (1), 117-123. (Year: 2001).*
Herold et al. Determinants of the assembly and function of antibody variable domains. Nature Scientific Reports, 7:12276, Sep. 25, 2017. (Year: 2017).*
Kehrl et al., "Molecular mechanisms regulating CD19, CD20 and CD22 gene expression", Immunology Today, 1994, pp. 432-436, vol. 19, No. 9.
International Search Report and Written Opinion relating to International Application No. PCT/EP2020/074071, dated Dec. 21, 2020; 18 pgs.
Ramos et al., "In Vivo Fate and Activity of Second- versus Third-Generation CD19-Specific CAR-T Cells in B Cell Non-Hodgkin's Lymphomas", Molecular Therapy, 2018, pp. 2727-2737, vol. 26, No. 12.

* cited by examiner

*Primary Examiner* — Julie Wu
*Assistant Examiner* — Amy M. Chattin
(74) *Attorney, Agent, or Firm* — Polsinelli PC

(57) ABSTRACT

Provided herein are immuno-responsive cells expressing a B cell targeting pCAR comprising a 2nd generation chimeric antigen receptor (CAR) and a chimeric co-stimulatory receptor (CCR). Also provided herein are methods of preparing the immuno-responsive cells and methods of directing T cell mediated immune response using the immuno-responsive cells.

16 Claims, 53 Drawing Sheets

Figures 1A, 1B:
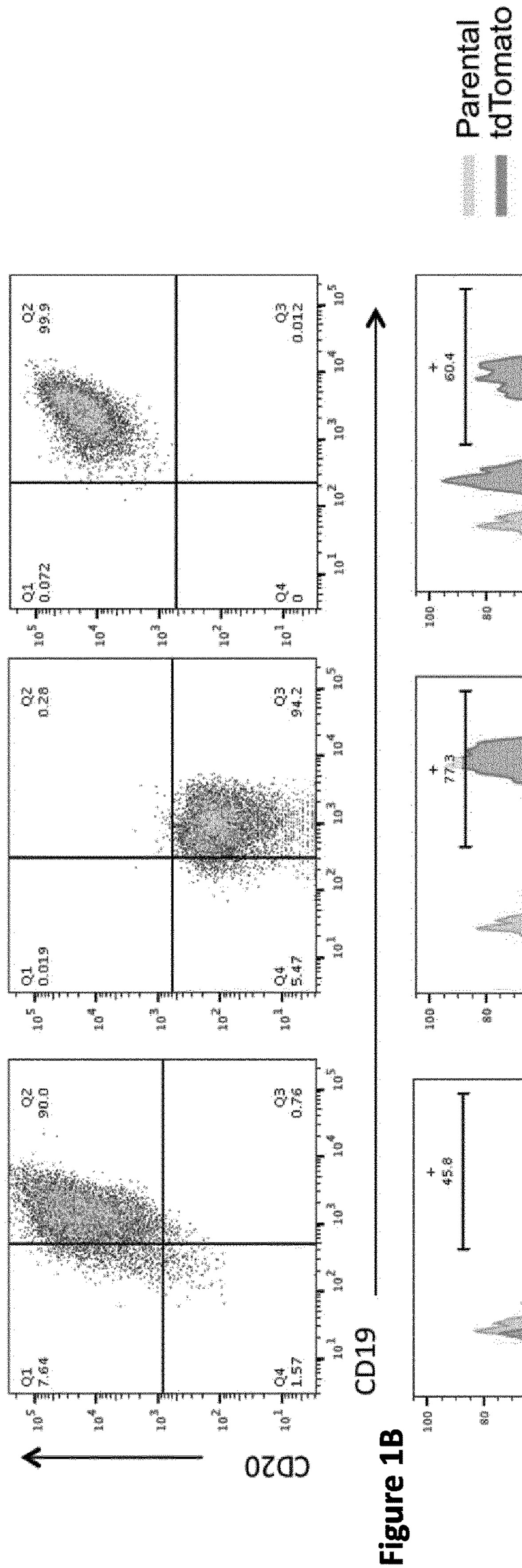

Specification includes a Sequence Listing.

FMC63 $V_H$ CDR3:

```
F-2:  HYYYGGSYAMDY
Y01:  -A----------
Y02:  --A---------
Y03:  ---A--------
G01:  ----A-------
G02:  -----A------
Y04:  -------A----
Y05:  -----------A
```

Figure 2B

Bioluminescence emission
($p$ values – unpaired Student's $t$ test)

| | | |
|---|---|---|
| pFBB/Y04 vs Y04 | $p<0.001$ | d7 |
| pFBB/Y04 vs Y04 | $p=0.008$ | d14 |
| pFBB/Y04 vs Y04 | $p=0.003$ | d21 |
| pFBB/Y04 vs Y04 | $p=0.031$ | d28 |
| pFBB/Y05 vs Y05 | $p=0.022$ | d35 |
| pFBB/G02 vs G02 | $p=0.038$ | d21 |

| | | |
|---|---|---|
| F-2 vs Y05 | $p=0.046$ | d4 |
| F-2 vs Y05 | $p=0.024$ | d7 |
| F-2 vs Y05 | $p=0.009$ | d27 |
| F-2 vs G02 | $p=0.005$ | d7 |
| F-2 vs G02 | $p=0.007$ | d27 |

Figure 20B

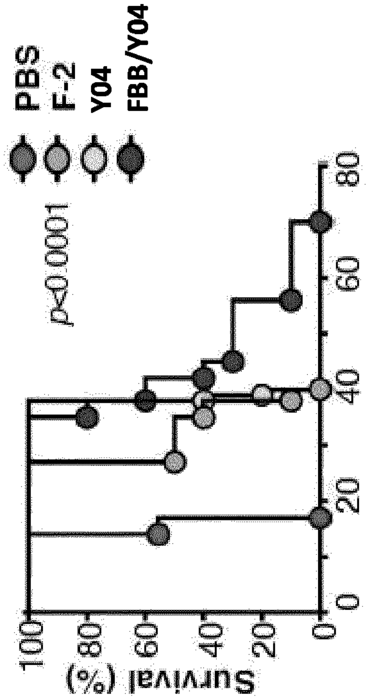
Figure 21A
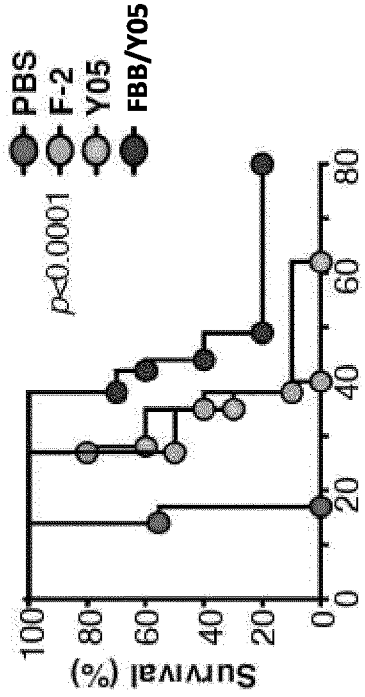
Figure 21B
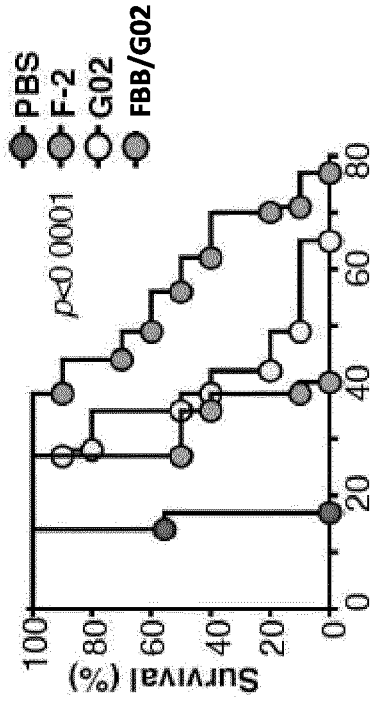
Figure 21C
| | Median survival |
|---|---|
| PBS | 17 days |
| F-2 | 31 days |
| Y04 | 38 days |
| Y05 | 35 days |
| G02 | 36.5 days |
| *FBB/Y04* | 42 days |
| *FBB/Y05* | 44 days |
| *FBB/G02* | 59 days |
Figure 21D

SEQUENCE LISTING

```
<160> NUMBER OF SEQ ID NOS: 135

<210> SEQ ID NO 1
<211> LENGTH: 112
<212> TYPE: PRT
<213> ORGANISM: Homo sapiens

<400> SEQUENCE: 1

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80
```

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 2
<211> LENGTH: 112
<212> TYPE: PRT
<213> ORGANISM: Homo sapiens

<400> SEQUENCE: 2

Arg Val Lys Phe Ser Arg Ser Ala Glu Pro Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 3
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Met Leu Arg Leu Leu Leu Ala Leu Asn Leu Phe Pro Ser Ile Gln Val
1 5 10 15

Thr Gly Asn Lys Ile Leu Val Lys Gln Ser Pro Met Leu Val Ala Tyr
20 25 30

Asp Asn Ala Val Asn Leu Ser Cys Lys Tyr Ser Tyr Asn Leu Phe Ser
35 40 45

Arg Glu Phe Arg Ala Ser Leu His Lys Gly Leu Asp Ser Ala Val Glu
50 55 60

Val Cys Val Val Tyr Gly Asn Tyr Ser Gln Gln Leu Gln Val Tyr Ser
65 70 75 80

Lys Thr Gly Phe Asn Cys Asp Gly Lys Leu Gly Asn Glu Ser Val Thr
85 90 95

Phe Tyr Leu Gln Asn Leu Tyr Val Asn Gln Thr Asp Ile Tyr Phe Cys
100 105 110

Lys Ile Glu Val Met Tyr Pro Pro Pro Tyr Leu Asp Asn Glu Lys Ser
115 120 125

Asn Gly Thr Ile Ile His Val Lys Gly Lys His Leu Cys Pro Ser Pro
130 135 140

Leu Phe Pro Gly Pro Ser Lys Pro Phe Trp Val Leu Val Val Val Gly
145 150 155 160

Gly Val Leu Ala Cys Tyr Ser Leu Leu Val Thr Val Ala Phe Ile Ile
165 170 175

Phe Trp Val Arg Ser Lys Arg Ser Arg Leu Leu His Ser Asp Tyr Met
180 185 190

Asn Met Thr Pro Arg Arg Pro Gly Pro Thr Arg Lys His Tyr Gln Pro
195 200 205

Tyr Ala Pro Pro Arg Asp Phe Ala Ala Tyr Arg Ser
210 215 220

<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro Phe Trp Val Leu Val Val Val Gly Gly
35 40 45

Val Leu Ala Cys Tyr Ser Leu Leu Val Thr Val Ala Phe Ile Ile Phe
50 55 60

Trp Val Arg Ser Lys Arg Ser Arg Leu Leu His Ser Asp Tyr Met Asn
65 70 75 80

Met Thr Pro Arg Arg Pro Gly Pro Thr Arg Lys His Tyr Gln Pro Tyr
85 90 95

Ala Pro Pro Arg Asp Phe Ala Ala Tyr Arg Ser
100 105

<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Glu Gln Lys Leu Ile Ser Glu Glu Asp Leu
1 5 10

<210> SEQ ID NO 6
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 6

Ile Glu Val Glu Gln Lys Leu Ile Ser Glu Glu Asp Leu Leu Asp Asn
1 5 10 15

Glu Lys Ser Asn Gly Thr Ile Ile His Val Lys Gly Lys His Leu Cys
20 25 30

```
Pro Ser Pro Leu Phe Pro Gly Pro Ser Lys Pro Phe Trp Val Leu Val
        35                  40                  45

Val Val Gly Gly Val Leu Ala Cys Tyr Ser Leu Leu Val Thr Val Ala
    50                  55                  60

Phe Ile Ile Phe Trp Val Arg Ser Lys Arg Ser Arg Leu Leu His Ser
65                  70                  75                  80

Asp Tyr Met Asn Met Thr Pro Arg Arg Pro Gly Pro Thr Arg Lys His
                85                  90                  95

Tyr Gln Pro Tyr Ala Pro Pro Arg Asp Phe Ala Ala Tyr Arg Ser
            100                 105                 110


<210> SEQ ID NO 7
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Asp Tyr Lys Asp Asp Asp Asp Lys
1               5


<210> SEQ ID NO 9
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu Asp Tyr Lys Asp Asp Asp
        35                  40                  45

Asp Lys
    50


<210> SEQ ID NO 10
<211> LENGTH: 7
<212> TYPE: PRT
```

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 10

Gly Val Ser Leu Pro Asp Tyr
1 5

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 11

Trp Gly Ser Glu Thr
1 5

<210> SEQ ID NO 12
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 12

His Tyr Tyr Tyr Gly Gly Ser Tyr Ala Met Asp Tyr
1 5 10

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 13

Arg Ala Ser Gln Asp Ile Ser Lys Tyr Leu Asn
1 5 10

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 14

His Thr Ser Arg Leu His Ser
1 5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 15

Gln Gln Gly Asn Thr Leu Pro Tyr Thr
1 5

<210> SEQ ID NO 16
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser
115 120

<210> SEQ ID NO 17
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr
100 105

<210> SEQ ID NO 18

<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ile Lys Asp Asn Ser Lys Ser Gln Val Phe Leu
65 70 75 80

Lys Met Asn Ser Leu Gln Thr Asp Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Ser Val Thr Val Ser Ser Gly Gly Gly Gly Ser Gly Gly Gly
115 120 125

Gly Ser Gly Gly Gly Gly Ser Asp Ile Gln Met Thr Gln Thr Thr Ser
130 135 140

Ser Leu Ser Ala Ser Leu Gly Asp Arg Val Thr Ile Ser Cys Arg Ala
145 150 155 160

Ser Gln Asp Ile Ser Lys Tyr Leu Asn Trp Tyr Gln Gln Lys Pro Asp
165 170 175

Gly Thr Val Lys Leu Leu Ile Tyr His Thr Ser Arg Leu His Ser Gly
180 185 190

Val Pro Ser Arg Phe Ser Gly Ser Gly Ser Gly Thr Asp Tyr Ser Leu
195 200 205

Thr Ile Ser Asn Leu Glu Gln Glu Asp Ile Ala Thr Tyr Phe Cys Gln
210 215 220

Gln Gly Asn Thr Leu Pro Tyr Thr Phe Gly Gly Gly Thr Lys Leu Glu
225 230 235 240

Ile Thr

<210> SEQ ID NO 19
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

```
Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 20
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

```
His Ala Tyr Tyr Gly Gly Ser Tyr Ala Met Asp Tyr
1               5                   10
```

<210> SEQ ID NO 21
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

```
His Tyr Ala Tyr Gly Gly Ser Tyr Ala Met Asp Tyr
1               5                   10
```

<210> SEQ ID NO 22
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

His Tyr Tyr Ala Gly Gly Ser Tyr Ala Met Asp Tyr
1 5 10

<210> SEQ ID NO 23
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 23

His Tyr Tyr Tyr Ala Gly Ser Tyr Ala Met Asp Tyr
1 5 10

<210> SEQ ID NO 24
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 24

His Tyr Tyr Tyr Gly Ala Ser Tyr Ala Met Asp Tyr
1 5 10

<210> SEQ ID NO 25
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 25

His Tyr Tyr Tyr Gly Gly Ser Ala Ala Met Asp Tyr
1 5 10

<210> SEQ ID NO 26
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 26

His Tyr Tyr Tyr Gly Gly Ser Tyr Ala Met Asp Ala
1 5 10

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 27

Gly Tyr Thr Phe Thr Ser Tyr
1 5

<210> SEQ ID NO 28
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Tyr Pro Gly Asn Gly Asp
1               5

<210> SEQ ID NO 29
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser His Tyr Gly Ser Asn Tyr Val Asp Tyr Phe Asp Tyr
1               5                   10

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Arg Ala Ser Ser Ser Leu Ser Phe Met His
1               5                   10

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Thr Ser Asn Leu Ala Ser
1               5

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

His Gln Trp Ser Ser Asn Pro Leu Thr
1               5

<210> SEQ ID NO 33
<211> LENGTH: 123

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 33

Gln Val Gln Leu Arg Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Asn Met His Trp Val Lys Gln Thr Pro Gly Gln Gly Leu Glu Trp Ile
35 40 45

Gly Ala Ile Tyr Pro Gly Asn Gly Asp Thr Ser Tyr Asn Gln Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Ser His Tyr Gly Ser Asn Tyr Val Asp Tyr Phe Asp Tyr Trp
100 105 110

Gly Gln Gly Thr Leu Val Thr Val Ser Thr Gly
115 120

<210> SEQ ID NO 34
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 34

Gln Ile Val Leu Ser Gln Ser Pro Ala Ile Leu Ser Ala Ser Pro Gly
1 5 10 15

Glu Lys Val Thr Met Thr Cys Arg Ala Ser Ser Ser Leu Ser Phe Met
20 25 30

His Trp Tyr Gln Gln Lys Pro Gly Ser Ser Pro Lys Pro Trp Ile Tyr
35 40 45

Ala Thr Ser Asn Leu Ala Ser Gly Val Pro Ala Arg Phe Ser Gly Ser
50 55 60

Gly Ser Gly Thr Ser Tyr Ser Leu Thr Ile Ser Arg Val Glu Ala Glu
65 70 75 80

Asp Ala Ala Thr Tyr Phe Cys His Gln Trp Ser Ser Asn Pro Leu Thr
85 90 95

Phe Gly Ala Gly Thr Lys Val Glu Ile Lys Arg Lys
100 105

<210> SEQ ID NO 35
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 35

Gln Val Gln Leu Arg Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser His Tyr Gly Ser Asn Tyr Val Asp Tyr Phe Asp Tyr Trp
            100                 105                 110

Gly Gln Gly Thr Leu Val Thr Val Ser Thr Gly Gly Ser Thr Ser Gly
        115                 120                 125

Ser Gly Lys Pro Gly Ser Gly Glu Gly Ser Thr Lys Gly Gln Ile Val
    130                 135                 140

Leu Ser Gln Ser Pro Ala Ile Leu Ser Ala Ser Pro Gly Glu Lys Val
145                 150                 155                 160

Thr Met Thr Cys Arg Ala Ser Ser Ser Leu Ser Phe Met His Trp Tyr
                165                 170                 175

Gln Gln Lys Pro Gly Ser Ser Pro Lys Pro Trp Ile Tyr Ala Thr Ser
            180                 185                 190

Asn Leu Ala Ser Gly Val Pro Ala Arg Phe Ser Gly Ser Gly Ser Gly
        195                 200                 205

Thr Ser Tyr Ser Leu Thr Ile Ser Arg Val Glu Ala Glu Asp Ala Ala
    210                 215                 220

Thr Tyr Phe Cys His Gln Trp Ser Ser Asn Pro Leu Thr Phe Gly Ala
225                 230                 235                 240

Gly Thr Lys Val Glu Ile Lys Arg Lys
                245

<210> SEQ ID NO 36
<211> LENGTH: 249
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Leu Ser Phe Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

```
Asp Ala Ala Thr Tyr Phe Cys His Gln Trp Ser Ser Asn Pro Leu Thr
                85                  90                  95

Phe Gly Ala Gly Thr Lys Val Glu Ile Lys Arg Lys Gly Ser Thr Ser
            100                 105                 110

Gly Ser Gly Lys Pro Gly Ser Gly Glu Gly Ser Thr Lys Gly Gln Val
        115                 120                 125

Gln Leu Arg Gln Pro Gly Ala Glu Leu Val Lys Pro Gly Ala Ser Val
    130                 135                 140

Lys Met Ser Cys Lys Ala Ser Gly Tyr Thr Phe Thr Ser Tyr Asn Met
145                 150                 155                 160

His Trp Val Lys Gln Thr Pro Gly Gln Gly Leu Glu Trp Ile Gly Ala
                165                 170                 175

Ile Tyr Pro Gly Asn Gly Asp Thr Ser Tyr Asn Gln Lys Phe Lys Gly
            180                 185                 190

Lys Ala Thr Leu Thr Ala Asp Lys Ser Ser Ser Thr Ala Tyr Met Gln
        195                 200                 205

Leu Ser Ser Leu Thr Ser Glu Asp Ser Ala Val Tyr Tyr Cys Ala Arg
    210                 215                 220

Ser His Tyr Gly Ser Asn Tyr Val Asp Tyr Phe Asp Tyr Trp Gly Gln
225                 230                 235                 240

Gly Thr Leu Val Thr Val Ser Thr Gly
                245


<210> SEQ ID NO 37
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Phe Ala Phe Ser Ile Tyr
1               5


<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ser Ser Gly Gly Gly Thr
1               5


<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

His Ser Gly Tyr Gly Ser Ser Tyr Gly Val Leu Phe Ala Tyr
1               5                   10
```

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

Arg Ala Ser Gln Asp Ile Ser Asn Tyr Leu Asn
1 5 10

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 41

Tyr Thr Ser Ile Leu His Ser
1 5

<210> SEQ ID NO 42
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

Gln Gln Gly Asn Thr Leu Pro Trp Thr
1 5

<210> SEQ ID NO 43
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Glu Val Gln Leu Val Glu Ser Gly Gly Gly Leu Val Lys Pro Gly Gly
1 5 10 15

Ser Leu Lys Leu Ser Cys Ala Ala Ser Gly Phe Ala Phe Ser Ile Tyr
20 25 30

Asp Met Ser Trp Val Arg Gln Thr Pro Glu Lys Arg Leu Glu Trp Val
35 40 45

Ala Tyr Ile Ser Ser Gly Gly Gly Thr Thr Tyr Tyr Pro Asp Thr Val
50 55 60

Lys Gly Arg Phe Thr Ile Ser Arg Asp Asn Ala Lys Asn Thr Leu Tyr
65 70 75 80

Leu Gln Met Ser Ser Leu Lys Ser Glu Asp Thr Ala Met Tyr Tyr Cys
85 90 95

Ala Arg His Ser Gly Tyr Gly Ser Ser Tyr Gly Val Leu Phe Ala Tyr
100 105 110

```
Trp Gly Gln Gly Thr Leu Val Thr Val Ser Ala
        115                 120


<210> SEQ ID NO 44
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105


<210> SEQ ID NO 45
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ile Tyr
            20                  25                  30

Asp Met Ser Trp Val Arg Gln Thr Pro Glu Lys Arg Leu Glu Trp Val
        35                  40                  45

Ala Tyr Ile Ser Ser Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ala Gly Ser Thr Ser Gly
        115                 120                 125

Ser Gly Lys Pro Gly Ser Gly Glu Gly Ser Thr Lys Gly Asp Ile Gln
    130                 135                 140

Met Thr Gln Thr Thr Ser Ser Leu Ser Ala Ser Leu Gly Asp Arg Val
145                 150                 155                 160
```

```
Thr Ile Ser Cys Arg Ala Ser Gln Asp Ile Ser Asn Tyr Leu Asn Trp
                165                 170                 175

Tyr Gln Gln Lys Pro Asp Gly Thr Val Lys Leu Leu Ile Tyr Tyr Thr
            180                 185                 190

Ser Ile Leu His Ser Gly Val Pro Ser Arg Phe Ser Gly Ser Gly Ser
        195                 200                 205

Gly Thr Asp Tyr Ser Leu Thr Ile Ser Asn Leu Glu Gln Glu Asp Phe
    210                 215                 220

Ala Thr Tyr Phe Cys Gln Gln Gly Asn Thr Leu Pro Trp Thr Phe Gly
225                 230                 235                 240

Gly Gly Thr Lys Leu Glu Ile Lys
                245


<210> SEQ ID NO 46
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys Gly Ser Thr Ser Gly
            100                 105                 110

Ser Gly Lys Pro Gly Ser Gly Glu Gly Ser Thr Lys Gly Glu Val Gln
        115                 120                 125

Leu Val Glu Ser Gly Gly Gly Leu Val Lys Pro Gly Gly Ser Leu Lys
    130                 135                 140

Leu Ser Cys Ala Ala Ser Gly Phe Ala Phe Ser Ile Tyr Asp Met Ser
145                 150                 155                 160

Trp Val Arg Gln Thr Pro Glu Lys Arg Leu Glu Trp Val Ala Tyr Ile
                165                 170                 175

Ser Ser Gly Gly Gly Thr Thr Tyr Tyr Pro Asp Thr Val Lys Gly Arg
            180                 185                 190

Phe Thr Ile Ser Arg Asp Asn Ala Lys Asn Thr Leu Tyr Leu Gln Met
        195                 200                 205

Ser Ser Leu Lys Ser Glu Asp Thr Ala Met Tyr Tyr Cys Ala Arg His
    210                 215                 220

Ser Gly Tyr Gly Ser Ser Tyr Gly Val Leu Phe Ala Tyr Trp Gly Gln
225                 230                 235                 240

Gly Thr Leu Val Thr Val Ser Ala
                245
```

<210> SEQ ID NO 47
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

```
Met Gly Pro Gly Val Leu Leu Leu Leu Leu Val Ala Thr Ala Trp His
1               5                   10                  15

Gly Gln Gly Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Gly Ser Gly Gly Gly Gly Ser Glu Val
    130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
            180                 185                 190

Ile Trp Gly Ser Glu Thr Thr Tyr Tyr Asn Ser Ala Leu Lys Ser Arg
        195                 200                 205

Leu Thr Ile Ile Lys Asp Asn Ser Lys Ser Gln Val Phe Leu Lys Met
    210                 215                 220

Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
                245                 250                 255

Ser Val Thr Val Ser Ser Ala Ala Ala Pro Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Asn
                325                 330                 335

His Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365
```

```
Phe Pro Glu Glu Glu Glu Gly Gly Cys Glu Leu Asp Tyr Lys Asp Asp
    370                 375                 380

Asp Asp Lys Arg Arg Lys Arg Ser Gly Ser Gly Ala Thr Asn Phe Ser
385                 390                 395                 400

Leu Leu Lys Gln Ala Gly Asp Val Glu Glu Asn Pro Gly Pro Asn Met
                405                 410                 415

Ala Leu Pro Val Thr Ala Leu Leu Leu Pro Leu Ala Leu Leu Leu His
            420                 425                 430

Ala Ala Arg Pro Asp Ile Gln Met Thr Gln Thr Thr Ser Ser Leu Ser
        435                 440                 445

Ala Ser Leu Gly Asp Arg Val Thr Ile Ser Cys Arg Ala Ser Gln Asp
    450                 455                 460

Ile Ser Lys Tyr Leu Asn Trp Tyr Gln Gln Lys Pro Asp Gly Thr Val
465                 470                 475                 480

Lys Leu Leu Ile Tyr His Thr Ser Arg Leu His Ser Gly Val Pro Ser
                485                 490                 495

Arg Phe Ser Gly Ser Gly Ser Gly Thr Asp Tyr Ser Leu Thr Ile Ser
            500                 505                 510

Asn Leu Glu Gln Glu Asp Ile Ala Thr Tyr Phe Cys Gln Gln Gly Asn
        515                 520                 525

Thr Leu Pro Tyr Thr Phe Gly Gly Gly Thr Lys Leu Glu Ile Thr Gly
    530                 535                 540

Gly Gly Gly Ser Gly Gly Gly Gly Ser Gly Gly Gly Gly Ser Glu Val
545                 550                 555                 560

Lys Leu Gln Glu Ser Gly Pro Gly Leu Val Ala Pro Ser Gln Ser Leu
                565                 570                 575

Ser Val Thr Cys Thr Val Ser Gly Val Ser Leu Pro Asp Tyr Gly Val
            580                 585                 590

Ser Trp Ile Arg Gln Pro Pro Arg Lys Gly Leu Glu Trp Leu Gly Val
        595                 600                 605

Ile Trp Gly Ser Glu Thr Thr Tyr Tyr Asn Ser Ala Leu Lys Ser Arg
    610                 615                 620

Leu Thr Ile Ile Lys Asp Asn Ser Lys Ser Gln Val Phe Leu Lys Met
625                 630                 635                 640

Asn Ser Leu Gln Thr Asp Asp Thr Ala Ile Tyr Tyr Cys Ala Lys His
                645                 650                 655

Tyr Tyr Tyr Ala Gly Ser Tyr Ala Met Asp Tyr Trp Gly Gln Gly Thr
            660                 665                 670

Ser Val Thr Val Ser Ser Ala Ala Ala Ile Glu Val Glu Gln Lys Leu
        675                 680                 685

Ile Ser Glu Glu Asp Leu Leu Asp Asn Glu Lys Ser Asn Gly Thr Ile
    690                 695                 700

Ile His Val Lys Gly Lys His Leu Cys Pro Ser Pro Leu Phe Pro Gly
705                 710                 715                 720

Pro Ser Lys Pro Phe Trp Val Leu Val Val Val Gly Gly Val Leu Ala
                725                 730                 735

Cys Tyr Ser Leu Leu Val Thr Val Ala Phe Ile Ile Phe Trp Val Arg
            740                 745                 750

Ser Lys Arg Ser Arg Leu Leu His Ser Asp Tyr Met Asn Met Thr Pro
        755                 760                 765

Arg Arg Pro Gly Pro Thr Arg Lys His Tyr Gln Pro Tyr Ala Pro Pro
    770                 775                 780
```

```
Arg Asp Phe Ala Ala Tyr Arg Ser Arg Val Lys Phe Ser Arg Ser Ala
785                 790                 795                 800

Asp Ala Pro Ala Tyr Gln Gln Gly Gln Asn Gln Leu Tyr Asn Glu Leu
                805                 810                 815

Asn Leu Gly Arg Arg Glu Glu Tyr Asp Val Leu Asp Lys Arg Arg Gly
            820                 825                 830

Arg Asp Pro Glu Met Gly Gly Lys Pro Arg Arg Lys Asn Pro Gln Glu
        835                 840                 845

Gly Leu Tyr Asn Glu Leu Gln Lys Asp Lys Met Ala Glu Ala Tyr Ser
    850                 855                 860

Glu Ile Gly Met Lys Gly Glu Arg Arg Arg Gly Lys Gly His Asp Gly
865                 870                 875                 880

Leu Tyr Gln Gly Leu Ser Thr Ala Thr Lys Asp Thr Tyr Asp Ala Leu
                885                 890                 895

His Met Gln Ala Leu Pro Pro Arg
            900


<210> SEQ ID NO 48
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Met Gly Pro Gly Val Leu Leu Leu Leu Leu Val Ala Thr Ala Trp His
1               5                   10                  15

Gly Gln Gly Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Gly Ser Gly Gly Gly Gly Ser Glu Val
    130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
            180                 185                 190

Ile Trp Gly Ser Glu Thr Thr Tyr Tyr Asn Ser Ala Leu Lys Ser Arg
        195                 200                 205

Leu Thr Ile Ile Lys Asp Asn Ser Lys Ser Gln Val Phe Leu Lys Met
    210                 215                 220
```

Asn Ser Leu Gln Thr Asp Asp Thr Ala Ile Tyr Tyr Cys Ala Lys His
225 230 235 240

Tyr Tyr Tyr Gly Gly Ser Tyr Ala Met Asp Tyr Trp Gly Gln Gly Thr
245 250 255

Ser Val Thr Val Ser Ser Ala Ala Ala Pro Thr Thr Thr Pro Ala Pro
260 265 270

Arg Pro Pro Thr Pro Ala Pro Thr Ile Ala Ser Gln Pro Leu Ser Leu
275 280 285

Arg Pro Glu Ala Cys Arg Pro Ala Ala Gly Gly Ala Val His Thr Arg
290 295 300

Gly Leu Asp Phe Ala Cys Asp Ile Tyr Ile Trp Ala Pro Leu Ala Gly
305 310 315 320

Thr Cys Gly Val Leu Leu Leu Ser Leu Val Ile Thr Leu Tyr Cys Asn
325 330 335

His Lys Arg Gly Arg Lys Lys Leu Leu Tyr Ile Phe Lys Gln Pro Phe
340 345 350

Met Arg Pro Val Gln Thr Thr Gln Glu Glu Asp Gly Cys Ser Cys Arg
355 360 365

Phe Pro Glu Glu Glu Glu Gly Gly Cys Glu Leu Asp Tyr Lys Asp Asp
370 375 380

Asp Asp Lys Arg Arg Lys Arg Ser Gly Ser Gly Ala Thr Asn Phe Ser
385 390 395 400

Leu Leu Lys Gln Ala Gly Asp Val Glu Glu Asn Pro Gly Pro Asn Met
405 410 415

Ala Leu Pro Val Thr Ala Leu Leu Leu Pro Leu Ala Leu Leu Leu His
420 425 430

Ala Ala Arg Pro Asp Ile Gln Met Thr Gln Thr Thr Ser Ser Leu Ser
435 440 445

Ala Ser Leu Gly Asp Arg Val Thr Ile Ser Cys Arg Ala Ser Gln Asp
450 455 460

Ile Ser Lys Tyr Leu Asn Trp Tyr Gln Gln Lys Pro Asp Gly Thr Val
465 470 475 480

Lys Leu Leu Ile Tyr His Thr Ser Arg Leu His Ser Gly Val Pro Ser
485 490 495

Arg Phe Ser Gly Ser Gly Ser Gly Thr Asp Tyr Ser Leu Thr Ile Ser
500 505 510

Asn Leu Glu Gln Glu Asp Ile Ala Thr Tyr Phe Cys Gln Gln Gly Asn
515 520 525

Thr Leu Pro Tyr Thr Phe Gly Gly Gly Thr Lys Leu Glu Ile Thr Gly
530 535 540

Gly Gly Gly Ser Gly Gly Gly Gly Ser Gly Gly Gly Gly Ser Glu Val
545 550 555 560

Lys Leu Gln Glu Ser Gly Pro Gly Leu Val Ala Pro Ser Gln Ser Leu
565 570 575

Ser Val Thr Cys Thr Val Ser Gly Val Ser Leu Pro Asp Tyr Gly Val
580 585 590

Ser Trp Ile Arg Gln Pro Pro Arg Lys Gly Leu Glu Trp Leu Gly Val
595 600 605

Ile Trp Gly Ser Glu Thr Thr Tyr Tyr Asn Ser Ala Leu Lys Ser Arg
610 615 620

Leu Thr Ile Ile Lys Asp Asn Ser Lys Ser Gln Val Phe Leu Lys Met
625 630 635 640

```
Asn Ser Leu Gln Thr Asp Asp Thr Ala Ile Tyr Tyr Cys Ala Lys His
                645                 650                 655

Tyr Tyr Tyr Gly Ala Ser Tyr Ala Met Asp Tyr Trp Gly Gln Gly Thr
            660                 665                 670

Ser Val Thr Val Ser Ser Ala Ala Ala Ile Glu Val Glu Gln Lys Leu
        675                 680                 685

Ile Ser Glu Glu Asp Leu Leu Asp Asn Glu Lys Ser Asn Gly Thr Ile
    690                 695                 700

Ile His Val Lys Gly Lys His Leu Cys Pro Ser Pro Leu Phe Pro Gly
705                 710                 715                 720

Pro Ser Lys Pro Phe Trp Val Leu Val Val Val Gly Gly Val Leu Ala
                725                 730                 735

Cys Tyr Ser Leu Leu Val Thr Val Ala Phe Ile Ile Phe Trp Val Arg
            740                 745                 750

Ser Lys Arg Ser Arg Leu Leu His Ser Asp Tyr Met Asn Met Thr Pro
        755                 760                 765

Arg Arg Pro Gly Pro Thr Arg Lys His Tyr Gln Pro Tyr Ala Pro Pro
    770                 775                 780

Arg Asp Phe Ala Ala Tyr Arg Ser Arg Val Lys Phe Ser Arg Ser Ala
785                 790                 795                 800

Asp Ala Pro Ala Tyr Gln Gln Gly Gln Asn Gln Leu Tyr Asn Glu Leu
                805                 810                 815

Asn Leu Gly Arg Arg Glu Glu Tyr Asp Val Leu Asp Lys Arg Arg Gly
            820                 825                 830

Arg Asp Pro Glu Met Gly Gly Lys Pro Arg Arg Lys Asn Pro Gln Glu
        835                 840                 845

Gly Leu Tyr Asn Glu Leu Gln Lys Asp Lys Met Ala Glu Ala Tyr Ser
    850                 855                 860

Glu Ile Gly Met Lys Gly Glu Arg Arg Arg Gly Lys Gly His Asp Gly
865                 870                 875                 880

Leu Tyr Gln Gly Leu Ser Thr Ala Thr Lys Asp Thr Tyr Asp Ala Leu
                885                 890                 895

His Met Gln Ala Leu Pro Pro Arg
            900


<210> SEQ ID NO 49
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Met Gly Pro Gly Val Leu Leu Leu Leu Leu Val Ala Thr Ala Trp His
1               5                   10                  15

Gly Gln Gly Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
65                  70                  75                  80
```

```
Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Gly Ser Gly Gly Gly Gly Ser Glu Val
    130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
            180                 185                 190

Ile Trp Gly Ser Glu Thr Thr Tyr Tyr Asn Ser Ala Leu Lys Ser Arg
        195                 200                 205

Leu Thr Ile Ile Lys Asp Asn Ser Lys Ser Gln Val Phe Leu Lys Met
    210                 215                 220

Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
                245                 250                 255

Ser Val Thr Val Ser Ser Ala Ala Ala Pro Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Asn
                325                 330                 335

His Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Asp Tyr Lys Asp Asp
    370                 375                 380

Asp Asp Lys Arg Arg Lys Arg Ser Gly Ser Gly Ala Thr Asn Phe Ser
385                 390                 395                 400

Leu Leu Lys Gln Ala Gly Asp Val Glu Glu Asn Pro Gly Pro Asn Met
                405                 410                 415

Ala Leu Pro Val Thr Ala Leu Leu Leu Pro Leu Ala Leu Leu Leu His
            420                 425                 430

Ala Ala Arg Pro Asp Ile Gln Met Thr Gln Thr Thr Ser Ser Leu Ser
        435                 440                 445

Ala Ser Leu Gly Asp Arg Val Thr Ile Ser Cys Arg Ala Ser Gln Asp
    450                 455                 460

Ile Ser Lys Tyr Leu Asn Trp Tyr Gln Gln Lys Pro Asp Gly Thr Val
465                 470                 475                 480

Lys Leu Leu Ile Tyr His Thr Ser Arg Leu His Ser Gly Val Pro Ser
                485                 490                 495
```

```
Arg Phe Ser Gly Ser Gly Ser Gly Thr Asp Tyr Ser Leu Thr Ile Ser
            500                 505                 510

Asn Leu Glu Gln Glu Asp Ile Ala Thr Tyr Phe Cys Gln Gln Gly Asn
        515                 520                 525

Thr Leu Pro Tyr Thr Phe Gly Gly Gly Thr Lys Leu Glu Ile Thr Gly
    530                 535                 540

Gly Gly Gly Ser Gly Gly Gly Gly Ser Gly Gly Gly Gly Ser Glu Val
545                 550                 555                 560

Lys Leu Gln Glu Ser Gly Pro Gly Leu Val Ala Pro Ser Gln Ser Leu
                565                 570                 575

Ser Val Thr Cys Thr Val Ser Gly Val Ser Leu Pro Asp Tyr Gly Val
            580                 585                 590

Ser Trp Ile Arg Gln Pro Pro Arg Lys Gly Leu Glu Trp Leu Gly Val
        595                 600                 605

Ile Trp Gly Ser Glu Thr Thr Tyr Tyr Asn Ser Ala Leu Lys Ser Arg
    610                 615                 620

Leu Thr Ile Ile Lys Asp Asn Ser Lys Ser Gln Val Phe Leu Lys Met
625                 630                 635                 640

Asn Ser Leu Gln Thr Asp Asp Thr Ala Ile Tyr Tyr Cys Ala Lys His
                645                 650                 655

Ala Tyr Tyr Gly Gly Ser Tyr Ala Met Asp Tyr Trp Gly Gln Gly Thr
            660                 665                 670

Ser Val Thr Val Ser Ser Ala Ala Ala Ile Glu Val Glu Gln Lys Leu
        675                 680                 685

Ile Ser Glu Glu Asp Leu Leu Asp Asn Glu Lys Ser Asn Gly Thr Ile
    690                 695                 700

Ile His Val Lys Gly Lys His Leu Cys Pro Ser Pro Leu Phe Pro Gly
705                 710                 715                 720

Pro Ser Lys Pro Phe Trp Val Leu Val Val Val Gly Gly Val Leu Ala
                725                 730                 735

Cys Tyr Ser Leu Leu Val Thr Val Ala Phe Ile Ile Phe Trp Val Arg
            740                 745                 750

Ser Lys Arg Ser Arg Leu Leu His Ser Asp Tyr Met Asn Met Thr Pro
        755                 760                 765

Arg Arg Pro Gly Pro Thr Arg Lys His Tyr Gln Pro Tyr Ala Pro Pro
    770                 775                 780

Arg Asp Phe Ala Ala Tyr Arg Ser Arg Val Lys Phe Ser Arg Ser Ala
785                 790                 795                 800

Asp Ala Pro Ala Tyr Gln Gln Gly Gln Asn Gln Leu Tyr Asn Glu Leu
                805                 810                 815

Asn Leu Gly Arg Arg Glu Glu Tyr Asp Val Leu Asp Lys Arg Arg Gly
            820                 825                 830

Arg Asp Pro Glu Met Gly Gly Lys Pro Arg Arg Lys Asn Pro Gln Glu
        835                 840                 845

Gly Leu Tyr Asn Glu Leu Gln Lys Asp Lys Met Ala Glu Ala Tyr Ser
    850                 855                 860

Glu Ile Gly Met Lys Gly Glu Arg Arg Arg Gly Lys Gly His Asp Gly
865                 870                 875                 880

Leu Tyr Gln Gly Leu Ser Thr Ala Thr Lys Asp Thr Tyr Asp Ala Leu
                885                 890                 895

His Met Gln Ala Leu Pro Pro Arg
            900
```

<210> SEQ ID NO 50
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Met Gly Pro Gly Val Leu Leu Leu Leu Leu Val Ala Thr Ala Trp His
1 5 10 15

Gly Gln Gly Gly Asp Ile Gln Met Thr Gln Thr Thr Ser Ser Leu Ser
20 25 30

Ala Ser Leu Gly Asp Arg Val Thr Ile Ser Cys Arg Ala Ser Gln Asp
35 40 45

Ile Ser Lys Tyr Leu Asn Trp Tyr Gln Gln Lys Pro Asp Gly Thr Val
50 55 60

Lys Leu Leu Ile Tyr His Thr Ser Arg Leu His Ser Gly Val Pro Ser
65 70 75 80

Arg Phe Ser Gly Ser Gly Ser Gly Thr Asp Tyr Ser Leu Thr Ile Ser
85 90 95

Asn Leu Glu Gln Glu Asp Ile Ala Thr Tyr Phe Cys Gln Gln Gly Asn
100 105 110

Thr Leu Pro Tyr Thr Phe Gly Gly Gly Thr Lys Leu Glu Ile Thr Gly
115 120 125

Gly Gly Gly Ser Gly Gly Gly Gly Ser Gly Gly Gly Gly Ser Glu Val
130 135 140

Lys Leu Gln Glu Ser Gly Pro Gly Leu Val Ala Pro Ser Gln Ser Leu
145 150 155 160

Ser Val Thr Cys Thr Val Ser Gly Val Ser Leu Pro Asp Tyr Gly Val
165 170 175

Ser Trp Ile Arg Gln Pro Pro Arg Lys Gly Leu Glu Trp Leu Gly Val
180 185 190

Ile Trp Gly Ser Glu Thr Thr Tyr Tyr Asn Ser Ala Leu Lys Ser Arg
195 200 205

Leu Thr Ile Ile Lys Asp Asn Ser Lys Ser Gln Val Phe Leu Lys Met
210 215 220

Asn Ser Leu Gln Thr Asp Asp Thr Ala Ile Tyr Tyr Cys Ala Lys His
225 230 235 240

Tyr Tyr Tyr Gly Gly Ser Tyr Ala Met Asp Tyr Trp Gly Gln Gly Thr
245 250 255

Ser Val Thr Val Ser Ser Ala Ala Ala Pro Thr Thr Thr Pro Ala Pro
260 265 270

Arg Pro Pro Thr Pro Ala Pro Thr Ile Ala Ser Gln Pro Leu Ser Leu
275 280 285

Arg Pro Glu Ala Cys Arg Pro Ala Ala Gly Gly Ala Val His Thr Arg
290 295 300

Gly Leu Asp Phe Ala Cys Asp Ile Tyr Ile Trp Ala Pro Leu Ala Gly
305 310 315 320

Thr Cys Gly Val Leu Leu Leu Ser Leu Val Ile Thr Leu Tyr Cys Asn
325 330 335

His Lys Arg Gly Arg Lys Lys Leu Leu Tyr Ile Phe Lys Gln Pro Phe
340 345 350

Met Arg Pro Val Gln Thr Thr Gln Glu Glu Asp Gly Cys Ser Cys Arg
355 360 365

```
Phe Pro Glu Glu Glu Glu Gly Gly Cys Glu Leu Asp Tyr Lys Asp Asp
    370                 375                 380

Asp Asp Lys Arg Arg Lys Arg Ser Gly Ser Gly Ala Thr Asn Phe Ser
385                 390                 395                 400

Leu Leu Lys Gln Ala Gly Asp Val Glu Glu Asn Pro Gly Pro Asn Met
                405                 410                 415

Ala Leu Pro Val Thr Ala Leu Leu Leu Pro Leu Ala Leu Leu Leu His
            420                 425                 430

Ala Ala Arg Pro Asp Ile Gln Met Thr Gln Thr Thr Ser Ser Leu Ser
        435                 440                 445

Ala Ser Leu Gly Asp Arg Val Thr Ile Ser Cys Arg Ala Ser Gln Asp
    450                 455                 460

Ile Ser Lys Tyr Leu Asn Trp Tyr Gln Gln Lys Pro Asp Gly Thr Val
465                 470                 475                 480

Lys Leu Leu Ile Tyr His Thr Ser Arg Leu His Ser Gly Val Pro Ser
                485                 490                 495

Arg Phe Ser Gly Ser Gly Ser Gly Thr Asp Tyr Ser Leu Thr Ile Ser
            500                 505                 510

Asn Leu Glu Gln Glu Asp Ile Ala Thr Tyr Phe Cys Gln Gln Gly Asn
        515                 520                 525

Thr Leu Pro Tyr Thr Phe Gly Gly Gly Thr Lys Leu Glu Ile Thr Gly
    530                 535                 540

Gly Gly Gly Ser Gly Gly Gly Gly Ser Gly Gly Gly Gly Ser Glu Val
545                 550                 555                 560

Lys Leu Gln Glu Ser Gly Pro Gly Leu Val Ala Pro Ser Gln Ser Leu
                565                 570                 575

Ser Val Thr Cys Thr Val Ser Gly Val Ser Leu Pro Asp Tyr Gly Val
            580                 585                 590

Ser Trp Ile Arg Gln Pro Pro Arg Lys Gly Leu Glu Trp Leu Gly Val
        595                 600                 605

Ile Trp Gly Ser Glu Thr Thr Tyr Tyr Asn Ser Ala Leu Lys Ser Arg
    610                 615                 620

Leu Thr Ile Ile Lys Asp Asn Ser Lys Ser Gln Val Phe Leu Lys Met
625                 630                 635                 640

Asn Ser Leu Gln Thr Asp Asp Thr Ala Ile Tyr Tyr Cys Ala Lys His
                645                 650                 655

Tyr Ala Tyr Gly Gly Ser Tyr Ala Met Asp Tyr Trp Gly Gln Gly Thr
            660                 665                 670

Ser Val Thr Val Ser Ser Ala Ala Ala Ile Glu Val Glu Gln Lys Leu
        675                 680                 685

Ile Ser Glu Glu Asp Leu Leu Asp Asn Glu Lys Ser Asn Gly Thr Ile
    690                 695                 700

Ile His Val Lys Gly Lys His Leu Cys Pro Ser Pro Leu Phe Pro Gly
705                 710                 715                 720

Pro Ser Lys Pro Phe Trp Val Leu Val Val Val Gly Gly Val Leu Ala
                725                 730                 735

Cys Tyr Ser Leu Leu Val Thr Val Ala Phe Ile Ile Phe Trp Val Arg
            740                 745                 750

Ser Lys Arg Ser Arg Leu Leu His Ser Asp Tyr Met Asn Met Thr Pro
        755                 760                 765

Arg Arg Pro Gly Pro Thr Arg Lys His Tyr Gln Pro Tyr Ala Pro Pro
    770                 775                 780
```

Arg Asp Phe Ala Ala Tyr Arg Ser Arg Val Lys Phe Ser Arg Ser Ala
785 790 795 800

Asp Ala Pro Ala Tyr Gln Gln Gly Gln Asn Gln Leu Tyr Asn Glu Leu
805 810 815

Asn Leu Gly Arg Arg Glu Glu Tyr Asp Val Leu Asp Lys Arg Arg Gly
820 825 830

Arg Asp Pro Glu Met Gly Gly Lys Pro Arg Arg Lys Asn Pro Gln Glu
835 840 845

Gly Leu Tyr Asn Glu Leu Gln Lys Asp Lys Met Ala Glu Ala Tyr Ser
850 855 860

Glu Ile Gly Met Lys Gly Glu Arg Arg Arg Gly Lys Gly His Asp Gly
865 870 875 880

Leu Tyr Gln Gly Leu Ser Thr Ala Thr Lys Asp Thr Tyr Asp Ala Leu
885 890 895

His Met Gln Ala Leu Pro Pro Arg
900

<210> SEQ ID NO 51
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

Met Gly Pro Gly Val Leu Leu Leu Leu Leu Val Ala Thr Ala Trp His
1 5 10 15

Gly Gln Gly Gly Asp Ile Gln Met Thr Gln Thr Thr Ser Ser Leu Ser
20 25 30

Ala Ser Leu Gly Asp Arg Val Thr Ile Ser Cys Arg Ala Ser Gln Asp
35 40 45

Ile Ser Lys Tyr Leu Asn Trp Tyr Gln Gln Lys Pro Asp Gly Thr Val
50 55 60

Lys Leu Leu Ile Tyr His Thr Ser Arg Leu His Ser Gly Val Pro Ser
65 70 75 80

Arg Phe Ser Gly Ser Gly Ser Gly Thr Asp Tyr Ser Leu Thr Ile Ser
85 90 95

Asn Leu Glu Gln Glu Asp Ile Ala Thr Tyr Phe Cys Gln Gln Gly Asn
100 105 110

Thr Leu Pro Tyr Thr Phe Gly Gly Gly Thr Lys Leu Glu Ile Thr Gly
115 120 125

Gly Gly Gly Ser Gly Gly Gly Gly Ser Gly Gly Gly Gly Ser Glu Val
130 135 140

Lys Leu Gln Glu Ser Gly Pro Gly Leu Val Ala Pro Ser Gln Ser Leu
145 150 155 160

Ser Val Thr Cys Thr Val Ser Gly Val Ser Leu Pro Asp Tyr Gly Val
165 170 175

Ser Trp Ile Arg Gln Pro Pro Arg Lys Gly Leu Glu Trp Leu Gly Val
180 185 190

Ile Trp Gly Ser Glu Thr Thr Tyr Tyr Asn Ser Ala Leu Lys Ser Arg
195 200 205

Leu Thr Ile Ile Lys Asp Asn Ser Lys Ser Gln Val Phe Leu Lys Met
210 215 220

```
Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
                245                 250                 255

Ser Val Thr Val Ser Ser Ala Ala Ala Pro Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Asn
                325                 330                 335

His Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Asp Tyr Lys Asp Asp
    370                 375                 380

Asp Asp Lys Arg Arg Lys Arg Ser Gly Ser Gly Ala Thr Asn Phe Ser
385                 390                 395                 400

Leu Leu Lys Gln Ala Gly Asp Val Glu Glu Asn Pro Gly Pro Asn Met
                405                 410                 415

Ala Leu Pro Val Thr Ala Leu Leu Leu Pro Leu Ala Leu Leu Leu His
            420                 425                 430

Ala Ala Arg Pro Asp Ile Gln Met Thr Gln Thr Thr Ser Ser Leu Ser
        435                 440                 445

Ala Ser Leu Gly Asp Arg Val Thr Ile Ser Cys Arg Ala Ser Gln Asp
    450                 455                 460

Ile Ser Lys Tyr Leu Asn Trp Tyr Gln Gln Lys Pro Asp Gly Thr Val
465                 470                 475                 480

Lys Leu Leu Ile Tyr His Thr Ser Arg Leu His Ser Gly Val Pro Ser
                485                 490                 495

Arg Phe Ser Gly Ser Gly Ser Gly Thr Asp Tyr Ser Leu Thr Ile Ser
            500                 505                 510

Asn Leu Glu Gln Glu Asp Ile Ala Thr Tyr Phe Cys Gln Gln Gly Asn
        515                 520                 525

Thr Leu Pro Tyr Thr Phe Gly Gly Gly Thr Lys Leu Glu Ile Thr Gly
    530                 535                 540

Gly Gly Gly Ser Gly Gly Gly Gly Ser Gly Gly Gly Gly Ser Glu Val
545                 550                 555                 560

Lys Leu Gln Glu Ser Gly Pro Gly Leu Val Ala Pro Ser Gln Ser Leu
                565                 570                 575

Ser Val Thr Cys Thr Val Ser Gly Val Ser Leu Pro Asp Tyr Gly Val
            580                 585                 590

Ser Trp Ile Arg Gln Pro Pro Arg Lys Gly Leu Glu Trp Leu Gly Val
        595                 600                 605

Ile Trp Gly Ser Glu Thr Thr Tyr Tyr Asn Ser Ala Leu Lys Ser Arg
    610                 615                 620

Leu Thr Ile Ile Lys Asp Asn Ser Lys Ser Gln Val Phe Leu Lys Met
625                 630                 635                 640
```

Asn Ser Leu Gln Thr Asp Asp Thr Ala Ile Tyr Tyr Cys Ala Lys His
645 650 655

Tyr Tyr Ala Gly Gly Ser Tyr Ala Met Asp Tyr Trp Gly Gln Gly Thr
660 665 670

Ser Val Thr Val Ser Ser Ala Ala Ala Ile Glu Val Glu Gln Lys Leu
675 680 685

Ile Ser Glu Glu Asp Leu Leu Asp Asn Glu Lys Ser Asn Gly Thr Ile
690 695 700

Ile His Val Lys Gly Lys His Leu Cys Pro Ser Pro Leu Phe Pro Gly
705 710 715 720

Pro Ser Lys Pro Phe Trp Val Leu Val Val Val Gly Gly Val Leu Ala
725 730 735

Cys Tyr Ser Leu Leu Val Thr Val Ala Phe Ile Ile Phe Trp Val Arg
740 745 750

Ser Lys Arg Ser Arg Leu Leu His Ser Asp Tyr Met Asn Met Thr Pro
755 760 765

Arg Arg Pro Gly Pro Thr Arg Lys His Tyr Gln Pro Tyr Ala Pro Pro
770 775 780

Arg Asp Phe Ala Ala Tyr Arg Ser Arg Val Lys Phe Ser Arg Ser Ala
785 790 795 800

Asp Ala Pro Ala Tyr Gln Gln Gly Gln Asn Gln Leu Tyr Asn Glu Leu
805 810 815

Asn Leu Gly Arg Arg Glu Glu Tyr Asp Val Leu Asp Lys Arg Arg Gly
820 825 830

Arg Asp Pro Glu Met Gly Gly Lys Pro Arg Arg Lys Asn Pro Gln Glu
835 840 845

Gly Leu Tyr Asn Glu Leu Gln Lys Asp Lys Met Ala Glu Ala Tyr Ser
850 855 860

Glu Ile Gly Met Lys Gly Glu Arg Arg Arg Gly Lys Gly His Asp Gly
865 870 875 880

Leu Tyr Gln Gly Leu Ser Thr Ala Thr Lys Asp Thr Tyr Asp Ala Leu
885 890 895

His Met Gln Ala Leu Pro Pro Arg
900

<210> SEQ ID NO 52
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

Met Gly Pro Gly Val Leu Leu Leu Leu Leu Val Ala Thr Ala Trp His
1 5 10 15

Gly Gln Gly Gly Asp Ile Gln Met Thr Gln Thr Thr Ser Ser Leu Ser
20 25 30

Ala Ser Leu Gly Asp Arg Val Thr Ile Ser Cys Arg Ala Ser Gln Asp
35 40 45

Ile Ser Lys Tyr Leu Asn Trp Tyr Gln Gln Lys Pro Asp Gly Thr Val
50 55 60

Lys Leu Leu Ile Tyr His Thr Ser Arg Leu His Ser Gly Val Pro Ser
65 70 75 80

```
Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Gly Ser Gly Gly Gly Gly Ser Glu Val
    130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
            180                 185                 190

Ile Trp Gly Ser Glu Thr Thr Tyr Tyr Asn Ser Ala Leu Lys Ser Arg
        195                 200                 205

Leu Thr Ile Ile Lys Asp Asn Ser Lys Ser Gln Val Phe Leu Lys Met
    210                 215                 220

Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
                245                 250                 255

Ser Val Thr Val Ser Ser Ala Ala Ala Pro Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Asn
                325                 330                 335

His Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Asp Tyr Lys Asp Asp
    370                 375                 380

Asp Asp Lys Arg Arg Lys Arg Ser Gly Ser Gly Ala Thr Asn Phe Ser
385                 390                 395                 400

Leu Leu Lys Gln Ala Gly Asp Val Glu Glu Asn Pro Gly Pro Asn Met
                405                 410                 415

Ala Leu Pro Val Thr Ala Leu Leu Leu Pro Leu Ala Leu Leu Leu His
            420                 425                 430

Ala Ala Arg Pro Asp Ile Gln Met Thr Gln Thr Thr Ser Ser Leu Ser
        435                 440                 445

Ala Ser Leu Gly Asp Arg Val Thr Ile Ser Cys Arg Ala Ser Gln Asp
    450                 455                 460

Ile Ser Lys Tyr Leu Asn Trp Tyr Gln Gln Lys Pro Asp Gly Thr Val
465                 470                 475                 480

Lys Leu Leu Ile Tyr His Thr Ser Arg Leu His Ser Gly Val Pro Ser
                485                 490                 495
```

```
Arg Phe Ser Gly Ser Gly Ser Gly Thr Asp Tyr Ser Leu Thr Ile Ser
            500                 505                 510

Asn Leu Glu Gln Glu Asp Ile Ala Thr Tyr Phe Cys Gln Gln Gly Asn
        515                 520                 525

Thr Leu Pro Tyr Thr Phe Gly Gly Gly Thr Lys Leu Glu Ile Thr Gly
    530                 535                 540

Gly Gly Gly Ser Gly Gly Gly Gly Ser Gly Gly Gly Gly Ser Glu Val
545                 550                 555                 560

Lys Leu Gln Glu Ser Gly Pro Gly Leu Val Ala Pro Ser Gln Ser Leu
                565                 570                 575

Ser Val Thr Cys Thr Val Ser Gly Val Ser Leu Pro Asp Tyr Gly Val
            580                 585                 590

Ser Trp Ile Arg Gln Pro Pro Arg Lys Gly Leu Glu Trp Leu Gly Val
        595                 600                 605

Ile Trp Gly Ser Glu Thr Thr Tyr Tyr Asn Ser Ala Leu Lys Ser Arg
    610                 615                 620

Leu Thr Ile Ile Lys Asp Asn Ser Lys Ser Gln Val Phe Leu Lys Met
625                 630                 635                 640

Asn Ser Leu Gln Thr Asp Asp Thr Ala Ile Tyr Tyr Cys Ala Lys His
                645                 650                 655

Tyr Tyr Tyr Gly Gly Ser Ala Ala Met Asp Tyr Trp Gly Gln Gly Thr
            660                 665                 670

Ser Val Thr Val Ser Ser Ala Ala Ala Ile Glu Val Glu Gln Lys Leu
        675                 680                 685

Ile Ser Glu Glu Asp Leu Leu Asp Asn Glu Lys Ser Asn Gly Thr Ile
    690                 695                 700

Ile His Val Lys Gly Lys His Leu Cys Pro Ser Pro Leu Phe Pro Gly
705                 710                 715                 720

Pro Ser Lys Pro Phe Trp Val Leu Val Val Val Gly Gly Val Leu Ala
                725                 730                 735

Cys Tyr Ser Leu Leu Val Thr Val Ala Phe Ile Ile Phe Trp Val Arg
            740                 745                 750

Ser Lys Arg Ser Arg Leu Leu His Ser Asp Tyr Met Asn Met Thr Pro
        755                 760                 765

Arg Arg Pro Gly Pro Thr Arg Lys His Tyr Gln Pro Tyr Ala Pro Pro
    770                 775                 780

Arg Asp Phe Ala Ala Tyr Arg Ser Arg Val Lys Phe Ser Arg Ser Ala
785                 790                 795                 800

Asp Ala Pro Ala Tyr Gln Gln Gly Gln Asn Gln Leu Tyr Asn Glu Leu
                805                 810                 815

Asn Leu Gly Arg Arg Glu Glu Tyr Asp Val Leu Asp Lys Arg Arg Gly
            820                 825                 830

Arg Asp Pro Glu Met Gly Gly Lys Pro Arg Arg Lys Asn Pro Gln Glu
        835                 840                 845

Gly Leu Tyr Asn Glu Leu Gln Lys Asp Lys Met Ala Glu Ala Tyr Ser
    850                 855                 860

Glu Ile Gly Met Lys Gly Glu Arg Arg Arg Gly Lys Gly His Asp Gly
865                 870                 875                 880

Leu Tyr Gln Gly Leu Ser Thr Ala Thr Lys Asp Thr Tyr Asp Ala Leu
                885                 890                 895

His Met Gln Ala Leu Pro Pro Arg
            900
```

<210> SEQ ID NO 53
<211> LENGTH: 904
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Met Gly Pro Gly Val Leu Leu Leu Leu Leu Val Ala Thr Ala Trp His
1               5                   10                  15

Gly Gln Gly Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Gly Ser Gly Gly Gly Gly Ser Glu Val
    130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
            180                 185                 190

Ile Trp Gly Ser Glu Thr Thr Tyr Tyr Asn Ser Ala Leu Lys Ser Arg
        195                 200                 205

Leu Thr Ile Ile Lys Asp Asn Ser Lys Ser Gln Val Phe Leu Lys Met
    210                 215                 220

Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
                245                 250                 255

Ser Val Thr Val Ser Ser Ala Ala Ala Pro Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Asn
                325                 330                 335

His Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365
```

```
Phe Pro Glu Glu Glu Glu Gly Gly Cys Glu Leu Asp Tyr Lys Asp Asp
    370                 375                 380

Asp Asp Lys Arg Arg Lys Arg Ser Gly Ser Gly Ala Thr Asn Phe Ser
385                 390                 395                 400

Leu Leu Lys Gln Ala Gly Asp Val Glu Glu Asn Pro Gly Pro Asn Met
                405                 410                 415

Ala Leu Pro Val Thr Ala Leu Leu Leu Pro Leu Ala Leu Leu Leu His
            420                 425                 430

Ala Ala Arg Pro Asp Ile Gln Met Thr Gln Thr Thr Ser Ser Leu Ser
        435                 440                 445

Ala Ser Leu Gly Asp Arg Val Thr Ile Ser Cys Arg Ala Ser Gln Asp
    450                 455                 460

Ile Ser Lys Tyr Leu Asn Trp Tyr Gln Gln Lys Pro Asp Gly Thr Val
465                 470                 475                 480

Lys Leu Leu Ile Tyr His Thr Ser Arg Leu His Ser Gly Val Pro Ser
                485                 490                 495

Arg Phe Ser Gly Ser Gly Ser Gly Thr Asp Tyr Ser Leu Thr Ile Ser
            500                 505                 510

Asn Leu Glu Gln Glu Asp Ile Ala Thr Tyr Phe Cys Gln Gln Gly Asn
        515                 520                 525

Thr Leu Pro Tyr Thr Phe Gly Gly Gly Thr Lys Leu Glu Ile Thr Gly
    530                 535                 540

Gly Gly Gly Ser Gly Gly Gly Gly Ser Gly Gly Gly Gly Ser Glu Val
545                 550                 555                 560

Lys Leu Gln Glu Ser Gly Pro Gly Leu Val Ala Pro Ser Gln Ser Leu
                565                 570                 575

Ser Val Thr Cys Thr Val Ser Gly Val Ser Leu Pro Asp Tyr Gly Val
            580                 585                 590

Ser Trp Ile Arg Gln Pro Pro Arg Lys Gly Leu Glu Trp Leu Gly Val
        595                 600                 605

Ile Trp Gly Ser Glu Thr Thr Tyr Tyr Asn Ser Ala Leu Lys Ser Arg
    610                 615                 620

Leu Thr Ile Ile Lys Asp Asn Ser Lys Ser Gln Val Phe Leu Lys Met
625                 630                 635                 640

Asn Ser Leu Gln Thr Asp Asp Thr Ala Ile Tyr Tyr Cys Ala Lys His
                645                 650                 655

Tyr Tyr Tyr Gly Gly Ser Tyr Ala Met Asp Ala Trp Gly Gln Gly Thr
            660                 665                 670

Ser Val Thr Val Ser Ser Ala Ala Ala Ile Glu Val Glu Gln Lys Leu
        675                 680                 685

Ile Ser Glu Glu Asp Leu Leu Asp Asn Glu Lys Ser Asn Gly Thr Ile
    690                 695                 700

Ile His Val Lys Gly Lys His Leu Cys Pro Ser Pro Leu Phe Pro Gly
705                 710                 715                 720

Pro Ser Lys Pro Phe Trp Val Leu Val Val Val Gly Gly Val Leu Ala
                725                 730                 735

Cys Tyr Ser Leu Leu Val Thr Val Ala Phe Ile Ile Phe Trp Val Arg
            740                 745                 750

Ser Lys Arg Ser Arg Leu Leu His Ser Asp Tyr Met Asn Met Thr Pro
        755                 760                 765

Arg Arg Pro Gly Pro Thr Arg Lys His Tyr Gln Pro Tyr Ala Pro Pro
    770                 775                 780
```

Arg Asp Phe Ala Ala Tyr Arg Ser Arg Val Lys Phe Ser Arg Ser Ala
785 790 795 800

Asp Ala Pro Ala Tyr Gln Gln Gly Gln Asn Gln Leu Tyr Asn Glu Leu
805 810 815

Asn Leu Gly Arg Arg Glu Glu Tyr Asp Val Leu Asp Lys Arg Arg Gly
820 825 830

Arg Asp Pro Glu Met Gly Gly Lys Pro Arg Arg Lys Asn Pro Gln Glu
835 840 845

Gly Leu Tyr Asn Glu Leu Gln Lys Asp Lys Met Ala Glu Ala Tyr Ser
850 855 860

Glu Ile Gly Met Lys Gly Glu Arg Arg Arg Gly Lys Gly His Asp Gly
865 870 875 880

Leu Tyr Gln Gly Leu Ser Thr Ala Thr Lys Asp Thr Tyr Asp Ala Leu
885 890 895

His Met Gln Ala Leu Pro Pro Arg
900

<210> SEQ ID NO 54
<211> LENGTH: 911
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 54

Met Gly Pro Gly Val Leu Leu Leu Leu Leu Val Ala Thr Ala Trp His
1 5 10 15

Gly Gln Gly Gly Gln Ile Val Leu Ser Gln Ser Pro Ala Ile Leu Ser
20 25 30

Ala Ser Pro Gly Glu Lys Val Thr Met Thr Cys Arg Ala Ser Ser Ser
35 40 45

Leu Ser Phe Met His Trp Tyr Gln Gln Lys Pro Gly Ser Ser Pro Lys
50 55 60

Pro Trp Ile Tyr Ala Thr Ser Asn Leu Ala Ser Gly Val Pro Ala Arg
65 70 75 80

Phe Ser Gly Ser Gly Ser Gly Thr Ser Tyr Ser Leu Thr Ile Ser Arg
85 90 95

Val Glu Ala Glu Asp Ala Ala Thr Tyr Phe Cys His Gln Trp Ser Ser
100 105 110

Asn Pro Leu Thr Phe Gly Ala Gly Thr Lys Val Glu Ile Lys Arg Lys
115 120 125

Gly Ser Thr Ser Gly Ser Gly Lys Pro Gly Ser Gly Glu Gly Ser Thr
130 135 140

Lys Gly Gln Val Gln Leu Arg Gln Pro Gly Ala Glu Leu Val Lys Pro
145 150 155 160

Gly Ala Ser Val Lys Met Ser Cys Lys Ala Ser Gly Tyr Thr Phe Thr
165 170 175

Ser Tyr Asn Met His Trp Val Lys Gln Thr Pro Gly Gln Gly Leu Glu
180 185 190

Trp Ile Gly Ala Ile Tyr Pro Gly Asn Gly Asp Thr Ser Tyr Asn Gln
195 200 205

Lys Phe Lys Gly Lys Ala Thr Leu Thr Ala Asp Lys Ser Ser Ser Thr
210 215 220

```
Ala Tyr Met Gln Leu Ser Ser Leu Thr Ser Glu Asp Ser Ala Val Tyr
225                 230                 235                 240

Tyr Cys Ala Arg Ser His Tyr Gly Ser Asn Tyr Val Asp Tyr Phe Asp
                245                 250                 255

Tyr Trp Gly Gln Gly Thr Leu Val Thr Val Ser Thr Gly Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn His Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Asp Tyr Lys Asp Asp Asp Asp Lys Arg Arg Lys Arg Ser Gly
385                 390                 395                 400

Ser Gly Ala Thr Asn Phe Ser Leu Leu Lys Gln Ala Gly Asp Val Glu
                405                 410                 415

Glu Asn Pro Gly Pro Asn Met Ala Leu Pro Val Thr Ala Leu Leu Leu
            420                 425                 430

Pro Leu Ala Leu Leu Leu His Ala Ala Arg Pro Asp Ile Gln Met Thr
        435                 440                 445

Gln Thr Thr Ser Ser Leu Ser Ala Ser Leu Gly Asp Arg Val Thr Ile
    450                 455                 460

Ser Cys Arg Ala Ser Gln Asp Ile Ser Lys Tyr Leu Asn Trp Tyr Gln
465                 470                 475                 480

Gln Lys Pro Asp Gly Thr Val Lys Leu Leu Ile Tyr His Thr Ser Arg
                485                 490                 495

Leu His Ser Gly Val Pro Ser Arg Phe Ser Gly Ser Gly Ser Gly Thr
            500                 505                 510

Asp Tyr Ser Leu Thr Ile Ser Asn Leu Glu Gln Glu Asp Ile Ala Thr
        515                 520                 525

Tyr Phe Cys Gln Gln Gly Asn Thr Leu Pro Tyr Thr Phe Gly Gly Gly
    530                 535                 540

Thr Lys Leu Glu Ile Thr Gly Gly Gly Gly Ser Gly Gly Gly Gly Ser
545                 550                 555                 560

Gly Gly Gly Gly Ser Glu Val Lys Leu Gln Glu Ser Gly Pro Gly Leu
                565                 570                 575

Val Ala Pro Ser Gln Ser Leu Ser Val Thr Cys Thr Val Ser Gly Val
            580                 585                 590

Ser Leu Pro Asp Tyr Gly Val Ser Trp Ile Arg Gln Pro Pro Arg Lys
        595                 600                 605

Gly Leu Glu Trp Leu Gly Val Ile Trp Gly Ser Glu Thr Thr Tyr Tyr
    610                 615                 620

Asn Ser Ala Leu Lys Ser Arg Leu Thr Ile Ile Lys Asp Asn Ser Lys
625                 630                 635                 640
```

```
Ser Gln Val Phe Leu Lys Met Asn Ser Leu Gln Thr Asp Asp Thr Ala
                645                 650                 655

Ile Tyr Tyr Cys Ala Lys His Tyr Tyr Tyr Gly Gly Ser Tyr Ala Met
            660                 665                 670

Asp Tyr Trp Gly Gln Gly Thr Ser Val Thr Val Ser Ser Ala Ala Ala
        675                 680                 685

Ile Glu Val Glu Gln Lys Leu Ile Ser Glu Glu Asp Leu Leu Asp Asn
    690                 695                 700

Glu Lys Ser Asn Gly Thr Ile Ile His Val Lys Gly Lys His Leu Cys
705                 710                 715                 720

Pro Ser Pro Leu Phe Pro Gly Pro Ser Lys Pro Phe Trp Val Leu Val
                725                 730                 735

Val Val Gly Gly Val Leu Ala Cys Tyr Ser Leu Leu Val Thr Val Ala
            740                 745                 750

Phe Ile Ile Phe Trp Val Arg Ser Lys Arg Ser Arg Leu Leu His Ser
        755                 760                 765

Asp Tyr Met Asn Met Thr Pro Arg Arg Pro Gly Pro Thr Arg Lys His
    770                 775                 780

Tyr Gln Pro Tyr Ala Pro Pro Arg Asp Phe Ala Ala Tyr Arg Ser Arg
785                 790                 795                 800

Val Lys Phe Ser Arg Ser Ala Asp Ala Pro Ala Tyr Gln Gln Gly Gln
                805                 810                 815

Asn Gln Leu Tyr Asn Glu Leu Asn Leu Gly Arg Arg Glu Glu Tyr Asp
            820                 825                 830

Val Leu Asp Lys Arg Arg Gly Arg Asp Pro Glu Met Gly Gly Lys Pro
        835                 840                 845

Arg Arg Lys Asn Pro Gln Glu Gly Leu Tyr Asn Glu Leu Gln Lys Asp
    850                 855                 860

Lys Met Ala Glu Ala Tyr Ser Glu Ile Gly Met Lys Gly Glu Arg Arg
865                 870                 875                 880

Arg Gly Lys Gly His Asp Gly Leu Tyr Gln Gly Leu Ser Thr Ala Thr
                885                 890                 895

Lys Asp Thr Tyr Asp Ala Leu His Met Gln Ala Leu Pro Pro Arg
            900                 905                 910


<210> SEQ ID NO 55
<211> LENGTH: 909
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Met Gly Pro Gly Val Leu Leu Leu Leu Leu Val Ala Thr Ala Trp His
1               5                   10                  15

Gly Gln Gly Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Leu Leu Ile Tyr Tyr Thr Ser Ile Leu His Ser Gly Val Pro Ser Arg
65                  70                  75                  80
```

```
Phe Ser Gly Ser Gly Ser Gly Thr Asp Tyr Ser Leu Thr Ile Ser Asn
                85                  90                  95

Leu Glu Gln Glu Asp Phe Ala Thr Tyr Phe Cys Gln Gln Gly Asn Thr
            100                 105                 110

Leu Pro Trp Thr Phe Gly Gly Gly Thr Lys Leu Glu Ile Lys Gly Ser
        115                 120                 125

Thr Ser Gly Ser Gly Lys Pro Gly Ser Gly Glu Gly Ser Thr Lys Gly
    130                 135                 140

Glu Val Gln Leu Val Glu Ser Gly Gly Gly Leu Val Lys Pro Gly Gly
145                 150                 155                 160

Ser Leu Lys Leu Ser Cys Ala Ala Ser Gly Phe Ala Phe Ser Ile Tyr
                165                 170                 175

Asp Met Ser Trp Val Arg Gln Thr Pro Glu Lys Arg Leu Glu Trp Val
            180                 185                 190

Ala Tyr Ile Ser Ser Gly Gly Gly Thr Thr Tyr Tyr Pro Asp Thr Val
        195                 200                 205

Lys Gly Arg Phe Thr Ile Ser Arg Asp Asn Ala Lys Asn Thr Leu Tyr
    210                 215                 220

Leu Gln Met Ser Ser Leu Lys Ser Glu Asp Thr Ala Met Tyr Tyr Cys
225                 230                 235                 240

Ala Arg His Ser Gly Tyr Gly Ser Ser Tyr Gly Val Leu Phe Ala Tyr
                245                 250                 255

Trp Gly Gln Gly Thr Leu Val Thr Val Ser Ala Ala Ala Ala Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Asp Tyr Lys Asp Asp Asp Asp Lys Arg Arg Lys Arg Ser Gly Ser Gly
385                 390                 395                 400

Ala Thr Asn Phe Ser Leu Leu Lys Gln Ala Gly Asp Val Glu Glu Asn
                405                 410                 415

Pro Gly Pro Asn Met Ala Leu Pro Val Thr Ala Leu Leu Leu Pro Leu
            420                 425                 430

Ala Leu Leu Leu His Ala Ala Arg Pro Asp Ile Gln Met Thr Gln Thr
        435                 440                 445

Thr Ser Ser Leu Ser Ala Ser Leu Gly Asp Arg Val Thr Ile Ser Cys
    450                 455                 460

Arg Ala Ser Gln Asp Ile Ser Lys Tyr Leu Asn Trp Tyr Gln Gln Lys
465                 470                 475                 480

Pro Asp Gly Thr Val Lys Leu Leu Ile Tyr His Thr Ser Arg Leu His
                485                 490                 495
```

```
Ser Gly Val Pro Ser Arg Phe Ser Gly Ser Gly Ser Gly Thr Asp Tyr
            500                 505                 510

Ser Leu Thr Ile Ser Asn Leu Glu Gln Glu Asp Ile Ala Thr Tyr Phe
        515                 520                 525

Cys Gln Gln Gly Asn Thr Leu Pro Tyr Thr Phe Gly Gly Gly Thr Lys
    530                 535                 540

Leu Glu Ile Thr Gly Gly Gly Gly Ser Gly Gly Gly Gly Ser Gly Gly
545                 550                 555                 560

Gly Gly Ser Glu Val Lys Leu Gln Glu Ser Gly Pro Gly Leu Val Ala
                565                 570                 575

Pro Ser Gln Ser Leu Ser Val Thr Cys Thr Val Ser Gly Val Ser Leu
            580                 585                 590

Pro Asp Tyr Gly Val Ser Trp Ile Arg Gln Pro Pro Arg Lys Gly Leu
        595                 600                 605

Glu Trp Leu Gly Val Ile Trp Gly Ser Glu Thr Thr Tyr Tyr Asn Ser
    610                 615                 620

Ala Leu Lys Ser Arg Leu Thr Ile Ile Lys Asp Asn Ser Lys Ser Gln
625                 630                 635                 640

Val Phe Leu Lys Met Asn Ser Leu Gln Thr Asp Asp Thr Ala Ile Tyr
                645                 650                 655

Tyr Cys Ala Lys His Tyr Tyr Tyr Gly Gly Ser Tyr Ala Met Asp Tyr
            660                 665                 670

Trp Gly Gln Gly Thr Ser Val Thr Val Ser Ser Ala Ala Ala Ile Glu
        675                 680                 685

Val Glu Gln Lys Leu Ile Ser Glu Glu Asp Leu Leu Asp Asn Glu Lys
    690                 695                 700

Ser Asn Gly Thr Ile Ile His Val Lys Gly Lys His Leu Cys Pro Ser
705                 710                 715                 720

Pro Leu Phe Pro Gly Pro Ser Lys Pro Phe Trp Val Leu Val Val Val
                725                 730                 735

Gly Gly Val Leu Ala Cys Tyr Ser Leu Leu Val Thr Val Ala Phe Ile
            740                 745                 750

Ile Phe Trp Val Arg Ser Lys Arg Ser Arg Leu Leu His Ser Asp Tyr
        755                 760                 765

Met Asn Met Thr Pro Arg Arg Pro Gly Pro Thr Arg Lys His Tyr Gln
    770                 775                 780

Pro Tyr Ala Pro Pro Arg Asp Phe Ala Ala Tyr Arg Ser Arg Val Lys
785                 790                 795                 800

Phe Ser Arg Ser Ala Asp Ala Pro Ala Tyr Gln Gln Gly Gln Asn Gln
                805                 810                 815

Leu Tyr Asn Glu Leu Asn Leu Gly Arg Arg Glu Glu Tyr Asp Val Leu
            820                 825                 830

Asp Lys Arg Arg Gly Arg Asp Pro Glu Met Gly Gly Lys Pro Arg Arg
        835                 840                 845

Lys Asn Pro Gln Glu Gly Leu Tyr Asn Glu Leu Gln Lys Asp Lys Met
    850                 855                 860

Ala Glu Ala Tyr Ser Glu Ile Gly Met Lys Gly Glu Arg Arg Arg Gly
865                 870                 875                 880

Lys Gly His Asp Gly Leu Tyr Gln Gly Leu Ser Thr Ala Thr Lys Asp
                885                 890                 895

Thr Tyr Asp Ala Leu His Met Gln Ala Leu Pro Pro Arg
            900                 905
```

```
<210> SEQ ID NO 56
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Ala Gly Ser Tyr Ala Met Asp Tyr Trp Gly Gln Gly
                245                 250                 255

Thr Ser Val Thr Val Ser Ser Ala Ala Ala Ile Glu Val Glu Gln Lys
            260                 265                 270

Leu Ile Ser Glu Glu Asp Leu Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365
```

Pro Arg Asp Phe Ala Ala Tyr Arg Ser Arg Val Lys Phe Ser Arg Ser
370 375 380

Ala Asp Ala Pro Ala Tyr Gln Gln Gly Gln Asn Gln Leu Tyr Asn Glu
385 390 395 400

Leu Asn Leu Gly Arg Arg Glu Glu Tyr Asp Val Leu Asp Lys Arg Arg
405 410 415

Gly Arg Asp Pro Glu Met Gly Gly Lys Pro Arg Arg Lys Asn Pro Gln
420 425 430

Glu Gly Leu Tyr Asn Glu Leu Gln Lys Asp Lys Met Ala Glu Ala Tyr
435 440 445

Ser Glu Ile Gly Met Lys Gly Glu Arg Arg Arg Gly Lys Gly His Asp
450 455 460

Gly Leu Tyr Gln Gly Leu Ser Thr Ala Thr Lys Asp Thr Tyr Asp Ala
465 470 475 480

Leu His Met Gln Ala Leu Pro Pro Arg
485

<210> SEQ ID NO 57
<211> LENGTH: 387
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

Met Gly Pro Gly Val Leu Leu Leu Leu Leu Val Ala Thr Ala Trp His
1 5 10 15

Gly Gln Gly Gly Asp Ile Gln Met Thr Gln Thr Thr Ser Ser Leu Ser
20 25 30

Ala Ser Leu Gly Asp Arg Val Thr Ile Ser Cys Arg Ala Ser Gln Asp
35 40 45

Ile Ser Lys Tyr Leu Asn Trp Tyr Gln Gln Lys Pro Asp Gly Thr Val
50 55 60

Lys Leu Leu Ile Tyr His Thr Ser Arg Leu His Ser Gly Val Pro Ser
65 70 75 80

Arg Phe Ser Gly Ser Gly Ser Gly Thr Asp Tyr Ser Leu Thr Ile Ser
85 90 95

Asn Leu Glu Gln Glu Asp Ile Ala Thr Tyr Phe Cys Gln Gln Gly Asn
100 105 110

Thr Leu Pro Tyr Thr Phe Gly Gly Gly Thr Lys Leu Glu Ile Thr Gly
115 120 125

Gly Gly Gly Ser Gly Gly Gly Gly Ser Gly Gly Gly Gly Ser Glu Val
130 135 140

Lys Leu Gln Glu Ser Gly Pro Gly Leu Val Ala Pro Ser Gln Ser Leu
145 150 155 160

Ser Val Thr Cys Thr Val Ser Gly Val Ser Leu Pro Asp Tyr Gly Val
165 170 175

Ser Trp Ile Arg Gln Pro Pro Arg Lys Gly Leu Glu Trp Leu Gly Val
180 185 190

Ile Trp Gly Ser Glu Thr Thr Tyr Tyr Asn Ser Ala Leu Lys Ser Arg
195 200 205

Leu Thr Ile Ile Lys Asp Asn Ser Lys Ser Gln Val Phe Leu Lys Met
210 215 220

Asn Ser Leu Gln Thr Asp Asp Thr Ala Ile Tyr Tyr Cys Ala Lys His
225 230 235 240

Tyr Tyr Tyr Gly Gly Ser Tyr Ala Met Asp Tyr Trp Gly Gln Gly Thr
245 250 255

Ser Val Thr Val Ser Ser Ala Ala Ala Pro Thr Thr Thr Pro Ala Pro
260 265 270

Arg Pro Pro Thr Pro Ala Pro Thr Ile Ala Ser Gln Pro Leu Ser Leu
275 280 285

Arg Pro Glu Ala Cys Arg Pro Ala Ala Gly Gly Ala Val His Thr Arg
290 295 300

Gly Leu Asp Phe Ala Cys Asp Ile Tyr Ile Trp Ala Pro Leu Ala Gly
305 310 315 320

Thr Cys Gly Val Leu Leu Leu Ser Leu Val Ile Thr Leu Tyr Cys Asn
325 330 335

His Lys Arg Gly Arg Lys Lys Leu Leu Tyr Ile Phe Lys Gln Pro Phe
340 345 350

Met Arg Pro Val Gln Thr Thr Gln Glu Glu Asp Gly Cys Ser Cys Arg
355 360 365

Phe Pro Glu Glu Glu Glu Gly Gly Cys Glu Leu Asp Tyr Lys Asp Asp
370 375 380

Asp Asp Lys
385

<210> SEQ ID NO 58
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ile Lys Asp Asn Ser Lys Ser Gln Val Phe Leu Lys
210 215 220

Met Asn Ser Leu Gln Thr Asp Asp Thr Ala Ile Tyr Tyr Cys Ala Lys
225 230 235 240

His Tyr Tyr Tyr Gly Ala Ser Tyr Ala Met Asp Tyr Trp Gly Gln Gly
245 250 255

Thr Ser Val Thr Val Ser Ser Ala Ala Ala Ile Glu Val Glu Gln Lys
260 265 270

Leu Ile Ser Glu Glu Asp Leu Leu Asp Asn Glu Lys Ser Asn Gly Thr
275 280 285

Ile Ile His Val Lys Gly Lys His Leu Cys Pro Ser Pro Leu Phe Pro
290 295 300

Gly Pro Ser Lys Pro Phe Trp Val Leu Val Val Val Gly Gly Val Leu
305 310 315 320

Ala Cys Tyr Ser Leu Leu Val Thr Val Ala Phe Ile Ile Phe Trp Val
325 330 335

Arg Ser Lys Arg Ser Arg Leu Leu His Ser Asp Tyr Met Asn Met Thr
340 345 350

Pro Arg Arg Pro Gly Pro Thr Arg Lys His Tyr Gln Pro Tyr Ala Pro
355 360 365

Pro Arg Asp Phe Ala Ala Tyr Arg Ser Arg Val Lys Phe Ser Arg Ser
370 375 380

Ala Asp Ala Pro Ala Tyr Gln Gln Gly Gln Asn Gln Leu Tyr Asn Glu
385 390 395 400

Leu Asn Leu Gly Arg Arg Glu Glu Tyr Asp Val Leu Asp Lys Arg Arg
405 410 415

Gly Arg Asp Pro Glu Met Gly Gly Lys Pro Arg Arg Lys Asn Pro Gln
420 425 430

Glu Gly Leu Tyr Asn Glu Leu Gln Lys Asp Lys Met Ala Glu Ala Tyr
435 440 445

Ser Glu Ile Gly Met Lys Gly Glu Arg Arg Arg Gly Lys Gly His Asp
450 455 460

Gly Leu Tyr Gln Gly Leu Ser Thr Ala Thr Lys Asp Thr Tyr Asp Ala
465 470 475 480

Leu His Met Gln Ala Leu Pro Pro Arg
485

<210> SEQ ID NO 59
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 59

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

```
Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Ala Tyr Tyr Gly Gly Ser Tyr Ala Met Asp Tyr Trp Gly Gln Gly
                245                 250                 255

Thr Ser Val Thr Val Ser Ser Ala Ala Ala Ile Glu Val Glu Gln Lys
            260                 265                 270

Leu Ile Ser Glu Glu Asp Leu Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445
```

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 60
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Ala Tyr Gly Gly Ser Tyr Ala Met Asp Tyr Trp Gly Gln Gly
                245                 250                 255

Thr Ser Val Thr Val Ser Ser Ala Ala Ala Ile Glu Val Glu Gln Lys
            260                 265                 270

Leu Ile Ser Glu Glu Asp Leu Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305 310 315 320

Ala Cys Tyr Ser Leu Leu Val Thr Val Ala Phe Ile Ile Phe Trp Val
325 330 335

Arg Ser Lys Arg Ser Arg Leu Leu His Ser Asp Tyr Met Asn Met Thr
340 345 350

Pro Arg Arg Pro Gly Pro Thr Arg Lys His Tyr Gln Pro Tyr Ala Pro
355 360 365

Pro Arg Asp Phe Ala Ala Tyr Arg Ser Arg Val Lys Phe Ser Arg Ser
370 375 380

Ala Asp Ala Pro Ala Tyr Gln Gln Gly Gln Asn Gln Leu Tyr Asn Glu
385 390 395 400

Leu Asn Leu Gly Arg Arg Glu Glu Tyr Asp Val Leu Asp Lys Arg Arg
405 410 415

Gly Arg Asp Pro Glu Met Gly Gly Lys Pro Arg Arg Lys Asn Pro Gln
420 425 430

Glu Gly Leu Tyr Asn Glu Leu Gln Lys Asp Lys Met Ala Glu Ala Tyr
435 440 445

Ser Glu Ile Gly Met Lys Gly Glu Arg Arg Arg Gly Lys Gly His Asp
450 455 460

Gly Leu Tyr Gln Gly Leu Ser Thr Ala Thr Lys Asp Thr Tyr Asp Ala
465 470 475 480

Leu His Met Gln Ala Leu Pro Pro Arg
485

<210> SEQ ID NO 61
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

```
Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Ala Gly Gly Ser Tyr Ala Met Asp Tyr Trp Gly Gln Gly
                245                 250                 255

Thr Ser Val Thr Val Ser Ser Ala Ala Ala Ile Glu Val Glu Gln Lys
            260                 265                 270

Leu Ile Ser Glu Glu Asp Leu Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

```
<210> SEQ ID NO 62
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Met Ala Leu Pro Val Thr Ala Leu Leu Leu Pro Leu Ala Leu Leu Leu
1               5                   10                  15
```

```
His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Ala Ala Met Asp Tyr Trp Gly Gln Gly
                245                 250                 255

Thr Ser Val Thr Val Ser Ser Ala Ala Ala Ile Glu Val Glu Gln Lys
            260                 265                 270

Leu Ile Ser Glu Glu Asp Leu Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430
```

Glu Gly Leu Tyr Asn Glu Leu Gln Lys Asp Lys Met Ala Glu Ala Tyr
435 440 445

Ser Glu Ile Gly Met Lys Gly Glu Arg Arg Arg Gly Lys Gly His Asp
450 455 460

Gly Leu Tyr Gln Gly Leu Ser Thr Ala Thr Lys Asp Thr Tyr Asp Ala
465 470 475 480

Leu His Met Gln Ala Leu Pro Pro Arg
485

<210> SEQ ID NO 63
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ile Lys Asp Asn Ser Lys Ser Gln Val Phe Leu Lys
210 215 220

Met Asn Ser Leu Gln Thr Asp Asp Thr Ala Ile Tyr Tyr Cys Ala Lys
225 230 235 240

His Tyr Tyr Tyr Gly Gly Ser Tyr Ala Met Asp Ala Trp Gly Gln Gly
245 250 255

Thr Ser Val Thr Val Ser Ser Ala Ala Ala Ile Glu Val Glu Gln Lys
260 265 270

Leu Ile Ser Glu Glu Asp Leu Leu Asp Asn Glu Lys Ser Asn Gly Thr
275 280 285

```
Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 64
<211> LENGTH: 489
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Glu
    130                 135                 140
```

```
Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Ala Ala Ala Ile Glu Val Glu Gln Lys
            260                 265                 270

Leu Ile Ser Glu Glu Asp Leu Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 65
<211> LENGTH: 394
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Met Gly Pro Gly Val Leu Leu Leu Leu Leu Val Ala Thr Ala Trp His
1               5                   10                  15

Gly Gln Gly Gly Gln Ile Val Leu Ser Gln Ser Pro Ala Ile Leu Ser
            20                  25                  30

Ala Ser Pro Gly Glu Lys Val Thr Met Thr Cys Arg Ala Ser Ser Ser
        35                  40                  45

Leu Ser Phe Met His Trp Tyr Gln Gln Lys Pro Gly Ser Ser Pro Lys
    50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Phe Cys His Gln Trp Ser Ser
            100                 105                 110

Asn Pro Leu Thr Phe Gly Ala Gly Thr Lys Val Glu Ile Lys Arg Lys
        115                 120                 125

Gly Ser Thr Ser Gly Ser Gly Lys Pro Gly Ser Gly Glu Gly Ser Thr
    130                 135                 140

Lys Gly Gln Val Gln Leu Arg Gln Pro Gly Ala Glu Leu Val Lys Pro
145                 150                 155                 160

Gly Ala Ser Val Lys Met Ser Cys Lys Ala Ser Gly Tyr Thr Phe Thr
                165                 170                 175

Ser Tyr Asn Met His Trp Val Lys Gln Thr Pro Gly Gln Gly Leu Glu
            180                 185                 190

Trp Ile Gly Ala Ile Tyr Pro Gly Asn Gly Asp Thr Ser Tyr Asn Gln
        195                 200                 205

Lys Phe Lys Gly Lys Ala Thr Leu Thr Ala Asp Lys Ser Ser Ser Thr
    210                 215                 220

Ala Tyr Met Gln Leu Ser Ser Leu Thr Ser Glu Asp Ser Ala Val Tyr
225                 230                 235                 240

Tyr Cys Ala Arg Ser His Tyr Gly Ser Asn Tyr Val Asp Tyr Phe Asp
                245                 250                 255

Tyr Trp Gly Gln Gly Thr Leu Val Thr Val Ser Thr Gly Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn His Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Asp Tyr Lys Asp Asp Asp Asp Lys
385                 390
```

```
<210> SEQ ID NO 66
<211> LENGTH: 392
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Met Gly Pro Gly Val Leu Leu Leu Leu Leu Val Ala Thr Ala Trp His
1               5                   10                  15

Gly Gln Gly Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn Tyr Leu Asn Trp Tyr Gln Gln Lys Pro Asp Gly Thr Val Lys
    50                  55                  60

Leu Leu Ile Tyr Tyr Thr Ser Ile Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Phe Ala Thr Tyr Phe Cys Gln Gln Gly Asn Thr
            100                 105                 110

Leu Pro Trp Thr Phe Gly Gly Gly Thr Lys Leu Glu Ile Lys Gly Ser
        115                 120                 125

Thr Ser Gly Ser Gly Lys Pro Gly Ser Gly Glu Gly Ser Thr Lys Gly
    130                 135                 140

Glu Val Gln Leu Val Glu Ser Gly Gly Gly Leu Val Lys Pro Gly Gly
145                 150                 155                 160

Ser Leu Lys Leu Ser Cys Ala Ala Ser Gly Phe Ala Phe Ser Ile Tyr
                165                 170                 175

Asp Met Ser Trp Val Arg Gln Thr Pro Glu Lys Arg Leu Glu Trp Val
            180                 185                 190

Ala Tyr Ile Ser Ser Gly Gly Gly Thr Thr Tyr Tyr Pro Asp Thr Val
        195                 200                 205

Lys Gly Arg Phe Thr Ile Ser Arg Asp Asn Ala Lys Asn Thr Leu Tyr
    210                 215                 220

Leu Gln Met Ser Ser Leu Lys Ser Glu Asp Thr Ala Met Tyr Tyr Cys
225                 230                 235                 240

Ala Arg His Ser Gly Tyr Gly Ser Ser Tyr Gly Val Leu Phe Ala Tyr
                245                 250                 255

Trp Gly Gln Gly Thr Leu Val Thr Val Ser Ala Ala Ala Ala Pro Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Asn His Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365
```

Gly Cys Ser Cys Arg Phe Pro Glu Glu Glu Glu Gly Gly Cys Glu Leu
370 375 380

Asp Tyr Lys Asp Asp Asp Asp Lys
385 390

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 101
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acggcggaag ctacgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 102
<211> LENGTH: 1470

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 102
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acgccggaag ctacgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 103
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 103
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acggcgccag ctacgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 104
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 104
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cacgcctact acggcggaag ctacgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 105
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 105
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactacgcct acggcggaag ctacgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 106
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactacg ccggcggaag ctacgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 107
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 107
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acggcggaag cgccgctatg gactactggg gccagggaac cagcgtgacc 780
gtgagcagcg cggccgctat cgaggtggag cagaagctga tcagcgagga ggacctgcta 840
gacaatgaga agagcaatgg aaccattatc catgtgaaag ggaaacacct ttgtccaagt 900
cccctatttc ccggaccttc taagcccttt tgggtgctgg tggtggttgg tggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgctaa 1470

<210> SEQ ID NO 108
<211> LENGTH: 1470
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 108
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420

```
ggaggcagcg aggtgaagct gcaggagagc ggccccggcc tggtggcccc cagccagagc    480

ctgagcgtga cctgcaccgt gagcggcgtg agcctgcccg actacggcgt gagctggatc    540

agacagcctc ccagaaaggg cctggagtgg ctgggcgtga tctggggcag cgagaccacc    600

tactacaaca gcgccctgaa gagcagactg accatcatta aggacaacag caagtcccag    660

gtgttcctga agatgaacag cctgcagacc gacgacaccg ccatctacta ctgcgccaag    720

cactactact acggcggaag ctacgctatg gacgcctggg gccagggaac cagcgtgacc    780

gtgagcagcg cggccgctat cgaggtggag cagaagctga tcagcgagga ggacctgcta    840

gacaatgaga agagcaatgg aaccattatc catgtgaaag ggaaacacct ttgtccaagt    900

cccctatttc ccggaccttc taagcccttt tgggtgctgg tggtggttgg tggagtcctg    960

gcttgctata gcttgctagt aacagtggcc tttattattt tctgggtgag gagtaagagg   1020

agcaggctcc tgcacagtga ctacatgaac atgactcccc gccgccccgg gcccacccgc   1080

aagcattacc agccctatgc cccaccacgc gacttcgcag cctatcgctc cagagtgaag   1140

ttcagcagga gcgcagacgc ccccgcgtac cagcagggcc agaaccagct ctataacgag   1200

ctcaatctag gacgaagaga ggagtacgat gttttggaca agagacgtgg ccgggaccct   1260

gagatggggg gaaagccgag aaggaagaac cctcaggaag gcctgtacaa tgaactgcag   1320

aaagataaga tggcggaggc ctacagtgag attgggatga aaggcgagcg ccggaggggc   1380

aaggggcacg atggccttta ccagggtctc agtacagcca ccaaggacac ctacgacgcc   1440

cttcacatgc aggccctgcc ccctcgctaa                                    1470
```

<210> SEQ ID NO 109
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 109

```
atgggcccag gagttctgct gctcctgctg gtggccacag cttggcatgg tcagggaggt     60

gacatccaga tgacacagac aacatcctcc ctctccgctt ccctcggaga cagggtcaca    120

atttcctgca gggcttccca ggacatttcc aagtacctca actggtacca gcagaagcct    180

gacggaacag tcaagctcct catttaccac acatccaggc tccactccgg agtcccttcc    240

aggttctccg gatccggatc cggaacagac tactccctca caatttccaa cctcgagcag    300

gaggacattg ctacatactt ctgccagcag ggaaacacac tcccttacac attcggagga    360

ggaacaaagc tcgagattac aggaggtggc ggttccggtg gtggaggctc cggtggtggt    420

ggatctgagg tcaagctcca ggagtccgga cctggacttg tcgctccttc tcagtctctc    480

tccgtcacat gcacagtctc cggagtctcc ctccctgatt atggagtctc ctggattagg    540

caacctccta ggaaaggact cgaatggctc ggagtcattt ggggatccga aacaacatat    600

tataattccg ctctcaaatc caggctcaca attattaaag ataattccaa atcccaagtc    660

tttctcaaga tgaactccct ccagacagac gacacagcta tttactactg cgctaagcac    720

tactactacg gggatctta cgctatggac tactggggac agggaacatc cgtcacagtc    780

tcttccgctg ctgctcccac caccacaccc gctcccagac cccctacccc tgcccccacc    840

atcgccagcc agcccctgag cctgagaccc gaggcctgca gacctgccgc cggcggagcc    900

gtgcacacca gaggcctgga cttcgcctgc gacatctaca tctgggctcc cctggccggc    960
```

acctgcggcg tgctgctgct gagcctggtg atcaccctgt actgcaacca caagagaggc 1020
agaaagaagc tgctgtacat cttcaagcag cccttcatga gacccgtgca gaccacccag 1080
gaggaggacg gctgcagctg cagattcccc gaggaggagg agggcggctg cgagctggac 1140
tacaaagacg atgacgacaa gcggagaaag cgcagcggct ccggcgccac gaacttctct 1200
ctgttaaagc aagcaggaga cgtggaagaa aaccccggtc ccaacatggc tctgcctgtg 1260
acagctctgc tgctgcctct ggctctgctg ctgcacgccg ctagacccga catccagatg 1320
acccagacca ccagcagcct gagcgccagc ctgggcgaca gagtgaccat cagctgcaga 1380
gccagccagg acatcagcaa gtacctgaac tggtaccagc agaagcccga cggcaccgtg 1440
aagctgctga tctaccacac cagcagactg cacagcggcg tgcccagcag attcagcggc 1500
agcggcagcg gcaccgacta cagcctgacc atcagcaacc tggagcagga ggacatcgcc 1560
acctacttct gccagcaggg caacaccctg ccctacacct tcggcggagg caccaagctg 1620
gagatcaccg gcggaggagg aagcggagga ggaggcagcg gaggaggagg cagcgaggtg 1680
aagctgcagg agagcggccc cggcctggtg gcccccagcc agagcctgag cgtgacctgc 1740
accgtgagcg gcgtgagcct gcccgactac ggcgtgagct ggatcagaca gcctcccaga 1800
aagggcctgg agtggctggg cgtgatctgg ggcagcgaga ccacctacta caacagcgcc 1860
ctgaagagca gactgaccat cattaaggac aacagcaagt cccaggtgtt cctgaagatg 1920
aacagcctgc agaccgacga caccgccatc tactactgcg ccaagcacta ctactacgcc 1980
ggaagctacg ctatggacta ctggggccag ggaaccagcg tgaccgtgag cagcgcggcc 2040
gctatcgagg tggagcagaa gctgatcagc gaggaggacc tgctggacaa cgagaagagc 2100
aacggcacca tcatccacgt gaagggcaag cacctgtgcc ccagccccct gttccccggc 2160
cccagcaagc ccttctgggt gctggtggtg gtgggcggcg tgctggcctg ctacagcctg 2220
ctggtgaccg tggccttcat catcttctgg gtgcggagca agcggagccg gctgctgcac 2280
agcgactaca tgaacatgac cccccggcgg cctgggccca cccgcaagca ttaccagccc 2340
tatgccccac cacgcgactt cgcagcctat cgctccagag tgaagttcag caggagcgca 2400
gacgcccccg cgtaccagca gggccagaac cagctctata acgagctcaa tctaggacga 2460
agagaggagt acgatgtttt ggacaagaga cgtggccggg accctgagat ggggggaaag 2520
ccgagaagga agaaccctca ggaaggcctg tacaatgaac tgcagaaaga taagatggcg 2580
gaggcctaca gtgagattgg gatgaaaggc gagcgccgga ggggcaaggg gcacgatggc 2640
ctttaccagg gtctcagtac agccaccaag gacacctacg acgcccttca catgcaggcc 2700
ctgccccctc gctaa 2715

<210> SEQ ID NO 110
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 110
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180

```
gacggaacag tcaagctcct catttaccac acatccaggc tccactccgg agtcccttcc    240
aggttctccg gatccggatc cggaacagac tactccctca caatttccaa cctcgagcag    300
gaggacattg ctacatactt ctgccagcag ggaaacacac tcccttacac attcggagga    360
ggaacaaagc tcgagattac aggaggtggc ggttccggtg gtggaggctc cggtggtggt    420
ggatctgagg tcaagctcca ggagtccgga cctggacttg tcgctccttc tcagtctctc    480
tccgtcacat gcacagtctc cggagtctcc ctccctgatt atggagtctc ctggattagg    540
caacctccta ggaaaggact cgaatggctc ggagtcattt ggggatccga aacaacatat    600
tataattccg ctctcaaatc caggctcaca attattaaag ataattccaa atcccaagtc    660
tttctcaaga tgaactccct ccagacagac gacacagcta tttactactg cgctaagcac    720
tactactacg gggggatctta cgctatggac tactggggac agggaacatc cgtcacagtc    780
tcttccgctg ctgctcccac caccacaccc gctcccagac cccctacccc tgcccccacc    840
atcgccagcc agcccctgag cctgagaccc gaggcctgca gacctgccgc cggcggagcc    900
gtgcacacca gaggcctgga cttcgcctgc gacatctaca tctgggctcc cctggccggc    960
acctgcggcg tgctgctgct gagcctggtg atcaccctgt actgcaacca caagagaggc   1020
agaaagaagc tgctgtacat cttcaagcag cccttcatga gacccgtgca gaccacccag   1080
gaggaggacg gctgcagctg cagattcccc gaggaggagg agggcggctg cgagctggac   1140
tacaaagacg atgacgacaa gcggagaaag cgcagcggct ccggcgccac gaacttctct   1200
ctgttaaagc aagcaggaga cgtggaagaa aaccccggtc ccaacatggc tctgcctgtg   1260
acagctctgc tgctgcctct ggctctgctg ctgcacgccg ctagacccga catccagatg   1320
acccagacca ccagcagcct gagcgccagc ctgggcgaca gagtgaccat cagctgcaga   1380
gccagccagg acatcagcaa gtacctgaac tggtaccagc agaagcccga cggcaccgtg   1440
aagctgctga tctaccacac cagcagactg cacagcggcg tgcccagcag attcagcggc   1500
agcggcagcg gcaccgacta cagcctgacc atcagcaacc tggagcagga ggacatcgcc   1560
acctacttct gccagcaggg caacaccctg ccctacacct tcggcggagg caccaagctg   1620
gagatcaccg gcggaggagg aagcggagga ggaggcagcg gaggaggagg cagcgaggtg   1680
aagctgcagg agagcggccc cggcctggtg gcccccagcc agagcctgag cgtgacctgc   1740
accgtgagcg gcgtgagcct gcccgactac ggcgtgagct ggatcagaca gcctcccaga   1800
aagggcctgg agtggctggg cgtgatctgg ggcagcgaga ccacctacta caacagcgcc   1860
ctgaagagca gactgaccat cattaaggac aacagcaagt cccaggtgtt cctgaagatg   1920
aacagcctgc agaccgacga caccgccatc tactactgcg ccaagcacta ctactacggc   1980
gccagctacg ctatggacta ctggggccag ggaaccagcg tgaccgtgag cagcgcggcc   2040
gctatcgagg tggagcagaa gctgatcagc gaggaggacc tgctggacaa cgagaagagc   2100
aacggcacca tcatccacgt gaagggcaag cacctgtgcc ccagccccct gttccccggc   2160
cccagcaagc ccttctgggt gctggtggtg gtgggcggcg tgctggcctg ctacagcctg   2220
ctggtgaccg tggccttcat catcttctgg gtgcggagca agcggagccg gctgctgcac   2280
agcgactaca tgaacatgac cccccggcgg cctgggccca cccgcaagca ttaccagccc   2340
tatgccccac cacgcgactt cgcagcctat cgctccagag tgaagttcag caggagcgca   2400
gacgcccccg cgtaccagca gggccagaac cagctctata acgagctcaa tctaggacga   2460
agagaggagt acgatgtttt ggacaagaga cgtggccggg accctgagat ggggggaaag   2520
ccgagaagga agaaccctca ggaaggcctg tacaatgaac tgcagaaaga taagatggcg   2580
```

gaggcctaca gtgagattgg gatgaaaggc gagcgccgga ggggcaaggg gcacgatggc 2640
ctttaccagg gtctcagtac agccaccaag gacacctacg acgcccttca catgcaggcc 2700
ctgccccctc gctaa 2715

<210> SEQ ID NO 111
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 111
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180
gacggaacag tcaagctcct catttaccac acatccaggc tccactccgg agtcccttcc 240
aggttctccg gatccggatc cggaacagac tactccctca caatttccaa cctcgagcag 300
gaggacattg ctacatactt ctgccagcag ggaaacacac tcccttacac attcggagga 360
ggaacaaagc tcgagattac aggaggtggc ggttccggtg gtggaggctc cggtggtggt 420
ggatctgagg tcaagctcca ggagtccgga cctggacttg tcgctccttc tcagtctctc 480
tccgtcacat gcacagtctc cggagtctcc ctccctgatt atggagtctc ctggattagg 540
caacctccta ggaaaggact cgaatggctc ggagtcattt ggggatccga aacaacatat 600
tataattccg ctctcaaatc caggctcaca attattaaag ataattccaa atcccaagtc 660
tttctcaaga tgaactccct ccagacagac gacacagcta tttactactg cgctaagcac 720
tactactacg gggatcttta cgctatggac tactggggac agggaacatc cgtcacagtc 780
tcttccgctg ctgctcccac caccacaccc gctcccagac cccctacccc tgcccccacc 840
atcgccagcc agcccctgag cctgagaccc gaggcctgca gacctgccgc cggcggagcc 900
gtgcacacca gaggcctgga cttcgcctgc gacatctaca tctgggctcc cctggccggc 960
acctgcggcg tgctgctgct gagcctggtg atcaccctgt actgcaacca caagagaggc 1020
agaaagaagc tgctgtacat cttcaagcag cccttcatga gacccgtgca gaccacccag 1080
gaggaggacg gctgcagctg cagattcccc gaggaggagg agggcggctg cgagctggac 1140
tacaaagacg atgacgacaa gcggagaaag cgcagcggct ccggcgccac gaacttctct 1200
ctgttaaagc aagcaggaga cgtggaagaa aaccccggtc ccaacatggc tctgcctgtg 1260
acagctctgc tgctgcctct ggctctgctg ctgcacgccg ctagacccga catccagatg 1320
acccagacca ccagcagcct gagcgccagc ctgggcgaca gagtgaccat cagctgcaga 1380
gccagccagg acatcagcaa gtacctgaac tggtaccagc agaagcccga cggcaccgtg 1440
aagctgctga tctaccacac cagcagactg cacagcggcg tgcccagcag attcagcggc 1500
agcggcagcg gcaccgacta cagcctgacc atcagcaacc tggagcagga ggacatcgcc 1560
acctacttct gccagcaggg caacaccctg ccctacacct tcggcggagg caccaagctg 1620
gagatcaccg gcggaggagg aagcggagga ggaggcagcg gaggaggagg cagcgaggtg 1680
aagctgcagg agagcggccc cggcctggtg gcccccagcc agagcctgag cgtgacctgc 1740
accgtgagcg gcgtgagcct gcccgactac ggcgtgagct ggatcagaca gcctcccaga 1800
aagggcctgg agtggctggg cgtgatctgg ggcagcgaga ccacctacta caacagcgcc 1860
ctgaagagca gactgaccat cattaaggac aacagcaagt cccaggtgtt cctgaagatg 1920
aacagcctgc agaccgacga caccgccatc tactactgcg ccaagcacgc ctactacggc 1980
ggaagctacg ctatggacta ctggggccag ggaaccagcg tgaccgtgag cagcgcggcc 2040
gctatcgagg tggagcagaa gctgatcagc gaggaggacc tgctagacaa tgagaagagc 2100
aatggaacca ttatccatgt gaaagggaaa cacctttgtc caagtcccct atttcccgga 2160
ccttctaagc ccttttgggt gctggtggtg gttggtggag tcctggcttg ctatagcttg 2220
ctagtaacag tggcctttat tattttctgg gtgaggagta agaggagcag gctcctgcac 2280
agtgactaca tgaacatgac tccccgccgc cccgggccca cccgcaagca ttaccagccc 2340
tatgccccac cacgcgactt cgcagcctat cgctccagag tgaagttcag caggagcgca 2400
gacgcccccg cgtaccagca gggccagaac cagctctata acgagctcaa tctaggacga 2460
agagaggagt acgatgtttt ggacaagaga cgtggccggg accctgagat ggggggaaag 2520
ccgagaagga agaaccctca ggaaggcctg tacaatgaac tgcagaaaga taagatggcg 2580
gaggcctaca gtgagattgg gatgaaaggc gagcgccgga ggggcaaggg gcacgatggc 2640
ctttaccagg gtctcagtac agccaccaag gacacctacg acgcccttca catgcaggcc 2700
ctgccccctc gctaa 2715

<210> SEQ ID NO 112
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 112
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180
gacggaacag tcaagctcct catttaccac acatccaggc tccactccgg agtcccttcc 240
aggttctccg gatccggatc cggaacagac tactccctca caatttccaa cctcgagcag 300
gaggacattg ctacatactt ctgccagcag ggaaacacac tcccttacac attcggagga 360
ggaacaaagc tcgagattac aggaggtggc ggttccggtg gtggaggctc cggtggtggt 420
ggatctgagg tcaagctcca ggagtccgga cctggacttg tcgctccttc tcagtctctc 480
tccgtcacat gcacagtctc cggagtctcc ctccctgatt atggagtctc ctggattagg 540
caacctccta ggaaaggact cgaatggctc ggagtcattt ggggatccga aacaacatat 600
tataattccg ctctcaaatc caggctcaca attattaaag ataattccaa atcccaagtc 660
tttctcaaga tgaactccct ccagacagac gacacagcta tttactactg cgctaagcac 720
tactactacg gggatctta cgctatggac tactggggac agggaacatc cgtcacagtc 780
tcttccgctg ctgctcccac caccacaccc gctcccagac cccctacccc tgcccccacc 840
atcgccagcc agcccctgag cctgagaccc gaggcctgca gacctgccgc cggcggagcc 900
gtgcacacca gaggcctgga cttcgcctgc gacatctaca tctgggctcc cctggccggc 960
acctgcggcg tgctgctgct gagcctggtg atcaccctgt actgcaacca caagagaggc 1020
agaaagaagc tgctgtacat cttcaagcag cccttcatga gacccgtgca gaccacccag 1080
gaggaggacg gctgcagctg cagattcccc gaggaggagg agggcggctg cgagctggac 1140
tacaaagacg atgacgacaa gcggagaaag cgcagcggct ccggcgccac gaacttctct 1200
ctgttaaagc aagcaggaga cgtggaagaa aaccccggtc ccaacatggc tctgcctgtg 1260
acagctctgc tgctgcctct ggctctgctg ctgcacgccg ctagacccga catccagatg 1320
acccagacca ccagcagcct gagcgccagc ctgggcgaca gagtgaccat cagctgcaga 1380
gccagccagg acatcagcaa gtacctgaac tggtaccagc agaagcccga cggcaccgtg 1440
aagctgctga tctaccacac cagcagactg cacagcggcg tgcccagcag attcagcggc 1500
agcggcagcg gcaccgacta cagcctgacc atcagcaacc tggagcagga ggacatcgcc 1560
acctacttct gccagcaggg caacaccctg ccctacacct tcggcggagg caccaagctg 1620
gagatcaccg gcggaggagg aagcggagga ggaggcagcg gaggaggagg cagcgaggtg 1680
aagctgcagg agagcggccc cggcctggtg gcccccagcc agagcctgag cgtgacctgc 1740
accgtgagcg gcgtgagcct gcccgactac ggcgtgagct ggatcagaca gcctcccaga 1800
aagggcctgg agtggctggg cgtgatctgg ggcagcgaga ccacctacta caacagcgcc 1860
ctgaagagca gactgaccat cattaaggac aacagcaagt cccaggtgtt cctgaagatg 1920
aacagcctgc agaccgacga caccgccatc tactactgcg ccaagcacta cgcctacggc 1980
ggaagctacg ctatggacta ctggggccag ggaaccagcg tgaccgtgag cagcgcggcc 2040
gctatcgagg tggagcagaa gctgatcagc gaggaggacc tgctggacaa cgagaagagc 2100
aacggcacca tcatccacgt gaagggcaag cacctgtgcc ccagcccccct gttccccggc 2160 cccagcaagc ccttctgggt gctggtggtg gtgggcggcg tgctggcctg ctacagcctg 2220
ctggtgaccg tggccttcat catcttctgg gtgcggagca agcggagccg gctgctgcac 2280
agcgactaca tgaacatgac cccccggcgg cctgggccca cccgcaagca ttaccagccc 2340
tatgccccac cacgcgactt cgcagcctat cgctccagag tgaagttcag caggagcgca 2400
gacgcccccg cgtaccagca gggccagaac cagctctata acgagctcaa tctaggacga 2460
agagaggagt acgatgtttt ggacaagaga cgtggccggg accctgagat ggggggaaag 2520
ccgagaagga agaaccctca ggaaggcctg tacaatgaac tgcagaaaga taagatggcg 2580
gaggcctaca gtgagattgg gatgaaaggc gagcgccgga ggggcaaggg gcacgatggc 2640
ctttaccagg gtctcagtac agccaccaag gacacctacg acgcccttca catgcaggcc 2700
ctgccccctc gctaa 2715

<210> SEQ ID NO 113
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 113
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180
gacggaacag tcaagctcct catttaccac acatccaggc tccactccgg agtcccttcc 240
aggttctccg gatccggatc cggaacagac tactccctca caatttccaa cctcgagcag 300

-continued

```
gaggacattg ctacatactt ctgccagcag ggaaacacac tcccttacac attcggagga    360
ggaacaaagc tcgagattac aggaggtggc ggttccggtg gtggaggctc cggtggtggt    420
ggatctgagg tcaagctcca ggagtccgga cctggacttg tcgctccttc tcagtctctc    480
tccgtcacat gcacagtctc cggagtctcc ctccctgatt atggagtctc ctggattagg    540
caacctccta ggaaaggact cgaatggctc ggagtcattt ggggatccga aacaacatat    600
tataattccg ctctcaaatc caggctcaca attattaaag ataattccaa atcccaagtc    660
tttctcaaga tgaactccct ccagacagac gacacagcta tttactactg cgctaagcac    720
tactactacg gggatcttta cgctatggac tactggggac agggaacatc cgtcacagtc    780
tcttccgctg ctgctcccac caccacaccc gctcccagac cccctacccc tgcccccacc    840
atcgccagcc agcccctgag cctgagaccc gaggcctgca gacctgccgc cggcggagcc    900
gtgcacacca gaggcctgga cttcgcctgc gacatctaca tctgggctcc cctggccggc    960
acctgcggcg tgctgctgct gagcctggtg atcaccctgt actgcaacca caagagaggc   1020
agaaagaagc tgctgtacat cttcaagcag cccttcatga gacccgtgca gaccacccag   1080
gaggaggacg gctgcagctg cagattcccc gaggaggagg agggcggctg cgagctggac   1140
tacaaagacg atgacgacaa gcggagaaag cgcagcggct ccggcgccac gaacttctct   1200
ctgttaaagc aagcaggaga cgtggaagaa aaccccggtc ccaacatggc tctgcctgtg   1260
acagctctgc tgctgcctct ggctctgctg ctgcacgccg ctagacccga catccagatg   1320
acccagacca ccagcagcct gagcgccagc ctgggcgaca gagtgaccat cagctgcaga   1380
gccagccagg acatcagcaa gtacctgaac tggtaccagc agaagcccga cggcaccgtg   1440
aagctgctga tctaccacac cagcagactg cacagcggcg tgcccagcag attcagcggc   1500
agcggcagcg gcaccgacta cagcctgacc atcagcaacc tggagcagga ggacatcgcc   1560
acctacttct gccagcaggg caacaccctg ccctacacct tcggcggagg caccaagctg   1620
gagatcaccg gcggaggagg aagcggagga ggaggcagcg gaggaggagg cagcgaggtg   1680
aagctgcagg agagcggccc cggcctggtg gcccccagcc agagcctgag cgtgacctgc   1740
accgtgagcg gcgtgagcct gcccgactac ggcgtgagct ggatcagaca gcctcccaga   1800
aagggcctgg agtggctggg cgtgatctgg ggcagcgaga ccacctacta caacagcgcc   1860
ctgaagagca gactgaccat cattaaggac aacagcaagt cccaggtgtt cctgaagatg   1920
aacagcctgc agaccgacga caccgccatc tactactgcg ccaagcacta ctacgccggc   1980
ggaagctacg ctatggacta ctggggccag ggaaccagcg tgaccgtgag cagcgcggcc   2040
gctatcgagg tggagcagaa gctgatcagc gaggaggacc tgctggacaa cgagaagagc   2100
aacggcacca tcatccacgt gaagggcaag cacctgtgcc ccagccccct gttccccggc   2160
cccagcaagc ccttctgggt gctggtggtg gtgggcggcg tgctggcctg ctacagcctg   2220
ctggtgaccg tggccttcat catcttctgg gtgcggagca agcggagccg gctgctgcac   2280
agcgactaca tgaacatgac cccccggcgg cctgggccca cccgcaagca ttaccagccc   2340
tatgccccac cacgcgactt cgcagcctat cgctccagag tgaagttcag caggagcgca   2400
gacgcccccg cgtaccagca gggccagaac cagctctata acgagctcaa tctaggacga   2460
agagaggagt acgatgtttt ggacaagaga cgtggccggg accctgagat ggggggaaag   2520
ccgagaagga agaaccctca ggaaggcctg tacaatgaac tgcagaaaga taagatggcg   2580
gaggcctaca gtgagattgg gatgaaaggc gagcgccgga ggggcaaggg gcacgatggc   2640
```

ctttaccagg gtctcagtac agccaccaag gacacctacg acgcccttca catgcaggcc 2700 ctgcccctc gctaa 2715

<210> SEQ ID NO 114
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 114
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180
gacggaacag tcaagctcct catttaccac acatccaggc tccactccgg agtcccttcc 240
aggttctccg gatccggatc cggaacagac tactccctca caatttccaa cctcgagcag 300
gaggacattg ctacatactt ctgccagcag ggaaacacac tcccttacac attcggagga 360
ggaacaaagc tcgagattac aggaggtggc ggttccggtg gtggaggctc cggtggtggt 420
ggatctgagg tcaagctcca ggagtccgga cctggacttg tcgctccttc tcagtctctc 480
tccgtcacat gcacagtctc cggagtctcc ctccctgatt atggagtctc ctggattagg 540
caacctccta ggaaaggact cgaatggctc ggagtcattt ggggatccga aacaacatat 600
tataattccg ctctcaaatc caggctcaca attattaaag ataattccaa atcccaagtc 660
tttctcaaga tgaactccct ccagacagac gacacagcta tttactactg cgctaagcac 720
tactactacg gggatcttta cgctatggac tactggggac agggaacatc cgtcacagtc 780
tcttccgctg ctgctcccac caccacaccc gctcccagac cccctacccc tgcccccacc 840
atcgccagcc agcccctgag cctgagaccc gaggcctgca gacctgccgc cggcggagcc 900
gtgcacacca gaggcctgga cttcgcctgc gacatctaca tctgggctcc cctggccggc 960
acctgcggcg tgctgctgct gagcctggtg atcaccctgt actgcaacca caagagaggc 1020
agaaagaagc tgctgtacat cttcaagcag cccttcatga gacccgtgca gaccacccag 1080
gaggaggacg gctgcagctg cagattcccc gaggaggagg agggcggctg cgagctggac 1140
tacaaagacg atgacgacaa gcggagaaag cgcagcggct ccggcgccac gaacttctct 1200
ctgttaaagc aagcaggaga cgtggaagaa aaccccggtc ccaacatggc tctgcctgtg 1260
acagctctgc tgctgcctct ggctctgctg ctgcacgccg ctagacccga catccagatg 1320
acccagacca ccagcagcct gagcgccagc ctgggcgaca gagtgaccat cagctgcaga 1380
gccagccagg acatcagcaa gtacctgaac tggtaccagc agaagcccga cggcaccgtg 1440
aagctgctga tctaccacac cagcagactg cacagcggcg tgcccagcag attcagcggc 1500
agcggcagcg gcaccgacta cagcctgacc atcagcaacc tggagcagga ggacatcgcc 1560
acctacttct gccagcaggg caacaccctg ccctacacct tcggcggagg caccaagctg 1620
gagatcaccg gcggaggagg aagcggagga ggaggcagcg gaggaggagg cagcgaggtg 1680
aagctgcagg agagcggccc cggcctggtg gcccccagcc agagcctgag cgtgacctgc 1740
accgtgagcg gcgtgagcct gcccgactac ggcgtgagct ggatcagaca gcctcccaga 1800
aagggcctgg agtggctggg cgtgatctgg ggcagcgaga ccacctacta caacagcgcc 1860
ctgaagagca gactgaccat cattaaggac aacagcaagt cccaggtgtt cctgaagatg 1920
aacagcctgc agaccgacga caccgccatc tactactgcg ccaagcacta ctactacggc 1980
ggaagcgccg ctatggacta ctggggccag ggaaccagcg tgaccgtgag cagcgcggcc 2040
gctatcgagg tggagcagaa gctgatcagc gaggaggacc tgctggacaa cgagaagagc 2100
aacggcacca tcatccacgt gaagggcaag cacctgtgcc ccagccccct gttccccggc 2160
cccagcaagc ccttctgggt gctggtggtg gtgggcggcg tgctggcctg ctacagcctg 2220
ctggtgaccg tggccttcat catcttctgg gtgcggagca agcggagccg gctgctgcac 2280
agcgactaca tgaacatgac cccccggcgg cctgggccca cccgcaagca ttaccagccc 2340
tatgccccac cacgcgactt cgcagcctat cgctccagag tgaagttcag caggagcgca 2400
gacgcccccg cgtaccagca gggccagaac cagctctata acgagctcaa tctaggacga 2460
agagaggagt acgatgtttt ggacaagaga cgtggccggg accctgagat gggggggaaag 2520 ccgagaagga agaaccctca ggaaggcctg tacaatgaac tgcagaaaga taagatggcg 2580
gaggcctaca gtgagattgg gatgaaaggc gagcgccgga ggggcaaggg gcacgatggc 2640
ctttaccagg gtctcagtac agccaccaag gacacctacg acgcccttca catgcaggcc 2700
ctgccccctc gctaa 2715

<210> SEQ ID NO 115
<211> LENGTH: 2715
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 115
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180
gacggaacag tcaagctcct catttaccac acatccaggc tccactccgg agtcccttcc 240
aggttctccg gatccggatc cggaacagac tactccctca caatttccaa cctcgagcag 300
gaggacattg ctacatactt ctgccagcag ggaaacacac tcccttacac attcggagga 360
ggaacaaagc tcgagattac aggaggtggc ggttccggtg gtggaggctc cggtggtggt 420
ggatctgagg tcaagctcca ggagtccgga cctggacttg tcgctccttc tcagtctctc 480
tccgtcacat gcacagtctc cggagtctcc ctccctgatt atggagtctc ctggattagg 540
caacctccta ggaaaggact cgaatggctc ggagtcattt ggggatccga aacaacatat 600
tataattccg ctctcaaatc caggctcaca attattaaag ataattccaa atcccaagtc 660
tttctcaaga tgaactccct ccagacagac gacacagcta tttactactg cgctaagcac 720
tactactacg gggatctta cgctatggac tactggggac agggaacatc cgtcacagtc 780
tcttccgctg ctgctcccac caccacaccc gctcccagac cccctacccc tgcccccacc 840
atcgccagcc agcccctgag cctgagaccc gaggcctgca gacctgccgc cggcggagcc 900
gtgcacacca gaggcctgga cttcgcctgc gacatctaca tctgggctcc cctggccggc 960
acctgcggcg tgctgctgct gagcctggtg atcaccctgt actgcaacca caagagaggc 1020
agaaagaagc tgctgtacat cttcaagcag cccttcatga gacccgtgca gaccacccag 1080
gaggaggacg gctgcagctg cagattcccc gaggaggagg agggcggctg cgagctggac 1140
tacaaagacg atgacgacaa gcggagaaag cgcagcggct ccggcgccac gaacttctct 1200
ctgttaaagc aagcaggaga cgtggaagaa aaccccggtc ccaacatggc tctgcctgtg 1260
acagctctgc tgctgcctct ggctctgctg ctgcacgccg ctagacccga catccagatg 1320
acccagacca ccagcagcct gagcgccagc ctgggcgaca gagtgaccat cagctgcaga 1380
gccagccagg acatcagcaa gtacctgaac tggtaccagc agaagcccga cggcaccgtg 1440
aagctgctga tctaccacac cagcagactg cacagcggcg tgcccagcag attcagcggc 1500
agcggcagcg gcaccgacta cagcctgacc atcagcaacc tggagcagga ggacatcgcc 1560
acctacttct gccagcaggg caacaccctg ccctacacct tcggcggagg caccaagctg 1620
gagatcaccg gcggaggagg aagcggagga ggaggcagcg gaggaggagg cagcgaggtg 1680
aagctgcagg agagcggccc cggcctggtg gcccccagcc agagcctgag cgtgacctgc 1740
accgtgagcg gcgtgagcct gcccgactac ggcgtgagct ggatcagaca gcctcccaga 1800
aagggcctgg agtggctggg cgtgatctgg ggcagcgaga ccacctacta caacagcgcc 1860
ctgaagagca gactgaccat cattaaggac aacagcaagt cccaggtgtt cctgaagatg 1920
aacagcctgc agaccgacga caccgccatc tactactgcg ccaagcacta ctactacggc 1980
ggaagctacg ctatggacgc ctggggccag ggaaccagcg tgaccgtgag cagcgcggcc 2040
gctatcgagg tggagcagaa gctgatcagc gaggaggacc tgctggacaa cgagaagagc 2100
aacggcacca tcatccacgt gaagggcaag cacctgtgcc ccagccccct gttccccggc 2160
cccagcaagc ccttctgggt gctggtggtg gtgggcggcg tgctggcctg ctacagcctg 2220
ctggtgaccg tggccttcat catcttctgg gtgcggagca agcggagccg gctgctgcac 2280
agcgactaca tgaacatgac cccccggcgg cctgggccca cccgcaagca ttaccagccc 2340
tatgccccac cacgcgactt cgcagcctat cgctccagag tgaagttcag caggagcgca 2400
gacgcccccg cgtaccagca gggccagaac cagctctata acgagctcaa tctaggacga 2460
agagaggagt acgatgtttt ggacaagaga cgtggccggg accctgagat ggggggaaag 2520
ccgagaagga agaaccctca ggaaggcctg tacaatgaac tgcagaaaga taagatggcg 2580
gaggcctaca gtgagattgg gatgaaaggc gagcgccgga ggggcaaggg gcacgatggc 2640
ctttaccagg gtctcagtac agccaccaag gacacctacg acgcccttca catgcaggcc 2700
ctgccccctc gctaa 2715

<210> SEQ ID NO 116
<211> LENGTH: 2736
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 116
atgggacctg gcgtgctgct gctgctgctg gtggccaccg cttggcatgg acagggagga 60
cagatcgtgc tgagccagag ccctgccatc ctgagcgcca gccctggcga gaaggtgacc 120
atgacctgca gagccagctc cagcctgagc ttcatgcact ggtaccagca gaagcccggc 180
agcagcccta agccctggat ctacgccacc agcaacctgg ccagcggcgt gcccgccaga 240
ttcagcggca gcggcagcgg caccagctac agcctgacca tcagcagagt ggaggccgag 300
gacgccgcca cctacttctg ccaccagtgg agcagcaacc ccctgacctt cggcgccggc 360
accaaggtgg agatcaagag aaagggcagc accagcggaa gcggcaagcc tggaagcgga 420
gagggcagca ccaagggaca ggtgcagctg agacagcctg gcgccgagct ggtgaagccc 480
ggcgccagcg tgaagatgag ctgcaaggcc agcggctaca ccttcaccag ctacaacatg 540
cactgggtga agcagacccc tggccagggc ctggagtgga tcggcgccat ctatcccggc 600
aacggcgaca ccagctacaa ccagaagttc aagggcaagg ccaccctgac cgccgacaag 660
agcagcagca ccgcctacat gcagctgagc agcctgacca gcgaggacag cgccgtgtac 720
tactgcgcca gaagccacta cggcagcaac tacgtggact acttcgacta ctggggccag 780
ggcaccctgg tgaccgtgag caccggcgcg gccgccccca ccaccacacc cgctcccaga 840
cccccctaccc ctgcccccac catcgccagc cagcccctga gcctgagacc cgaggcctgc 900
agacctgccg ccggcggagc cgtgcacacc agaggcctgg acttcgcctg cgacatctac 960
atctgggctc ccctggccgg cacctgcggc gtgctgctgc tgagcctggt gatcaccctg 1020
tactgcaacc acaagagagg cagaaagaag ctgctgtaca tcttcaagca gcccttcatg 1080
agacccgtgc agaccaccca ggaggaggac ggctgcagct gcagattccc cgaggaggag 1140
gagggcggct gcgagctgga ctacaaagac gatgacgaca agagaagaaa gagaagcggc 1200
agcggcgcca cgaacttctc tctgttaaag caagcaggag acgtggaaga aaaccccggt 1260
cccaacatgg ctctgcctgt gacagctctg ctgctgcctc tggctctgct gctgcacgcc 1320
gctagacccg acatccagat gacccagacc accagcagcc tgagcgccag cctgggcgac 1380
agagtgacca tcagctgcag agccagccag gacatcagca agtacctgaa ctggtaccag 1440
cagaagcccg acggcaccgt gaagctgctg atctaccaca ccagcagact gcacagcggc 1500
gtgcccagca gattcagcgg cagcggcagc ggcaccgact acagcctgac catcagcaac 1560
ctggagcagg aggacatcgc cacctacttc tgccagcagg gcaacaccct gccctacacc 1620
ttcggcggag gcaccaagct ggagatcacc ggcggaggag gaagcggagg aggaggcagc 1680
ggaggaggag gcagcgaggt gaagctgcag gagagcggcc ccggcctggt ggcccccagc 1740
cagagcctga gcgtgacctg caccgtgagc ggcgtgagcc tgcccgacta cggcgtgagc 1800
tggatcagac agcctcccag aaagggcctg gagtggctgg gcgtgatctg gggcagcgag 1860
accacctact acaacagcgc cctgaagagc agactgacca tcattaagga caacagcaag 1920
tcccaggtgt tcctgaagat gaacagcctg cagaccgacg acaccgccat ctactactgc 1980
gccaagcact actactacgg cggaagctac gctatggact actggggcca gggaaccagc 2040
gtgaccgtga gcagcgcggc cgctatcgag gtggagcaga agctgatcag cgaggaggac 2100
ctgctagaca atgagaagag caatggaacc attatccatg tgaaagggaa acacctttgt 2160
ccaagtcccc tatttcccgg accttctaag cccttttggg tgctggtggt ggttggtgga 2220
gtcctggctt gctatagctt gctagtaaca gtggccttta ttattttctg ggtgaggagt 2280
aagaggagca ggctcctgca cagtgactac atgaacatga ctccccgccg ccccgggccc 2340
acccgcaagc attaccagcc ctatgcccca ccacgcgact tcgcagccta tcgctccaga 2400
gtgaagttca gcaggagcgc agacgccccc gcgtaccagc agggccagaa ccagctctat 2460
aacgagctca atctaggacg aagagaggag tacgatgttt tggacaagag acgtggccgg 2520
gaccctgaga tgggggggaaa gccgagaagg aagaaccctc aggaaggcct gtacaatgaa 2580
ctgcagaaag ataagatggc ggaggcctac agtgagattg ggatgaaagg cgagcgccgg 2640
aggggcaagg ggcacgatgg cctttaccag ggtctcagta cagccaccaa ggacacctac 2700
gacgcccttc acatgcaggc cctgccccct cgctaa 2736

<210> SEQ ID NO 117
<211> LENGTH: 2730
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 117
atgggccctg gagtgctgct gctcctgctg gtggccacag cttggcacgg ccagggagat 60
atccagatga cccagactac atcctccctg tctgcctctc tgggagacag agtcaccatt 120
agttgcaggg caagtcagga cattagcaat tatttaaact ggtatcagca gaaaccagat 180
ggaactgtta aactcctgat ctactacaca tcaatattac actcaggagt cccatcaagg 240
ttcagtggca gtgggtctgg aacagattat tctctcacca ttagcaacct ggagcaagaa 300
gattttgcca cttacttttg ccaacagggt aatacgcttc cgtggacgtt cggtggaggc 360
accaagctgg aaatcaaagg cagcaccagc ggaagcggca agcctggaag cggagagggc 420
agcaccaagg gagaagtgca gctggtggag tctgggggag gcttagtgaa gcctggaggg 480
tccctgaaac tctcctgtgc agcctctgga ttcgctttca gtatctatga catgtcttgg 540
gttcgccaga ctccggagaa gaggctggag tgggtcgcat acattagtag tggtggtggt 600
accacctact atccagacac tgtgaagggc cgattcacca tctccagaga caatgccaag 660
aacaccctgt acctgcaaat gagcagtctg aagtctgagg acacagccat gtattactgt 720
gcaagacata gtggctacgg tagtagctac ggggttttgt ttgcttactg gggccaaggg 780
actctggtca ctgtctctgc cgcggccgcc cccaccacca cacccgctcc cagacccccct 840 acccctgccc ccaccatcgc cagccagccc ctgagcctga gacccgaggc ctgcagacct 900
gccgccggcg gagccgtgca caccagaggc ctggacttcg cctgcgacat ctacatctgg 960
gctcccctgg ccggcacctg cggcgtgctg ctgctgagcc tggtgatcac cctgtactgc 1020
aaccacaaga gaggcagaaa gaagctgctg tacatcttca agcagccctt catgagaccc 1080
gtgcagacca cccaggagga ggacggctgc agctgcagat tccccgagga ggaggagggc 1140
ggctgcgagc tggactacaa agacgatgac gacaagcgga gaaagcgcag cggctccggc 1200
gccacgaact tctctctgtt aaagcaagca ggagacgtgg aagaaaaccc cggtcccaac 1260
atggctctgc ctgtgacagc tctgctgctg cctctggctc tgctgctgca cgccgctaga 1320
cccgacatcc agatgaccca gaccaccagc agcctgagcg ccagcctggg cgacagagtg 1380
accatcagct gcagagccag ccaggacatc agcaagtacc tgaactggta ccagcagaag 1440
cccgacggca ccgtgaagct gctgatctac cacaccagca gactgcacag cggcgtgccc 1500
agcagattca gcggcagcgg cagcggcacc gactacagcc tgaccatcag caacctggag 1560
caggaggaca tcgccaccta cttctgccag cagggcaaca ccctgcccta caccttcggc 1620
ggaggcacca agctggagat caccggcgga ggaggaagcg gaggaggagg cagcggagga 1680
ggaggcagcg aggtgaagct gcaggagagc ggccccggcc tggtggcccc cagccagagc 1740
ctgagcgtga cctgcaccgt gagcggcgtg agcctgcccg actacggcgt gagctggatc 1800
agacagcctc ccagaaaggg cctggagtgg ctgggcgtga tctggggcag cgagaccacc 1860
tactacaaca gcgccctgaa gagcagactg accatcatta aggacaacag caagtcccag 1920
gtgttcctga agatgaacag cctgcagacc gacgacaccg ccatctacta ctgcgccaag 1980

```
cactactact acggcggaag ctacgctatg gactactggg gccagggaac cagcgtgacc   2040

gtgagcagcg cggccgctat cgaggtggag cagaagctga tcagcgagga ggacctgcta   2100

gacaatgaga agagcaatgg aaccattatc catgtgaaag ggaaacacct ttgtccaagt   2160

cccctatttc ccggaccttc taagcccttt tgggtgctgg tggtggttgg tggagtcctg   2220

gcttgctata gcttgctagt aacagtggcc tttattattt tctgggtgag gagtaagagg   2280

agcaggctcc tgcacagtga ctacatgaac atgactcccc gccgccccgg gcccacccgc   2340

aagcattacc agccctatgc cccaccacgc gacttcgcag cctatcgctc cagagtgaag   2400

ttcagcagga gcgcagacgc ccccgcgtac cagcagggcc agaaccagct ctataacgag   2460

ctcaatctag gacgaagaga ggagtacgat gttttggaca agagacgtgg ccgggaccct   2520

gagatggggg gaaagccgag aaggaagaac cctcaggaag gcctgtacaa tgaactgcag   2580

aaagataaga tggcggaggc ctacagtgag attgggatga aaggcgagcg ccggaggggc   2640

aaggggcacg atggccttta ccagggtctc agtacagcca ccaaggacac ctacgacgcc   2700

cttcacatgc aggccctgcc ccctcgctaa                                    2730
```

<210> SEQ ID NO 118
<211> LENGTH: 790
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 118

```
atggctctgc ctgtgacagc tctgctgctg cctctggctc tgctgctgca cgccgctaga     60

cccgacatcc agatgaccca gaccaccagc agcctgagcg ccagcctggg cgacagagtg    120

accatcagct gcagagccag ccaggacatc agcaagtacc tgaactggta ccagcagaag    180

cccgacggca ccgtgaagct gctgatctac cacaccagca gactgcacag cggcgtgccc    240

agcagattca gcggcagcgg cagcggcacc gactacagcc tgaccatcag caacctggag    300

caggaggaca tcgccaccta cttctgccag cagggcaaca ccctgcccta caccttcggc    360

ggaggcacca agctggagat caccggcgga ggaggaagcg gaggaggagg cagcggagga    420

ggaggcagcg aggtgaagct gcaggagagc ggccccggcc tggtggcccc cagccagagc    480

ctgagcgtga cctgcaccgt gagcggcgtg agcctgcccg actacggcgt gagctggatc    540

agacagcctc ccagaaaggg cctggagtgg ctgggcgtga tctggggcag cgagaccacc    600

tactacaaca gcgccctgaa gagcagactg accatcatta aggacaacag caagtcccag    660

gtgttcctga agatgaacag cctgcagacc gacgacaccg ccatctacta ctgcgccaag    720

cactactact acggcggaag ctacgctatg gactactggg gccagggaac cagcgtgacc    780

gtgagcagcg                                                           790
```

<210> SEQ ID NO 119
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 119
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acgccggaag ctacgctatg gactactggg gccagggaac cagcgtgacc 780
gtgagcagc 789

<210> SEQ ID NO 120
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 120
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acggcgccag ctacgctatg gactactggg gccagggaac cagcgtgacc 780
gtgagcagc 789

<210> SEQ ID NO 121
<211> LENGTH: 789
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 121
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cacgcctact acggcggaag ctacgctatg gactactggg gccagggaac cagcgtgacc 780
gtgagcagc 789

<210> SEQ ID NO 122
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactacgcct acggcggaag ctacgctatg gactactggg gccagggaac cagcgtgacc 780
gtgagcagc 789

<210> SEQ ID NO 123
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 123
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactacg ccggcggaag ctacgctatg gactactggg gccagggaac cagcgtgacc 780
gtgagcagc 789

<210> SEQ ID NO 124
<211> LENGTH: 789
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 124
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acggcggaag cgccgctatg gactactggg gccagggaac cagcgtgacc 780
gtgagcagc 789

<210> SEQ ID NO 125
<211> LENGTH: 789
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 125
atggctctgc ctgtgacagc tctgctgctg cctctggctc tgctgctgca cgccgctaga 60
cccgacatcc agatgaccca gaccaccagc agcctgagcg ccagcctggg cgacagagtg 120
accatcagct gcagagccag ccaggacatc agcaagtacc tgaactggta ccagcagaag 180
cccgacggca ccgtgaagct gctgatctac cacaccagca gactgcacag cggcgtgccc 240
agcagattca gcggcagcgg cagcggcacc gactacagcc tgaccatcag caacctggag 300
caggaggaca tcgccaccta cttctgccag cagggcaaca ccctgcccta caccttcggc 360
ggaggcacca agctggagat caccggcgga ggaggaagcg gaggaggagg cagcggagga 420
ggaggcagcg aggtgaagct gcaggagagc ggccccggcc tggtggcccc cagccagagc 480
ctgagcgtga cctgcaccgt gagcggcgtg agcctgcccg actacggcgt gagctggatc 540
agacagcctc ccagaaaggg cctggagtgg ctgggcgtga tctggggcag cgagaccacc 600
tactacaaca gcgccctgaa gagcagactg accatcatta aggacaacag caagtcccag 660
gtgttcctga agatgaacag cctgcagacc gacgacaccg ccatctacta ctgcgccaag 720
cactactact acggcggaag ctacgctatg gacgcctggg gccagggaac cagcgtgacc 780
gtgagcagc 789

<210> SEQ ID NO 126
<211> LENGTH: 807
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 126
atgggacctg gcgtgctgct gctgctgctg gtggccaccg cttggcatgg acagggagga 60
cagatcgtgc tgagccagag ccctgccatc ctgagcgcca gccctggcga gaaggtgacc 120
atgacctgca gagccagctc cagcctgagc ttcatgcact ggtaccagca gaagcccggc 180
agcagcccta agccctggat ctacgccacc agcaacctgg ccagcggcgt gcccgccaga 240
ttcagcggca gcggcagcgg caccagctac agcctgacca tcagcagagt ggaggccgag 300
gacgccgcca cctacttctg ccaccagtgg agcagcaacc ccctgacctt cggcgccggc 360
accaaggtgg agatcaagag aaagggcagc accagcggaa gcggcaagcc tggaagcgga 420
gagggcagca ccaagggaca ggtgcagctg agacagcctg gcgccgagct ggtgaagccc 480
ggcgccagcg tgaagatgag ctgcaaggcc agcggctaca ccttcaccag ctacaacatg 540
cactgggtga agcagacccc tggccagggc ctggagtgga tcggcgccat ctatcccggc 600
aacggcgaca ccagctacaa ccagaagttc aagggcaagg ccaccctgac cgccgacaag 660
agcagcagca ccgcctacat gcagctgagc agcctgacca gcgaggacag cgccgtgtac 720
tactgcgcca gaagccacta cggcagcaac tacgtggact acttcgacta ctggggccag 780
ggcaccctgg tgaccgtgag caccggc 807

<210> SEQ ID NO 127
<211> LENGTH: 804

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127
atgggacctg gcgtgctgct gctgctgctg gtggccaccg cttggcatgg acagggagga 60
gatatccaga tgacccagac tacatcctcc ctgtctgcct ctctgggaga cagagtcacc 120
attagttgca gggcaagtca ggacattagc aattatttaa actggtatca gcagaaacca 180
gatggaactg ttaaactcct gatctactac acatcaatat tacactcagg agtcccatca 240
aggttcagtg gcagtgggtc tggaacagat tattctctca ccattagcaa cctggagcaa 300
gaagattttg ccacttactt ttgccaacag ggtaatacgc ttccgtggac gttcggtgga 360
ggcaccaagc tggaaatcaa aggcagcacc agcggaagcg gcaagcctgg aagcggagag 420
ggcagcacca agggagaagt gcagctggtg gagtctgggg gaggcttagt gaagcctgga 480
gggtccctga aactctcctg tgcagcctct ggattcgctt tcagtatcta tgacatgtct 540
tgggttcgcc agactccgga gaagaggctg gagtgggtcg catacattag tagtggtggt 600
ggtaccacct actatccaga cactgtgaag ggccgattca ccatctccag agacaatgcc 660
aagaacaccc tgtacctgca aatgagcagt ctgaagtctg aggacacagc catgtattac 720
tgtgcaagac atagtggcta cggtagtagc tacggggttt tgtttgctta ctggggccaa 780
gggactctgg tcactgtctc tgca 804

<210> SEQ ID NO 128
<211> LENGTH: 1137
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 128
atgggcccag gagttctgct gctcctgctg gtggccacag cttggcatgg tcagggaggt 60
gacatccaga tgacacagac aacatcctcc ctctccgctt ccctcggaga cagggtcaca 120
atttcctgca gggcttccca ggacatttcc aagtacctca actggtacca gcagaagcct 180
gacggaacag tcaagctcct catttaccac acatccaggc tccactccgg agtcccttcc 240
aggttctccg gatccggatc cggaacagac tactccctca caatttccaa cctcgagcag 300
gaggacattg ctacatactt ctgccagcag ggaaacacac tcccttacac attcggagga 360
ggaacaaagc tcgagattac aggaggtggc ggttccggtg gtggaggctc cggtggtggt 420
ggatctgagg tcaagctcca ggagtccgga cctggacttg tcgctccttc tcagtctctc 480
tccgtcacat gcacagtctc cggagtctcc ctccctgatt atggagtctc ctggattagg 540
caacctccta ggaaaggact cgaatggctc ggagtcattt ggggatccga aacaacatat 600
tataattccg ctctcaaatc caggctcaca attattaaag ataattccaa atcccaagtc 660
tttctcaaga tgaactccct ccagacagac gacacagcta tttactactg cgctaagcac 720
tactactacg gggatctta cgctatggac tactggggac agggaacatc cgtcacagtc 780
tcttccgctg ctgctcccac caccacaccc gctcccagac cccctacccc tgcccccacc 840
atcgccagcc agcccctgag cctgagaccc gaggcctgca gacctgccgc cggcggagcc 900
gtgcacacca gaggcctgga cttcgcctgc gacatctaca tctgggctcc cctggccggc 960
acctgcggcg tgctgctgct gagcctggtg atcaccctgt actgcaacca caagagaggc 1020
agaaagaagc tgctgtacat cttcaagcag cccttcatga gacccgtgca gaccacccag 1080
gaggaggacg gctgcagctg cagattcccc gaggaggagg agggcggctg cgagctg 1137

<210> SEQ ID NO 129
<211> LENGTH: 1158
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 129
atgggacctg gcgtgctgct gctgctgctg gtggccaccg cttggcatgg acagggagga 60
cagatcgtgc tgagccagag ccctgccatc ctgagcgcca gccctggcga gaaggtgacc 120
atgacctgca gagccagctc cagcctgagc ttcatgcact ggtaccagca gaagcccggc 180
agcagcccta agccctggat ctacgccacc agcaacctgg ccagcggcgt gcccgccaga 240
ttcagcggca gcggcagcgg caccagctac agcctgacca tcagcagagt ggaggccgag 300
gacgccgcca cctacttctg ccaccagtgg agcagcaacc ccctgacctt cggcgccggc 360
accaaggtgg agatcaagag aaagggcagc accagcggaa gcggcaagcc tggaagcgga 420
gagggcagca ccaagggaca ggtgcagctg agacagcctg gcgccgagct ggtgaagccc 480
ggcgccagcg tgaagatgag ctgcaaggcc agcggctaca ccttcaccag ctacaacatg 540
cactgggtga agcagacccc tggccagggc ctggagtgga tcggcgccat ctatcccggc 600
aacggcgaca ccagctacaa ccagaagttc aagggcaagg ccaccctgac cgccgacaag 660
agcagcagca ccgcctacat gcagctgagc agcctgacca gcgaggacag cgccgtgtac 720
tactgcgcca gaagccacta cggcagcaac tacgtggact acttcgacta ctggggccag 780
ggcaccctgg tgaccgtgag caccggcgcg gccgccccca ccaccacacc cgctcccaga 840
ccccctaccc ctgcccccac catcgccagc cagcccctga gcctgagacc cgaggcctgc 900
agacctgccg ccggcggagc cgtgcacacc agaggcctgg acttcgcctg cgacatctac 960
atctgggctc ccctggccgg cacctgcggc gtgctgctgc tgagcctggt gatcaccctg 1020
tactgcaacc acaagagagg cagaaagaag ctgctgtaca tcttcaagca gcccttcatg 1080
agacccgtgc agaccaccca ggaggaggac ggctgcagct gcagattccc cgaggaggag 1140
gagggcggct gcgagctg 1158

<210> SEQ ID NO 130
<211> LENGTH: 1152
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130
atgggccctg gagtgctgct gctcctgctg gtggccacag cttggcacgg ccagggagat 60
atccagatga cccagactac atcctccctg tctgcctctc tgggagacag agtcaccatt 120
agttgcaggg caagtcagga cattagcaat tatttaaact ggtatcagca gaaaccagat 180
ggaactgtta aactcctgat ctactacaca tcaatattac actcaggagt cccatcaagg 240

```
ttcagtggca gtgggtctgg aacagattat tctctcacca ttagcaacct ggagcaagaa    300

gattttgcca cttacttttg ccaacagggt aatacgcttc cgtggacgtt cggtggaggc    360

accaagctgg aaatcaaagg cagcaccagc ggaagcggca agcctggaag cggagagggc    420

agcaccaagg gagaagtgca gctggtggag tctgggggag gcttagtgaa gcctggaggg    480

tccctgaaac tctcctgtgc agcctctgga ttcgctttca gtatctatga catgtcttgg    540

gttcgccaga ctccggagaa gaggctggag tgggtcgcat acattagtag tggtggtggt    600

accacctact atccagacac tgtgaagggc cgattcacca tctccagaga caatgccaag    660

aacaccctgt acctgcaaat gagcagtctg aagtctgagg acacagccat gtattactgt    720

gcaagacata gtggctacgg tagtagctac ggggttttgt ttgcttactg gggccaaggg    780

actctggtca ctgtctctgc cgcggccgcc cccaccacca cacccgctcc cagaccccct    840

acccctgccc ccaccatcgc cagccagccc ctgagcctga gacccgaggc ctgcagacct    900

gccgccggcg gagccgtgca caccagaggc ctggacttcg cctgcgacat ctacatctgg    960

gctcccctgg ccggcacctg cggcgtgctg ctgctgagcc tggtgatcac cctgtactgc   1020

aaccacaaga gaggcagaaa gaagctgctg tacatcttca agcagccctt catgagaccc   1080

gtgcagacca cccaggagga ggacggctgc agctgcagat tccccgagga ggaggagggc   1140

ggctgcgagc tg                                                       1152
```

<210> SEQ ID NO 131
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 131

```
Glu Gln Lys Leu Ile Ser Glu Glu Asp Leu
1               5                   10
```

<210> SEQ ID NO 132
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 132

```
Asp Tyr Lys Asp Asp Asp Asp Lys
1               5
```

<210> SEQ ID NO 133
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 133

```
Met Tyr Pro Pro Pro Tyr
1               5
```

```
<210> SEQ ID NO 134
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Ser Gly Ser Gly
1


<210> SEQ ID NO 135
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

His Tyr Tyr Tyr Gly Gly Ser Tyr Ala Met Asp Ala
1               5                   10
```

B CELL TARGETED PARALLEL CAR (pCAR) THERAPEUTIC AGENTS

CROSS-REFERENCE TO RELATED APPLICATIONS

This application is a U.S. National Stage Application of International Application No. PCT/EP2020/074071, filed Aug. 28, 2020, which claims the benefit of, and priority to, U.S. Provisional Patent Application No. 62/892,936, filed Aug. 28, 2019 and 62/983,451, filed Feb. 28, 2020, the contents of which are hereby incorporated by reference in their entirety.

SEQUENCE LISTING

This application contains a Sequence Listing that has been submitted electronically in ASCII format and is hereby incorporated by reference in its entirety. The ASCII copy, created on May 21, 2025, is named 44312US_CRF_sequencelisting.txt and is 222,334 bytes in size.

1. BACKGROUND

Chimeric antigen receptors (CARs), which are at times referred to as artificial T cell receptors, chimeric T cell receptors (cTCR), or chimeric immunoreceptors, are engineered receptors now well known in the art. They are used primarily to transform immune effector cells, in particular T cells, to provide those cells with a desired engineered specificity. Adoptive cell therapies using CAR-T cells are particularly under investigation in the field of cancer therapy. In these therapies, T cells are removed from a patient and modified so that they express CARs specific to the antigens found in a particular form of cancer. The CAR-T cells, which can then recognize and kill the cancer cells, are reintroduced into the patient.

First generation CARs provide a TCR-like signal, most commonly using a CD3 zeta (z) intracellular signaling domain, and thereby elicit tumoricidal functions. However, the engagement of CD3z-chain fusion receptors may not suffice to elicit substantial IL-2 secretion and/or T cell proliferation in the absence of a concomitant co-stimulatory signal. In physiological T cell responses, optimal lymphocyte activation requires the engagement of one or more co-stimulatory receptors such as CD28 or 4-1BB.

Second ($2^{nd}$) generation CARs have been constructed to transduce a functional antigen-dependent co-stimulatory signal in human primary T cells in addition to antigen-dependent TCR-like signal, permitting T cell proliferation in addition to tumoricidal activity. Second generation CARs most commonly provide co-stimulation using co-stimulatory domains (synonymously, co-stimulatory signaling regions) derived from CD28 or 4-1BB. The combined delivery of co-stimulation plus a CD3 zeta signal renders $2^{nd}$ generation CARs clearly superior in terms of function as compared to their first generation counterparts (CD3z signal alone). An example of a $2^{nd}$ generation CAR is found in U.S. Pat. No. 7,446,190, incorporated herein by reference.

More recently, so-called $3^{rd}$ generation CARs have been prepared. These combine multiple co-stimulatory domains (synonymously, co-stimulatory signaling regions) with a TCR-like signaling domain in cis, such as CD28+4-1BB+CD3z or CD28+OX40+CD3z, to further augment potency. In the $3^{rd}$ generation CARs, the co-stimulatory domains are aligned in series in the CAR endodomain and are generally placed upstream of CD3z or its equivalent.

In general, however, the results achieved with these third generation CARs have been disappointing, showing only a marginal improvement over $2^{nd}$ generation configurations, with some $3^{rd}$ generation CARs being inferior to $2^{nd}$ generation configurations.

We have recently described a new format in which immuno-responsive cells such as T cells are engineered to express two constructs in parallel, a $2^{nd}$ generation CAR and a chimeric co-stimulatory receptor (CCR). The $2^{nd}$ generation CAR comprises, from C-terminus to N-terminus (from intracellular to extracellular), the following domains: (a) a signaling region; (b) a co-stimulatory signaling region; (c) a transmembrane domain; and (d) a first binding element that specifically interacts with a first epitope on a first target antigen. The CCR comprises, from C-terminus to N-terminus (from intracellular to extracellular), (a) a co-stimulatory signaling region which is different from the co-stimulatory signaling region of the CAR; (b) a transmembrane domain; and (c) a second binding element that specifically interacts with an epitope on a target antigen. The CAR and CCR may recognize an identical epitope, different epitopes on the same antigen, or epitopes found on two distinct antigens. Unlike the CAR, the CCR lacks a TCR-like signaling region such as CD3z. These parallel CAR (pCAR)-engineered T cells demonstrate superior activity and resistance to exhaustion as compared to $1^{st}$ generation CAR-T cells, $2^{nd}$ generation CAR-T cells, and $3^{rd}$ generation CAR-T cells. See US pre-grant publication 2019/0002521, incorporated herein by reference in its entirety.

These properties of pCAR-T cells make them attractive candidates for treatment of refractory malignancies, where $1^{st}$, $2^{nd}$, and $3^{rd}$ generation CAR-T cells show limited efficacy in part due to T cell exhaustion. However, there is an additional need for antigen target combinations that enable the broadened therapeutic application of this technology.

2. SUMMARY OF THE INVENTION

The applicants have found that effective T cell responses can be induced using a combination of constructs in which multiple co-stimulatory regions are arranged in distinct constructs. In particular, provided herein are effective pCAR-T cells having parallel CAR (pCAR) constructs that bind to one or more antigens present on a target cell derived from the B cell lineage. In some embodiments, the pCAR constructs comprise a CAR (chimeric antigen receptor) comprising a binding element that specifically binds to an epitope found in CD19 on a target cell and a CCR (chimeric costimulatory receptor) that binds either to CD19, or to another B cell lineage specific marker. Examples of the latter include, but are not restricted to CD20, CD22, CD23, CD79a and CD79b.

Thus, according to some embodiments, provided herein is an immuno-responsive cell expressing:

- i. a second generation chimeric antigen receptor (CAR) comprising
  - a) a signaling region;
  - b) a first co-stimulatory signaling region;
  - c) a first transmembrane domain; and
  - d) a first binding element that specifically interacts with an epitope on CD19 target antigen; and
- ii. a chimeric co-stimulatory receptor (CCR) comprising
  - e) a second co-stimulatory signaling region, wherein the second co-stimulatory signaling region is different from the first co-stimulatory signaling region;
  - f) a second transmembrane domain; and g) a second binding element that specifically interacts with a second epitope on a second target antigen, wherein the second target antigen is CD19 or another B cell associated target antigen.

When a T cell expressing a B cell targeting pCAR construct binds to a cell expressing one or more antigens with both epitope targets (for the CAR and CCR), both the CAR and CCR send stimulatory signals to enhance the response of the T cell.

Constructs of the type of the invention may be called "parallel chimeric activating receptors" or "pCAR." The applicants have found that the pCARs described herein are superior to $2^{nd}$ generation CAR-T cells having similar elements in both in vitro and in vivo experiments.

In addition, the proliferation of the T cells, their ability to retain cytotoxic potency and to release IL-2 is maintained over many repeated rounds of stimulation with antigen-expressing tumor cells.

In some embodiments, the first epitope recognized by the CAR component of the pCAR is an epitope on a CD19 target antigen. In some embodiments, said first binding element comprises the complementarity determining regions (CDRs) of the FMC63 antibody and have sequences of SEQ ID NO: 10, 11, 12, 13, 14 and 15. In some embodiments, said first binding element comprises the variable heavy ($V_H$; GenBank accession number CAA74659.1) and variable light ($V_L$; GenBank accession number CAA74660.1) domains of the FMC63 antibody and have sequences of SEQ ID NO: 16 and 17. In some embodiments, said first binding element comprises an FMC63 single-chain variable fragment (scFv), which comprises the variable heavy ($V_H$) and variable light ($V_L$) domains of the FMC63 antibody and has the sequence of SEQ ID NO: 18 or 19. In some embodiments, the FMC63 scFv was expressed from a polynucleotide or set of polynucleotides of SEQ ID NO: 118.

In some preferred embodiments, the said first binding element comprises a variant of the FMC63 antibody or scFv in which a single G→A or Y→A mutation has been introduced into the CDR3 of the $V_H$ domain and have the modified $V_H$ CDR3 sequences of SEQ ID NO: 20, 21, 22, 23, 24, 25 and 26. In some preferred embodiments, the mutated FMC63 scFv was expressed from a polynucleotide or set of polynucleotides of SEQ ID NO: 119, 120, 121, 122, 123, 124 or 125.

In some embodiments, the second epitope recognized by the chimeric co-stimulatory receptor (CCR) component of the pCAR is also an epitope on a CD19 target antigen. In some embodiments, the second binding element comprises the complementarity determining regions (CDRs) of the FMC63 antibody and have sequences of SEQ ID NO: 10, 11, 12, 13, 14 and 15. In some embodiments, the second binding element comprises the variable heavy ($V_H$) and variable light ($V_L$) domains of the FMC63 antibody and have sequences of SEQ ID NO: 16 and 17. In some preferred embodiments, said second binding element comprises an FMC63 antibody or scFv, which comprises the variable heavy ($V_H$) and variable light ($V_L$) domains of the FMC63 antibody and has the sequence of SEQ ID NO: 18 or 19. In some preferred embodiments, the FMC63 scFv was expressed from a polynucleotide or set of polynucleotides of SEQ ID NO: 118.

In some embodiments, the CAR and CCR bind to the same epitope within the CD19 antigen. In some preferred embodiments, the pCARs were designated FBB/G01, FBB/G02, FBB/Y01, FBB/Y02, FBB/Y03, FBB/Y04 and FBB/Y05 respectively and have the sequence of SEQ ID NO: 47, 48, 49, 50, 51, 52 or 53. Nomenclature derives from an abbreviation of the following elements: CCR binder (FMC63 scFv), CCR signaling domain (4-1BB)/CAR binder (G01-Y05 mutated scFv respectively). In some embodiments, the CAR of FBB/G01, FBB/G02, FBB/Y01, FBB/Y02, FBB/Y03, FBB/Y04 and FBB/Y05 comprises the sequences of SEQ ID NOs: 56, 58, 59, 60, 61, 62, and 63 respectively and the CCR comprises the sequence of SEQ ID NO: 57. In some preferred embodiments, these pCARs were expressed from a polynucleotide or set of polynucleotides of SEQ ID NO: 109, 110, 111, 112, 113, 114 or 115 respectively. In some embodiments, the pCAR is a polypeptide having at least 85%, 90%, 95%, 97%, 98%, 99% or 100% sequence identity to SEQ ID NO: 47, 48, 49, 50, 51, 52 or 53. In some embodiments, the pCAR is a polypeptide having at least about 85%, 90%, 95%, 97%, 98%, 99% or 100% sequence identity to SEQ ID NO: 47, 48, 49, 50, 51, 52 or 53.

In some embodiments, the CAR and CCR bind to distinct epitopes within the CD19 antigen.

In some embodiments, the CAR binds to CD19 while the CCR binds to a distinct B cell lineage antigen, such as CD20, CD22, CD23, CD79a or CD79b.

In some embodiments, the CAR binds to CD19 while the CCR binds to CD20. In some preferred embodiments, the second binding element which directs CCR specificity comprises the complementarity determining regions (CDRs) of the 1F5 antibody and have sequences of SEQ ID NO: 27, 28, 29, 30, 31 and 32. In some preferred embodiments, said second binding element comprises the variable heavy ($V_H$; GenBank accession number AAL27650.1) and variable light ($V_L$; GenBank accession number AAL27649.1) domains of the 1F5 antibody and have sequences of SEQ ID NO: 33 and 34. In some preferred embodiments, said second binding element comprises an 1F5 scFv, which comprises the variable heavy ($V_H$) and variable light ($V_L$) domains of the 1F5 antibody and has the sequence of SEQ ID NO: 35 or 36. In some preferred embodiments, the 1F5 scFv was expressed from a polynucleotide or set of polynucleotides of SEQ ID NO: 126. In some preferred embodiments, the pCAR was designated 1BB/F and has the sequence of SEQ ID NO: 54. Nomenclature derives from an abbreviation of the following elements: CCR binder (1F5 scFv), CCR signaling domain (4-1BB)/CAR binder (FMC63 scFv). In some embodiments, the CAR of 1BB/F comprises the sequence of SEQ ID NO: 64 and the CCR of 1BB/F comprises the sequence of SEQ ID NO: 65. In some preferred embodiments, the 1BB/F pCAR was expressed from a polynucleotide or set of polynucleotides of SEQ ID NO: 116. In some embodiments, the pCAR is a polypeptide having at least 85%, 90%, 95%, 97%, 98%, 99% or 100% sequence identity to SEQ ID NO: 54. In some embodiments, the pCAR is a polypeptide having at least about 85%, 90%, 95%, 97%, 98%, 99% or 100% sequence identity to SEQ ID NO: 54.

In some embodiments, the CAR binds to CD19 while the CCR binds to CD22. In some preferred embodiments, the second binding element which directs CCR specificity comprises the complementarity determining regions (CDRs) of the RFB4 antibody and have sequences of SEQ ID NO: 37, 38, 39, 40, 41 and 42. In some preferred embodiments, said second binding element comprises the variable heavy ($V_H$; GenBank accession number CAJ09937.1) and variable light ($V_L$; GenBank accession number CAJ09936.1) domains of the RFB4 antibody and have sequences of SEQ ID NO: 43 and 44. In some preferred embodiments, said second binding element comprises an RFB4 scFv, which comprises the variable heavy ($V_H$) and variable light ($V_L$) domains of the RFB4 antibody and have the sequence of SEQ ID NO: 45 or 46. In some preferred embodiments, the RFB4 scFv was expressed from a polynucleotide or set of polynucleotides of SEQ ID NO: 127. In some preferred embodiments, the pCAR was designated RBB/F and has the sequence of SEQ ID NO: 55. Nomenclature derives from an abbreviation of the following elements: CCR binder (RFB4 scFv), CCR signaling domain (4-1BB)/CAR binder (FMC63 scFv). In some embodiments, the CAR of 1BB/F comprises the sequence of SEQ ID NO: 64 and the CCR of 1BB/F comprises the sequence of SEQ ID NO: 66. In some preferred embodiments, the RBB/F pCAR was expressed from a polynucleotide or set of polynucleotides of SEQ ID NO: 117. In some embodiments, the pCAR is a polypeptide having at least 85%, 90%, 95%, 97%, 98%, 99% or 100% sequence identity to SEQ ID NO: 55. In some embodiments, the pCAR is a polypeptide having at least about 85%, 90%, 95%, 97%, 98%, 99% or 100% sequence identity to SEQ ID NO: 55.

In some embodiments, said immuno-responsive cell is an αβ T cell, γδ T cell, or a Natural Killer (NK) cell. In some embodiments, said T cell is an αβ T cell. In some embodiments, said T cell is a γδ T-cell.

In some embodiments, the polynucleotide or set of polynucleotides comprise: (a) a first nucleic acid encoding a CCR that binds to a B cell lineage antigen and; (b) a second nucleic acid encoding a CAR that binds to CD19. In some embodiments, said first nucleic acid and said second nucleic acid are in a single vector. In some embodiments, said first nucleic acid and said second nucleic acid are in two separate vectors.

In one aspect, the present invention provides a method of preparing the immuno-responsive cell, said method comprising transfecting or transducing the polynucleotide or set of polynucleotides provided herein into an immuno-responsive cell.

In another aspect, the present disclosure provides a method for directing a T cell-mediated immune response to a target cell in a patient in need thereof, said method comprising the administration to the patient of the immuno-responsive cell, wherein the target cell is a B cell.

In yet another aspect, the present disclosure provides a method of treating cancer, said method comprising the administration to the patient of an effective amount of the immuno-responsive cell. In some embodiments, the patient's cancer expresses CD19. In some embodiments, the patient has a cancer arising from the B cell lineage. In some embodiments, the patient has a cancer selected from the group consisting of acute or chronic B cell leukemia or B cell lymphoma.

In another aspect, the present disclosure provides the use of immuno-responsive cells for use in a therapy or as a medicament. The disclosure further provides immuno-responsive cells in the manufacture of a medicament for the treatment of a pathological disorder. In some embodiments, the pathological disorder is cancer.

3. BRIEF DESCRIPTION OF THE DRAWINGS

The drawings are not necessarily to scale, emphasis instead being placed upon illustrating the principles of various embodiments of the invention.

FIGS. 1A and 1B—Flow Cytometric Analysis of Malignant B Cell Lines

FIG. 1A demonstrates the expression profile of CD19 and CD20 on a panel of human lymphoma and leukemia cell lines (Daudi, Nalm-6 and Raji). In accordance with published data, the analysis confirmed that CD19 was detectable on the cell surface of these tumor cells at a high level and CD20 was detectable on both Raji and Daudi cell lines. The Nalm-6 cell line had no detectable expression of CD20.

To enable bioluminescence and fluorescence imaging of cells and derived xenografts, tumor cell lines were transduced with the LT retroviral vector that encodes for both firefly luciferase enzyme and the red fluorescent protein (RFP), tandem dimer (td) Tomato. Expression of RFP was confirmed using flow cytometry, as indicated in FIG. 1B.

FIG. 2—Design and Construction of CARs and pCARs

FIGS. 2A-2E provide schematic diagrams showing salient features of certain 2$^{nd}$ generation CAR and pCAR constructs used in the experiments described herein. The cell membrane is shown as parallel horizontal lines, with the extracellular domains depicted above the membrane and intracellular domains shown below the membrane. F-2 is a 2$^{nd}$ generation CAR similar to that originally described in Kochenderfer et al., *J. Immunother.* 32:689-702 (2009), incorporated herein by reference in its entirety. It comprises, from C-terminus to N-terminus (intracellular to extracellular), a CD3z signaling region, CD28 co-stimulatory and transmembrane domains, a CD28 hinge/spacer domain that contains an embedded myc epitope tag and a human CD19-targeting FMC63 single chain antibody (scFv) domain. Cells transduced with F-2 alone are standard 2$^{nd}$ generation CAR-T cells and are used for comparative purposes.

Figure 2A:
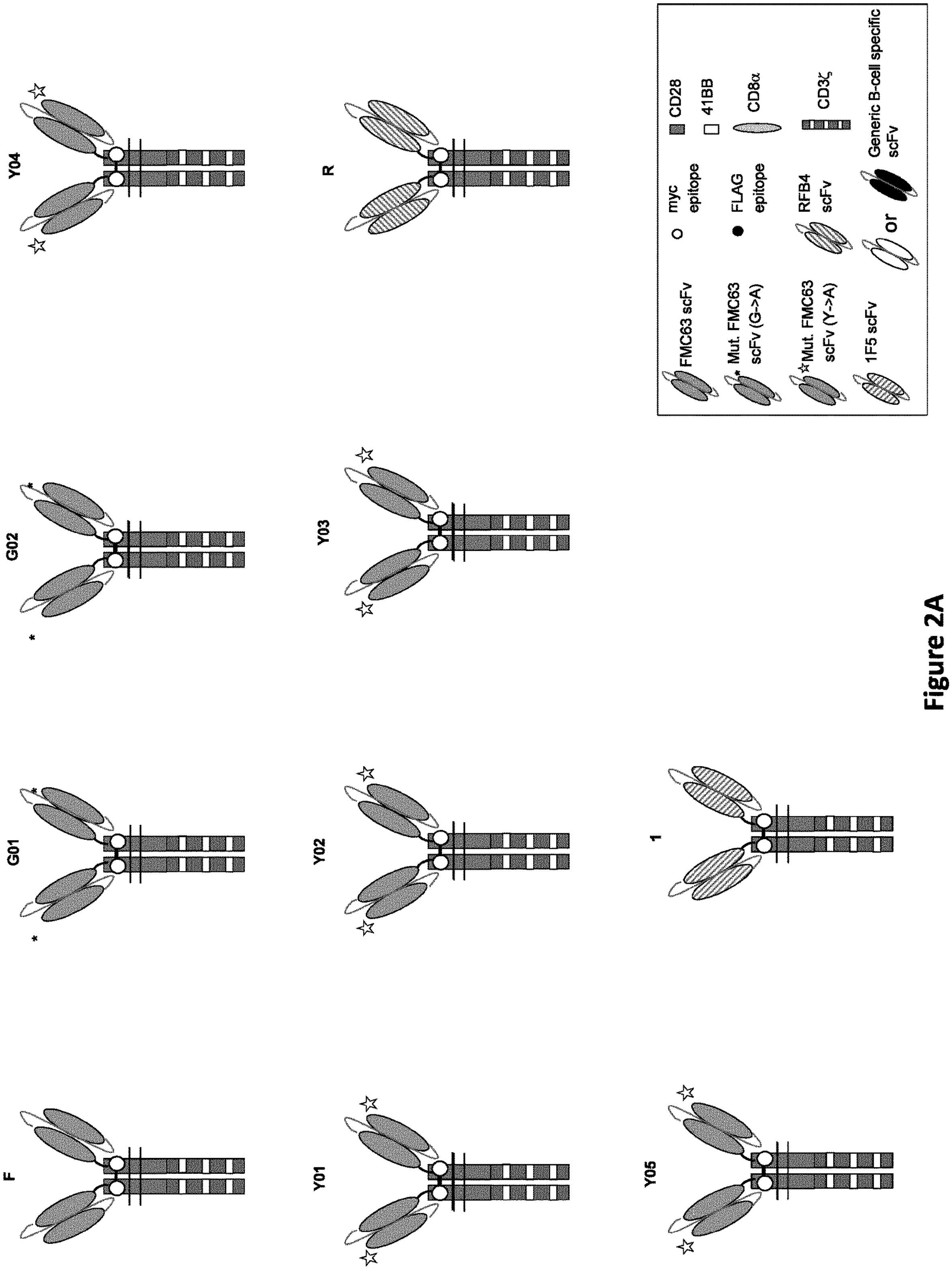

The CDR3 region of the $V_H$ domain within the FMC63 scFv was identified usingabysis.org. To generate variants with an altered ability to bind CD19, an alanine (A) residue was substituted for the first or second glycine (G01, G02) or alternatively for the first, second, third, fourth or fifth tyrosine (Y01-Y05) within CDR3 of the said $V_H$ domain, as illustrated in FIGS. 2A and 2B. These modified CD19-specific 2$^{nd}$ generation CARs are designated G01, G02, Y01, Y02, Y03, Y04 and Y05 respectively.

1-2 is a 2$^{nd}$ generation CAR in which targeting is achieved using the 1F5 scFv, as described in Budde et al., *PLOS One* 8 (12): e82742 (2013) and incorporated herein by reference in its entirety. It comprises, from C-terminus to N-terminus (intracellular to extracellular), a CD3z signaling region, CD28 co-stimulatory and transmembrane domains, a CD28 hinge/spacer domain that contains an embedded myc epitope tag and a human CD20-targeting 1F5 single chain antibody (scFv) domain. Cells transduced with 1-2 alone are standard 2$^{nd}$ generation CAR-T cells and are used for comparative purposes.

R-2) is a 2nd generation CAR in which targeting is achieved using the RFB4 scFv, as described in James et al., *J. Immunol.* 180 (10): 7028-38 (2008) and incorporated herein by reference in its entirety. It comprises, from C-terminus to N-terminus (intracellular to extracellular), a CD3z signaling region, CD28 co-stimulatory and transmembrane domains, a CD28 hinge/spacer domain that contains an embedded myc epitope tag and a human CD22-targeting RFB4 single chain antibody (scFv) domain. Cells transduced with R-2 alone are standard 2$^{nd}$ generation CAR-T cells and are used for comparative purposes.

Figure 2C:
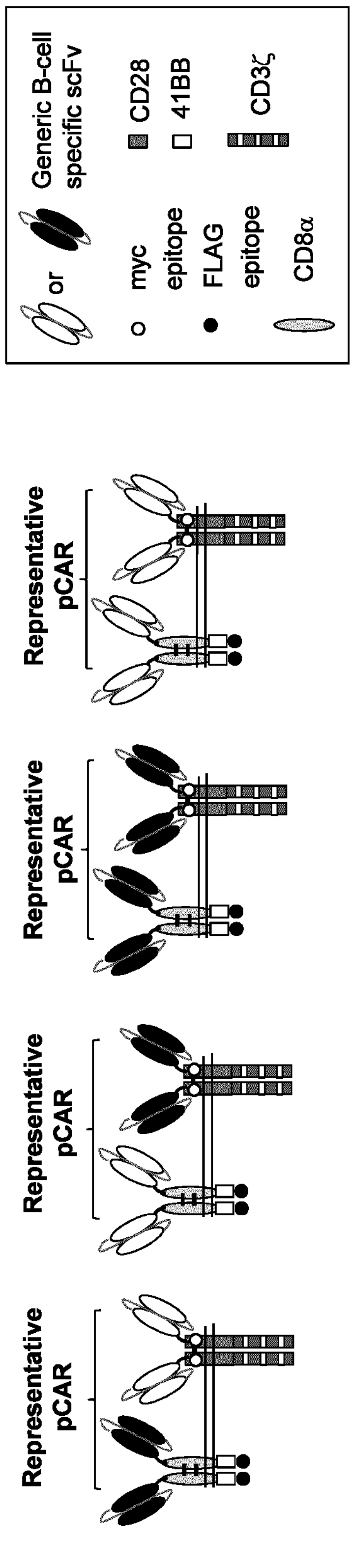
Figure 2D:
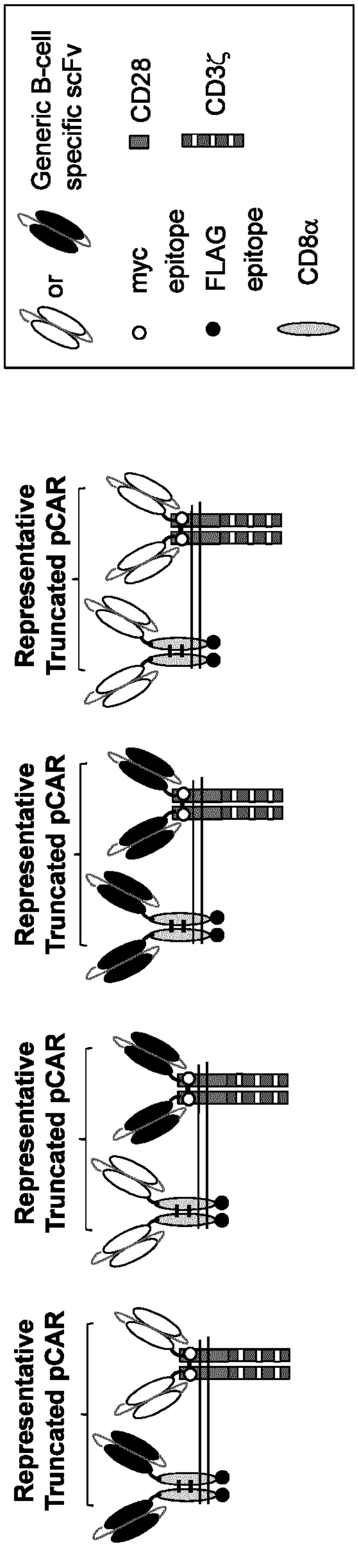
Figure 2E:
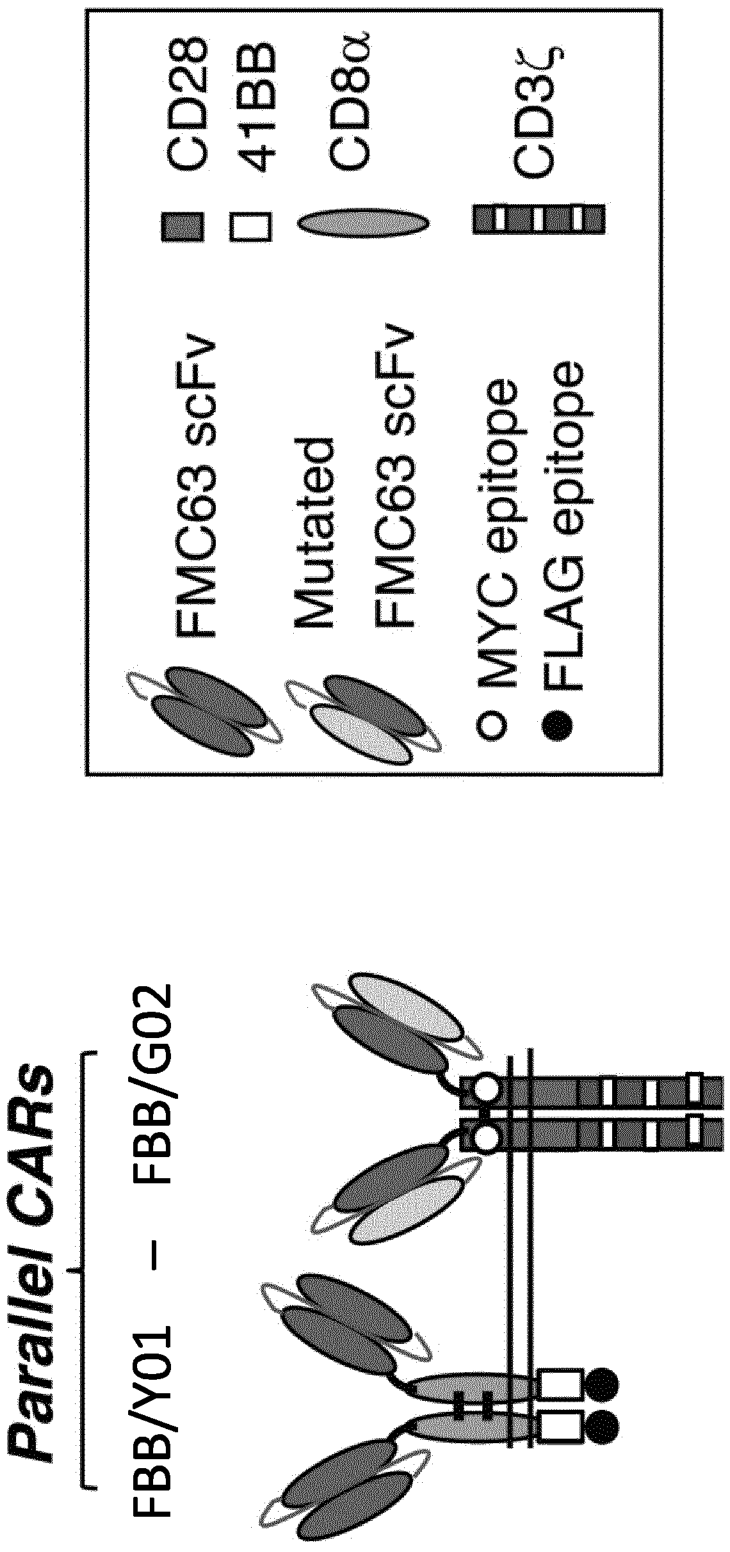
Figure 2F:
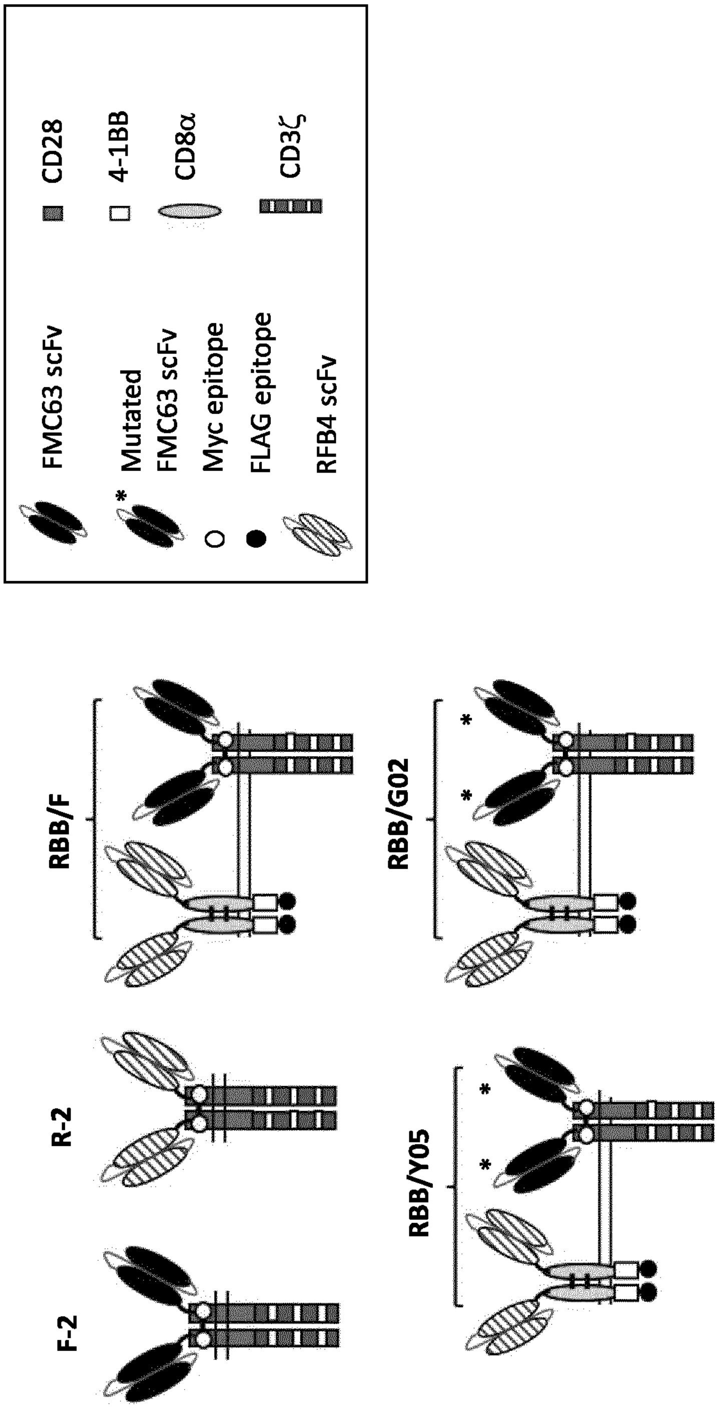

A series of B cell targeted pCARs (FIGS. 2C, 2D and 2E) have been engineered using combinations of the aforementioned binding moieties. Nomenclature derives from an ordered abbreviation of the following elements: CCR binder, CCR signaling domain/CAR binder. For example, 1BB/F is a pCAR in which a CCR targeted by a 1F5 scFv and containing a 4-1BB endodomain is co-expressed with an FMC63 scFv-targeted CD28-containing 2$^{nd}$ generation CAR. FBB/Y01 is a pCAR in which an FMC63 scFv-targeted CCR is co-expressed with a CD28-containing 2$^{nd}$ generation CAR that is targeted by a FMC63 (Y01) scFv. Similarly, FTr/Y05 is a control pCAR in which an FMC63 scFv-targeted CCR that has a Truncated signaling domain is co-expressed with a CD28-containing 2nd generation CAR that is targeted by an FMC63(Y05) scFv. Generic structure of B cell targeted pCARs and truncated controls is indicated in FIGS. 2C, 2D and 2E. FIG. 2F provides a schematic of the CD19-CD22 dual targeting pCARs RBB/F, RBB/Y05, and RBB/G02, as well as the 2nd generation CARs F-2 and R-2 that target CD19 and CD22, respectively. RBB/F is a pCAR with the RBB CCR (CD22-specific RFB4 scFv fused via a CD8a spacer and transmembrane domain to a 4-1BB signaling domain) and a CD19-specific CD28-containing 2nd generation CAR (F). RBB/Y05 is a pCAR in which an RFB4 scFv-targeted CCR is co-expressed with a CD28-containing 2nd generation CAR that is targeted by an FMC63(Y05) scFv. RBB/G02 is a pCAR in which an RFB4 scFv-targeted CCR is co-expressed with a CD28-containing 2nd generation CAR that is targeted by an FMC63(G02) scFv.

FIG. 3—Expression of CD19-Specific CARs in Human T Cells

Figure 3A:
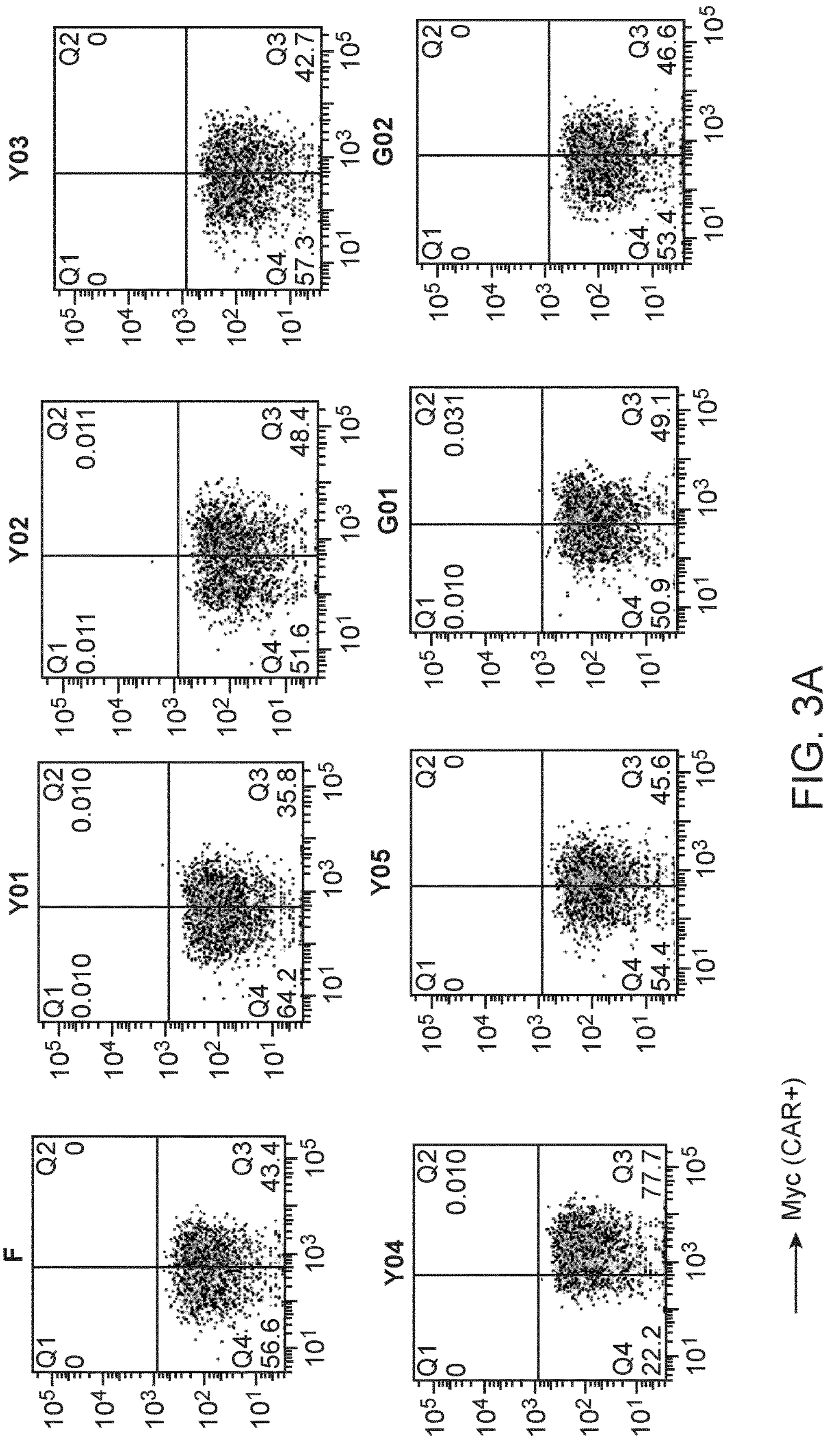
Figure 3B:
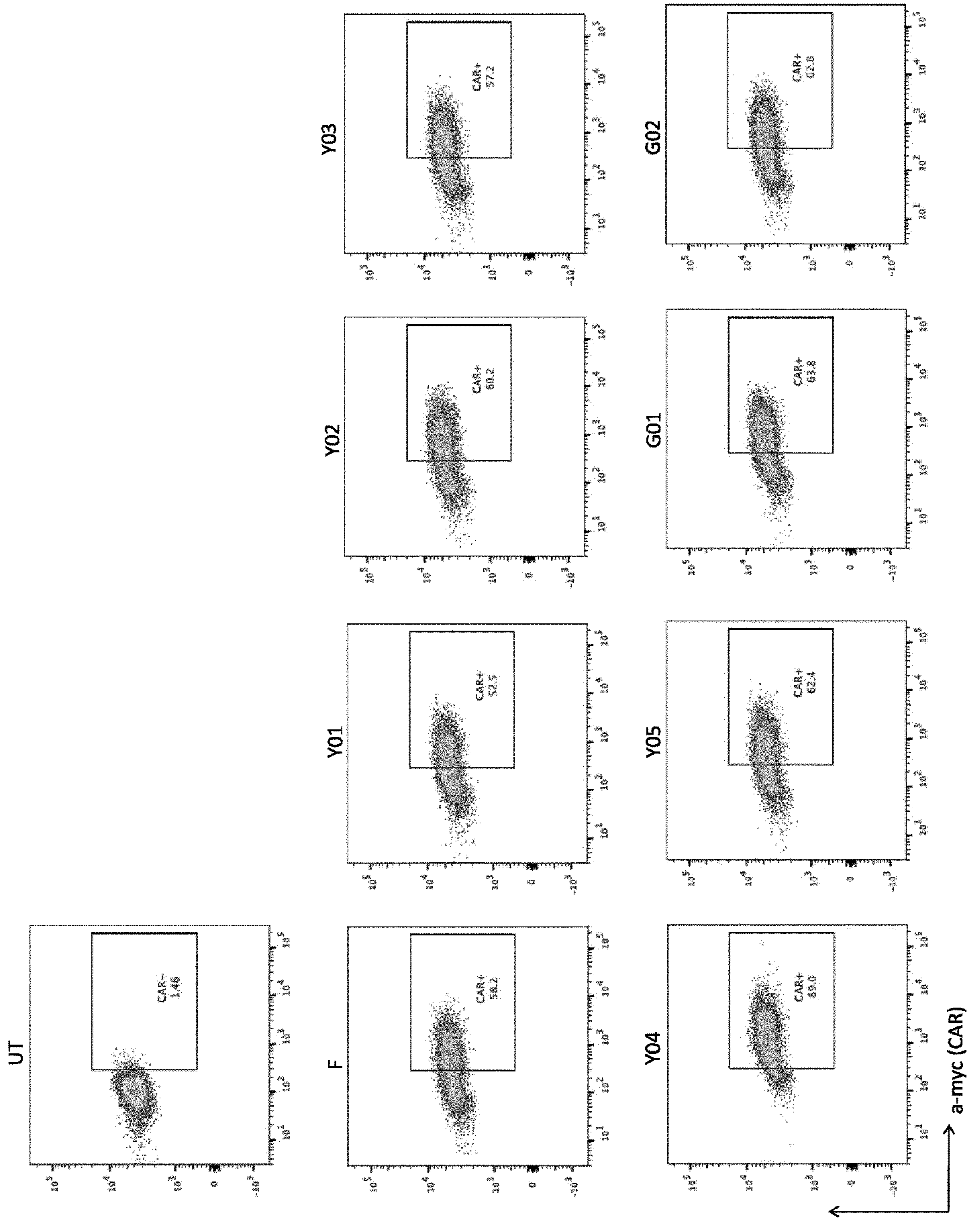

FIGS. 3A-3B show two representative examples in which CD19-specific 2nd generation CARs containing a mutated FMC63 scFv were expressed in human CAR T cells. Cell surface expression was detected using 9e10 antibody, which binds to a myc epitope tag (EQKLISEEDL) that had been inserted into the CD28 spacer domain of the CAR. The F-2 2nd generation CAR was expressed as a control.

FIG. 4—Expression of CD19-Specific pCARs in Human T Cells

Figure 4A:
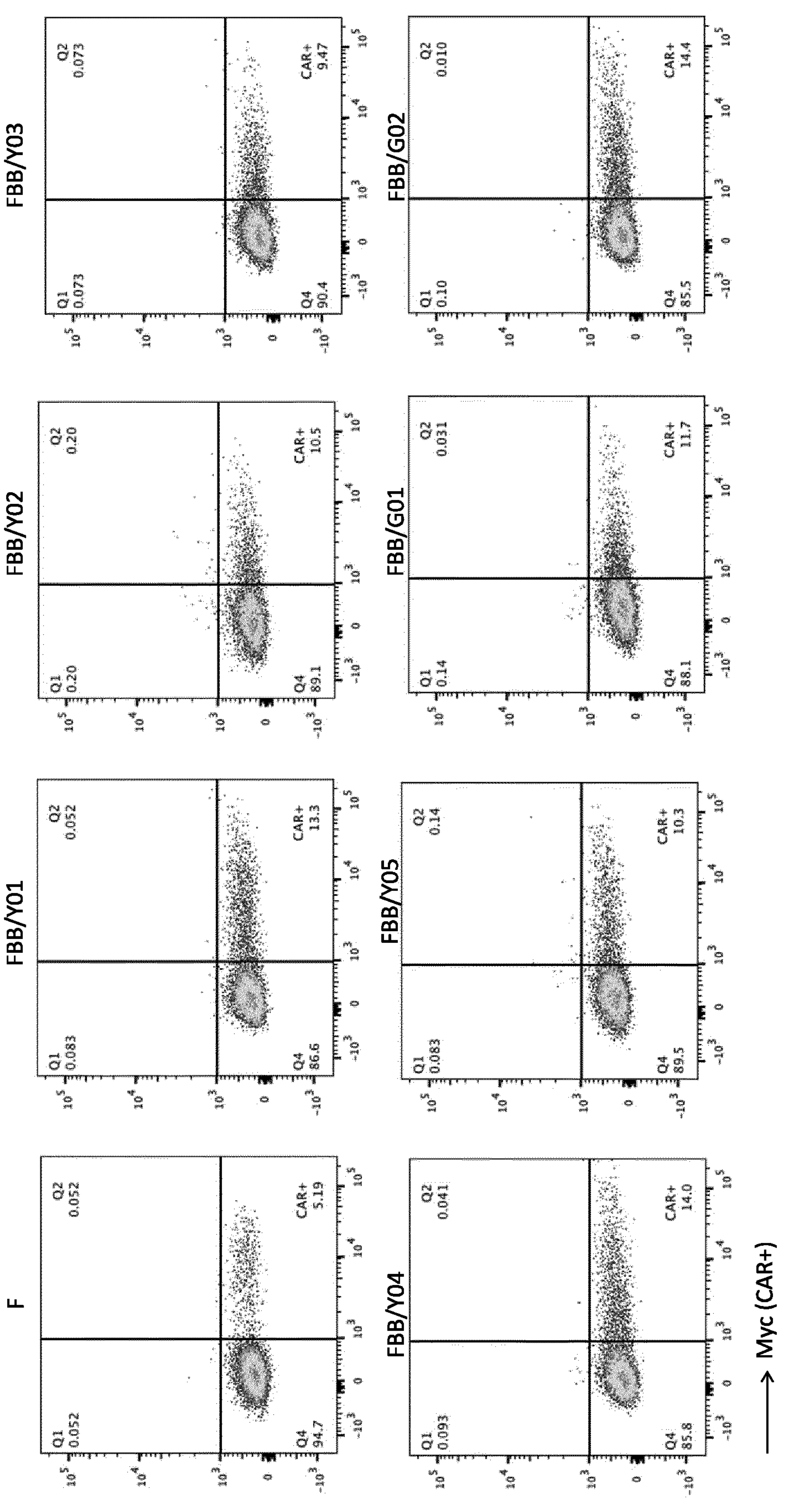
Figure 4B:
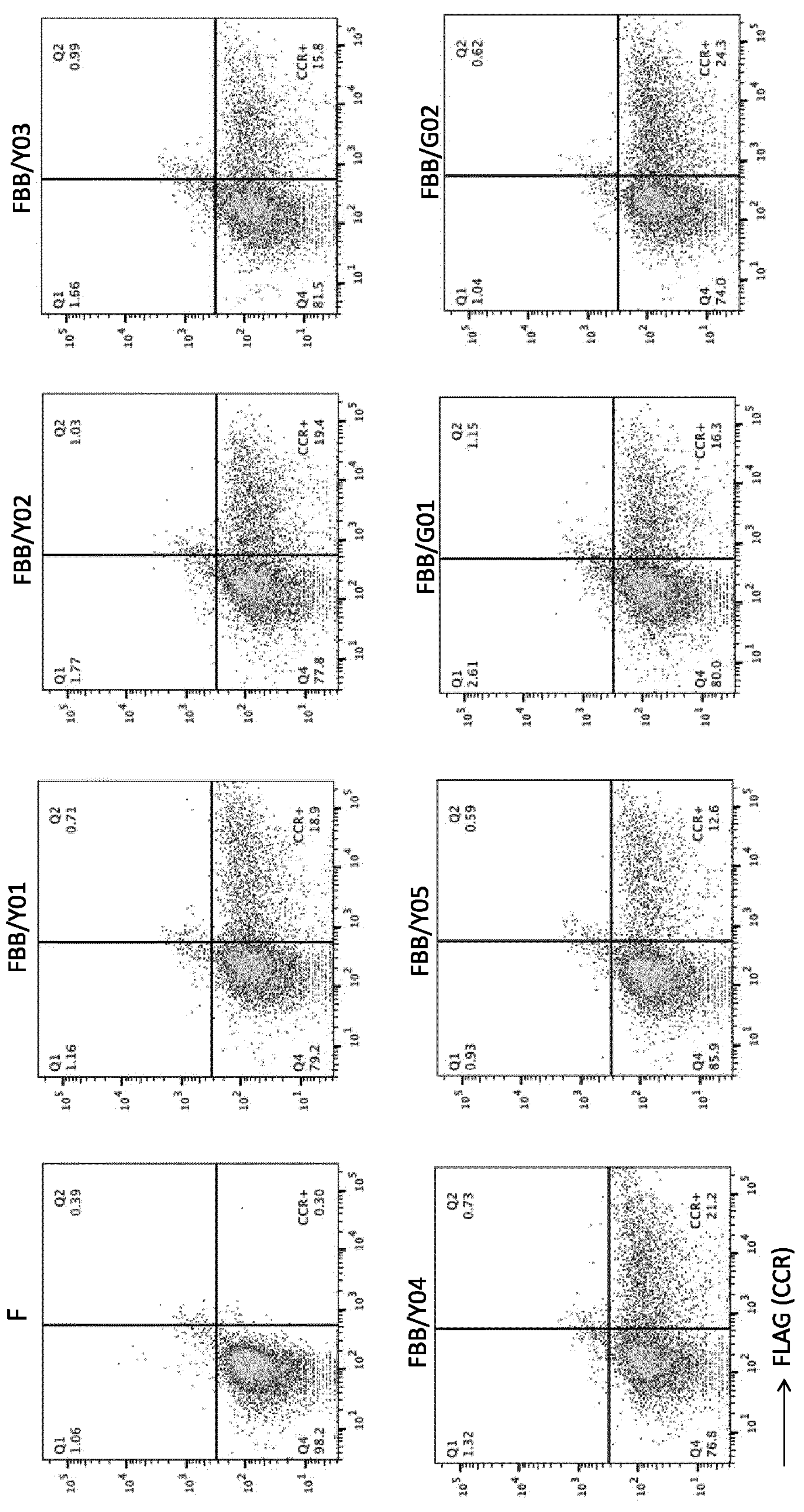

FIGS. 4A and 4B show representative examples in which CD19-specific pCARs were expressed in human T cells. In all CD19-specific pCARs, the FBB CCR (CD19-specific FMC63 scFv fused via a CD8α spacer and transmembrane domain to a 4-1BB signaling domain) is co-expressed with a CD19-specific CD28-containing 2nd generation CAR in which the FMC63 $V_H$ chain contains the indicated CDR3 mutation. The F-2 2nd generation CAR was expressed as a control here. Expression of CARs, or the CAR component of pCARs, was detected using 9e10 antibody which binds to a myc epitope tag (EQKLISEEDL), as explained above (FIG. 4A). Expression of the CCR component of pCARs was detected by intracellular staining using a FLAG epitope tag (DYKDDDDK)-specific antibody (FIG. 4B).

Figure 5:
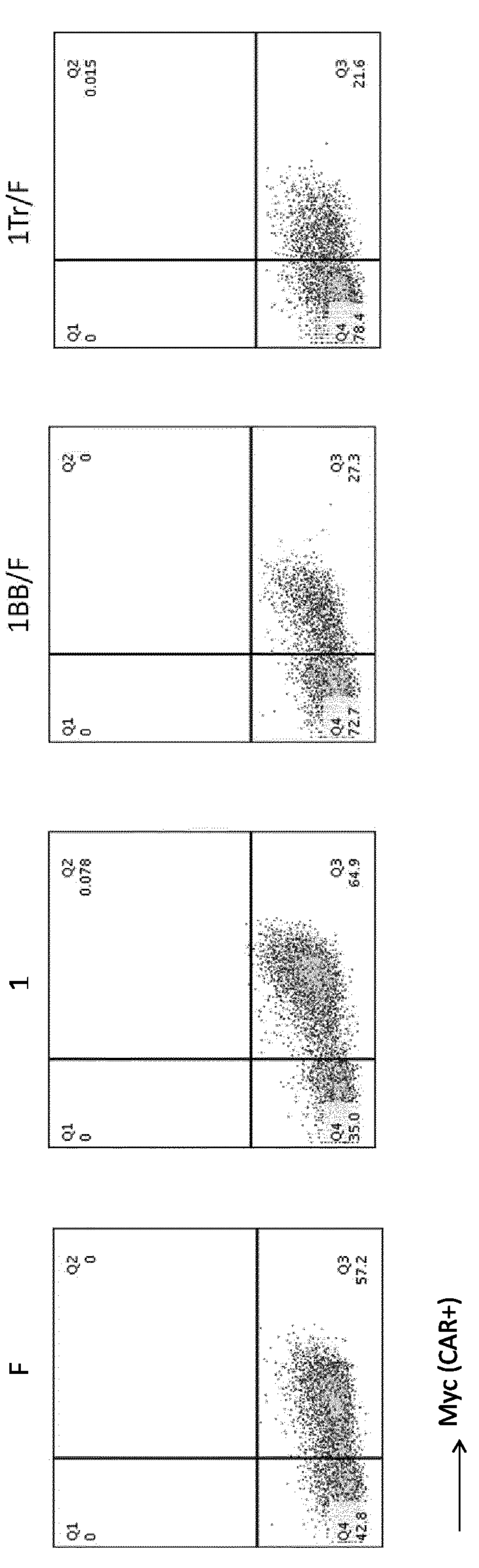

FIG. 5—Expression of pCARs that Co-Target CD19 and CD20 in Human T Cells

FIG. 5 shows a representative example in which the 1BB/F pCAR was expressed in human T cells. In 1BB/F, the 1BB CCR (CD20-specific 1F5 scFv fused via a CD8a spacer and transmembrane domain to a 4-1BB signaling domain) is co-expressed with a CD19-specific CD28-containing 2nd generation CAR (F). In 1Tr/F, the 1BB CCR having a Truncated signaling domain is co-expressed with a CD19-specific CD28-containing 2nd generation CAR (F). 1-2 is a CD28-containing 2nd generation CAR control that binds to CD20. Both F-2 and 1-2 were expressed as controls here. Expression of CARs, or the CAR component of pCARs, was detected using 9e10 antibody, as explained above.

Figure 6:
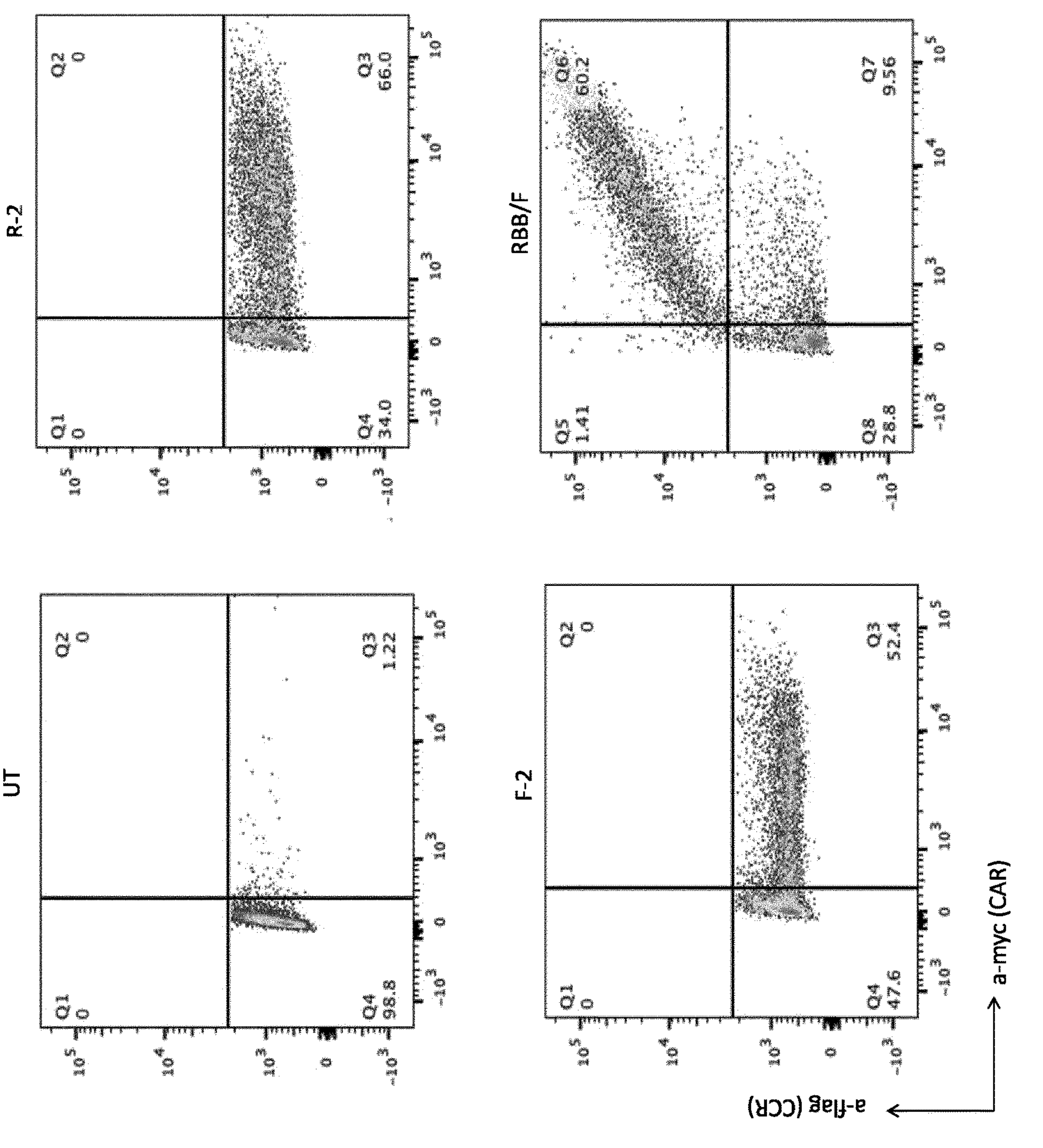

FIG. 6—Expression of pCAR that Co-Targets CD19 and CD22 in Human T Cells

FIG. 6 shows a representative example in which the RBB/F pCAR was expressed in human T cells. In RBB/F, the RBB CCR (CD22-specific RFB4 scFv fused via a CD8a spacer and transmembrane domain to a 4-1BB signaling domain) is co-expressed with a CD19-specific CD28-containing 2nd generation CAR (F). R-2 is a CD28-containing 2nd generation CAR control that binds to CD22. Both F-2 and R-2 were expressed as controls. Expression of CARs, or the CAR component of pCARs, was detected using the 9e10 MYC epitope tag-specific antibody as explained above. Expression of the CCR component of pCARs was detected by intracellular staining using a FLAG epitope tag-specific antibody.

Figure 7A:
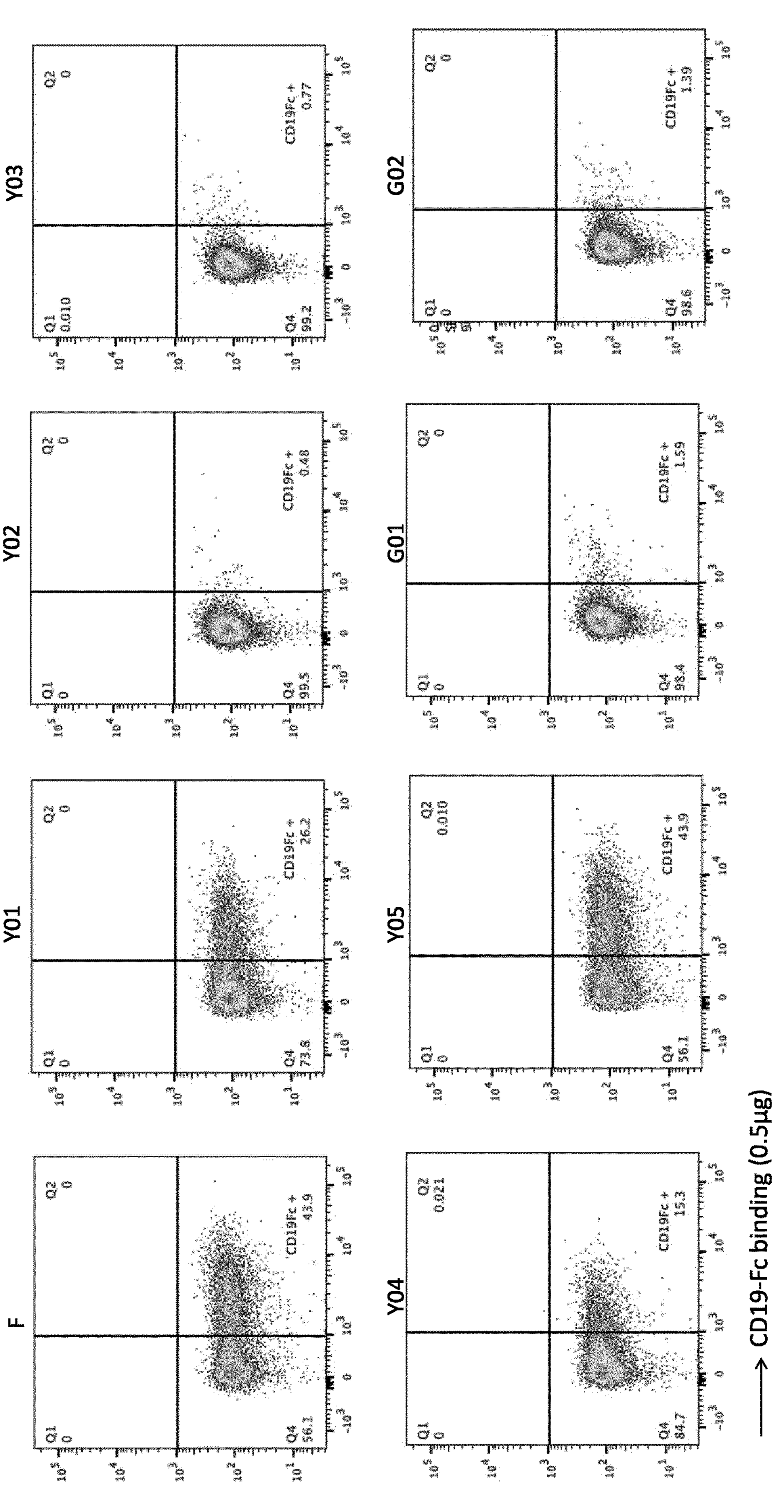
Figure 7B:
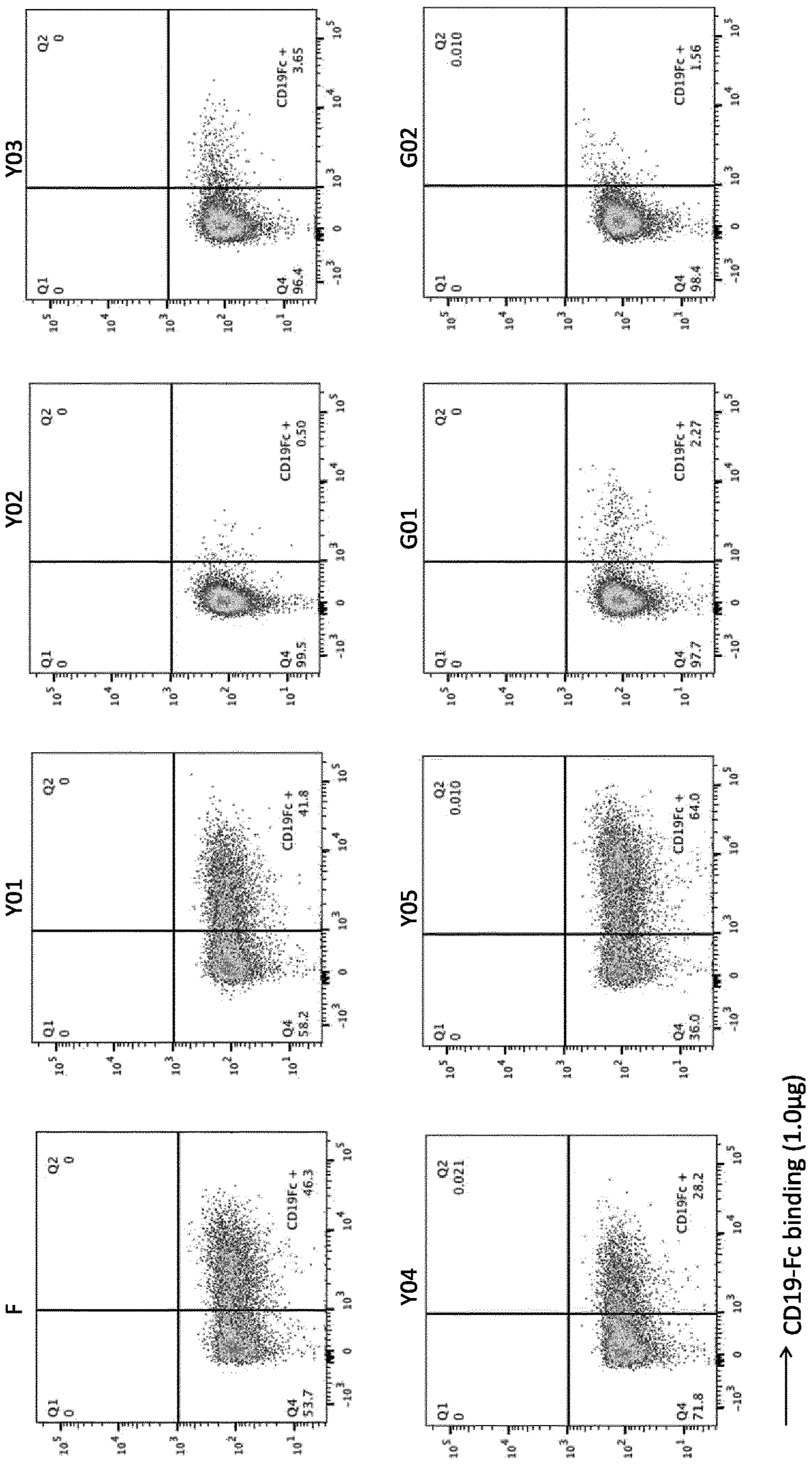
Figure 7C:
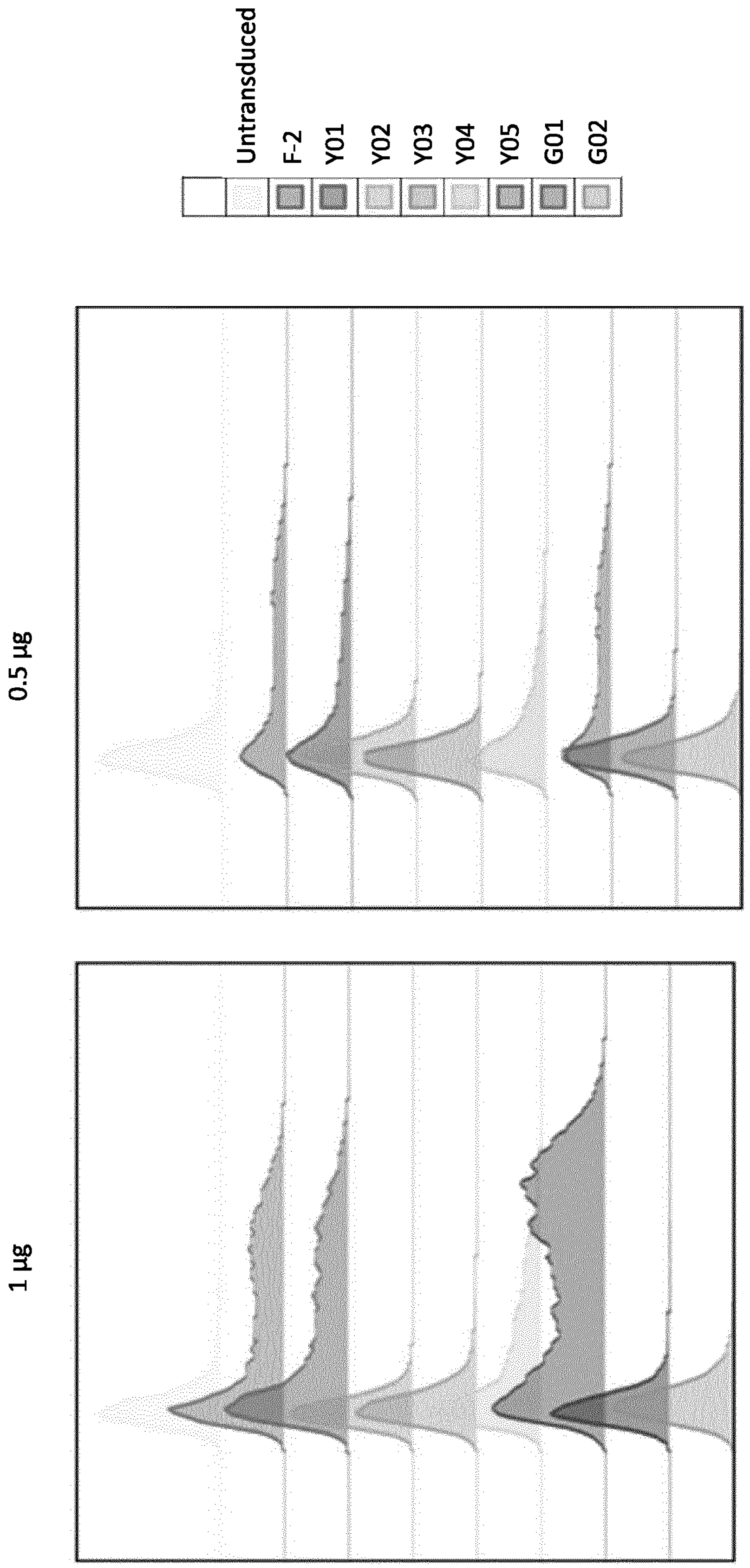
Figure 7D:
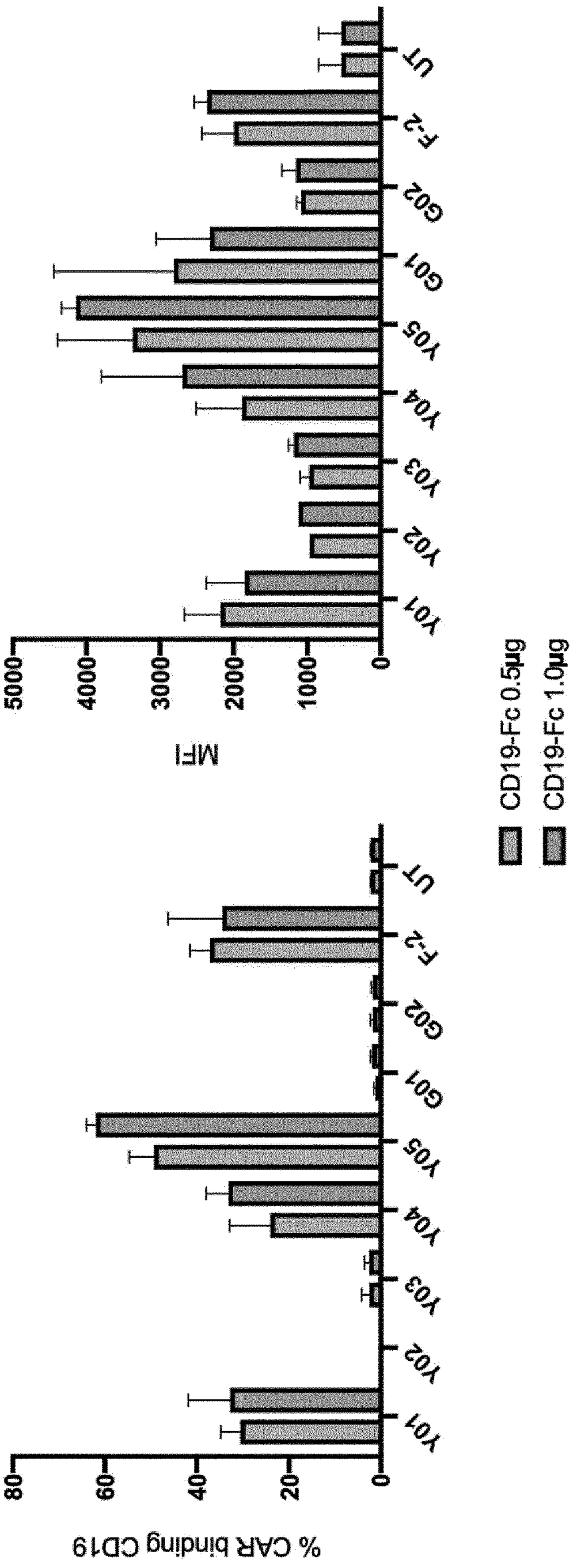

FIG. 7—Binding of CD19 to Parental and CDR3 $V_H$ mutated FMC63-Based 2nd Generation CARs FIGS. 7A-7D show the results of a representative experiment in which T cells that express F-2, G01, G02, Y01, Y02, Y03, Y04 or Y05 second generation CARs were incubated with two concentrations of a soluble CD19-Fc fusion protein—0.5 μg (FIG. 7A, FIG. 7C (right)) and 1.0 μg (FIG. 7B, FIG. 7C (left)). Binding was measured by flow cytometry after incubation with Alexa-fluor 488-conjugated anti-human IgG. The percentage of transduced T cells present in each case is shown in FIG. 3A. Binding of the T cells to CD19-Fc as measured by flow cytometry is plotted in histogram form in FIG. 7C and numeralized as percent binding and mean fluorescence intensity (MFI) after incubation with CD19-Fc (FIG. 7D left and right respectively). Note the spectrum of binding efficiencies of the mutated CARs from low (e.g. G01, G02) to intermediate (e.g. Y04) to increased (e.g. Y05), when compared to F-2.

FIG. 8—Titration of Tumor Cell Killing by F-2 and Mutant Derivative 2nd Generation CAR T Cells FIGS. 8A-8D show three experiments that compare the cytotoxic activity of F-2 and mutant derivative 2nd generation CAR T cells against the malignant CD19-expressing B cell lymphoma cell lines, Nalm-6 (FIG. 8A and FIG. 8C) or Raji (FIG. 8B and FIG. 8D), making comparison with untransduced (UT) control T cells.

FIG. 9—In Vitro Cytokine Release (at 24 Hours)

Figure 9A:
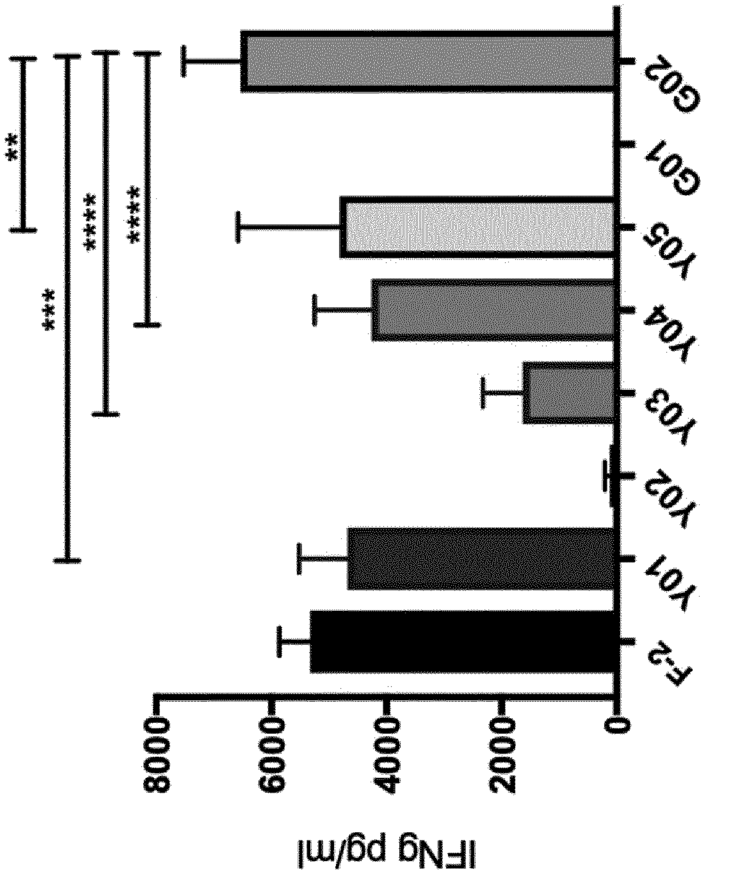
Figure 9B:
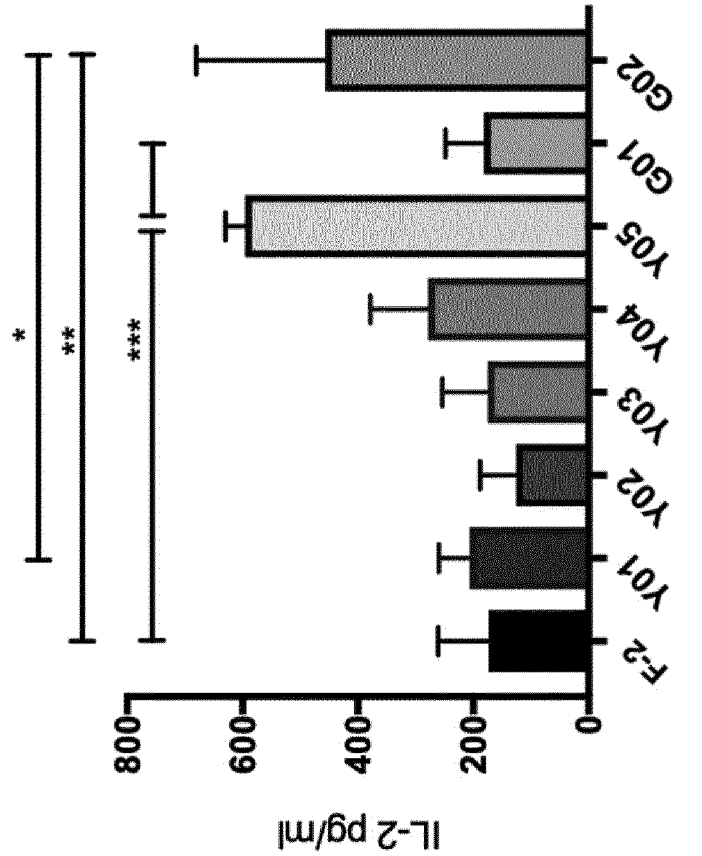
Figure 9C:
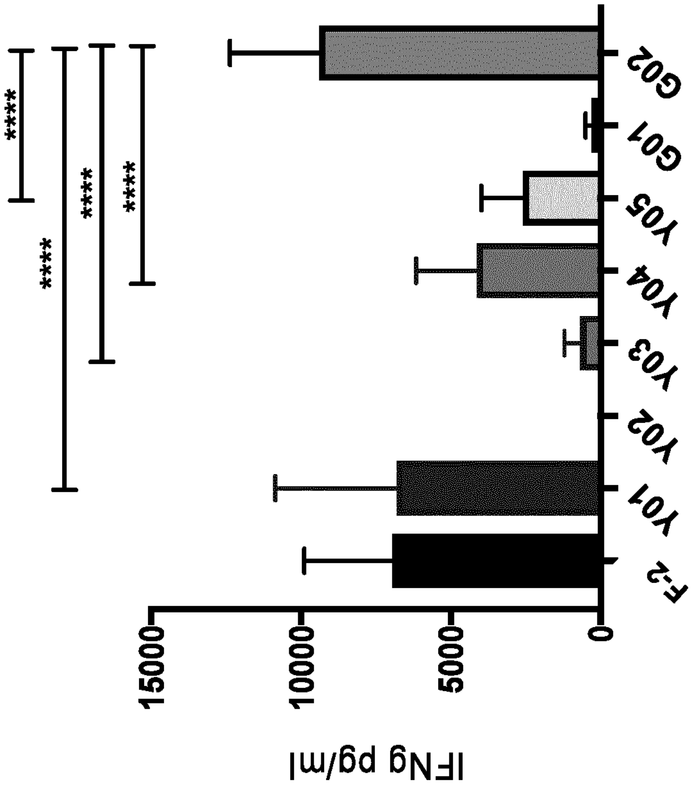
Figure 9D:
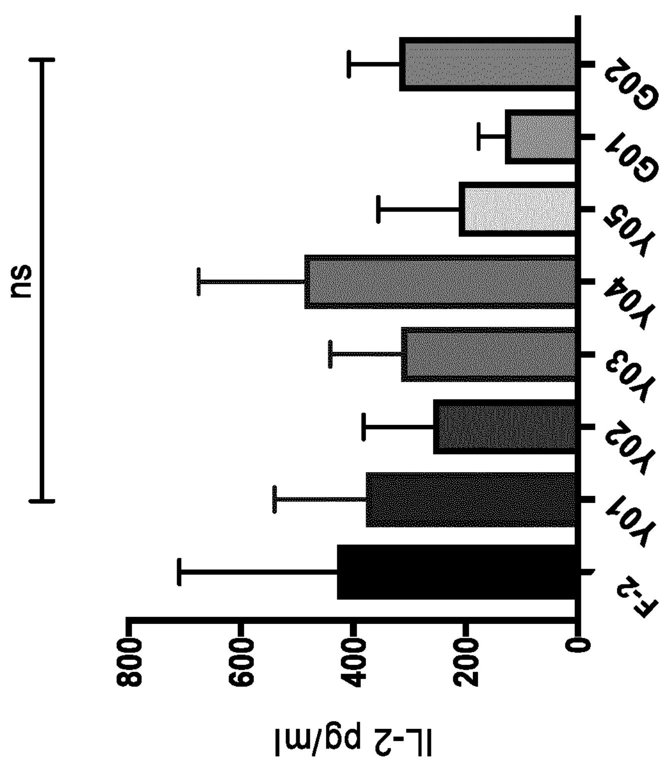

FIGS. 9A and 9B show pooled data indicating the release of IFN-γ (FIG. 9A) and IL-2 (FIG. 9B) by CD19-specific CAR-T cells when cultured with Nalm-6 cells. FIGS. 9C and 9D show pooled data indicating the release of IFN-γ (FIG. 9C) and IL-2 (FIG. 9D) by CD19-specific CAR-T cells when cultured with Raji cells. Comparison is made to the CD19-specific 2nd generation CAR, F-2.

FIG. 10—In Vitro Cytokine Release (at 24 Hours)

Figure 10B:
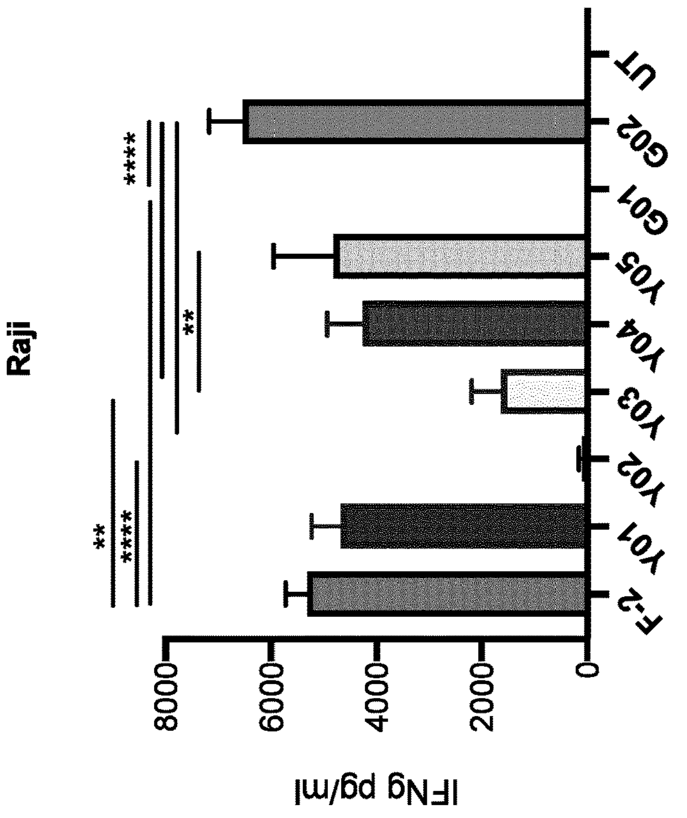
Figure 10A:
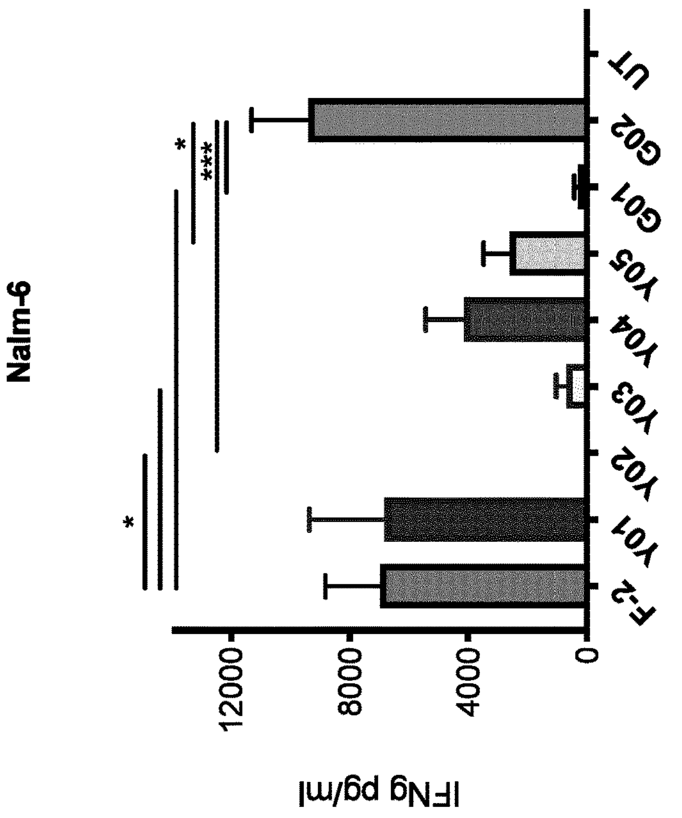
Figure 10D:
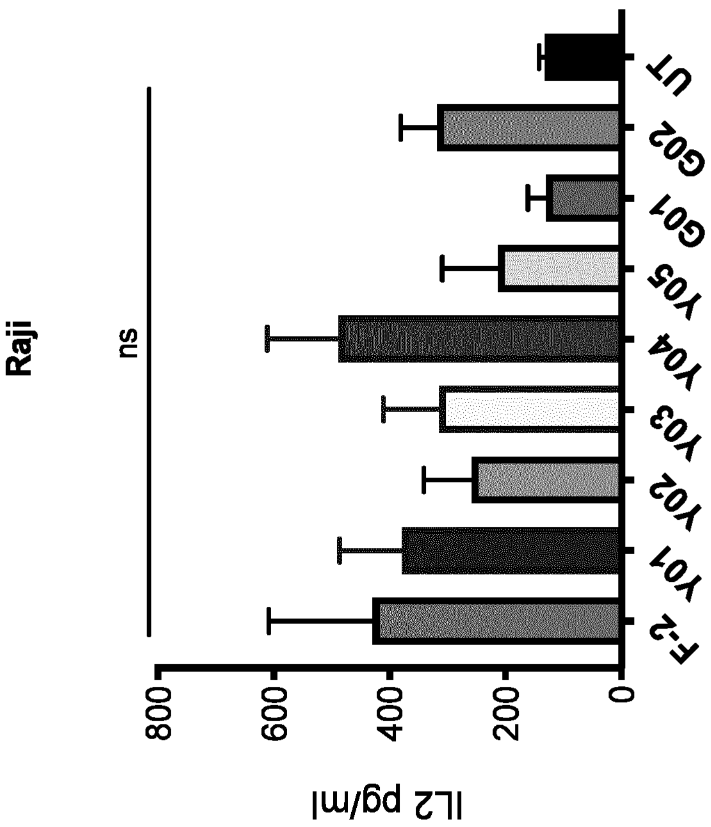
Figure 10C:
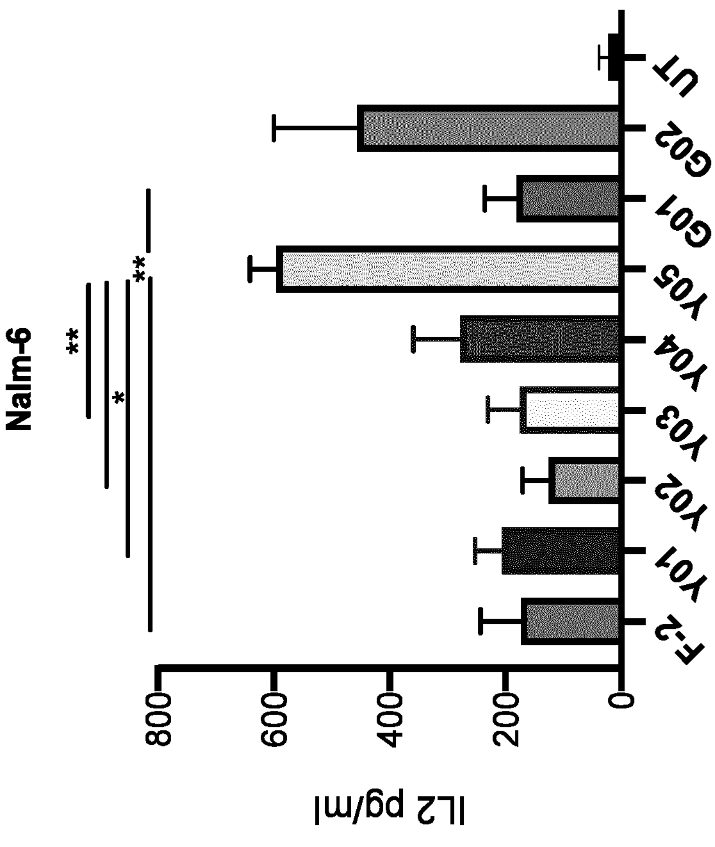

FIGS. 10A and 10B show pooled data indicating the release of IFN-γ by CD19-specific CAR-T cells when cultured with Nalm-6 cells (FIG. 10A) or Raji cells (FIG. 10B). FIGS. 10C and 10D show pooled data indicating the release of IL-2 by CD19-specific CAR-T cells when cultured with Nalm-6 cells (FIG. 10C) or Raji cells (FIG. 10D).

FIG. 11—In Vitro Re-Stimulation Potential

Figure 11A:
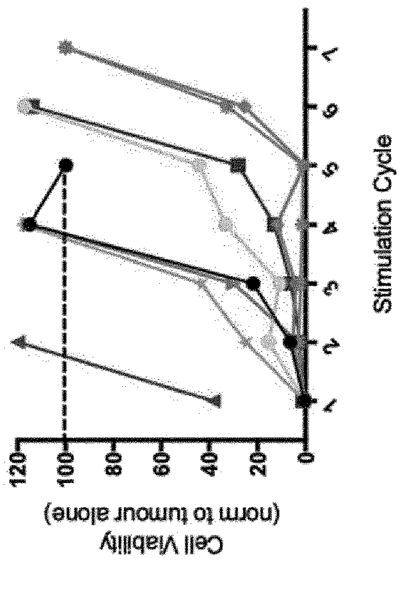
Figure 11B:
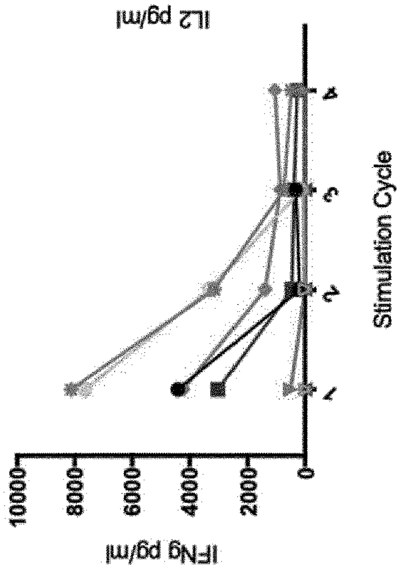
Figure 11C:
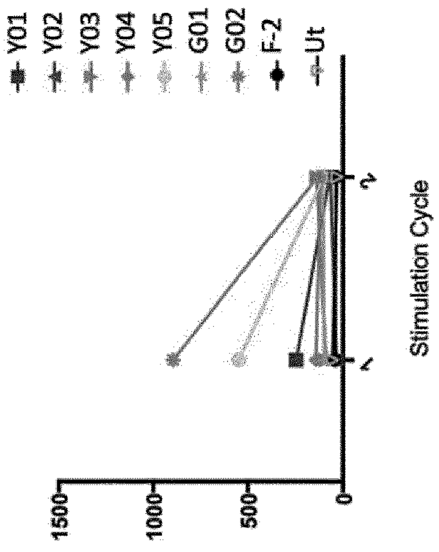

FIG. 11A show tumor cell killing activity of the 2nd generation CD19-specific CARs of FIG. 3A when iteratively re-stimulated by addition of Nalm-6 cells. FIGS. 11B and 11C shows IFN-γ (FIG. 11B) and IL-2 (FIG. 11C) production by the iteratively stimulated CAR T cells.

Figure 12:
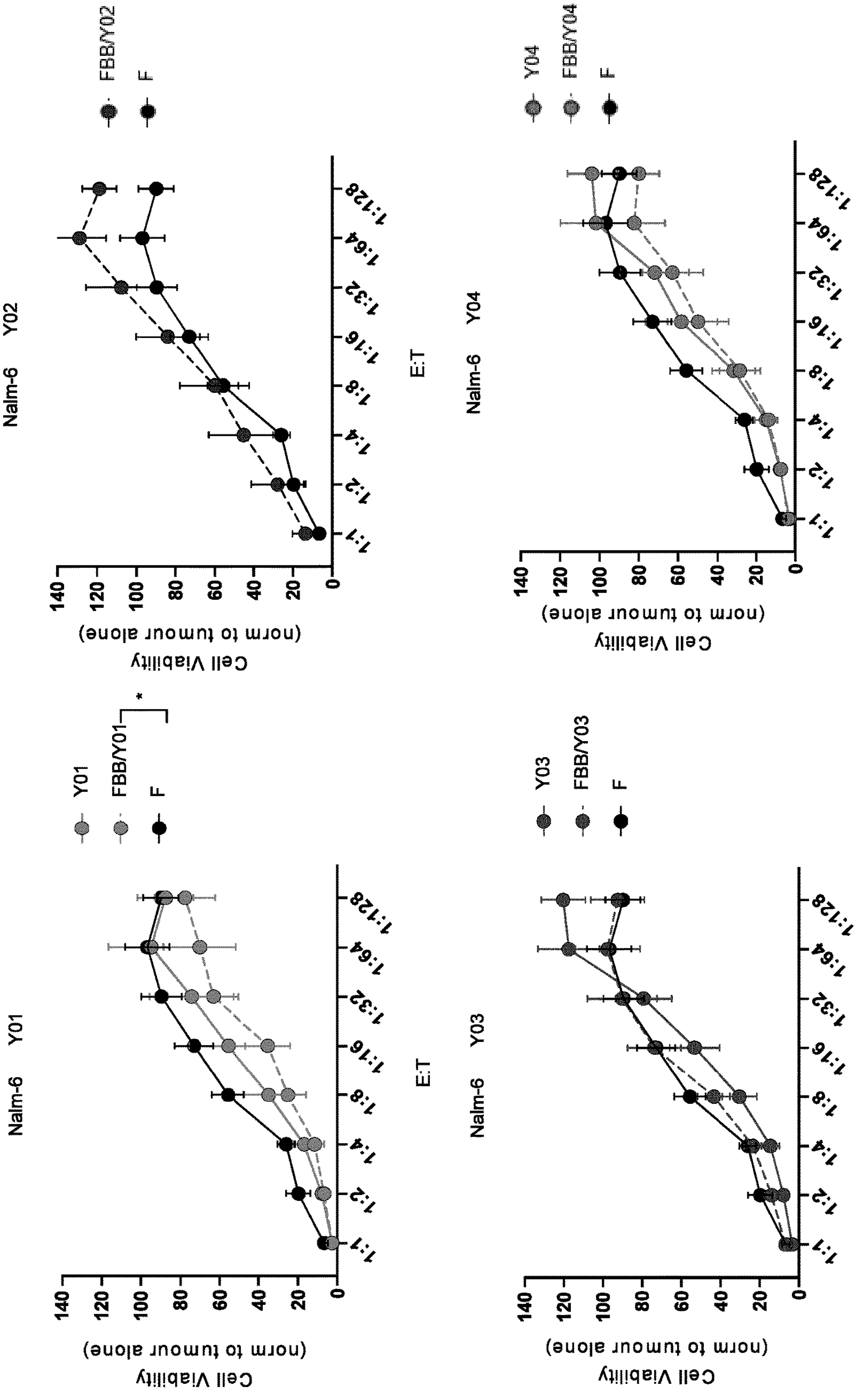
Figure 12:
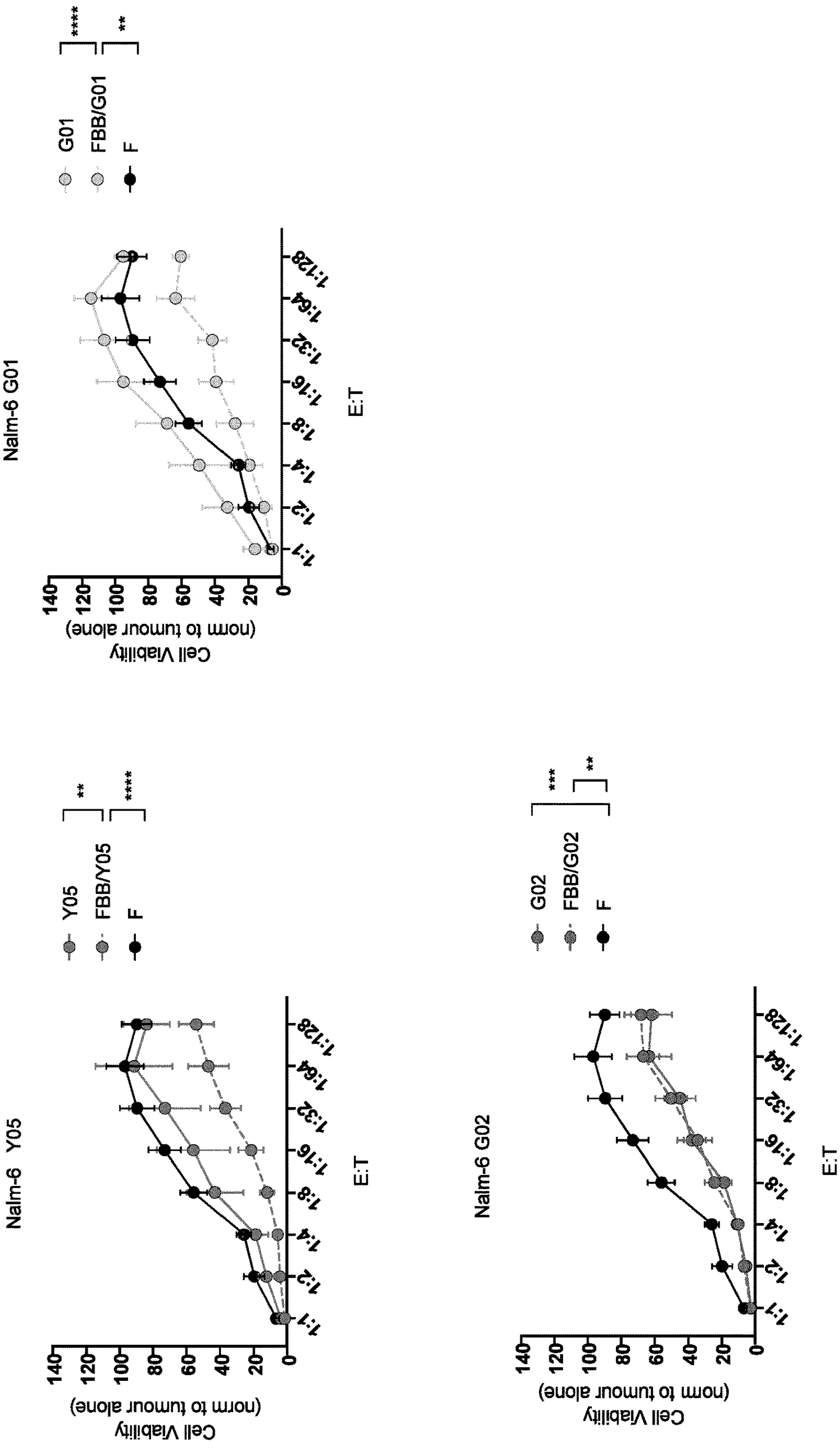

FIG. 12—Titration of Tumor Cell Killing by CAR and pCAR T Cells Targeted Against CD19

FIG. 12 shows pooled data in which cytotoxic activity of CDR3 $V_H$-mutated FMC63-based 2nd generation CAR T cells and pCAR T cells was titrated against Nalm-6 leukemic cells, making comparison with F-2 as control.

FIG. 13—In Vitro Re-Stimulation Potential of CD19-Specific pCAR T Cells

Figure 13A:
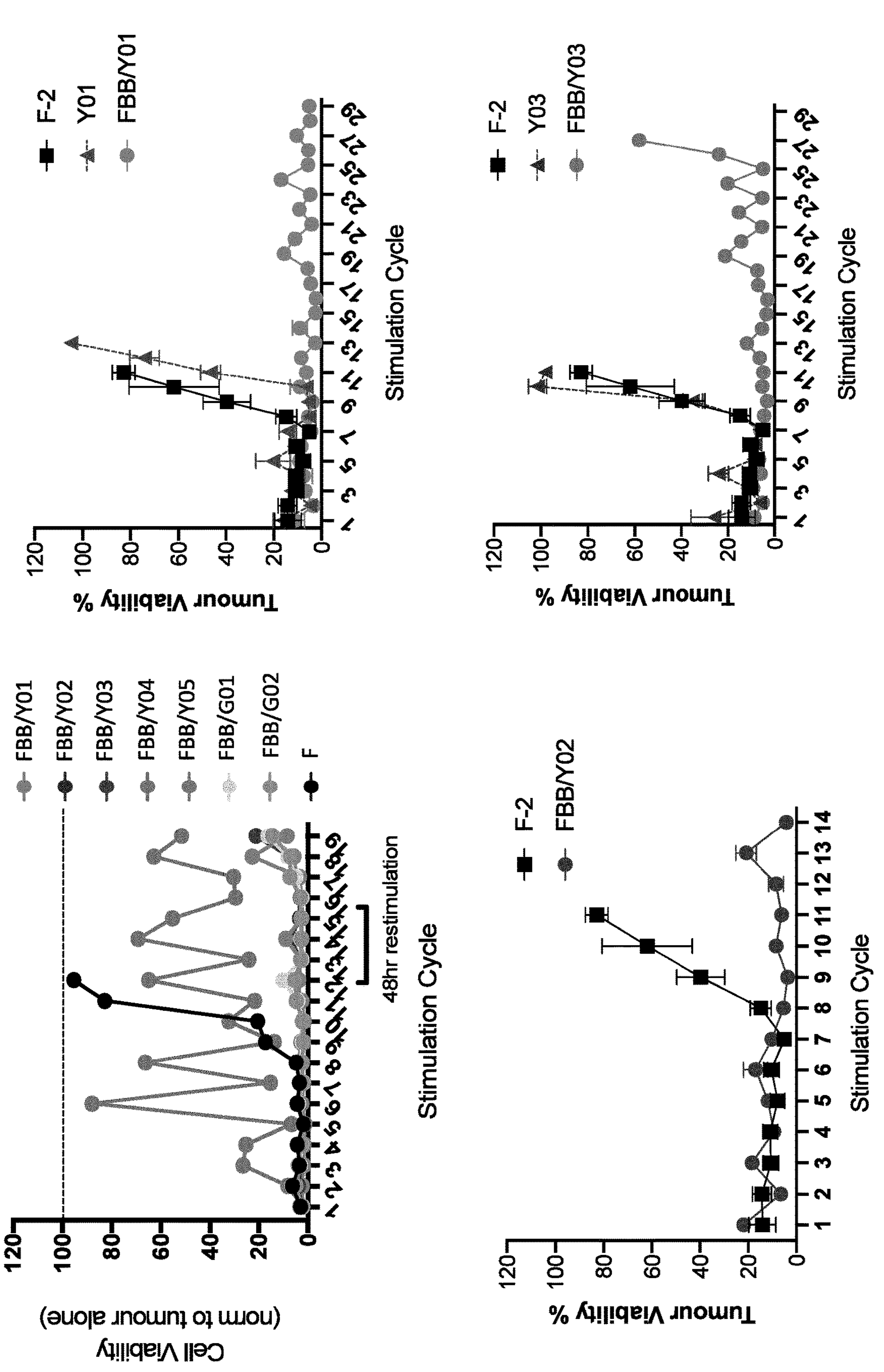
Figure 13A:
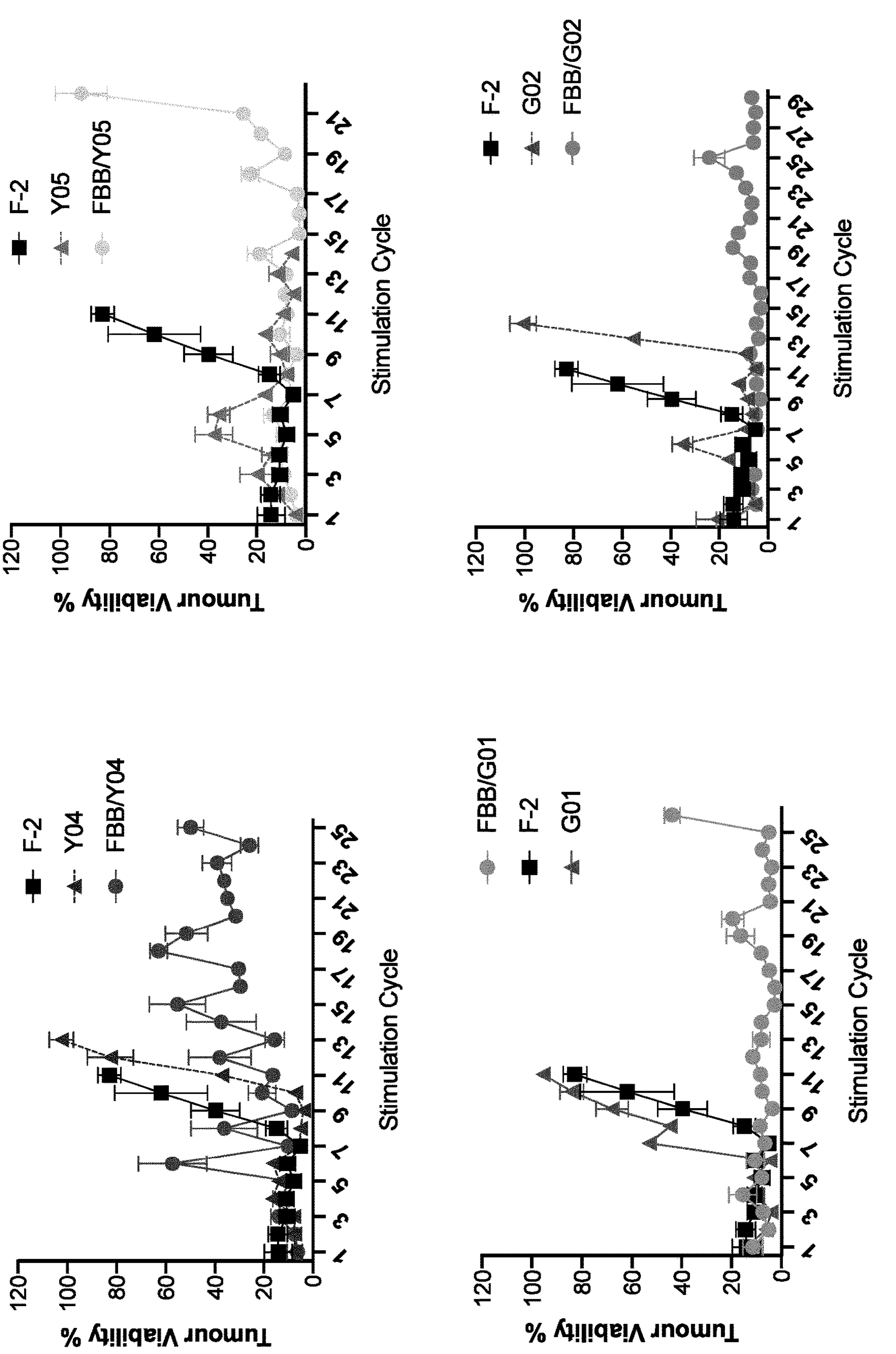
Figure 13B:
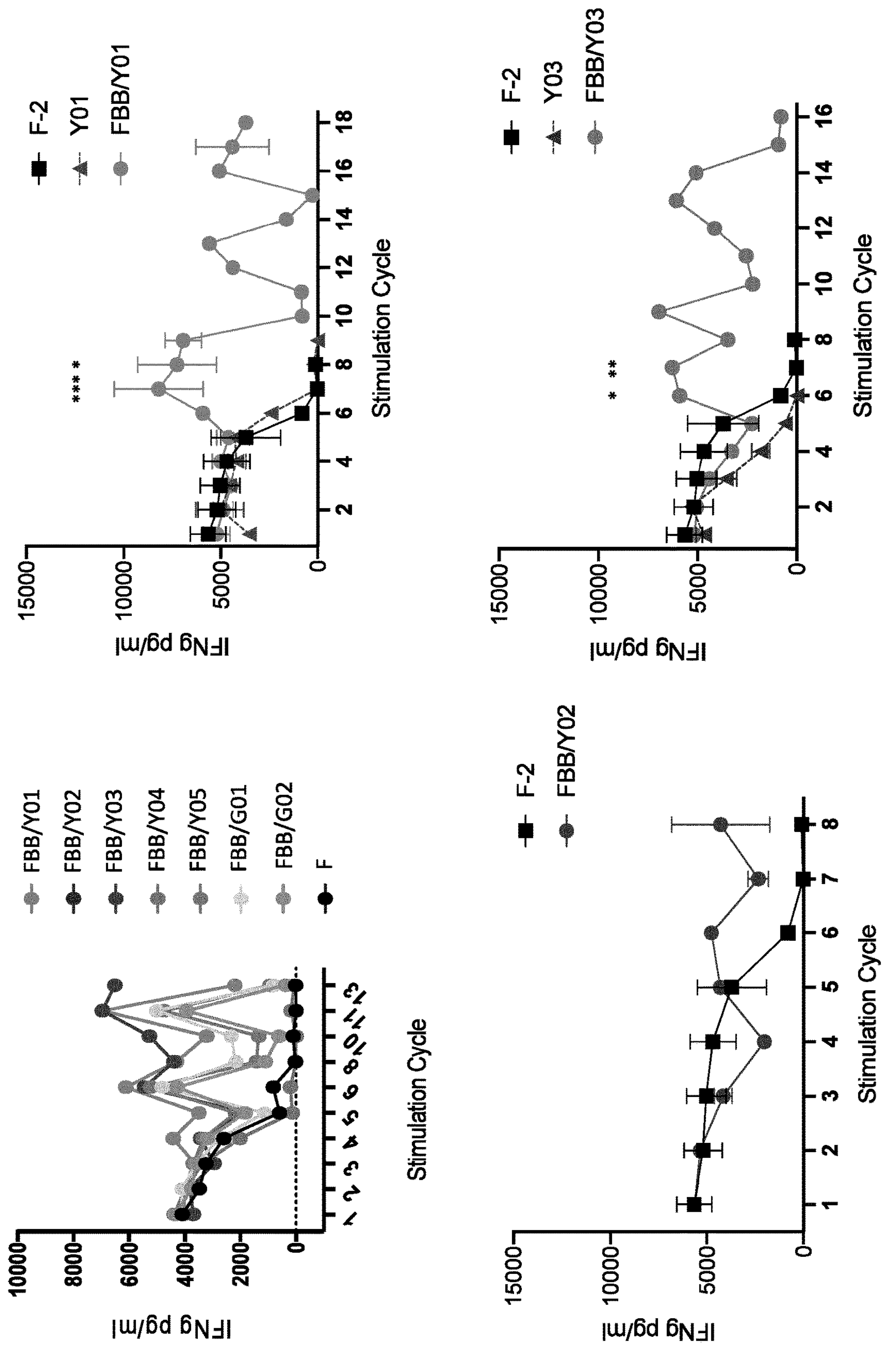
Figure 13B:
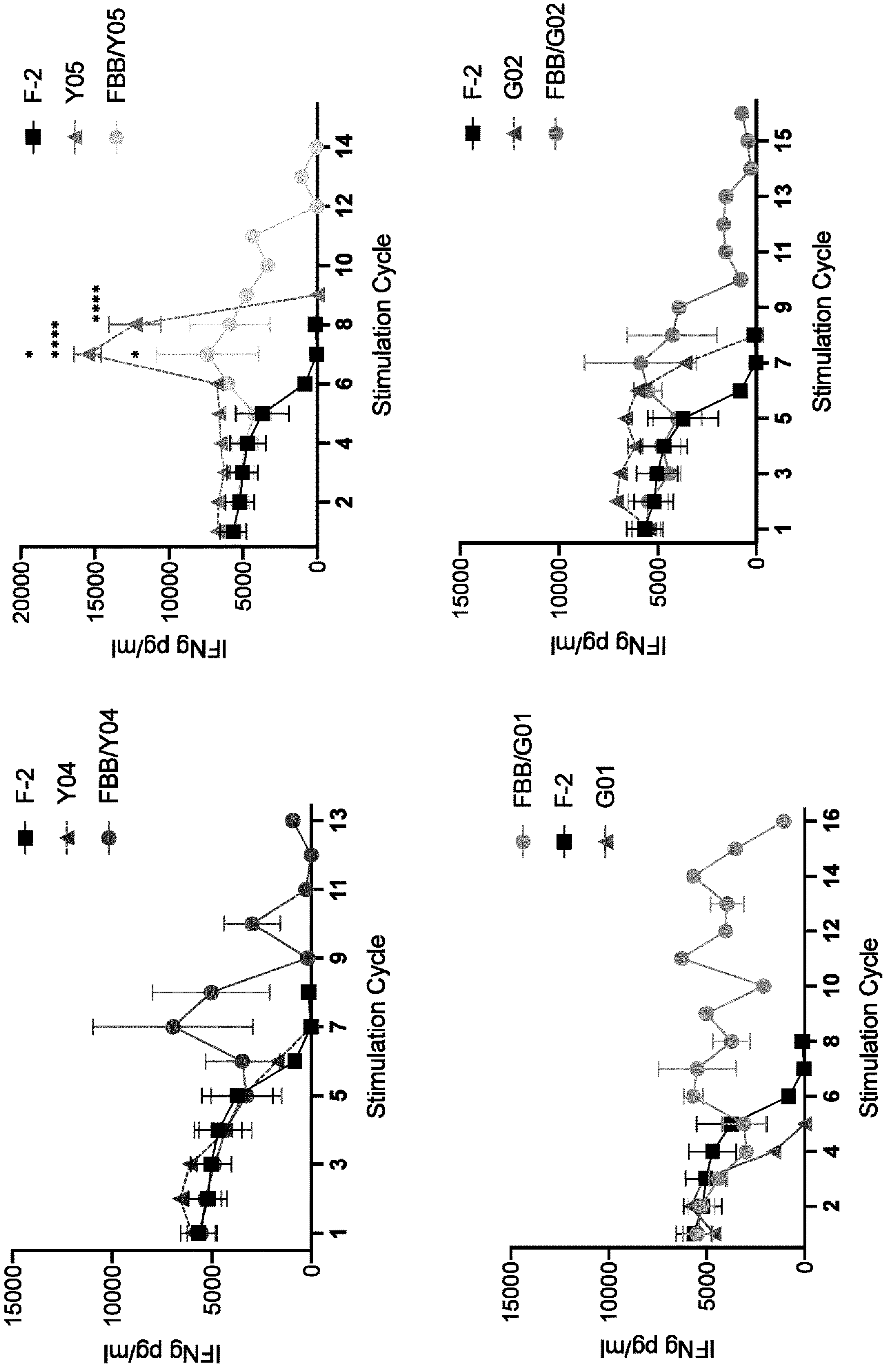
Figure 13C:
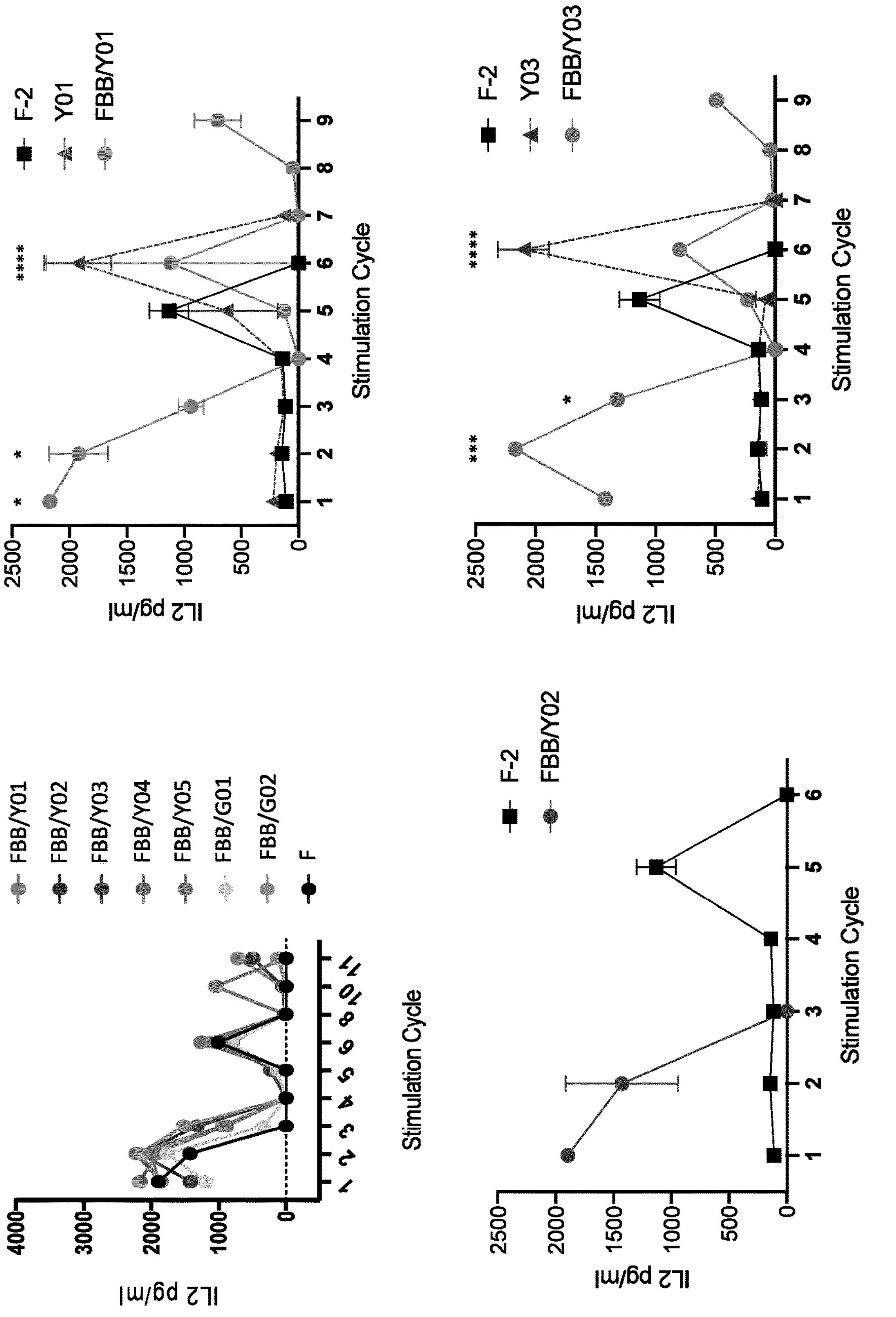
Figure 13C:
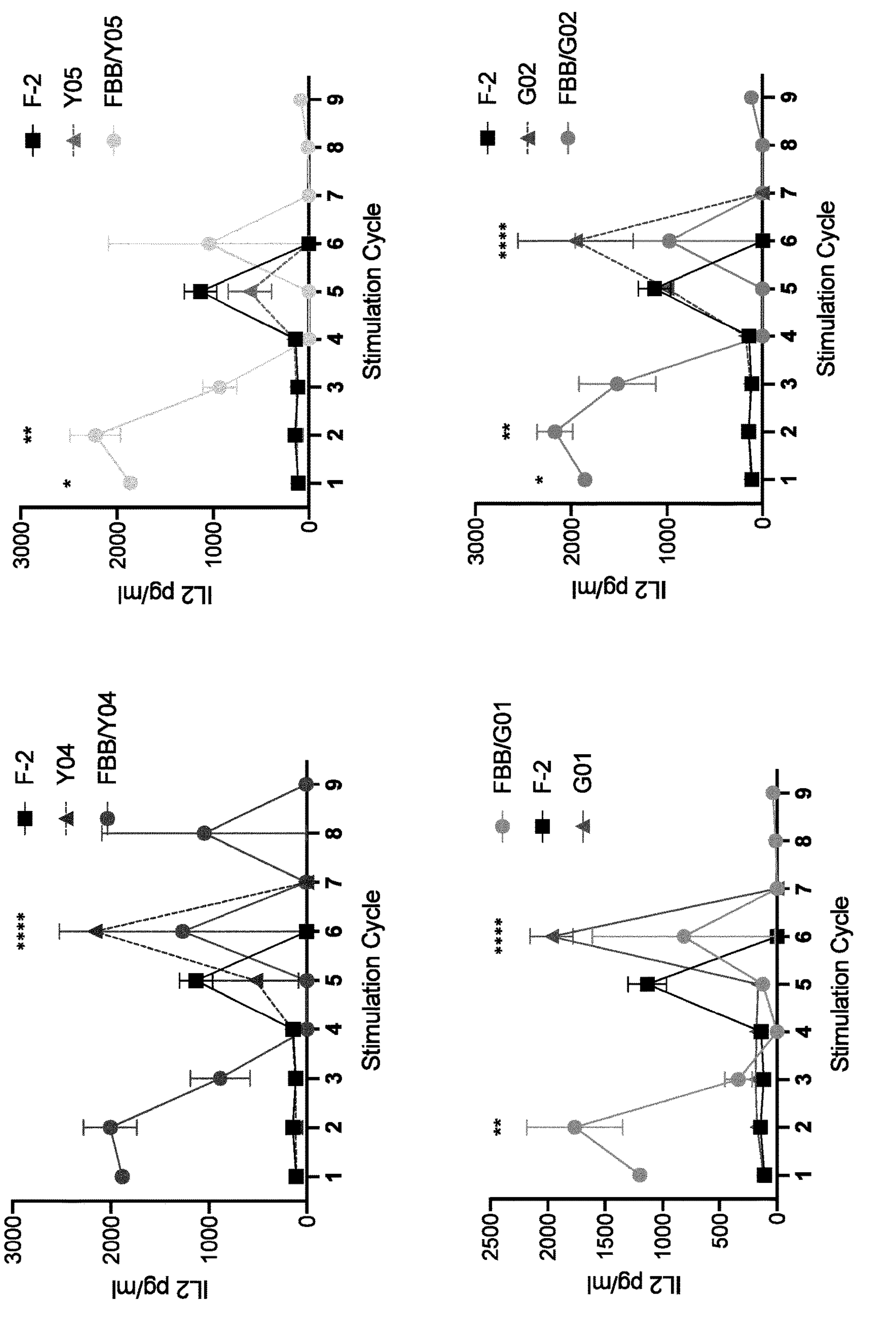

FIG. 13A shows tumor cell killing activity of CD19-specific pCAR T cells when iteratively re-stimulated by co-culture with CD19-expressing LO68 tumor cells. FIGS. 13B and 13C respectively show IFN-γ and IL-2 production by the iteratively stimulated CAR-T and pCAR-T cells.

FIG. 14—In Vivo Anti-Tumor Activity of CD19-Specific CAR and pCAR T-Cells (NSG Mice)

Figure 14A:
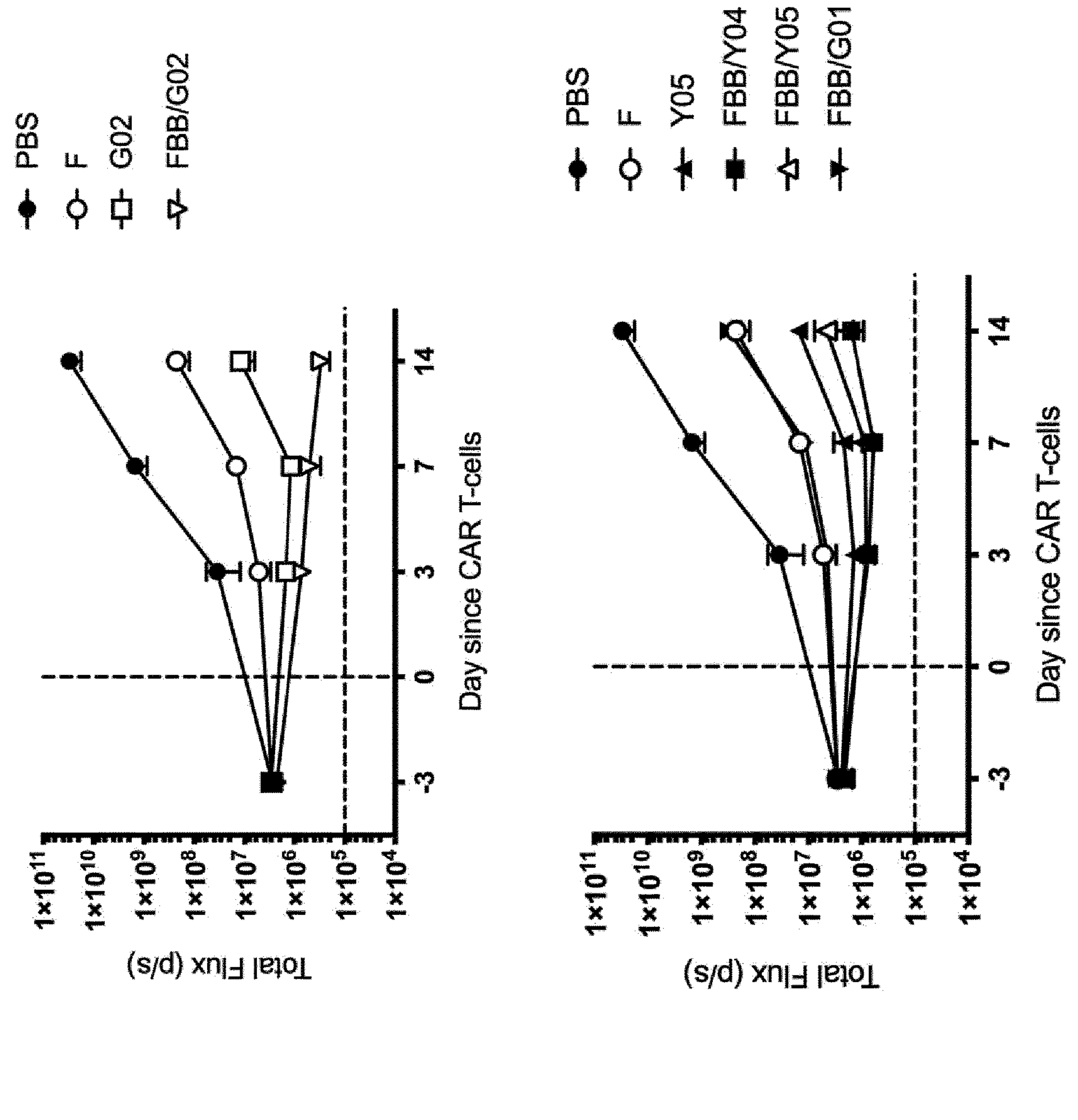
Figure 14B:
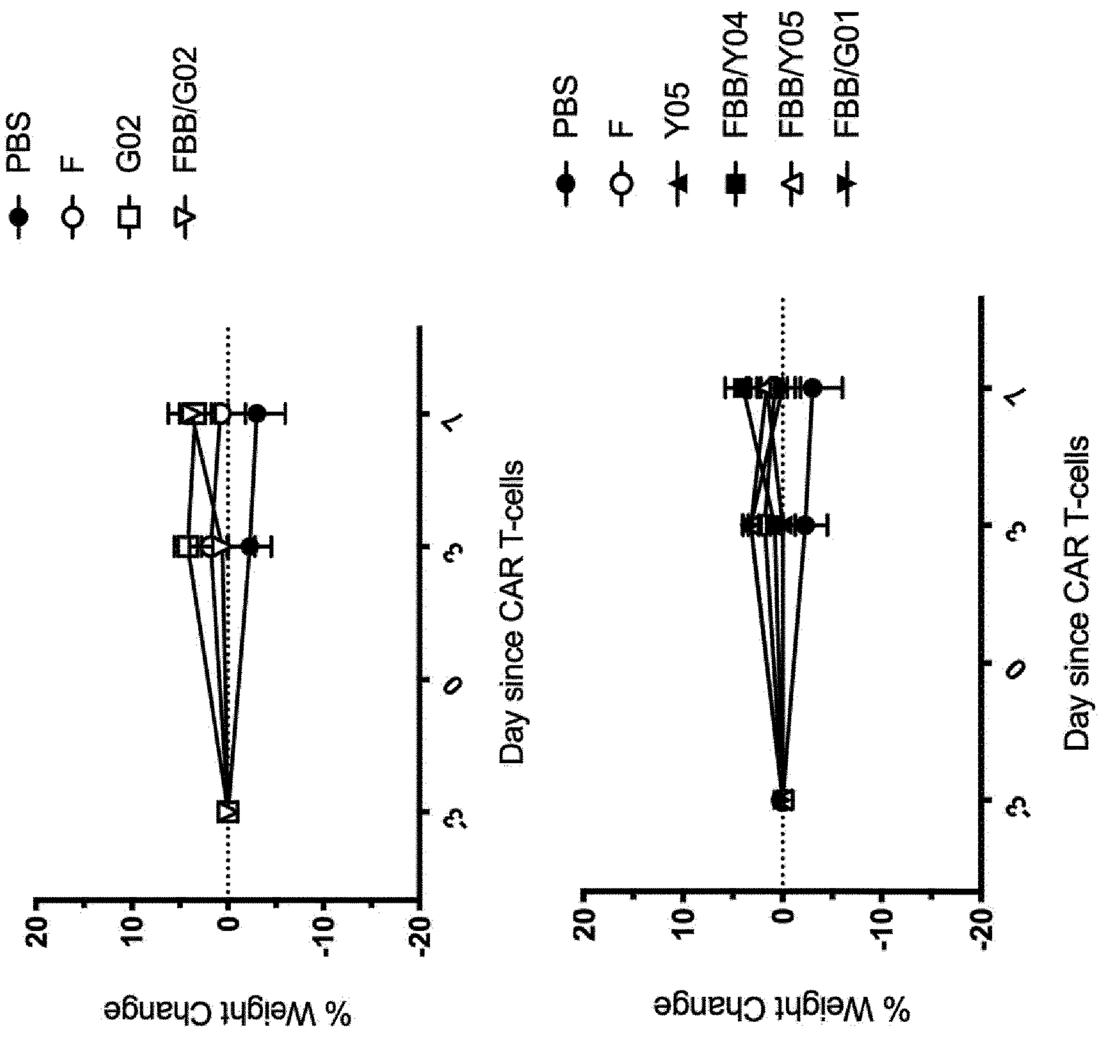

FIGS. 14A and 14B show the results of therapeutic evaluation of CD19-specific CAR or pCAR-T cells against an established luciferase-expressing Nalm-6 leukemic xenograft in NSG mice. FIG. 14A shows total flux emission from mice treated with CD19-specific CAR or pCAR-T cells and FIG. 14B shows percentage weight change of mice before and after the treatment.

FIG. 15—In Vitro Re-Stimulation Potential and Cytotoxicity of pCAR T Cells that Co-Target CD19 and CD20

Figure 15A:
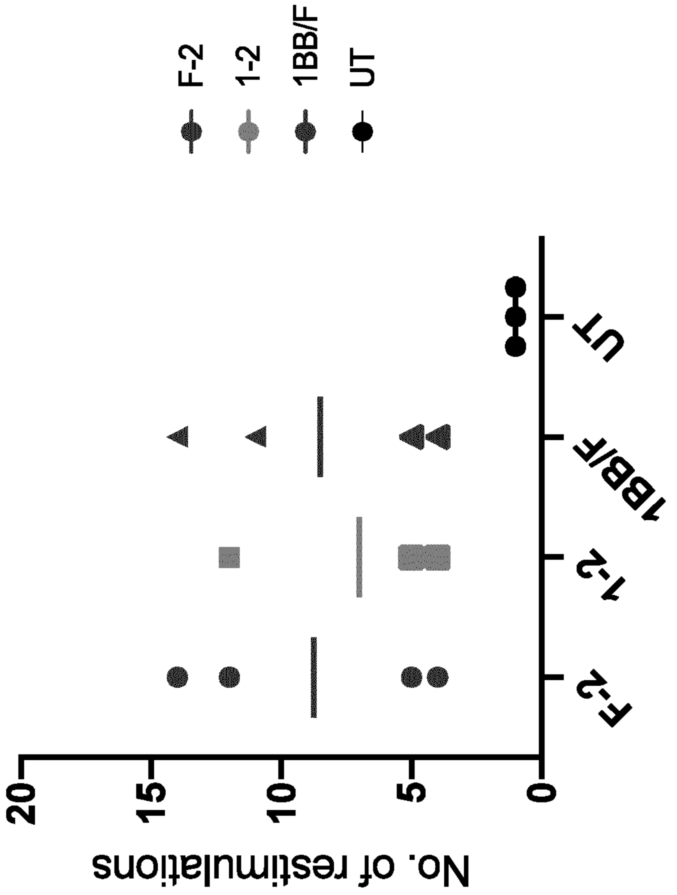
Figure 15B:
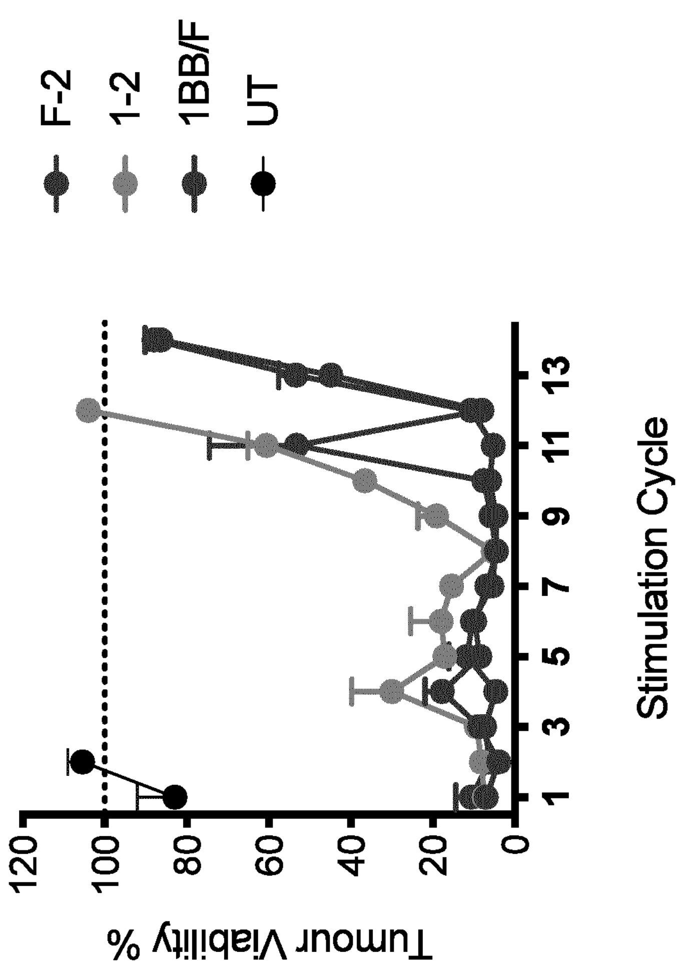
Figure 15C:
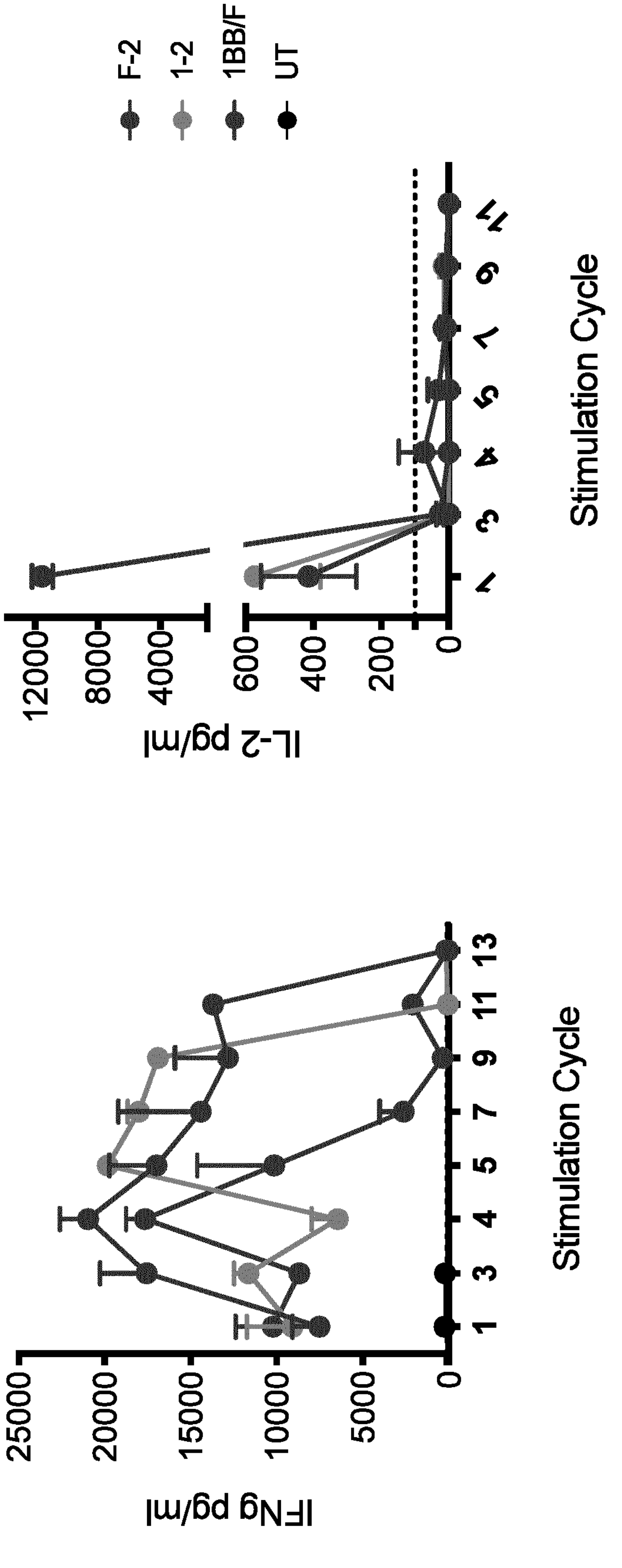
Figure 15D:
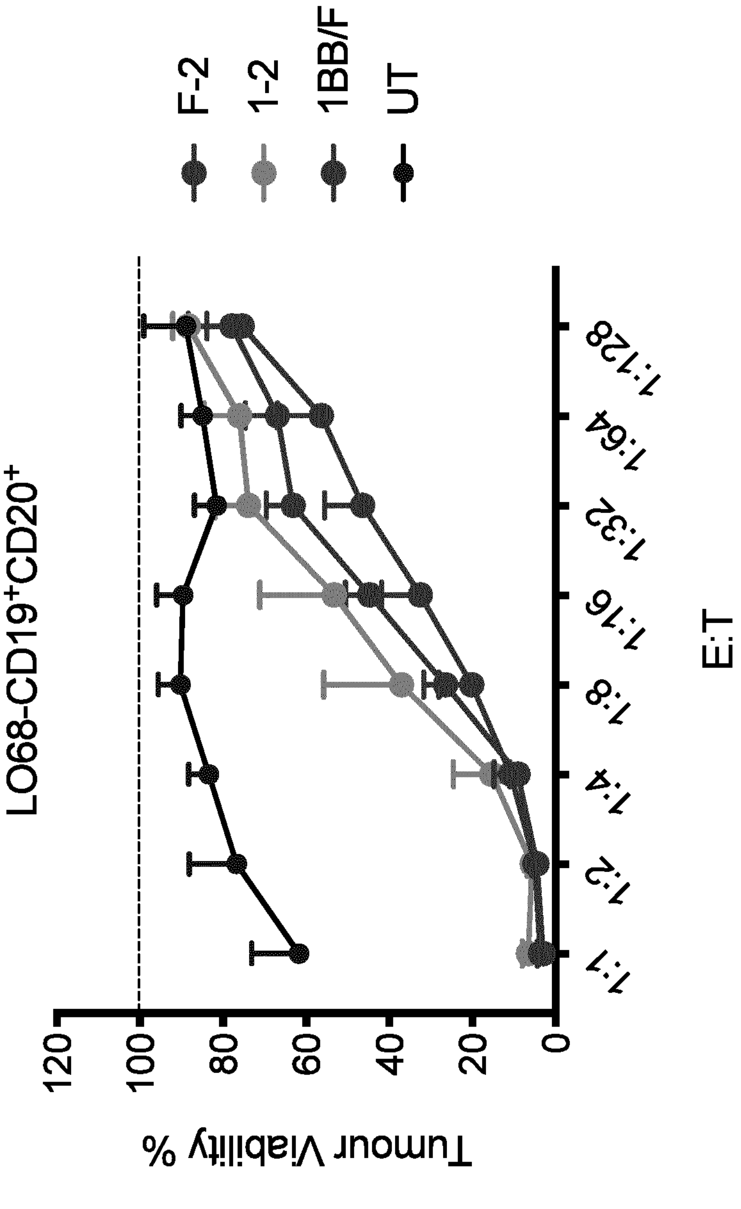
Figure 15E:
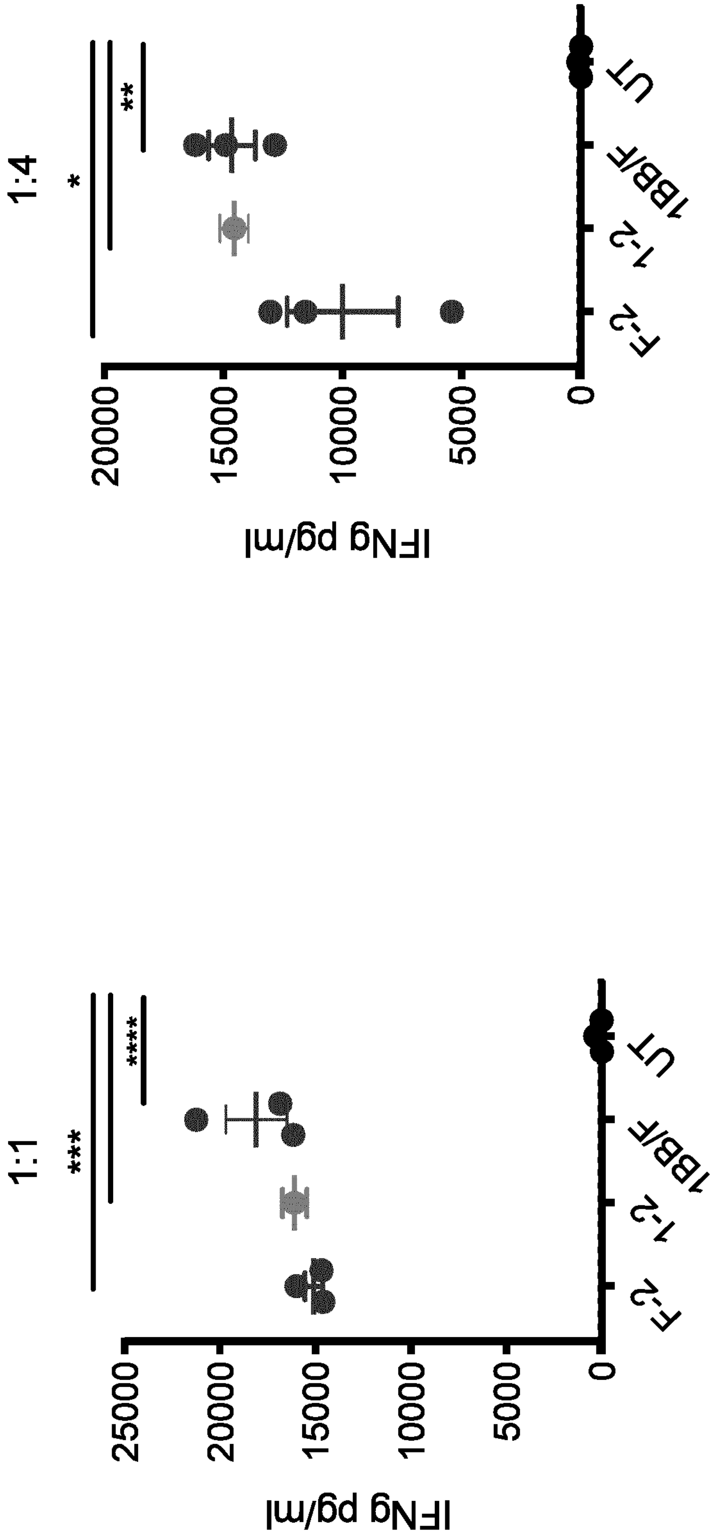
Figure 15F:
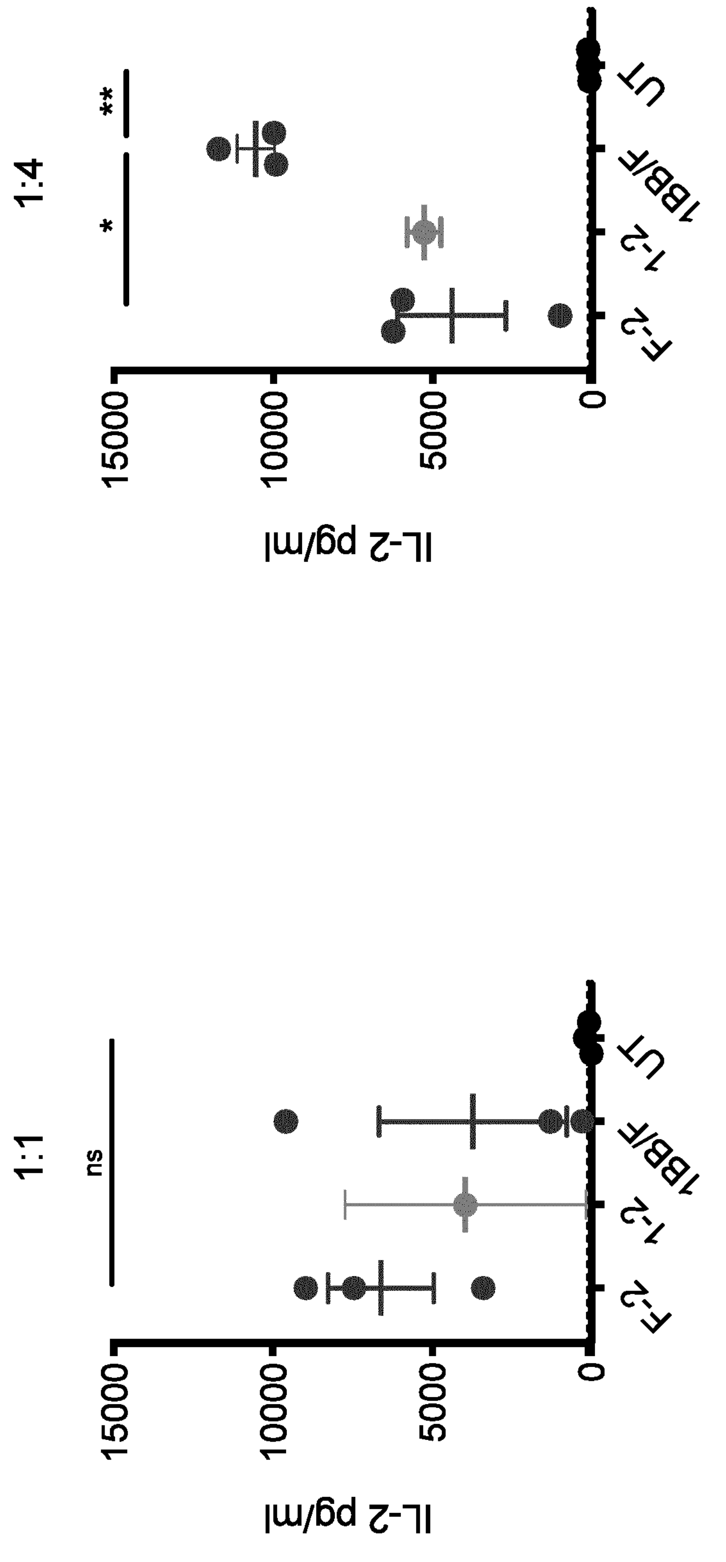

FIG. 15A shows number of restimulation cycles completed following co-cultivation of transduced 1BB/F pCAR T cells which co-target CD19 (CAR) and CD20 (CCR) with LO68 tumor cells that co-express both CD19 and CD20. Every 72 hours, T cells were transferred to a fresh monolayer of LO68 cells. FIG. 15B shows the pooled data of tumor cell killing activity of 1BB/F pCAR T cells co-cultivated with LO68 tumor cells. FIG. 15C shows the amount of IFN-γ (left panel) and IL-2 (right panel) released following each stimulation cycle. FIG. 15D shows pooled experiments in which cytotoxic activity of CAR and pCAR T cells was titrated using LO68 tumor cells that co-express both CD19 and CD20. FIGS. 15E-15F show the amount of IFN-γ (FIG. 15E) and IL-2 (FIG. 15F) released following 24 hours of co-cultivation at effector to target ratios of 1:1 and 1:4.

FIG. 16—Titration of Tumor Cell Killing by pCAR T Cells Co-Targeted Against CD19 and CD22

Figure 16A:
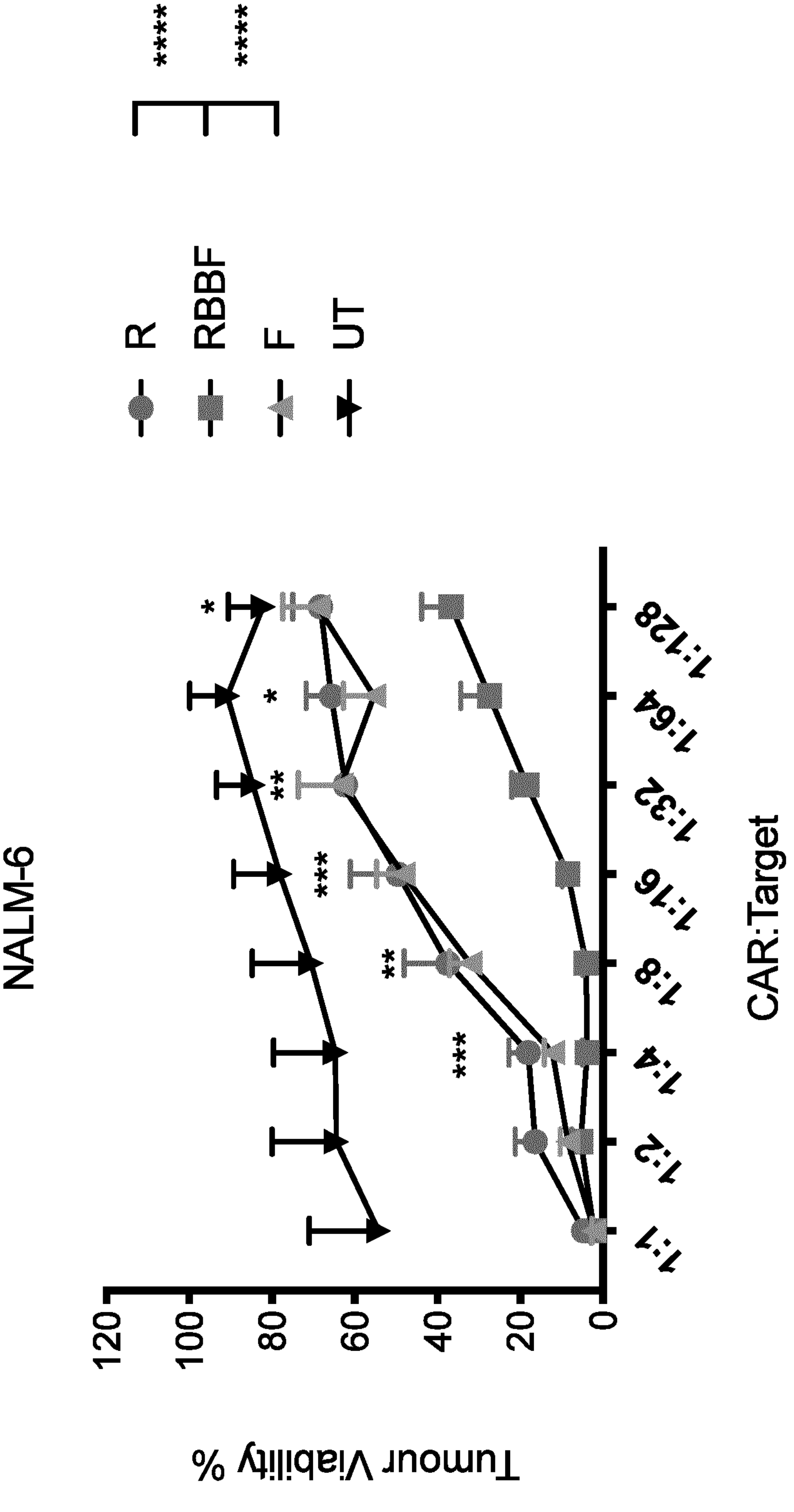
Figure 16B:
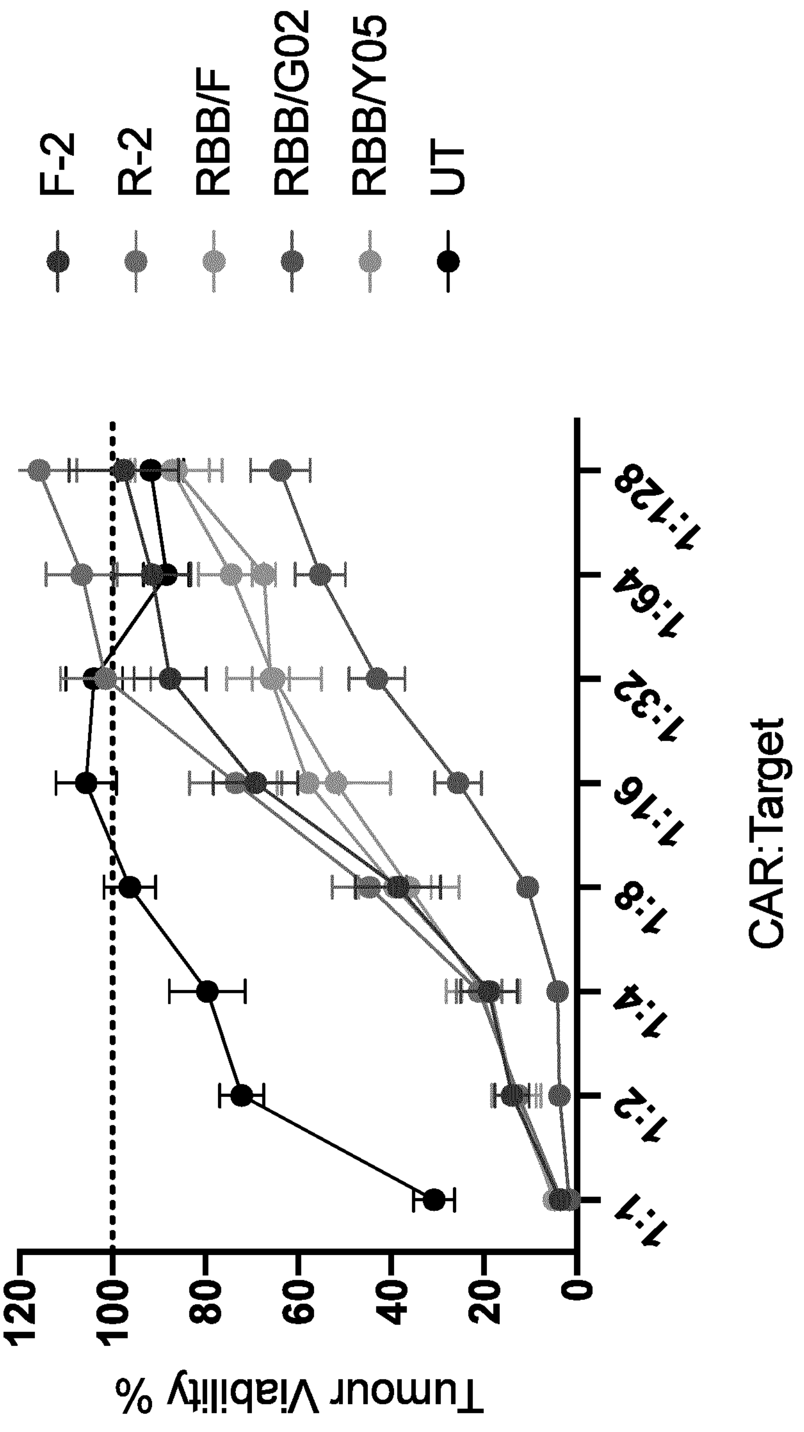

FIG. 16A-16B show the cytotoxic activity of RBB/F, RBB/G02 and RBB/Y05 pCAR T cells that co-target CD19 (CAR) and CD22 (CCR) against Nalm-6 leukemic cells. Comparison is made to the 2$^{nd}$ generation CD19 and CD22 targeting second generation CARs, F-2 and R-2 respectively.

FIG. 17—Binding Affinity of CD19-Specific CAR-T Cells

Figure 17A:
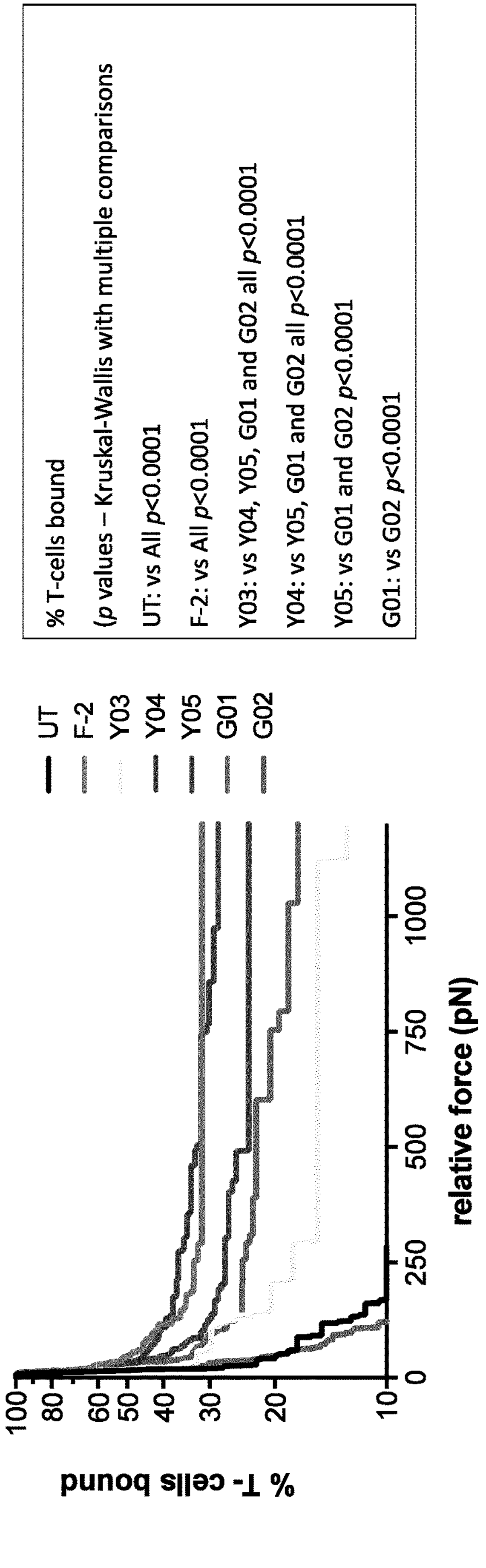
Figure 17B:
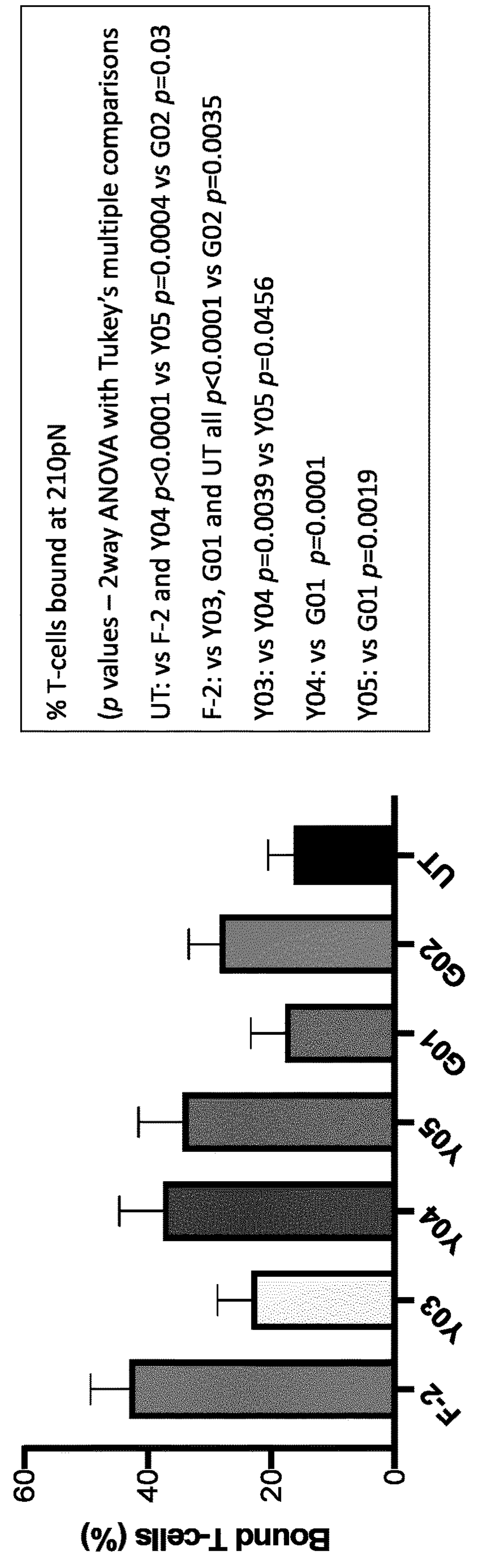
Figure 17C:
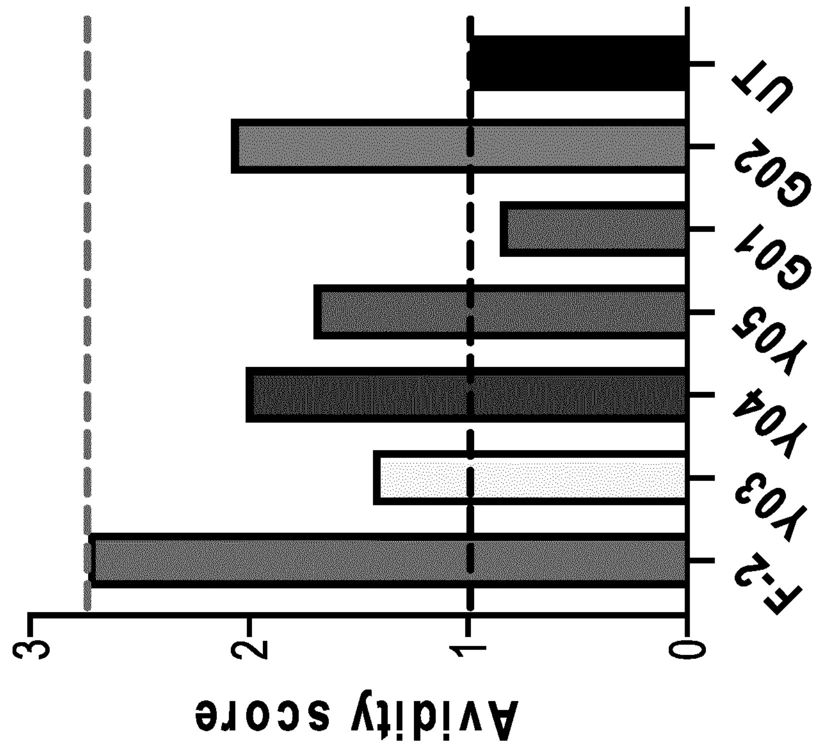
Figure 17D:
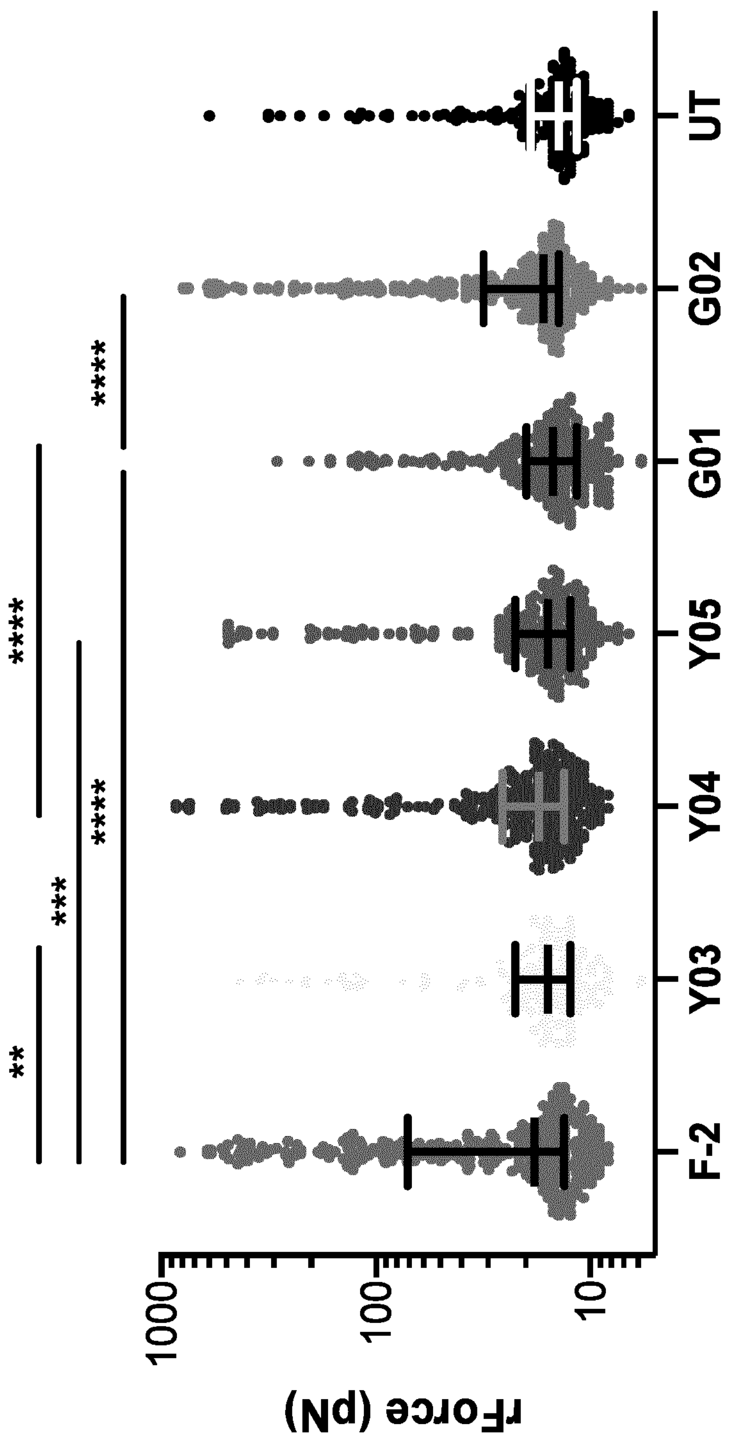

FIGS. 17A-17D show the binding affinity of CD19-specific CAR-T cells to CD19$^{+}$ LO68 tumor cells in a z-Movi microfluidic chip. T-cells were engineered to express the CD19-specific F-2 CAR or derivates that contain a mutation in $V_H$ CDR3 region. After flow sorting to purity, CAR T-cells were incubated on a monolayer of CD19$^{+}$ LO68 tumor cells in a z-Movi microfluidic chip. Increasing fluidic force was applied and the percentage of bound T-cells was determined (median, n=3) (FIG. 17A). FIG. 17B shows the overall mean percentage of bound T cells after applying minimal force to detach a mean of 90% untransduced T cells. FIG. 17C is a bar plot representing the avidity score or the mean rForce required to detach T cells from the monolayer of CD19$^{+}$ LO68 tumor cells compared to untransduced T cells (the black dotted line represents the avidity score of untransduced T cells; the red dotted line represents the avidity score of F-2 CAR T cells. The dot plot in FIG. 17D shows the rForce per cell required to detach from the tumor cell monolayer where each dot represents a single cell.

FIG. 18—Expression of CD19-Specific CAR or pCARs

Figure 18A:
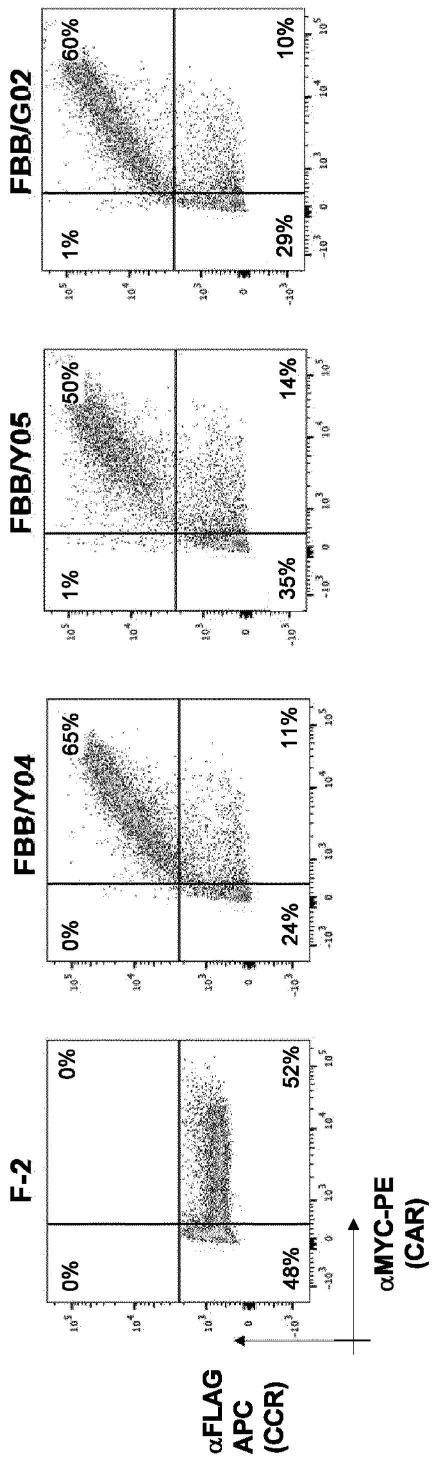
Figure 18B:
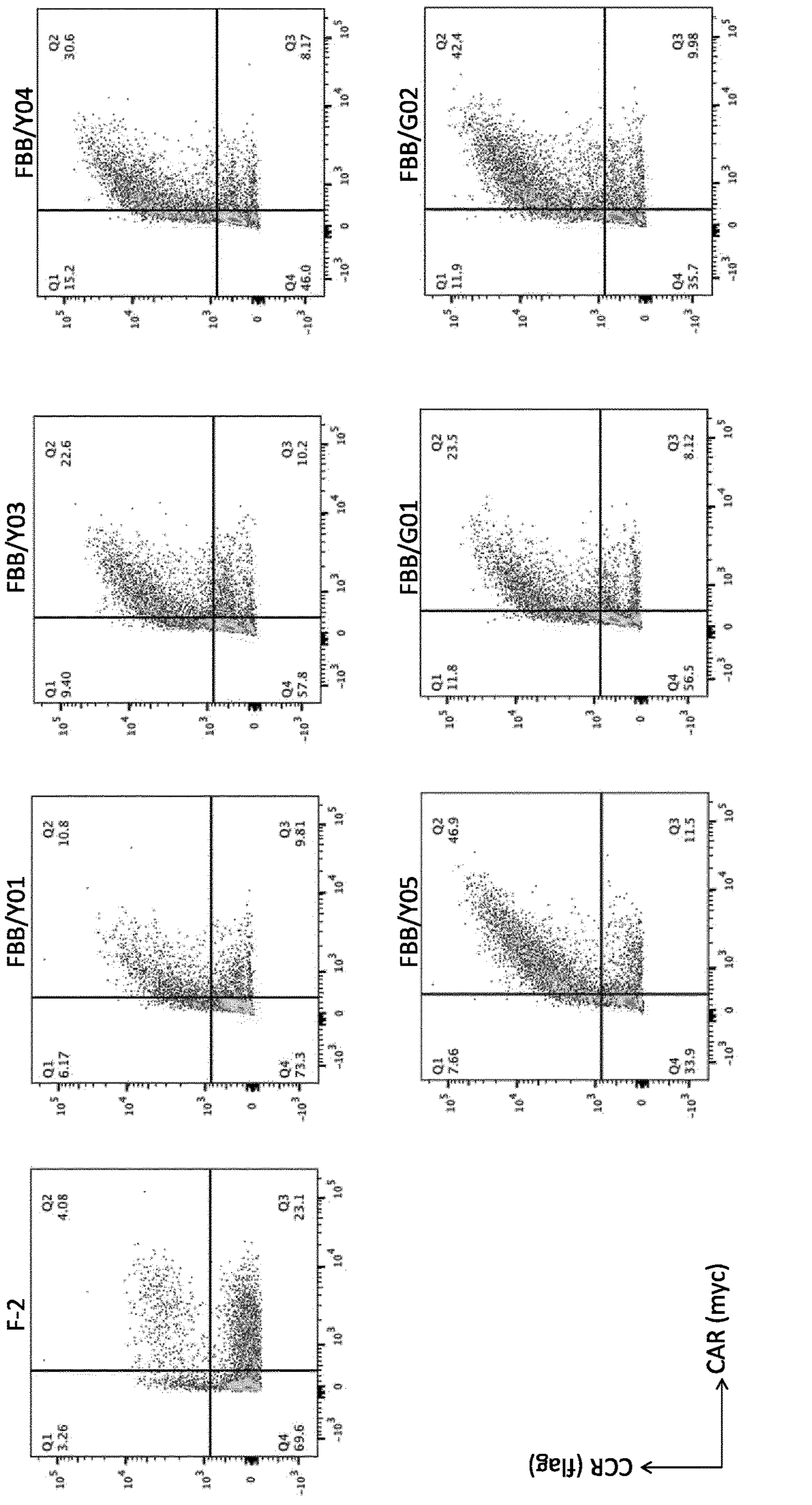

FIGS. 18A-18B show the expression of CD19-specific CAR or pCARs in human T cells analyzed by flow cytometry. Human T-cells were engineered by retroviral transduction to express the indicated CAR or pCAR. T-cells were incubated with antibodies directed against both MYC (CAR) and FLAG (CCR) epitope tags and then analyzed by flow cytometry. Data are representative of three independent replicate experiments (FIG. 18B) or greater than seven independent replicate experiments (FIG. 18A).

Figure 19:
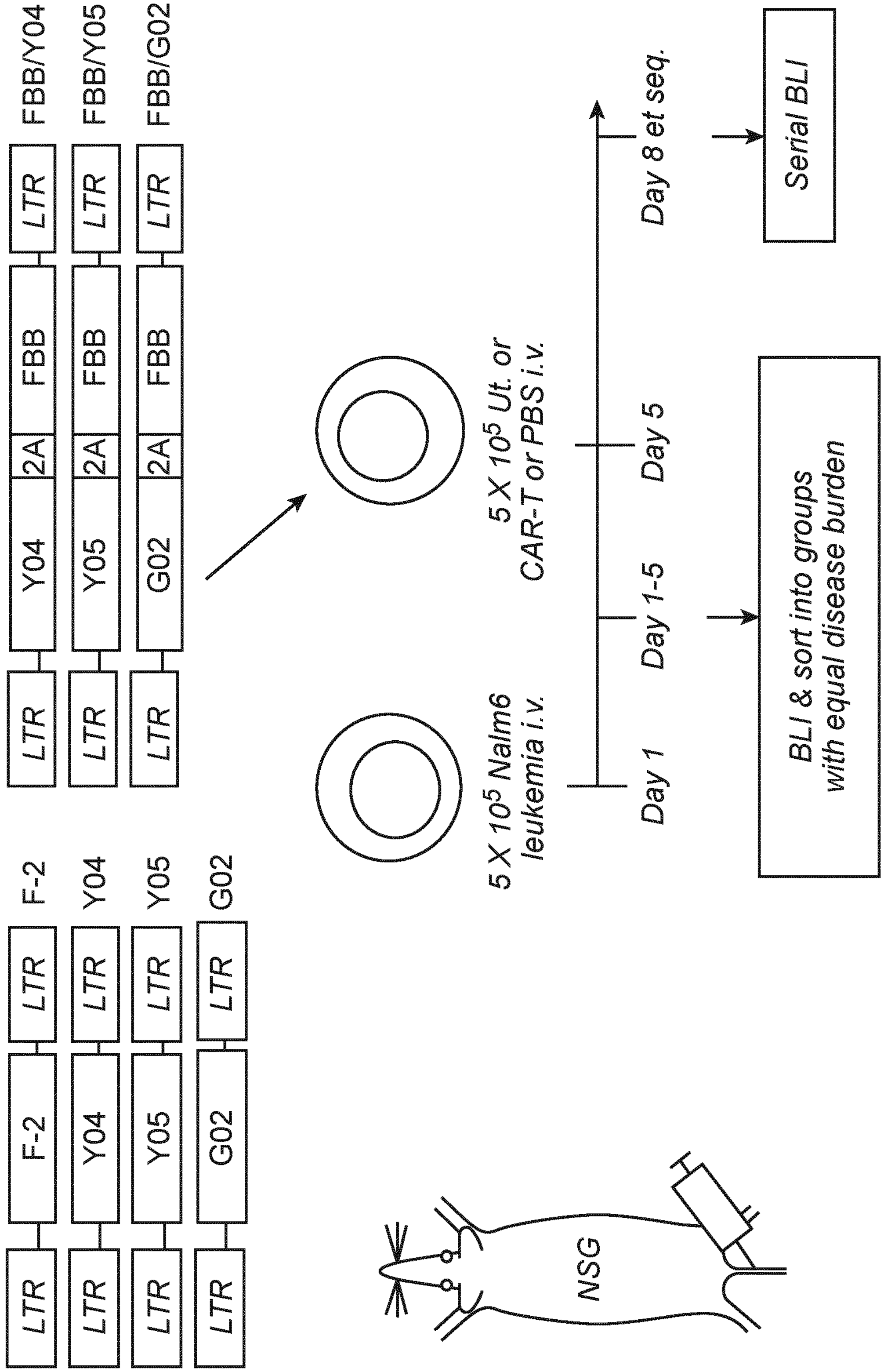

FIG. 19—Experimental Design of In Vivo Anti-Tumor Activity Testing (NSG Mice)

FIG. 19 shows the experimental design for testing the engineered CD19-specific CAR-T or pCAR-T cells in vivo. RFP/ffLuc$^{+}$ Nalm6 cells ($5\times10^5$ cells) were injected i.v. in NSG mice. Mice were sorted into groups of equal disease burden using BLI. On day 5, $5\times10^5$ of the indicated CAR or pCAR T-cells were administered i.v. Disease burden was monitored by BLI from day 8.

Figure 20A:
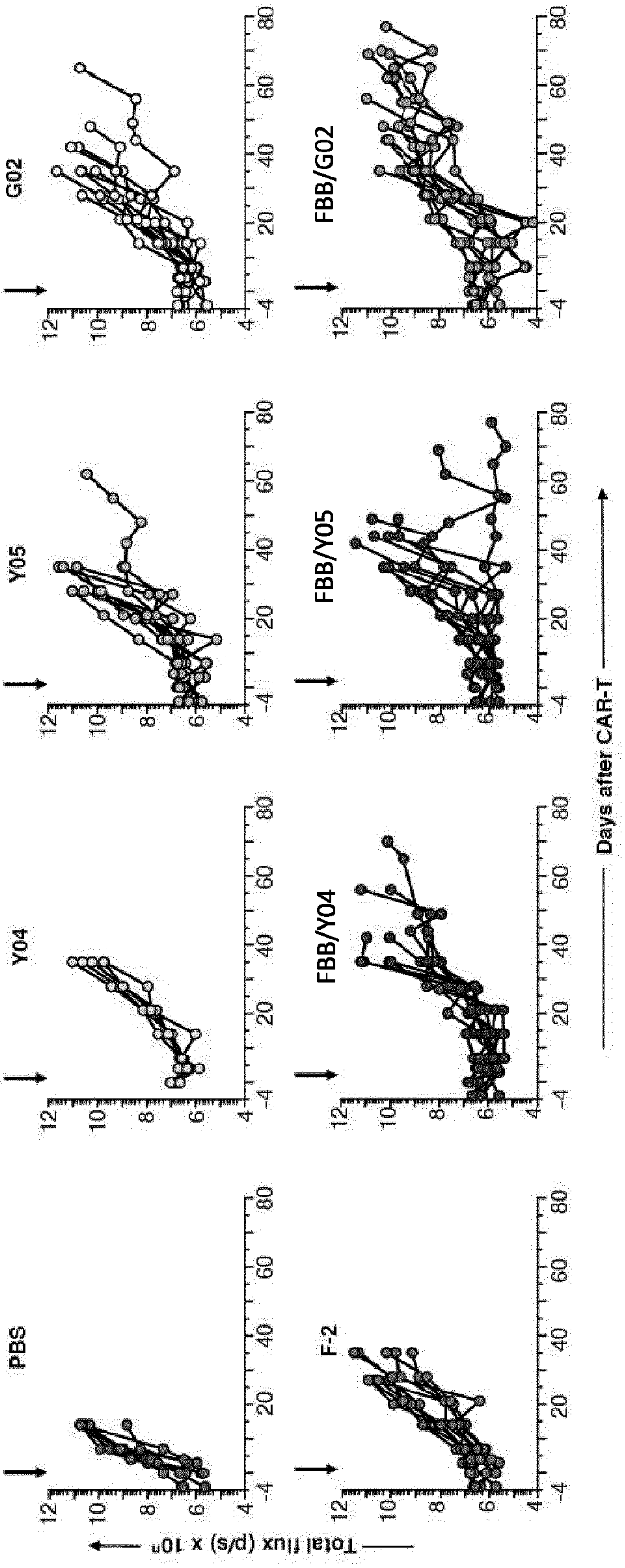

FIGS. 20A and 20B—In Vivo Anti-Tumor Activity of CD19-Specific CAR-T or pCAR-T Cells FIGS. 20A and 20B show the anti-tumor activity of CD19-specific CAR-T or pCAR-T cells in NSG mice bearing established luciferase-expressing Nalm6 leukemic xenografts. FIG. 20A shows the total flux emission (e.g. leukemic burden) of mice treated with indicated CD19-specific CAR-T or pCAR-T cells. FIG. 20B shows the p values of selected pCAR vs its corresponding 2G CAR with a mutation in $V_H$ CDR3 region and the p values of 2G CAR F-2 vs the indicated 2G CAR with a mutation in $V_H$ CDR3 region.

FIGS. 21A, 21B, 21C, and 21D—Survival of NSG Mice Treated with CD19-Specific CAR-T or pCAR-T Cells FIGS. 21A, 21B, 21C, and 21D show the survival curves of PBS, CD19 specific CAR-T cell- and CD19 specific pCAR-T cell-treated groups. FIG. 21A shows the survival curves of PBS, F-2 CAR-T cells, Y04 CAR-T cells, and FBB/Y04 pCAR-T cells-treated groups. FIG. 21B shows the survival curves of PBS, F-2 CAR-T cells, Y05 CAR-T cells, and FBB/Y05 pCAR-T cells treated-groups. FIG. 21C shows the survival curves of PBS, F-2 CAR-T cells, G02 CAR-T cells, and FBB/G02 pCAR-T cells-treated groups. FIG. 21D shows the median survival of each treatment group shown in FIGS. 21A-21C.

4. DETAILED DESCRIPTION

The details of various embodiments of the invention are set forth in the description below. Other features, objects, and advantages of the invention will be apparent from the description and the drawings, and from the claims.

4.1. Definitions

Unless otherwise defined herein, all technical and scientific terms used herein have the meaning commonly understood by a person skilled in the art to which this invention belongs. As used herein, the following terms have the meanings ascribed to them below.

As used herein, the term "variant" refers to a polypeptide sequence which is a naturally occurring polymorphic form of the basic sequence as well as synthetic variants, in which one or more amino acids within the chain are inserted, removed or replaced. However, the variant produces a biological effect which is similar to that of the basic sequence. For example, a variant of the intracellular domain of human CD3 zeta chain will act in a manner similar to that of the intracellular domain of human CD3 zeta chain. Amino acid substitutions may be regarded as "conservative" where an amino acid is replaced with a different amino acid in the same class with broadly similar properties. Non-conservative substitutions are where amino acids are replaced with amino acids of a different type or class.

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation. Non-conservative substitutions may also be possible provided that these do not interrupt the function of the polypeptide as described above. Broadly speaking, fewer non-conservative substitutions will be possible without altering the biological activity of the polypeptides. In general, variants will have amino acid sequences that will be at least 70%, for instance at least 71%, 75%, 79%, 81%, 84%, 87%, 90%, 93%, 95%, 96% or 98% identical to the basic sequence, for example SEQ ID NO: 1 or SEQ ID NO: 2. Identity in this context may be determined using the BLASTP computer program with SEQ ID NO: 1, SEQ ID NO: 2, or a fragment thereof, in particular a fragment as described below, as the base sequence. The BLAST software is publicly available.

As used herein, the term "antigen" refers to any member of a specific binding pair that will bind to the binding elements. The term includes receptors on target cells.

As used herein and with regard to the binding element to a target molecule, the terms "bind," "specific binding," "specifically binds to," "specifically interacts with," "specific for," "selectively binds," "selectively interacts with," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule.

The term "pCAR" as used herein refers to a parallel chimeric antigen receptor which comprises the combination of a $2^{nd}$ generation chimeric antigen receptor (CAR) and, in parallel, a chimeric co-stimulatory receptor (CCR). pCAR has been described in WO2017/021701, which is incorporated by reference in its entirety herein.

4.2. Other Interpretational Conventions

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

4.3. Immuno-Responsive Cells

In a first aspect, immuno-responsive cells are provided. The immuno-responsive cells express a pCAR which comprises the combination of a $2^{nd}$ generation chimeric antigen receptor (CAR) and, in parallel, a chimeric co-stimulatory receptor (CCR).

The CAR comprises, from C-terminus to N-terminus (from intracellular to extracellular as expressed within the immuno-responsive cell), (a) a signaling region; (b) a first co-stimulatory signaling region; (c) a first transmembrane domain; and (d) a first binding element that specifically interacts with a first epitope on a CD19 target antigen.

The CCR comprises, from C-terminus to N-terminus (from intracellular to extracellular as expressed within the immuno-responsive cell), (e) a second co-stimulatory signaling region which is different from that of the first co-stimulatory signaling region of the CAR; (f) a second transmembrane domain; and (g) a second binding element that specifically interacts with a second epitope on a second antigen. The second epitope can be identical to or distinct from the first epitope. The second antigen can be CD19 or an alternative B cell lineage-specific antigen.

4.3.1. Cells

In typical embodiments, the immuno-responsive cells are T cells.

In certain embodiments, the immuno-responsive cells are αβ T cells. In particular embodiments, the immuno-responsive cells are cytotoxic αβ T cells. In particular embodiments, the immuno-responsive cells are αβ helper T cells. In particular embodiments, the immuno-responsive cells are regulatory αβ T cells (Tregs).

In certain embodiments, the immuno-responsive cells are γδ T cells. In particular embodiments, the immuno-responsive cells are $V\delta2^{+}$ γδ T cells. In particular embodiments, the immuno-responsive cells are $V\delta2^{-}$ T cells. In specific embodiments, the $V\delta2^{-}$ T cells are $V\delta1^{+}$ cells.

In certain embodiments, the immuno-responsive cells are Natural Killer (NK) cells.

In some embodiments, the immuno-responsive cell expresses no additional exogenous proteins. In other embodiments, the immuno-responsive cell is engineered to express additional exogenous proteins, such as a cytokine, receptor or derivative thereof.

In some embodiments, the immuno-responsive cells are obtained from peripheral blood mononuclear cells (PBMCs). In some embodiments, the immuno-responsive cells are obtained from tumors. In particular embodiments, the immuno-responsive cells obtained from tumors are tumor infiltrating lymphocytes (TILs). In specific embodiments, the TILs are αβ T cells. In other specific embodiments, the TILs are γδ T cells, and in particular, $V\delta2^{+}$ or $V\delta2^{-}$ γδ T cells.

4.4. Chimeric Antigen Receptor Structure

4.4.1. Signaling Region

The CAR construct comprises a signaling region at its C-terminus. In some embodiments, the signaling region comprises an Immune-receptor-Tyrosine-based-Activation-Motif (ITAM), as reviewed for example by Love et al., *Cold Spring Harbor Perspect. Biol.* 2(6)1 a002485 (2010). In some embodiments, the signaling region comprises the intracellular domain of human CD3 zeta chain, as described for example in U.S. Pat. No. 7,446,190, incorporated by reference herein, or a variant thereof. In particular embodiments, the signaling region comprises the domain which spans amino acid residues 52-163 of the full-length human CD3 zeta chain. The CD3 zeta chain has a number of known polymorphic forms, (e.g. Sequence ID: gb|AAF34793.1 and gb|AAA60394.1), all of which are useful herein, and shown respectively as SEQ ID NO: 1 and 2:

```
                                             (SEQ ID NO: 1)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR;

                                             (SEQ ID NO: 2)
RVKFSRSAEPPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR.
```

Alternative signaling regions to the CD3 zeta domain include other ITAM containing units such as FcεrIγ, CD3ϑ, DAP12 and multi-ITAM. See Eshhar Z et al., "Specific activation and targeting of cytotoxic lymphocytes through chimeric single chains consisting of antibody-binding domains and the gamma or zeta subunits of the immunoglobulin and T-cell receptors," *Proc Natl Acad Sci USA* 90:720-724 (1993); Nolan et al., "Bypassing immunization: optimized design of "designer T cells" against carcinoembryonic antigen (CEA)-expressing tumors, and lack of suppression by soluble CEA," *Clin Cancer Res* 5:3928-3941 (1999); Zhao et al., "A herceptin-based chimeric antigen receptor with modified signaling domains leads to enhanced survival of transduced T lymphocytes and antitumor activity," *J Immunol* 183:5563-5574 (2009), Töpfer et al. DAP12-based activating chimeric antigen receptor for NK cell tumor immunotherapy. *J Immunol* 194:3201-3212 (2015); and James J R, "Tuning ITAM multiplicity on T cell receptors can control potency and selectivity to ligand density," *Sci Signal* 11(531) eaan1088 (2018), the disclosures of which are incorporated herein by reference in their entireties.

4.4.2. Co-Stimulatory Signaling Region

In the CAR, the co-stimulatory signaling region is suitably located between the signaling region and transmembrane domain, and remote from the binding element.

In the CCR, the co-stimulatory signaling region is suitably located adjacent the transmembrane domain and remote from the binding element.

Suitable co-stimulatory signaling regions are well known in the art, and include the co-stimulatory signaling regions of members of the B7/CD28 family such as B7-1, B7-2, B7-H1, B7-H2, B7-H3, B7-H4, B7-H6, B7-H7, BTLA, CD28, CTLA-4, Gi24, ICOS, PD-1, PD-L2 or PDCD6; or ILT/CD85 family proteins such as LILRA3, LILRA4, LILRB1, LILRB2, LILRB3 or LILRB4; or tumor necrosis factor (TNF) superfamily members such as 4-1BB, BAFF, BAFF R, CD27, CD30, CD40, DR3, GITR, HVEM, LIGHT, Lymphotoxin-alpha, OX40, RELT, TACI, TLIA, TNF-alpha, or TNF RII; or members of the SLAM family such as 2B4, BLAME, CD2, CD2F-10, CD48, CD8, CD84, CD229, CRACC, NTB-A or SLAM; or members of the TIM family such as TIM-1, TIM-3 or TIM-4; or other co-stimulatory molecules such as CD7, CD96, CD160, CD200, CD300a, CRTAM, DAP12, Dectin-1, DPPIV, EphB6, Integrin alpha 4 beta 1, Integrin alpha 4 beta 7/LPAM-1, LAG-3 or TSLP R. See Mondino A et al., "Surface proteins involved in T cell costimulation," *J Leukoc Biol.* 55:805-815 (1994); Thompson C B, "Distinct roles for the costimulatory ligands B7-1 and B7-2 in T helper cell differentiation?," *Cell.* 81:979-982 (1995); Somoza C and Lanier L L, "T-cell costimulation via CD28-CD80/CD86 and CD40-CD40 ligand interactions," *Res Immunol.* 146:171-176 (1995); Rhodes D A et al., "Regulation of immunity by butyrophilins," *Annu Rev Immunol.* 34:151-172 (2016); Foell J et al., "T cell costimulatory and inhibitory receptors as therapeutic targets for inducing anti-tumor immunity", *Curr Cancer Drug Targets.* 7:55-70 (2007); Greenwald R J et al., *Annu Rev Immunol., "The B*7 family revisited," 23:515-548 (2005); Flem-Karlsen K et al., "B7-H3 in cancer—beyond immune regulation," *Trends Cancer.* 4:401-404 (2018); Flies D B et al., "The new B7s: playing a pivotal role in tumor immunity," *J Immunother.* 30:251-260 (2007); Gavrieli M et al., "BTLA and HVEM cross talk regulates inhibition and costimulation," *Adv Immunol.* 92:157-185 (2006); Zhu Y et al., "B7-H5 costimulates human T cells via CD28H," *Nat Commun.* 4:2043 (2013); Omar H A et al., "Tacking molecular targets beyond PD-1/PD-L1: Novel approaches to boost patients' response to cancer immunotherapy," *Crit Rev Oncol Hematol.* 135:21-29 (2019); Hashemi M et al., "Association of PDCD6 polymorphisms with the risk of cancer: Evidence from a meta-analysis," *Oncotarget.* 9:24857-24868 (2018); Kang X et al., "Inhibitory leukocyte immunoglobulin-like receptors: Immune checkpoint proteins and tumor sustaining factors," *Cell Cycle.* 15:25-40 (2016); Watts T H, "TNF/TNFR family members in costimulation of T cell responses," *Annu Rev Immunol.* 23:23-68 (2005); Bryceson Y T et al., "Activation, coactivation, and costimulation of resting human natural killer cells," *Immunol Rev.* 214:73-91 (2006); Sharpe A H, "Analysis of lymphocyte costimulation in vivo using transgenic and 'knockout' mice," *Curr Opin Immunol.* 7:389-395 (1995); Wingren A G et al., "T cell activation pathways: B7, LFA-3, and ICAM-1 shape unique T cell profiles," *Crit Rev Immunol.* 15:235-253 (1995), the disclosures of which are incorporated herein by reference in their entireties.

The co-stimulatory signaling regions may be selected depending upon the particular use intended for the immunoresponsive cell. In particular, the co-stimulatory signaling regions can be selected to work additively or synergistically together. In some embodiments, the co-stimulatory signaling regions are selected from the co-stimulatory signaling regions of CD28, CD27, ICOS, 4-1BB, OX40, CD30, GITR, HVEM, DR3 and CD40.

In a particular embodiment, one co-stimulatory signaling region of the pCAR is the co-stimulatory signaling region of CD28 and the other is the co-stimulatory signaling region of 4-1BB. In a specific embodiment, the co-stimulatory signaling region of the CAR is the co-stimulatory signaling region of CD28 and the co-stimulatory signaling region of the CCR is the co-stimulatory signaling region of 4-1BB.

In a particular embodiment, one co-stimulatory signaling region of the pCAR is the co-stimulatory signaling region of CD28 and the other is the co-stimulatory signaling region of CD27. In a specific embodiment, the co-stimulatory signaling region of the CAR is the co-stimulatory signaling region of CD28 and the co-stimulatory signaling region of the CCR is the co-stimulatory signaling region of CD27.

4.4.3. Transmembrane Domains

The transmembrane domains for the CAR and CCR constructs may be the same or different. In currently preferred embodiments, when the CAR and CCR constructs are expressed from a single vector, the transmembrane domains of the CAR and CCR are different, to ensure separation of the constructs on the surface of the cell. Selection of different transmembrane domains may also enhance stability of the expression vector since inclusion of a direct repeat nucleic acid sequence in the viral vector renders it prone to rearrangement, with deletion of sequences between the direct repeats. In embodiments in which the transmembrane domains of the CAR and CCR of the pCAR are chosen to be the same, this risk can be reduced by modifying or "wobbling" the codons selected to encode the same protein sequence.

Suitable transmembrane domains are known in the art and include for example, the transmembrane domains of CD8α, CD28, CD4 or CD3z. Selection of CD3z as transmembrane domain may lead to the association of the CAR or CCR with other elements of TCR/CD3 complex. This association may recruit more ITAMs but may also lead to the competition between the CAR/CCR and the endogenous TCR/CD3.

In certain embodiments, one transmembrane domain of the pCAR is the transmembrane domain of CD28 and the other is the transmembrane domain of CD8a. In a particular pCAR embodiment, the transmembrane domain of the CAR is the transmembrane domain of CD28 and the transmembrane domain of the CCR is the transmembrane domain of CD8a.

4.4.4. Co-Stimulatory Signal Domain and Transmembrane Domain

In embodiments in which the co-stimulatory signaling region of the CAR or CCR is, or comprises, the co-stimulatory signaling region of CD28, the CD28 transmembrane domain represents a suitable, often preferred, option for the transmembrane domain. The full length CD28 protein is a 220 amino acid protein of SEQ ID NO: 3, where the transmembrane domain is shown in bold type:

(SEQ ID NO: 3)
MLRLLLALNLFPSIQVTGNKILVKQSPMLVAYDNAVNLSCKYSYNLFSR

EFRASLHKGLDSAVEVCVVYGNYSQQLQVYSKTGFNCDGKLGNESVTFY

LQNLYVNQTDIYFCKIEVMYPPPYLDNEKSNGTIIHVKGKHLCPSPLFP

GPSKPFWVLVVVGGVLACYSLLVTVAFIIFWVRSKRSRLLHSDYMNMTP

RRPGPTRKHYQPYAPPRDFAAYRS.

In some embodiments, one of the co-stimulatory signaling regions is based upon the hinge region and suitably also the transmembrane domain and endodomain of CD28. In some embodiments, the co-stimulatory signaling region comprises amino acids 114-220 of SEQ ID NO: 3, shown below as SEQ ID NO: 4:

(SEQ ID NO: 4)
IEVMYPPPYLDNEKSNGTIIHVKGKHLCPSPLFPGPSKPFWVLVVVGGV
LACYSLLVTVAFIIFWVRSKRSRLLHSDYMNMTPRRPGPTRKHYQPYAP
PRDFAAYRS.

In a particular embodiment, one of the co-stimulatory signaling regions is a modified form of SEQ ID NO: 4 which includes a c-myc tag of SEQ ID NO: 5:

(SEQ ID NO: 5)
EQKLISEEDL.

The c-myc tag may be added to the co-stimulatory signaling region by insertion into the ectodomain or by replacement of a region in the ectodomain, which is therefore within the region of amino acids 1-152 of SEQ ID NO: 3.

In a particularly preferred embodiment, the c-myc tag replaces MYPPPY motif in the CD28 sequence. This motif represents a potentially hazardous sequence. It is responsible for interactions between CD28 and its natural ligands, CD80 and CD86, so that it provides potential for off-target toxicity when CAR-T cells or pCAR-T cells encounter a target cell that expresses either of these ligands. By replacement of this motif with a tag sequence as described above, the potential for unwanted side-effects is reduced. Thus, in a particular embodiment, the co-stimulatory signaling region of the CAR construct comprises SEQ ID NO: 6:

(SEQ ID NO: 6)
IEVEQKLISEEDLLDNEKSNGTIIHVKGKHLCPSPLFPGPSKPFWVLVV
VGGVLACYSLLVTVAFIIFWVRSKRSRLLHSDYMNMTPRRPGPTRKHYQ
PYAPPRDFAAYRS.

Furthermore, the inclusion of a c-myc epitope facilitates detection of the pCAR-T cells using a monoclonal antibody to the c-myc epitope. This is very useful since flow cytometric detection had proven unreliable when using some available antibodies.

In addition, the provision of a c-myc epitope tag could facilitate the antigen-independent expansion of targeted CAR-T cells, for example by cross-linking of the CAR using the appropriate monoclonal antibody, either in solution or immobilized onto a solid phase (e.g., a bag).

Moreover, expression of the epitope for the anti-human c-myc antibody, 9e10, within the variable region of a TCR has previously been shown to be sufficient to enable antibody-mediated and complement mediated cytotoxicity both in vitro and in vivo. See Kieback et al. *Proc. Natl. Acad. Sci. USA,* 105(2) 623-8 (2008). Thus, the provision of such epitope tags could also be used as a "suicide system," whereby an antibody could be used to deplete pCAR-T cells in vivo in the event of toxicity.

In some embodiments, one of the co-stimulatory signaling regions is based upon the endodomain of 4-1BB. In some embodiments, the co-stimulatory signaling region comprises amino acids 214-255 of 4-1BB shown below as SEQ ID NO: 7:

(SEQ ID NO: 7)
KRGRKKLLYIFKQPFMRPVQTTQEEDGCSCRFPEEEEGGCEL.

In a particular embodiment, one of the co-stimulatory signaling regions is a modified form of SEQ ID NO: 7 which includes a FLAG epitope tag of SEQ ID NO: 8:

(SEQ ID NO: 8)
DYKDDDDK.

In a particularly preferred embodiment, the FLAG epitope tag is appended to the C-terminus of the 4-1BB endodomain. Thus, in a particular embodiment, the co-stimulatory signaling region of the CCR comprises SEQ ID NO: 9:

(SEQ ID NO: 9)
KRGRKKLLYIFKQPFMRPVQTTQEEDGCSCRFPEEEEGGCELDYKDDDDK.

4.4.5. Chimeric Antigen Receptor Binding Elements

The binding elements of the CAR and CCR constructs of the pCAR respectively bind a first epitope and a second epitope which may be identical or distinct.

In some embodiments, the binding elements of the CAR and CCR constructs are identical. More commonly however, these binding elements are different from one another.

In various embodiments, the binding elements of the CAR and CCR specifically bind to a first epitope and second epitope of the same antigen. In certain of these embodiments, the binding elements of the CAR and CCR specifically bind to the same, overlapping, or different epitopes of the same antigen. In embodiments in which the first and second epitopes are the same or overlapping, the binding elements on the CAR and CCR can compete in their binding. In such embodiments, elements that bind with different affinity may be employed in order to achieve an optimal balance of signaling by the CAR and CCR components of the pCAR.

In various embodiments, the binding elements of the CAR and CCR components of the pCAR bind to different antigens. In certain embodiments, the antigens are different but may be associated with the same disease, such as the same specific cancer derived from the B cell lineage.

In a preferred embodiment, the CAR binds to CD19 while the CCR binds either to CD19 or to another B cell lineage-specific marker. Examples of the latter include, but are not restricted to CD20, CD22, CD23, CD79a and CD79b.

Thus, suitable binding elements may be any element which provides the pCAR with the ability to recognize a target of interest. The target to which the pCARs of the invention are directed can be any target of clinical interest to which it would be desirable to direct a T cell response.

In various embodiments, the binding elements used in the CARs and CCRs of the pCARs described herein are antigen binding sites (ABS) of antibodies. In typical embodiments, the ABS used as the binding element is formatted into an scFv or is a single domain antibody from a camelid, human or other species.

Alternatively, a binding element of a pCAR may comprise ligand(s) that bind to a surface protein of interest.

Alternatively, a binding element of a pCAR may comprise peptide(s) that bind to a surface protein of interest.

In some embodiments, the binding element is associated with a leader sequence which facilitates expression on the cell surface. Many leader sequences are known in the art, and these include the macrophage colony stimulating factor receptor (FMS) leader sequence, the CD8a leader sequence or the CD124 leader sequence.

4.5. Parallel CARs Targeted Against B Cell Antigens

4.5.1. Binding Elements for Use in pCARs

In particular embodiments, the binding element of CAR or the binding element of CCR specifically interacts with an epitope on the CD19 target antigen. CD19 is a B-lymphocyte antigen encoded by the CD19 gene and is found on the surface of B cells. It is a known target for the treatment of B cell malignancies such as leukemia or non-Hodgkin's lymphoma. It has also been implicated in autoimmune diseases and so may be a target in the treatment of such conditions.

In some embodiments, the binding element of the CAR specifically interacts with an epitope on the CD19 antigen. In some embodiments, the binding element of the CCR specifically interacts with an epitope on the CD19 target antigen. In certain embodiments, the binding element of the CAR specifically interacts with an epitope on the CD19 antigen and the binding element of the CCR specifically interacts with the same, overlapping, or different epitope on the CD19 target antigen.

In currently preferred embodiments, the CAR and/or the CCR binding element specifically interacts with a first epitope on the CD19 target antigen. In some embodiments, the CAR or the CCR binding element comprises the antigen binding site of the FMC63 antibody. In certain embodiments, the CAR or the CCR binding element comprises the CDRs of the FMC63 antibody. The CDR sequences of the FMC63 antibody were determined using abysis.org and are shown as SEQ ID NO: 10-15 below.

$V_H$ CDR1 (SEQ ID NO: 10)
GVSLPDY.

$V_H$ CDR2 (SEQ ID NO: 11)
WGSET.

$V_H$ CDR3 (SEQ ID NO: 12)
HYYYGGSYAMDY.

$V_L$ CDR1 (SEQ ID NO: 13)
RASQDISKYLN.

$V_L$ CDR2 (SEQ ID NO: 14)
HTSRLHS.

$V_L$ CDR3 (SEQ ID NO: 15)
QQGNTLPYT.

In certain embodiments, the CAR or the CCR binding element comprises the $V_H$ and $V_L$ domains of the FMC63 antibody. The $V_H$ and $V_L$ domain sequences of the FMC63 antibody are shown below as SEQ ID NO: 16-17.

$V_H$: (SEQ ID NO: 16)
EVKLQESGPGLVAPSQSLSVTCTVSGVSLPDYGVSWIRQPPRKGLEWLGVI
WGSETTYYNSALKSRLTIIKDNSKSQVFLKMNSLQTDDTAIYYCAKHYYYG
GSYAMDYWGQGTSVTVSS.

$V_L$: (SEQ ID NO: 17)
DIQMTQTTSSLSASLGDRVTISCRASQDISKYLNWYQQKPDGTVKLLIYHT
SRLHSGVPSRFSGSGSGTDYSLTISNLEQEDIATYFCQQGNTLPYTFGGGT
KLEIT.

In particularly preferred embodiments, the CAR or the CCR binding element comprises the antigen binding site of the FMC63 antibody formatted as an scFv, either arranged as $V_H$-linker-$V_L$ or as $V_L$-linker-$V_H$. These sequences are presented as SEQ ID NO: 18 and 19 below. In each case, the linker sequence between the $V_H$ and $V_L$ domains has been underlined and italicized.

$V_H$-$V_L$: (SEQ ID NO: 18)
EVKLQESGPGLVAPSQSLSVTCTVSGVSLPDYGVSWIRQPPRKGLEWLGVI
WGSETTYYNSALKSRLTIIKDNSKSQVFLKMNSLQTDDTAIYYCAKHYYYG

-continued

GSYAMDYWGQGTSVTVSSGGGG*SGGGGSGGGGS*DIQMTQTTSSLSASLGDR

VTISCRASQDISKYLNWYQQKPDGTVKLLIYHTSRLHSGVPSRFSGSGSGT

DYSLTISNLEQEDIATYFCQQGNTLPYTFGGGTKLEIT.

$V_L$-$V_H$:

(SEQ ID NO: 19)

DIQMTQTTSSLSASLGDRVTISCRASQDISKYLNWYQQKPDGTVKLLIYHT

SRLHSGVPSRFSGSGSGTDYSLTISNLEQEDIATYFCQQGNTLPYTFGGGT

KLEIT*GGGGSGGGGSGGGGS*EVKLQESGPGLVAPSQSLSVTCTVSGVSLPD

YGVSWIRQPPRKGLEWLGVIWGSETTYYNSALKSRLTIIKDNSKSQVFLKM

NSLQTDDTAIYYCAKHYYYGGSYAMDYWGQGTSVTVSS.

In certain embodiments, the CAR or the CCR binding element comprises the amino acid sequence that is 70%, 75%, 80%, 85%, 90%, 95%, 97%, 99%, or 100% identical to the sequence of scFv of the FMC63 antibody, SEQ ID NO: 18 or 19.

In particularly preferred embodiments, the CAR or the CCR binding element comprises the CDR3 region of a variant of an FMC63 scFv. Specifically, the variant includes a mutation within the FMC $V_H$ domain (SEQ ID NO: 12) in order to modify affinity of the scFv for CD19. Particularly preferred embodiments contain a substitution of alanine (A) for either tyrosine (Y) or glycine (G) within CDR3 of the $V_H$ domain. These variants are shown below as SEQ ID NO: 20-26.

Y01

(SEQ ID NO: 20)

HAYYGGSYAMDY.

Y02

(SEQ ID NO: 21)

HYAYGGSYAMDY.

Y03

(SEQ ID NO: 22)

HYYAGGSYAMDY.

G01

(SEQ ID NO: 23)

HYYYAGSYAMDY.

G02

(SEQ ID NO: 24)

HYYYGASYAMDY.

Y04

(SEQ ID NO: 25)

HYYYGGSAAMDY.

Y05

(SEQ ID NO: 26)

HYYAGGSYAMDA.

In some embodiments, the CAR or the CCR binding element specifically interacts with an epitope on the CD20 antigen. In some embodiments, the CAR or the CCR binding element comprises the 1F5 antibody, which binds to CD20. See Ledbetter and Clark, *Hum. Immunol.* 15(1):30-43 (1986), incorporated herein by reference in its entirety. CD20 is an integral membrane protein expressed on the surface of all B cells beginning at the pro-B phase and progressively increasing in concentration until maturity. In humans, CD20 is encoded by the MS4A1 gene. Antibodies which target CD20 are used in treatment of B cell lymphomas and leukemias, as well as in the treatment of autoimmune diseases such as arthritis, in particular rheumatoid arthritis, Multiple Sclerosis (MS) and systemic lupus erythematosus. In certain embodiments, the CCR binding element comprises the CDRs of the 1F5 antibody. The CDR sequences of the 1F5 antibody were determined using abysis.org and are shown below as SEQ ID NO: 27-32.

$V_H$ CDR1

(SEQ ID NO: 27)

GYTFTSY.

$V_H$ CDR2

(SEQ ID NO: 28)

YPGNGD.

$V_H$ CDR3

(SEQ ID NO: 29)

SHYGSNYVDYFDY.

$V_L$ CDR1

(SEQ ID NO: 30)

RASSSLSFMH.

$V_L$ CDR2

(SEQ ID NO: 31)

ATSNLAS.

$V_L$ CDR3

(SEQ ID NO: 32)

HQWSSNPLT.

In certain embodiments, the CAR or the CCR binding element comprises the $V_H$ and $V_L$ domains of the 1F5 antibody. The $V_H$ and $V_L$ domain sequences of the 1F5 antibody are shown below as SEQ ID NO: 33-34.

$V_H$:

(SEQ ID NO: 33)

QVQLRQPGAELVKPGASVKMSCKASGYTFTSYNMHWVKQTPGQGLEWIGAI

YPGNGDTSYNQKFKGKATLTADKSSSTAYMQLSSLISEDSAVYYCARSHYG

SNYVDYFDYWGQGTLVTVSTG.

$V_L$:

(SEQ ID NO: 34)

QIVLSQSPAILSASPGEKVTMTCRASSSLSFMHWYQQKPGSSPKPWIYATS

NLASGVPARFSGSGSGTSYSLTISRVEAEDAATYFCHQWSSNPLTFGAGTK

VEIKRK.

In particularly preferred embodiments, the CAR or the CCR binding element comprises the antigen binding site of the 1F5 antibody formatted as a scFv, either arranged as $V_H$-linker-$V_L$ or $V_L$-linker-$V_H$. These sequences are presented as SEQ ID NO: 35 and 36 below. In each case, the linker sequence between the $V_H$ and $V_L$ domains has been underlined and italicized.

$V_H$-$V_L$:

(SEQ ID NO: 35)

QVQLRQPGAELVKPGASVKMSCKASGYTFTSYNMHWVKQTPGQGLEWIGAI

YPGNGDTSYNQKFKGKATLTADKSSSTAYMQLSSLTSEDSAVYYCARSHYG

SNYVDYFDYWGQGTLVTVSTG*GSTSGSGKPGSGEGSTKG*QIVLSQSPAILS

ASPGEKVTMTCRASSSLSFMHWYQQKPGSSPKPWIYATSNLASGVPARFSG

SGSGTSYSLTISRVEAEDAATYFCHQWSSNPLTFGAGTKVEIKRK.

-continued $V_L$-$V_H$:

(SEQ ID NO: 36)

QIVLSQSPAILSASPGEKVTMTCRASSSLSFMHWYQQKPGSSPKPWIYATS

NLASGVPARFSGSGSGTSYSLTISRVEAEDAATYFCHQWSSNPLTFGAGTK

VEIKRK*GSTSGSGKPGSGEGSTKG*QVQLRQPGAELVKPGASVKMSCKASGY

TFTSYNMHWVKQTPGQGLEWIGAIYPGNGDTSYNQKFKGKATLTADKSSST

AYMQLSSLTSEDSAVYYCARSHYGSNYVDYFDYWGQGTLVTVSTG.

In certain embodiments, the CAR or the CCR binding element comprises a variant of the scFv of the 1F5 antibody. The variant is 70%, 75%, 80%, 85%, 90%, 95%, 97%, 99%, or 100% identical to SEQ ID NO: 35 or 36, as shown above.

In some embodiments, the CAR or the CCR binding element specifically interacts with an epitope on the CD22 antigen. In some embodiments, the CAR or the CCR binding element is RFB4 antibody, which binds to CD22. See Campana et al., *J. Immunol.* 134(3):1524-30 (1985), incorporated herein by reference in its entirety. CD22 is a 135-kDa, B cell-specific adhesion molecule that is expressed on the cells of 60% to 90% of B cell malignancies. It is not expressed on hematopoietic stem cells or on any other non-lymphoid hematopoietic or nonhematopoietic cells. The CDR sequences of the RFB4 antibody were determined using abysis.org and are shown below as SEQ ID NO: 37-42.

$V_H$ CDR1

(SEQ ID NO: 37)

GFAFSIY.

$V_H$ CDR2

(SEQ ID NO: 38)

SSGGGT.

$V_H$ CDR3

(SEQ ID NO: 39)

HSGYGSSYGVLFAY.

$V_L$ CDR1

(SEQ ID NO: 40)

RASQDISNYLN.

$V_L$ CDR2

(SEQ ID NO: 41)

YTSILHS.

$V_L$ CDR3

(SEQ ID NO: 42)

QQGNTLPWT.

In certain embodiments, the CAR or the CCR binding element comprises the $V_H$ and $V_L$ domains of the RFB4 antibody. The $V_H$ and $V_L$ domain sequences of the RFB4 antibody are shown below as SEQ ID NO: 43-44:

$V_H$:

(SEQ ID NO: 43)

EVQLVESGGGLVKPGGSLKLSCAASGFAFSIYDMSWVRQTPEKRLEWVAYI

SSGGGTTYYPDTVKGRFTISRDNAKNTLYLQMSSLKSEDTAMYYCARHSGY

GSSYGVLFAYWGQGTLVTVS.

-continued

VL:

(SEQ ID NO: 44)

DIQMTQTTSSLSASLGDRVTISCRASQDISNYLNWYQQKPDGTVKLLIYYT

SILHSGVPSRFSGSGSGTDYSLTISNLEQEDFATYFCQQGNTLPWTFGGGT

KLEIK.

In particularly preferred embodiments, the CAR or the CCR binding element comprises the antigen binding site of the RFB4 antibody formatted as a scFv, either arranged as $V_H$-linker-$V_L$ or $V_L$-linker-$V_H$. These sequences are presented as SEQ ID NO: 45 and 46 below. In each case, the linker sequence between the $V_H$ and $V_L$ domains has been underlined and italicized.

$V_H$-$V_L$:

(SEQ ID NO: 45)

EVQLVESGGGLVKPGGSLKLSCAASGFAFSIYDMSWVRQTPEKRLEWVAYI

SSGGGTTYYPDTVKGRFTISRDNAKNTLYLQMSSLKSEDTAMYYCARHSGY

GSSYGVLFAYWGQGTLVTVS*GSTSGSGKPGSGEGSTKG*DIQMTQTTSSLSA

SLGDRVTISCRASQDISNYLNWYQQKPDGTVKLLIYYTSILHSGVPSRFSG

SGSGTDYSLTISNLEQEDFATYFCQQGNTLPWTFGGGTKLEIK.

$V_L$-$V_H$:

(SEQ ID NO: 46)

DIQMTQTTSSLSASLGDRVTISCRASQDISNYLNWYQQKPDGTVKLLIYYT

SILHSGVPSRFSGSGSGTDYSLTISNLEQEDFATYFCQQGNTLPWTFGGGT

KLEIK*GSTSGSGKPGSGEGSTKG*EVQLVESGGGLVKPGGSLKLSCAASGFA

FSIYDMSWVRQTPEKRLEWVAYISSGGGTTYYPDTVKGRFTISRDNAKNTL

YLQMSSLKSEDTAMYYCARHSGYGSSYGVLFAYWGQGTLVTVS.

In certain embodiments, the CAR or the CCR binding element comprises a variant of the scFv of the RFB4 antibody. The variant is 70%, 75%, 80%, 85%, 90%, 95%, 97%, 99%, or 100% identical to SEQ ID NO: 45 or 46, as shown above.

4.5.2. Representative Examples of Sequences Encoding B Cell Specific pCARs

Combinations of the aforementioned B cell antigen-specific binding elements have been used to engineer pCARs in which the CAR and CCR elements bind to an identical epitope within CD19, or to different epitopes found on CD19 and a second lineage-specific B cell antigen. Many additional moieties that bind specifically to CD19 and to other lineage-specific B cell antigens are known in the art, meaning that a large number of B cell specific pCARs could be engineered using similar methodologies. Consequently, the following pCAR examples are offered for illustrative purposes only and are not intended to limit the scope of the present invention. Nomenclature of pCARs derives from the following order: CCR binder, CCR signaling domain/CAR binder.

The protein sequence of FBB/G01 pCAR is shown below as SEQ ID NO: 47. The FBB/G01 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a $2^{nd}$ generation CAR comprising a linear fusion of the following elements: a CD8a leader peptide, a variant of FMC63 scFv in which the first glycine in $V_H$ CDR3 of FMC63 scFv has been substituted by alanine ("G01"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 47)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNELQEDIATYFCQQGNTL

PYTFGGGTKLEITGGGGSGGGGSGGGGSEVKLQESGPGLVAPSQSLSVTCTVSGVSL

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDKRRK*RSGSGATNF

SLLKQAGDVEENPGPNMALPVTALLLPLALLLHAARPDIQMTQTTSSLSASLGDRVT

ISCRASQDISKYLNWYQQKPDGTVKLLIYHTSRLHSGVPSRFSGSGSGTDYSLTISN

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHYYYAGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of FBB/G02 pCAR is shown below as SEQ ID NO: 48. The FBB/G02 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a 2nd generation CAR comprising a linear fusion of the following elements: a CD8a leader peptide, a variant of FMC63 scFv in which the second glycine in $V_H$ CDR3 of FMC63 scFv has been substituted by alanine ("G02"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 48)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNELQEDIATYFCQQGNTL

PYTFGGGTKLEITGGGGSGGGGSGGGGSEVKLQESGPGLVAPSQSLSVTCTVSGVSL

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

-continued

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDK*RRKRSGSGATNF

SLLKQAGDVEENPGPNMALPVTALLLPLALLLHAARPDIQMTQTTSSLSASLGDRVT

ISCRASQDISKYLNWYQQKPDGTVKLLIYHTSRLHSGVPSRFSGSGSGTDYSLTISN

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHYYYAGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of FBB/Y01 pCAR is shown below as SEQ ID NO: 49. The FBB/Y01 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a 2nd generation CAR comprising a linear fusion of the following elements: a CD8a leader peptide, a variant of FMC63 scFv in which the first tyrosine in $V_H$ CDR3 of FMC63 scFv has been substituted by alanine ("Y01"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 49)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNLEQEDIATYFCQQGNTL

PYTFGGGTKLEITGGGGSGGGGSGGGGSEVKLQESGPGLVAPSQSLSVTCTVSGVSL

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDK*RRKRSGSGATNF

SLLKQAGDVEENPGPNMALPVTALLLPLALLLHAARPDIQMTQTTSSLSASLGDRVT

ISCRASQDISKYLNWYQQKPDGTVKLLIYHTSRLHSGVPSRFSGSGSGTDYSLTISN

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHAYYGGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of FBB/Y02 pCAR is shown below as SEQ ID NO: 50. The FBB/Y02 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a 2nd generation CAR comprising a linear fusion of the following elements: a CD8a leader peptide, a variant of FMC63 scFv in which the second tyrosine in $V_H$ CDR3 of FMC63 scFv has been substituted by alanine ("Y02"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 50)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNLEQEDIATYFCQQGNTL

PYTFGGGTKLEITGGGGSGGGGSGGGGSEVKLQESGPGLVAPSQSLSVTCTVSGVSL

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDK*RRKRSGSGATNF

SLLKQAGDVEENPGPNMALPVTALLLPLALLLHAARPDIQMTQTTSSLSASLGDRVT

ISCRASQDISKYLNWYQQKPDGTVKLLIYHTSRLHSGVPSRFSGSGSGTDYSLTISN

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHYYYGGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of FBB/Y03 pCAR is shown below as SEQ ID NO: 51. The FBB/Y03 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a 2nd generation CAR comprising a linear fusion of the following elements: a CD8a leader peptide, a variant of FMC63 scFv in which the third tyrosine in $V_H$ CDR3 of FMC63 scFv has been substituted by alanine ("Y03"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 51)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNLEQEDIATYFCQQGNTL

PYTFGGGTKLEITGGGGSGGGGSGGGGSEVKLQESGPGLVAPSQSLSVTCTVSGVSL

-continued

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDK*RRKRSGSGATNF

SLLKQAGDVEENPGPNMALPVTALLLPLALLLHAARPDIQMTQTTSSLSASLGDRVT

APSQSLSVTCTVSGVSLPDYGVSWIRQPPRKGLEWLGVIWGSETTYYNSALKSRLTI

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHYYYGGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of FBB/Y04 pCAR is shown below as SEQ ID NO: 52. The FBB/Y04 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a 2nd generation CAR comprising a linear fusion of the following elements: a CD8a leader peptide, a variant of FMC63 scFv in which the fourth tyrosine in $V_H$ CDR3 of FMC63 scFv has been substituted by alanine ("Y04"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 52)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNLEQEDIATYFCQQGNTL

PYTFGGGTKLEITGGGGSGGGGSGGGGSEVKLQESGPGLVAPSQSLSVTCTVSGVSL

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDK*RRKRSGSGATNF

SLLKQAGDVEENPGPNMALPVTALLLPLALLLHAARPDIQMTQTTSSLSASLGDRVT

APSQSLSVTCTVSGVSLPDYGVSWIRQPPRKGLEWLGVIWGSETTYYNSALKSRLTI

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHYYYGGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of FBB/Y05 pCAR is shown below as SEQ ID NO: 53. The FBB/Y05 pCAR comprises:

(i) a CCR comprising a linear fusion of the following elements: a macrophage colony-stimulating factor receptor leader peptide, FMC63 scFv binding domain ($V_L$-$V_H$ order), CD8a spacer and transmembrane domain, a 4-1BB co-stimulatory endodomain, FLAG epitope tag ("FBB") and (ii) a 2nd generation CAR comprising a linear fusion of the following elements: a CD8a leader peptide, a variant of FMC63 scFv in which the fifth tyrosine in $V_H$ CDR3 of FMC63 scFv has been substituted by alanine ("Y05"; $V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and P2A ribosomal skip peptide. Codon wobbling has been used to minimize direct repeats within the scFv modules. The $V_H$ and the $V_L$ domains of scFv sequences are underlined and in bold. Epitope tags are italicized.

(SEQ ID NO: 53)

MGPGVLLLLLVATAWHGQGGDIQMTQTTSSLSASLGDRVTISCRASQDISKYLNWYQ

QKPDGTVKLLIYHTSRLHSGVPSRFSGSGSGTDYSLTISNLEQEDIATYFCQQGNTL

PYTFGGGTKLEITGGGGSGGGGSGGGGSEVKLQESGPGLVAPSQSLSVTCTVSGVSL

PDYGVSWIRQPPRKGLEWLGVIWGSETTYYNSALKSRLTIIKDNSKSQVFLKMNSLQ

TDDTAIYYCAKHYYYGGSYAMDYWGQGTSVTVSSAAAPTTTPAPRPPTPAPTIASQP

LSLRPEACRPAAGGAVHTRGLDFACDIYIWAPLAGTCGVLLLSLVITLYCNHKRGRK

KLLYIFKQPFMRPVQTTQEEDGCSCRFPEEEEGGCEL*DYKDDDDK*RRKRSGSGATNF

SLLKQAGDVEENPGPNMALPVTALLLPLALLLHAARPDIQMTQTTSSLSASLGDRVT

APSQSLSVTCTVSGVSLPDYGVSWIRQPPRKGLEWLGVIWGSETTYYNSALKSRLTI

LEQEDIATYFCQQGNTLPYTFGGGTKLEITGGGGSGGGGSGGGGSEVKLQESGPGLV

APSQSLSVTCTVSGVSLPDYGVSWIRQPPRKGLEWLGVIWGSETTYYNSALKSRLTI

IKDNSKSQVFLKMNSLQTDDTAIYYCAKHYYYGGSYAMDYWGQGTSVTVSSAAAIEV

*EQKLISEEDL*LDNEKSNGTIIHVKGKHLCPSPLFPGPSKPFWVLVVVGGVLACYSLL

VTVAFIIFWVRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR.

The protein sequence of 1BB/F pCAR is shown below as SEQ ID NO: 54. The 1BB/F pCAR comprises:

(i) a CCR comprising a linear fusion of the following elements: a macrophage colony-stimulating factor receptor leader peptide, 1F5 scFv binding domain ($V_L$-$V_H$ order), CD8a spacer and transmembrane domain, a 4-1BB co-stimulatory endodomain, FLAG epitope tag ("1BB") and (ii) a 2nd generation CAR comprising a linear fusion of the following elements: a CD8a leader peptide, FMC63 scFv ($V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and T2A ribosomal skip peptide. Codon wobbling has been used to minimize direct repeats within the scFv modules. Alternative spacers have been used within both scFvs for the same motive. The $V_H$ and the $V_L$ domains of scFv sequences are underlined and in bold. Epitope tags are italicized.

(SEQ ID NO: 54)

MGPGVLLLLLVATAWHGQGGQIVLSQSPAILSASPGEKVTMTCRASSSLSFMHWYQQKPGSS

PKPWIYATSNLASGVPARFSGSGSGTSYSLTISRVEAEDAATYFCHQWSSNPLTFGAGTKVE

IKRKGSTSGSGKPGSGEGSTKGQVQLRQPGAELVKPGASVKMSCKASGYTFTSYNMHWVKQT

-continued

PGQGLEWIGAIYPGNGDTSYNQKFKGKATLTADKSSSTAYMQLSSLTSEDSAVYYCARSHYG

SNYVDYFDYWGQGTLVTVSTGAAAPTTTPAPRPPTPAPTIASQPLSLRPEACRPAAGGAVHT

RGLDFACDIYIWAPLAGTCGVLLLSLVITLYCNHKRGRKKLLYIFKQPFMRPVQTTQEEDGC

SCRFPEEEEGGCEL*DYKDDDDK*RRKRSGSGATNFSLLKQAGDVEENPGPNMALPVTALLLPL

ALLLHAARPDIQMTQTTSSLSASLGDRVYISCRASQDISKYLNWYQQKPDGTVKLLIYHTSR

LHSGVPSRFSGSGSGTDYLSTISNLEQEDIATYFCQQGNTLPYTFGGGTKLEITGGGGSGGG

GSGGGGSEVKLQESGPGLVAPSQSLSVTCTVSGVSLPDYGVSWIRQPPRKGLEWLGVIWGSE

TTYYNSALKSRLTIIKDNSKSQVFLKMNSLQTDDTAIYYCAKHYYYGGSYAMDYWGQGTSVT

VSSAAAIEV*EQKLISEEDL*LDNEKSNGTIIHVKGKHLCPSPLFPGPSKPFWVLVVVGGVLAC

YSLLVTVAFIIFWVRSKRSRLLHSDYMNMTPRRPGPTRKHYQPYAPPRDFAAYRSRVKFSRS

ADAPAYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPR.

The protein sequence of RBB/F pCAR is shown below as SEQ ID NO: 55. The RBB/F pCAR comprises:

(i) a CCR comprising a linear fusion of the following elements: a macrophage colony-stimulating factor receptor leader peptide, RFB4 scFv binding domain ($V_L$-$V_H$ order), CD8a spacer and transmembrane domain, a 4-1BB co-stimulatory endodomain, FLAG epitope tag ("RBB") and (ii) a 2nd generation CAR comprising a linear fusion of the following elements: a CD8a leader peptide, FMC63 scFv ($V_L$-$V_H$ order), CD28 spacer containing an embedded myc epitope tag, CD28 transmembrane and endodomain, CD3z endodomain.

The CCR and the CAR are linked by a furin cleavage site, Ser-Gly linker (SGSG), and T2A ribosomal skip peptide. Codon wobbling has been used to minimize direct repeats within the scFv modules. Alternative spacers have been used within both scFvs for the same motive. The $V_H$ and the $V_L$ domains of scFv sequences are underlined and in bold. Epitope tags are italicized.

(SEQ ID NO: 55)

MGPGVLLLLLVATAWHGQGDIQMTQTTSSLSASLGDRVTISCRASQDISKYLNWYQQKPDGT

VKLLIYHTSRLHSGVPSRFSGSGSGTDYSLTISNLEQEDIATYFCQQGNTLPWTFGGGTKLE

IKGSTSGSGKPGSGEGSTKGEVQLVESGGGLVKPGGSLKLSCAASGFAFSIYDMSWVRQTPE

KRLEWVAYISSGGGTTYYPDTVKGRFTISRDNAKNTLYLQMSSLKSEDTAMYYCARHSGYGS

SYGVLFAYWGQGTLVTVSAAAAPTTTPAPRPPTPAPTIASQPLSLRPEACRPAAGGAVHTRG

LDFACDIYIWAPLAGTCGVLLLSLVITLYCNHKRGRKKLLYIFKQPFMRPVQTTQEEDGCSC

RFPEEEEGGCEL*DYKDDDDK*RRKRSGSGATNFSLLKQAGDVEENPGPNMALPVTALLLPLAL

LLHAARPDIQMTQTTSSLSASLGDRVTISCRASQDISKYLNWYQQKPDGTVKLLIYHTSRLH

SGVPSRFSGSGSGTDYSLTISNLEQEDIATYFCQQGNTLPYTFGGGTKLEITGGGGSGGGGS

GGGGSEVKLQESGPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAMDYWGQGTSVTVS

SAAAIEV*EQKLISEEDL*LDNEKSNGTIIHVKGKHLCPSPLFPGPSKPFWVLVVVGGVLACYS

LLVTVAFIIFWVRSKRSRLLHSDYMNMTPRRPGPTRKHYQPYAPPRDFAAYRSRVKFSRSAD

APAYQQGQNQLYNELNLGRREEYDVLDKRRGRDPEMGGKPRRKNPQEGLYNELQKDKMAEAY

SEIGMKGERRRGKGHDGLYQGLSTATKDTYDALHMQALPPR.

4.6. Nucleic Acids and Methods of Making pCAR-T Cells

Also provided herein is a combination of a first nucleic acid encoding a $2^{nd}$ generation CAR as described above and a second nucleic acid encoding a CCR as described above. As indicated above, for convenience herein, the CAR and CCR combination is referred to in the singular as a pCAR, although the CAR and CCR are separate, co-expressed, proteins. Suitable sequences for the nucleic acids will be apparent to a skilled person based on the description of the CAR and CCR above. The sequences may be optimized for use in the required immuno-responsive cell. However, in some cases, as discussed above, codons may be varied from the optimum or "wobbled" in order to avoid repeat sequences. Particular examples of such nucleic acids will encode the preferred embodiments described above. In some embodiments, the B cell specific pCAR comprises the polypeptide of a sequence selected from SEQ ID NOs: 47-55. In some embodiments, the nucleic acid which encodes for the pCAR is selected from the group consisting of SEQ ID NOs: 109-117.

In some embodiments, the nucleic acid which encodes the CCR component of the pCAR is selected from the group consisting of SEQ ID NOs: 128, 129 and 130.

In some embodiments, the nucleic acid which encodes the CAR component of the pCAR is selected from the group consisting of SEQ ID NOs: 101-108.

In order to achieve transduction, the nucleic acids encoding the pCAR are suitably introduced into one or more vectors, such as a plasmid, a retroviral or lentiviral vector, or a non-viral vector. Such vectors, including plasmid vectors, or cell lines containing them, form a further aspect of the invention.

In typical embodiments, the immuno-responsive cells are subjected to genetic modification, for example by retroviral or lentiviral mediated transduction, to introduce CAR and CCR coding nucleic acids into the host T cell genome, thereby permitting stable pCAR expression. They may then be reintroduced into the patient, optionally after expansion, to provide a beneficial therapeutic effect, as described below.

The first and second nucleic acids encoding the CAR and CCR can be expressed from the same vector or from different vectors. The vector or vectors containing them can be combined in a kit, which is supplied with a view to generating immuno-responsive cells of the first aspect disclosed herein.

In some embodiments, the T cells may also be engineered to co-express a chimeric cytokine receptor such as 4αβ, which comprises a fusion of the ectodomain of IL-4 receptor-α and the transmembrane and endodomain of the shared IL-2/15 receptor-β chain. In this case, the expansion step may include an ex vivo culture step in a medium which comprises the cytokine, such as a medium comprising IL-4 as the sole cytokine support in the case of 4αβ. Alternatively, the chimeric cytokine receptor may comprise the ectodomain of the IL-4 receptor-α chain joined to the receptor endodomain used by a common γ cytokine with distinct properties, such as IL-7. Expansion of the cells in IL-4 may result in less cell differentiation under these circumstances. In this way, selective expansion and enrichment of genetically engineered T cells with the desired state of differentiation can be ensured.

4.6. Methods of Treatment Using pCAR T Cells Targeted Against B Cell Antigens As discussed above, the immuno-responsive pCAR cells are useful in therapy to direct a T cell-mediated immune response to a target cell. Thus, in another aspect, methods for directing a T cell-mediated immune response to a target cell in a patient in need thereof are provided. The method comprises the administration to the patient a population of immuno-responsive cells as described above, wherein the binding elements are specific for the target cell. In some embodiments, the target cell expresses CD19 and/or other B cell antigens.

In another aspect, methods for treating cancer in a patient in need thereof are provided. The method comprises administering to the patient a population of immuno-responsive cells as described above, wherein the binding elements are specific for the target cell. In some embodiments, the target cell expresses CD19 and/or other B cell antigens. In some embodiments, the patient has acute or chronic B cell leukemia or B cell lymphoma.

In various embodiments, a therapeutically effective number of the immuno-responsive cells is administered to the patient. In certain embodiments, the immuno-responsive cells are administered by intravenous infusion. In certain embodiments, the immuno-responsive cells are administered by intratumoral injection. In certain embodiments, the immuno-responsive cells are administered by peritumoral injection. In certain embodiments, the immuno-responsive cells are administered by a plurality of routes selected from intravenous infusion, intratumoral injection, and peritumoral injection.

5. EXAMPLES

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should, of course, be allowed for.

5.1. Methods

5.1.1. Culture of Cell Lines

All tumor cells and 293T cells were grown in DMEM supplemented with L-Glutamine and 10% FBS. Where indicated, tumor cells were transduced to express a firefly luciferase and tandem dimer Tomato red fluorescent protein (LT) SFG vector, followed by flow sorting for red fluorescent protein expression. LO68 $CD19^+$ cells and LO68 $CD19^+/CD20^+$ cells were generated by transduction of LO68-LT cells with an SFG retroviral vector that encodes for human CD19 and/or human CD20.

5.1.2. Retrovirus Production 293T cells were triple transfected in Genejuice (MilliporeSigma, Merck KGaA, Darmstadt, Germany) with (i) SFG retroviral vectors encoding the indicated CAR/pCAR, (ii) RDF plasmid encoding the RD114 envelope and (iii) Peq-Pam plasmid encoding gag-pol, as recommended by the manufacturers. For transfection of $1.5\times10^6$ 293T cells in a 100 mm plate, 4.6875 μg SFG retroviral vector, 4.6875 μg Peq-Pam plasmid, and 3.125 μg RDF plasmid were used. Viral vector containing medium was collected 48 and 72 h post-transfection, snap-frozen and stored at −80° C. In some cases, stable packaging cell lines were then created by transduction of 293 VEC GALV cells with retrovirus. Virus prepared from either source was used interchangeably for transduction of target cells.

5.1.3. T Cell Culture and Transduction

Peripheral blood mononuclear cells (PBMCs) were isolated from healthy donor peripheral blood samples by density gradient centrifugation using Ficoll-Paque (Ethical approval no. 18/WS/0047). T cells were cultured in RPMI with GlutaMax supplemented with 5% human AB serum. Activation of T cells was achieved by culture in the presence of 5 μg/mL phytohemagglutinin leucoagglutinin (PHA-L) for 24-48 h after which the cells were grown in IL-2 (100 U/mL) for a further 24 h prior to gene transfer. T cell transduction was achieved using RetroNectin (Takara Bio) coated-plates according to the Manufacturer's protocol. Activated PBMCs ($1\times10^6$ cells) were added per well of a RetroNectin coated 6-well plate. Retrovirus-containing medium (3 mL) was then added per well with 100 U/mL IL2.

5.1.4. Cytotoxicity Assays

Tumor cells were seeded at $2\times10^4$ or $1\times10^5$ cells/well in a 24 or 96 well plate and were incubated with T cells at specified target to effector ratios. In some cases, destruction of tumor cells by T cells was quantified using an MTT assay. To achieve this, MTT (Sigma) was added at 500 μg/ml in D10 medium for 2 hours at 37° C. and 5% CO2. After removal of the supernatant, formazan crystals were re-suspended in 100 μL DMSO. Absorbance was measured at 560 nm. Alternatively, tumor cell viability was monitored by luciferase assays. D-luciferin (PerkinElmer, Waltham MA) was added at 150 mg/mL immediately prior to luminescence reading. In either case, tumor cell viability was calculated as follows: (absorbance or luminescence of tumor cells cultured with T cells/absorbance or luminescence of untreated monolayer alone)×100%.

5.1.5. Detection of CAR and CCR Expression by Flow Cytometry

Expression of CARs was detected using 9e10 antibody, which binds to a myc epitope tag (EQKLISEEDL), followed by PE-conjugated goat anti-mouse antibody. Expression of the CCR component of pCARs was detected by intracellular staining using a PE-conjugated antibody, which binds to a FLAG epitope tag (DYKDDDDK).

5.1.6. Detection of IFN-γ and IL-2 by ELISA

Supernatant was collected at 24 hours from co-cultures of tumor cells with CAR T cells. Cytokine levels were quantified using a human IFN-γ (Bio-Techne) or human IL-2 ELISA kit (Invitrogen) according to the Manufacturer's protocol.

5.1.7. Repeated Antigen Stimulation Assays

Suspension tumor cells were co-cultured with CAR-T/pCAR-T cells at an initial effector:target (E:T) ratio of 1:1 for 72-96 h. Residual tumor cell viability was then assessed by luciferase assay. D-luciferin (PerkinElmer) was added at 150 mg/mL immediately prior to luminescence reading. Fresh tumor cells ($10^5$ cells) were then added and this procedure was repeated until T cell cultures failed to expand.

Alternatively, adherent LO68 tumor cell lines were plated in triplicate at $1\times10^5$ cells per well in a 24-well culture plate 24 h prior to addition of T cells. CAR-T/pCAR-T cells were added at a 1:1 effector:target ratio. Tumor cell killing was measured after 48-72 h using an MTT assay, performed as described above. T cells were then collected and restimulated by addition to a new tumor cell monolayer provided that >20% tumor cells were killed compared to untreated cells. Tumor cell viability was calculated as described in section 5.1.4.

5.1.8. In Vivo Study

PBMCs from healthy donors were engineered to express the indicated CARs/pCARs or were untransduced. After 11 days of expansion in IL-2 (100 U/mL, added every 2-3 days), cells were analyzed by flow cytometry for expression of the CAR and CCR as described above. Female NSG mice were injected i.v. with $5\times10^5$ cells Nalm-6 LT cells. After 4 days, $5\times10^5$ CAR$^+$ (or untransduced) T cells were injected i.v. in 200 μl of PBS, making comparison with PBS as control. Tumor status was monitored by bioluminescence imaging (BLI), performed under isoflurane anaesthesia 20 minutes after injection of StayBrite™ D-Luciferin, Potassium Salt in 200 μl PBS (150 mg/kg). Image acquisition was performed at the indicated time points using an IVIS® Lumina III (PerkinElmer) with Living Image software (PerkinElmer) set for automatically optimized exposure time, binning and F/stop. Animals were humanely killed when experimental endpoints had been reached.

5.1.9. CD19 CAR Binding Studies—z-Movi.

CD19-engineered L068 tumor cells were seeded in a z-Movi microfluidic chip and cultured for 16 hours. The next day, flow sorted CAR-T cells were serially flowed in the chips and incubated with the target cells for 5 minutes prior to initializing a 3-minute linear force ramp. Cell detachment was determined using post-experiment using image analysis techniques.

5.2. Example 1: In Vitro Activity of CD19-Specific CAR-T Cells

T cells were engineered by retroviral transduction to express a CD28-containing 2$^{nd}$ generation CAR designated F-2, or $V_H$ CDR3 mutated derivatives designated Y01, Y02, Y03, Y04, Y05, G01 or G02, or were untransduced (FIGS. 3A and 3B).

To test binding to CD19, transduced T cells were incubated with CD19-Fc at two different concentrations, 0.5 μg (FIG. 7A) and 1.0 μg (FIG. 7B). Binding of CD19-Fc to CARs was detected by flow cytometry, following incubation with PE-conjugated anti-human IgG. FIGS. 7A-7D show that CDR3 mutated variants of F-2 exhibit variable efficiency of binding to CD19.

To further test the relative CD19 binding capacity of the 2G CAR, F-2, and its mutated derivatives, the engineered CAR-T cells were incubated on a monolayer of CD19+ LO68 tumor cells in a z-Movi microfluidic chip. Increasing fluidic force was applied and the percentage of bound T-cells was determined (median, n=3). T cells expressing the $V_H$ CDR3 mutated CARs presented a spectrum of binding activities for CD19. Most of the $V_H$ CDR3 mutated derivatives exhibited reduced binding activity for CD19 as compared with the 2G CAR F. Data from representative experiments are shown in FIGS. 17A-17D. Data are presented as median rForce which is the relative force required to elicit cell detachment, calibrated to 10 μM polystyrene beads. Since data were not normally distributed, they are presented as median rForce which is the relative force required to elicit cell detachment and calibrated to 10 μM polystyrene beads. FIG. 17B shows the overall mean percentage of bound T cells after applying the minimal rForce (210 pN) required to detach a mean of 90% untransduced T cells. Data shown are mean±standard error (n=11 runs, 3 independent donors). FIG. 17C shows the avidity score (e.g., the ratio of the mean rForce per cell required to detach T cells from the monolayer of CD19$^+$ LO68 tumor cells for each of the $V_H$ CDR3 mutated derivatives compared to untransduced T cells. The black dotted line represents the avidity score of untransduced T cells; the red dotted line represents the avidity score of F-2 CAR T cells. FIG. 17D shows the rForce per cell required to detach from the tumor cell monolayer where each dot in the dot plot represents a single cell. Bars indicate the median+interquartile range. Statistical analysis was performed using Kruskal-Wallis test with Dunnett's multiple comparisons test where p=<0.0001 (**), 0.0007 (*), or 0.005 (). For clarity, a single representative run for one healthy donor is plotted in which each dot represents a single cell. Collectively, these dots generate the avidity curve shown in FIG. 17**A. The avidity curves therefore represent more than 1000 single cell observations per donor.

Figure 8A:
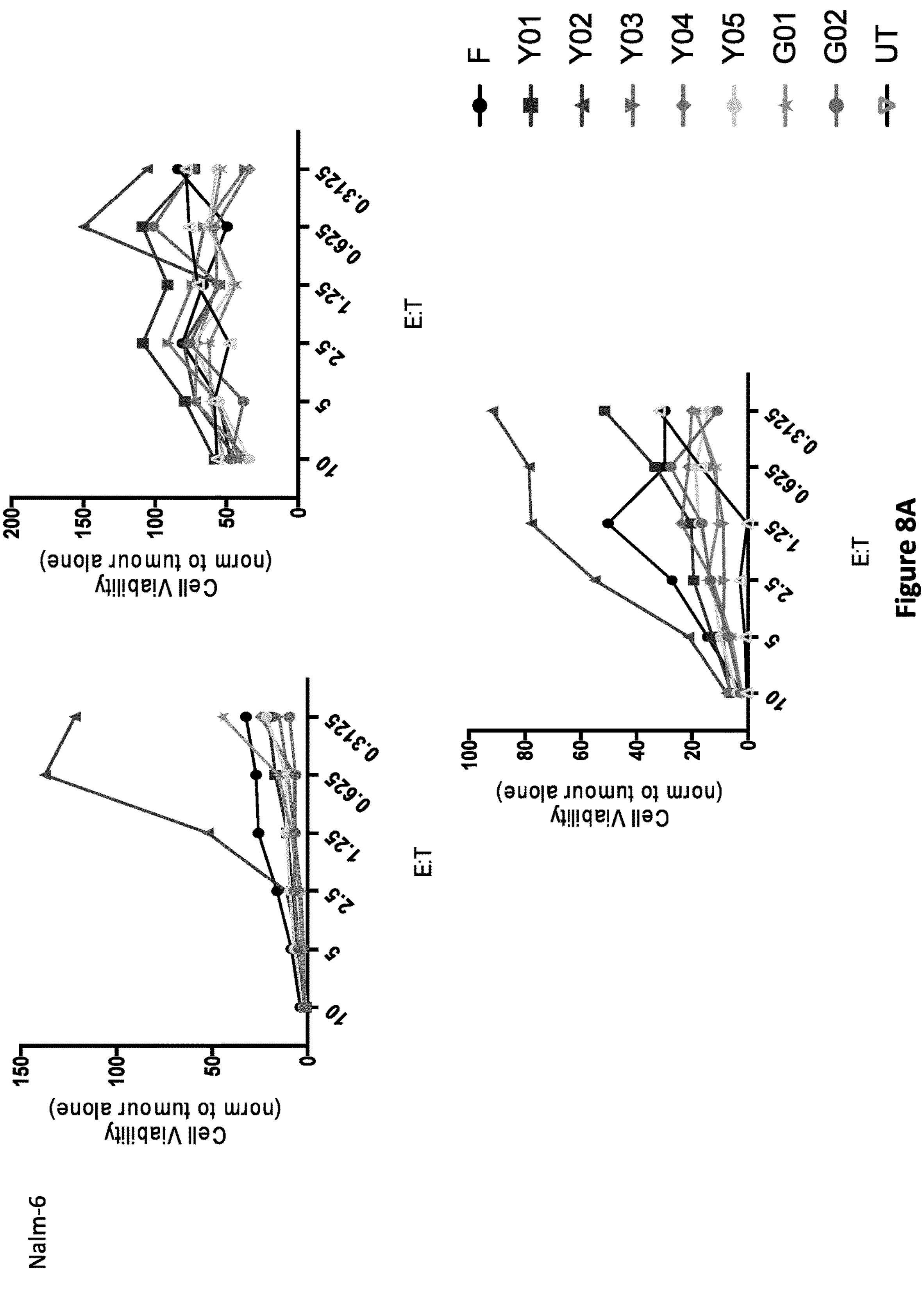
Figure 8B:
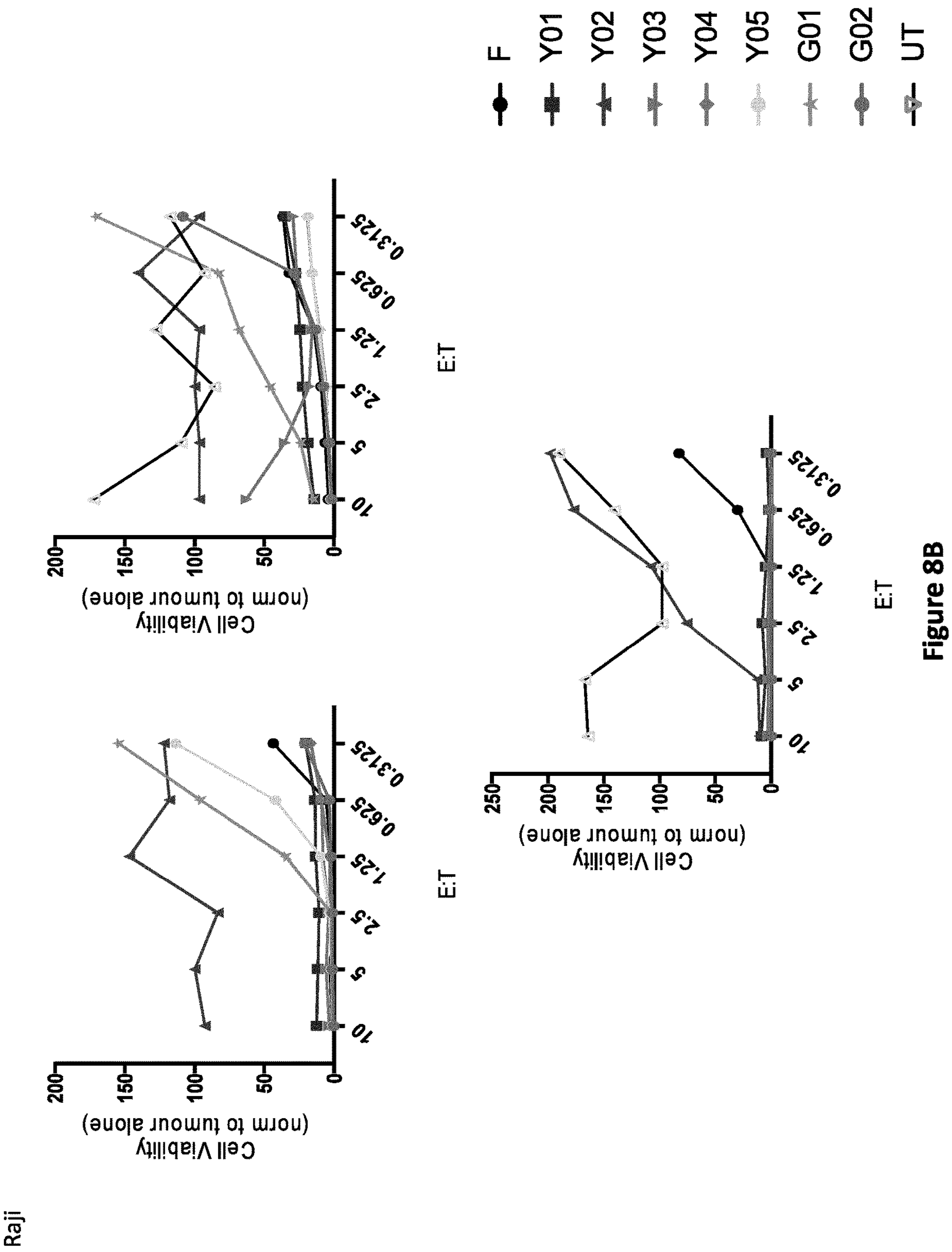

To evaluate anti-tumor activity, transduced T cells were co-cultivated in vitro with Nalm-6 LT or Raji LT cells, both of which naturally express CD19 (FIG. 1A). The E:T ratio ranged from 10 to 0.31, including 5, 2.5, 1.25 and 0.63. Data obtained using cells from three representative donors are shown in FIGS. 8A-8B. Residual viable cancer cells after the co-culture were quantified by luciferase assay after 72 hours. The percentage survival of Nalm-6 and Raji tumor cells after co-culture with the CAR-T cells is presented in FIGS. 8A and 8B respectively.

Figure 8D:
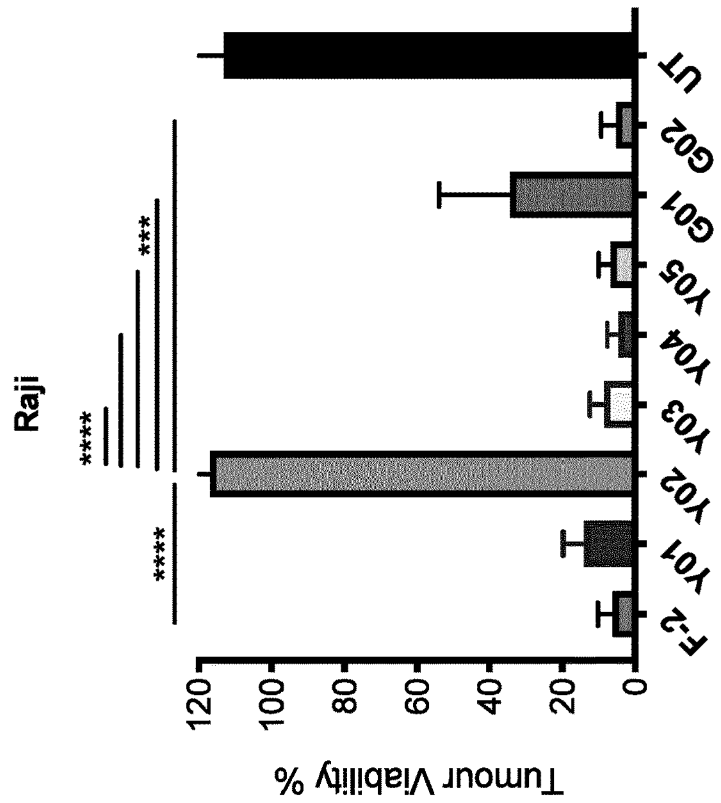
Figure 8C:
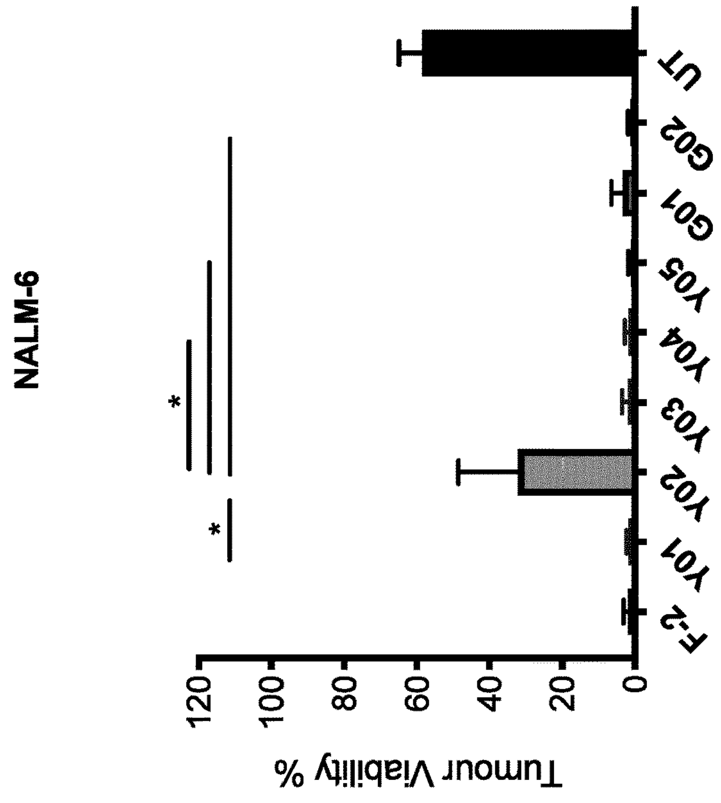

To further evaluate cytotoxic activity, $2\times10^4$ transduced T cells were co-cultivated in duplicate with an equal number of Nalm-6 (FIG. 8C) or Raji (FIG. 8D) cells. After 72 hours, viability of tumor cells was quantified by luciferase assay. Mean±standard error (n=3 biological replicates) of the mean levels of viable cancer cells are shown in FIGS. 8C-8D. Statistical analysis was performed using one-way ANOVA followed by Tukey's multiple comparison test where p<0.0001 (**), ≤0.001 (*), or ≤0.01 (**).

Transduced T cells were co-cultivated in vitro with Nalm-6 LT (FIG. 9A-9B) or Raji LT cells (FIG. 9C-9D), at an effector:target ratio of 1.25 tumor cells:1 CAR-expressing T cell. Mean±standard error (n=3 biological replicates) of the mean levels of IFN-γ and IL-2 concentration present in supernatant collected after 24 hours are presented in FIGS. 9A-9D. In each case, statistical analysis was performed using two-way ANOVA with Tukey's multiple comparisons test where p=0.033 (*), 0.002 (), 0.0002 (*) or <0.0001 (****). NS—not significant.

Following the co-cultivation experiments described above (data shown in FIGS. 8C-8D), cell supernatants were collected after 24 hours and analyzed for IFN-γ (FIGS. 10A-10B) and IL-2 (FIGS. 10C-10D) by ELISA. Data shown are mean±standard error (n=3 biological replicates). Statistical analysis was performed using one-way ANOVA followed by Tukey's multiple comparison test where p<0.0001 (**), ≤0.001 (*), ≤0.01 (**), or ≤0.05 (*). NS—not significant.

Transduced T cells were subjected to successive rounds of antigen (Ag) stimulation in the absence of exogenous cytokine IL-2. Triplicate cultures containing $10^5$ engineered T cells were re-stimulated twice weekly by addition of $10^5$ Nalm-6 tumor cells. FIG. 11A shows tumor cell viability which was measured by luciferase assay 72 hours after each tumor cell challenge. FIGS. 11B and 11C respectively show IFN-γ and IL-2 levels in supernatant, which was collected 24 hours after each tumor cell challenge.

5.3. Example 2: In Vitro Activity of CD19-Specific pCAR-T Cells

FIGS. 4A-4B and FIGS. 18A-18B show expression of a panel of CD19-specific pCARs in human T cells, making comparison with the $2^{nd}$ generation control CAR, (F-2). Nomenclature of pCARs derives from an ordered abbreviation of the following elements: CCR binder (FMC63 scFv), CCR signaling domain (4-1BB)/CAR binder (G01-Y05 respectively). Cell surface expression of the CD28-containing CAR within each pCAR was detected by flow cytometry after incubation of cells with 9e10 antibody, which binds to a myc epitope tag within the CAR ectodomain. Expression of the CCR component within each pCAR was detected by intracellular staining of permeabilized cells using anti-FLAG antibody, which binds to a FLAG epitope tag located at a distal position in the CCR endodomain. Locations of epitope tags are illustrated schematically in FIGS. 2C-2F.

FIG. 12 shows pooled data from five biological replicate experiments, each conducted in duplicate in which CDR3 $V_H$-mutated FMC63-based $2^{nd}$ generation CAR and pCAR T cells were co-cultivated in vitro with Nalm-6 LT tumor cells, making comparison with parental $2^{nd}$ generation CAR T cells (F-2). In each experiment, cultures were established in which T cells were co-cultivated with $2\times10^4$ tumor cells. The E:T ratio ranged from 1:1 to 1:128, including 1:2, 1:4, 1:8, 1:16, 1:32 and 1:64. Residual viable cancer cells were quantified by luciferase assay after 72 hours. The percentage survival of Nalm-6 tumor cells after co-culture with the CAR-T cells is presented (mean±standard error of the mean, n=10 data points). Statistical analysis was performed using two-way ANOVA with Tukey's multiple comparisons test where p=0.033 (*), 0.002 (), 0.0002 (*) or <0.0001 (****). NS—not significant. Some of the CDR3 $V_H$-mutated FMC63-based $2^{nd}$ generation CARs outperformed the parental $2^{nd}$ generation CAR, F-2. Equivalent or further enhancement of cytotoxicity was noted for derived pCARs with the same mutated $V_H$ CDR3.

FIGS. 13A-13C show representative data from experiments in which $10^5$ pCAR-T cells were iteratively restimulated on LO68 tumor monolayers that express CD19 in the absence of exogenous cytokine. FIG. 13A shows tumor cell viability which was measured by luciferase assay 24 hours after each round of stimulation. Levels of IFN-γ and IL-2 present in supernatants collected 24 hours after each round of stimulation are shown in FIG. 13B and FIG. 13C respectively. Note the superior anti-tumor activity of some pCAR variants when compared to the parental $2^{nd}$ generation CAR, F-2.

5.4. Example 3: In Vivo Activity of CD19-Specific pCAR-T Cells in NSG Mice

The anti-tumor activity of the CD19-specific CAR-T and pCAR-T cells was assessed in vivo in NSG mice bearing established Nalm-6 leukemic xenografts. RFP/ffLuc$^+$ Nalm6 cells ($5\times10^5$ cells) were injected i.v. in NSG mice. On day 5, animals were arranged into groups of 5-10 mice with equal disease burden (according to BLI). Mice were then treated with $5\times10^5$ of the indicated CAR or pCAR T-cells, administered i.v. Comparison was made with PBS. Pooled bioluminescence emission ("total flux") from leukemic xenografts was measured for each treatment from day 8 (FIG. 19). At the modest T-cell dose employed ($5\times10^5$ cells), F-2 CAR T-cells elicited transient delay in disease progression while the mutated 2G derivates, Y05 and G02, achieved superior anti-leukemic activity. All of the tested pCARs, FBB/Y04, FBB/Y05, and FBB/G02, achieved further enhancement of disease control (FIG. 14A, FIGS. 20A and 20B). The tested pCARs FBB/Y04, FBB/Y05, and FBB/G02 also achieved superior after treatment survival (FIGS. 21A-21D) without weight loss (FIG. 14B).

These results indicate that the CD19-specific pCAR-T cells have superior anti-tumor activity in vivo compared to the 2G CAR-T cells in NSG mice with established leukemic burden.

5.6. Example 4: In Vitro Anti-Tumor Activity of pCAR-T Cells that Co-Target CD19 and CD20

T cells were engineered to express the CD19- or CD20-specific $2^{nd}$ generation CAR T cells (F-2 and 1-2, respectively) or the 1BB/F pCAR. 1×10[5] transduced CAR or pCAR T cells were co-cultivated in triplicate with an equal number of LO68-CD19⁺CD20⁺ tumor cells. After 72 hours, T cells were transferred to a fresh monolayer of LO68-CD19⁺CD20⁺ cells. Data plotted in FIG. 15A show the number of re-stimulation cycles completed for each co-cultivation condition. Cultures were terminated when tumor cell viability was 80% or greater.

FIG. 15B shows data in which $10^5$ of 1BB/F pCAR-T cells were combined with an equal number of LO68 tumor cells that co-express CD19 and CD20. Cultures were established in the absence of exogenous cytokine. Comparison is made with CD19- or CD20-specific $2^{nd}$ generation CAR T cells (F-2 and 1-2, respectively) or untransduced T cells. Tumor cell cytotoxicity was assessed after 72 hours by MTT assay. T cells were re-stimulated twice weekly by co-culture with $10^5$ tumor cells and MTT assay performed after 72 hours to assess tumor cell viability. This procedure was repeated until T cell cultures failed. Data shown are mean±SEM, n=4. Supernatant was removed from the co-cultures one day after each cycle of stimulation and was analyzed by ELISA for release of IFN-γ and IL-2 (FIG. 15C). Data shown are mean±standard error (n=4).

In FIG. 15D, T cells were co-cultivated in vitro for 72 hours with $10^5$ of LO68 tumor cells that co-express CD19 and CD20. The effector:target (T cell:tumor cell) ratio ranged from 1:1 to 1:128, including 1:2, 1:4, 1:8, 1:16, 1:32 and 1:64. Cultures were established in the absence of exogenous cytokine. Residual viable cancer cells were quantified by MTT assay after 72 hours. Similar anti-tumor activity was noted in vitro for CAR- and pCAR-engineered T cells. Data shown are mean±SEM, n=4.

CAR or pCAR T cells were co-cultivated with LO68-$CD19^+CD20^+$ tumor cells at an effector:target (T cell:tumor cell) ratio of 1:1 and 1:4. Supernatants were collected after 24 hours of co-cultivations and were analyzed for IFN-γ (FIG. 15E) and IL-2 (FIG. 15F).

5.7. Example 5: In Vitro Anti-Tumor Activity of pCAR-T Cells that Co-Target CD19 and CD22

FIGS. 6A-6B show expression in human T cells of the RBB/F pCAR that co-targets CD19 and CD22, making comparison with CD19- or CD22-specific $2^{nd}$ generation CAR T cells (F-2 and R-2, respectively) or untransduced T cells. Expression of CARs, or the CAR component of pCARs was detected by flow cytometry after incubation of cells with 9e10 antibody, which binds to a myc epitope tag within the CAR ectodomain. Expression of the CCR component within the pCAR was detected by intracellular staining of permeabilized cells using anti-FLAG antibody, which binds to a FLAG epitope tag located at a distal position in the CCR endodomain. Locations of epitope tags are illustrated schematically in FIG. 2F.

FIG. 16A shows the cytotoxic activity of RBB/F pCAR T cells against Nalm-6 leukemic cells, making comparisons with CD19-specific (F-2) or CD22-specific (R-2) $2^{nd}$ generation CAR T cells. T cells were co-cultivated in vitro for 72 hours with tumor cells. The effector:target (T cell:tumor cell) ratio ranged from 1:1 to 1:128, including 1:2, 1:4, 1:8, 1:16, 1:32 and 1:64. Residual viable cancer cells were then quantified by luciferase assay. Note the enhanced anti-tumor activity of pCAR T cells at lower E:T ratios. Data shown are mean±SEM, n=5. Statistical analysis was performed with two-way ANOVA followed by Tukey post hoc test. $p=0.0216$ (*), 0.0021 (), 0.0002 (*), $<0.0001$ (****)

FIG. 16B shows the cytotoxic activity of RBB/G02 and RBB/Y05 pCAR T cells against Nalm-6 leukemic cells, making comparisons with RBB/F pCAR T cells and CD19-specific (F-2) or CD22-specific (R-2) $2^{nd}$ generation CAR T cells. Experiments were performed as described above, with viability of the target cells quantified by luciferase assay following 72 hours of co-cultivation. Data shown are mean±standard error (n=3-7 biological replicates).

6. SEQUENCES

| ID | SEQ |
|---|---|
| SEQ ID NO: 1<br>CD3 zeta chain (a polymorphic form) | RVKFSRSADAPAYQQGQNQLYNELNLGRREEYDVLDKRRGRDPE<br>MGGKPRRKNPQEGLYNELQKDKMAEAYSEIGMKGERRRGKGHD<br>GLYQGLSTATKDTYDALHMQALPPR |
| SEQ ID NO: 2<br>CD3 zeta chain (a polymorphic form) | RVKFSRSAEPPAYQQGQNQLYNELNLGRREEYDVLDKRRGRDPEM<br>GGKPRRKNPQEGLYNELQKDKMAEAYSEIGMKGERRRGKGHDGL<br>YQGLSTATKDTYDALHMQALPPR |
| SEQ ID NO: 3<br>CD28 protein | MLRLLLALNLFPSIQVTGNKILVKQSPMLVAYDNAVNLSCKYSYNL<br>FSREFRASLHKGLDSAVEVCVVYGNYSQQLQVYSKTGFNCDGKLG<br>NESVTFYLQNLYVNQTDIYFCKIEVMYPPPYLDNEKSNGTIIHVKG<br>KHLCPSPLFPGPSKPFWVLVVVGGVLACYSLLVTVAFIIFWVRSKRS<br>RLLHSDYMNMTPRRPGPTRKHYQPYAPPRDFAAYRS |
| SEQ ID NO: 4<br>Hinge, transmembrane and co-stimulatory region in CD28 protein | IEVMYPPPYLDNEKSNGTIIHVKGKHLCPSPLFPGPSKPFWVLVVVG<br>GVLACYSLLVTVAFIIFWVRSKRSRLLHSDYMNMTPRRPGPTRKHY<br>QPYAPPRDFAAYRS |
| SEQ ID NO: 5<br>c-myc tag | EQKLISEEDL |
| SEQ ID NO: 6<br>Hinge (containing myc tag), transmembrane and co-stimulatory region in CD28 protein | IEVEQKLISEEDLLDNEKSNGTIIHVKGKHLCPSPLFPGPSKPFWVLV<br>VVGGVLACYSLLVTVAFIIFWVRSKRSRLLHSDYMNMTPRRPGPTR<br>KHYQPYAPPRDFAAYRS |

-continued

| 6. SEQUENCES | |
|---|---|
| ID | SEQ |
| SEQ ID NO: 7<br>4-1BB endodomain | KRGRKKLLYIFKQPFMRPVQTTQEEDGCSCRFPEEEEGGCEL |
| SEQ ID NO: 8<br>FLAG epitope tag | DYKDDDDK |
| SEQ ID NO: 9<br>4-1BB endodomain fused to FLAG epitope tag | KRGRKKLLYIFKQPFMRPVQTTQEEDGCSCRFPEEEEGGCELDYKD<br>DDDK |
| SEQ ID NO: 10<br>$V_H$ CDR1 FMC63 | GVSLPDY |
| SEQ ID NO: 11<br>$V_H$ CDR2 FMC63 | WGSET |
| SEQ ID NO: 12<br>$V_H$ CDR3 FMC63 | HYYYGGSYAMDY |
| SEQ ID NO: 13<br>$V_L$ CDR1 FMC63 | RASQDISKYLN |
| SEQ ID NO: 14<br>$V_L$ CDR2 FMC63 | HTSRLHS |
| SEQ ID NO: 15<br>$V_L$ CDR3 FMC63 | QQGNTLPYT |
| SEQ ID NO: 16<br>$V_H$ of the FMC63 antibody | EVKLQESGPGLVAPSQSLSVTCTVSGVSLPDYGVSWIRQPPRKGLE<br>WLGVIWGSETTYYNSALKSRLTIIKDNSKSQVFLKMNSLQTDDTAI<br>YYCAKHYYYGGSYAMDYWGQGTSVTVSS |
| SEQ ID NO: 17<br>$V_L$ of the FMC63 antibody | DIQMTQTTSSLSASLGDRVTISCRASQDISKYLNWYQQKPDGTVKL<br>LIYHTSRLHSGVPSRFSGSGSGTDYSLTISNLEQEDIATYFCQQGNTL<br>PYTFGGGTKLEIT |
| SEQ ID NO: 18<br>scFv of the FMC63 antibody ($V_H$-$V_L$ format) | EVKLQESGPGLVAPSQSLSVTCTVSGVSLPDYGVSWIRQPPRKGLE<br>WLGVIWGSETTYYNSALKSRLTIIKDNSKSQVFLKMNSLQTDDTAI<br>YYCAKHYYYGGSYAMDYWGQGTSVTVSSGGGGSGGGGSGGGGS<br>DIQMTQTTSSLSASLGDRVTISCRASQDISKYLNWYQQKPDGTVKL<br>LIYHTSRLHSGVPSRFSGSGSGTDYSLTISNLEQEDIATYFCQQGNTL<br>PYTFGGGTKLEIT |
| SEQ ID NO: 19<br>scFv of the FMC63 antibody ($V_L$-$V_H$ format) | DIQMTQTTSSLSASLGDRVTISCRASQDISKYLNWYQQKPDGTVKL<br>LIYHTSRLHSGVPSRFSGSGSGTDYSLTISNLEQEDIATYFCQQGNTL<br>LPYTFGGGTKLEITGGGGSGGGGSGGGGSEVKLQESGPGLVAPSQSL<br>SVTCTVSGVSLPDYGVSWIRQPPRKGLEWLGVIWGSETTYYNSAL<br>KSRLTIIKDNSKSQVFLKMNSLQTDDTAIYYCAKHYYYGGSYAMD<br>YWGQGTSVTVSS |
| SEQ ID NO: 20<br>$V_H$ CDR3 FMC63 Y01 (Y->A mutation) | HAYYGGSYAMDY |
| SEQ ID NO: 21<br>$V_H$ CDR3 FMC63 Y02 (Y->A mutation) | HYAYGGSYAMDY |
| SEQ ID NO: 22<br>$V_H$ CDR3 FMC63 Y03 (Y->A mutation) | HYYAGGSYAMDY |
| SEQ ID NO: 23<br>$V_H$ CDR3 FMC63 G01 (G->A mutation) | HYYYAGSYAMDY |
| SEQ ID NO: 24<br>$V_H$ CDR3 FMC63 G02 (G->A mutation) | HYYYGASYAMDY |
| SEQ ID NO: 25<br>$V_H$ CDR3 FMC63 Y04 (Y->A mutation) | HYYYGGSAAMDY |

-continued

| 6. SEQUENCES | |
|---|---|
| ID | SEQ |
| SEQ ID NO: 26<br>$V_H$ CDR3 FMC63 Y05<br>(Y->A mutation) | HYYAGGSYAMDA |
| SEQ ID NO: 27<br>$V_H$ CDR1 1F5 | GYTFTSY |
| SEQ ID NO: 28<br>$V_H$ CDR2 1F5 | YPGNGD |
| SEQ ID NO: 29<br>$V_H$ CDR3 1F5 | SHYGSNYVDYFDY |
| SEQ ID NO: 30<br>$V_L$ CDR1 1F5 | RASSSLSFMH |
| SEQ ID NO: 31<br>$V_L$ CDR2 1F5 | ATSNLAS |
| SEQ ID NO: 32<br>$V_L$ CDR3 1F5 | HQWSSNPLT |
| SEQ ID NO: 33<br>$V_H$ 1F5 | QVQLRQPGAELVKPGASVKMSCKASGYTFTSYNMHWVKQTPGQG<br>LEWIGAIYPGNGDTSYNQKFKGKATLTADKSSSTAYMQLSSLTSED<br>SAVYYCARSHYGSNYVDYFDYWGQGTLVTVSTG |
| SEQ ID NO: 34<br>$V_L$ 1F5 | QIVLSQSPAILSASPGEKVTMTCRASSSLSFMHWYQQKPGSSPKPWI<br>YATSNLASGVPARFSGSGSGTSYSLTISRVEAEDAATYFCHQWSSN<br>PLTFGAGTKVEIKRK |
| SEQ ID NO: 35<br>scFv of the 1F5<br>antibody ($V_H$-$V_L$<br>format) | QVQLRQPGAELVKPGASVKMSCKASGYTFTSYNMHWVKQTPGQG<br>LEWIGAIYPGNGDTSYNQKFKGKATLTADKSSSTAYMQLSSLTSED<br>SAVYYCARSHYGSNYVDYFDYWGQGTLVTVSTGGSTSGSGKPGS<br>GEGSTKGQIVLSQSPAILSASPGEKVTMTCRASSSLSFMHWYQQKP<br>GSSPKPWIYATSNLASGVPARFSGSGSGTSYSLTISRVEAEDAATYF<br>CHQWSSNPLTFGAGTKVEIKRK |
| SEQ ID NO: 36<br>scFv of the 1F5<br>antibody ($V_L$-$V_H$<br>format) | QIVLSQSPAILSASPGEKVTMTCRASSSLSFMHWYQQKPGSSPKPWI<br>YATSNLASGVPARFSGSGSGTSYSLTISRVEAEDAATYFCHQWSSN<br>PLTFGAGTKVEIKRKGSTSGSGKPGSGEGSTKGQVQLRQPGAELVK<br>PGASVKMSCKASGYTFTSYNMHWVKQTPGQGLEWIGAIYPGNGD<br>TSYNQKFKGKATLTADKSSSTAYMQLSSLTSEDSAVYYCARSHYG<br>SNYVDYFDYWGQGTLVTVSTG |
| SEQ ID NO: 37<br>$V_H$ CDR1 RFB4 | GFAFSIY |
| SEQ ID NO: 38<br>$V_H$ CDR2 RFB4 | SSGGGT |
| SEQ ID NO: 39<br>$V_H$ CDR3 RFB4 | HSGYGSSYGVLFAY |
| SEQ ID NO: 40<br>$V_L$ CDR1 RFB4 | RASQDISNYLN |
| SEQ ID NO: 41<br>$V_L$ CDR2 RFB4 | YTSILHS |
| SEQ ID NO: 42<br>$V_L$ CDR3 RFB4 | QQGNTLPWT |
| SEQ ID NO: 43<br>$V_H$ RFB4 | EVQLVESGGGLVKPGGSLKLSCAASGFAFSIYDMSWVRQTPEKRLEV<br>VAYISSGGGTTYYPDTVKGRFTISRDNAKNTLYLQMSSLKSEDTAMY<br>CARHSGYGSSYGVLFAYWGQGTLVTVSA |
| SEQ ID NO: 44<br>$V_L$ RFB4 | DIQMTQTTSSLSASLGDRVTISCRASQDISNYLNWYQQKPDGTVKLLI<br>YTSILHSGVPSRFSGSGSGTDYSLTISNLEQEDFATYFCQQGNTLPWTI<br>GGTKLEIK |
| SEQ ID NO: 45<br>scFv of the RFB4<br>antibody ($V_H$-$V_L$<br>format) | EVQLVESGGGLVKPGGSLKLSCAASGFAFSIYDMSWVRQTPEKRLE<br>WVAYISSGGGTTYYPDTVKGRFTISRDNAKNTLYLQMSSLKSEDTA<br>MYYCARHSGYGSSYGVLFAYWGQGTLVTVSAGSTSGSGKPGSGE<br>GSTKGDIQMTQTTSSLSASLGDRVTISCRASQDISNYLNWYQQKPD |

-continued

6. SEQUENCES

| ID | SEQ |
|---|---|
| | GTVKLLIYYTSILHSGVPSRFSGSGSGTDYSLTISNLEQEDFATYFCQ QGNTLPWTFGGGTKLEIK |
| SEQ ID NO: 46 scFv of the RFB4 antibody ($V_L$-$V_H$ format) | DIQMTQTTSSLSASLGDRVTISCRASQDISNYLNWYQQKPDGTVKL LIYYTSILHSGVPSRFSGSGSGTDYSLTISNLEQEDFATYFCQQGNTL PWTFGGGTKLEIKGSTSGSGKPGSGEGSTKGEVQLVESGGGLVKPG GSLKLSCAASGFAFSIYDMSWVRQTPEKRLEWVAYISSGGGTTYYP DTVKGRFTISRDNAKNTLYLQMSSLKSEDTAMYYCARHSGYGSSY GVLFAYWGQGTLVTVSA |
| SEQ ID NO: 47 FBB/G01 pCAR | MGPGVLLLLLVATAWHGQGGDIQMTQTTSSLSASLGDRVTISCRA SQDISKYLNWYQQKPDGTVKLLIYHTSRLHSGVPSRFSGSGSGTDY SLTISNLEQEDIATYFCQQGNTLPYTFGGGTKLEITGGGGSGGGGSG GGGSEVKLQESGPGLVAPSQSLSVTCTVSGVSLPDYGVSWIRQPPR KGLEWLGVIWGSETTYYNSALKSRLTIIKDNSKSQVFLKMNSLQTD DTAIYYCAKHYYYGGSYAMDYWGQGTSVTVSSAAAPTTTPAPRPP TPAPTIASQPLSLRPEACRPAAGGAVHTRGLDFACDIYIWAPLAGTC GVLLLSLVITLYCNHKRGRKKLLYIFKQPFMRPVQTTQEEDGCSCR FPEEEEGGCELDYKDDDDKRRKRSGSGATNFSLLKQAGDVEENPG PNMALPVTALLLPLALLLHAARPDIQMTQTTSSLSASLGDRVTISCR ASQDISKYLNWYQQKPDGTVKLLIYHTSRLHSGVPSRFSGSGSGTD YSLTISNLEQEDIATYFCQQGNTLPYTFGGGTKLEITGGGGSGGGGS GGGGSEVKLQESGPGLVAPSQSLSVTCTVSGVSLPDYGVSWIRQPP RKGLEWLGVIWGSETTYYNSALKSRLTIIKDNSKSQVFLKMNSLQT DDTAIYYCAKHYYYAGSYAMDYWGQGTSVTVSSAAAIEVEQKLIS EEDLLDNEKSNGTIIHVKGKHLCPSPLFPGPSKPFWVLVVVGGVLA CYSLLVTVAFIIFWVRSKRSRLLHSDYMNMTPRRPGPTRKHYQPYA PPRDFAAYRSRVKFSRSADAPAYQQGQNQLYNELNLGRREEYDVL DKRRGRDPEMGGKPRRKNPQEGLYNELQKDKMAEAYSEIGMKGE RRRGKGHDGLYQGLSTATKDTYDALHMQALPPR |
| SEQ ID NO: 48 FBB/G02 pCAR | MGPGVLLLLLVATAWHGQGGDIQMTQTTSSLSASLGDRVTISCRA SQDISKYLNWYQQKPDGTVKLLIYHTSRLHSGVPSRFSGSGSGTDY SLTISNLEQEDIATYFCQQGNTLPYTFGGGTKLEITGGGGSGGGGSG GGGSEVKLQESGPGLVAPSQSLSVTCTVSGVSLPDYGVSWIRQPPR KGLEWLGVIWGSETTYYNSALKSRLTIIKDNSKSQVFLKMNSLQTD DTAIYYCAKHYYYGGSYAMDYWGQGTSVTVSSAAAPTTTPAPRPP TPAPTIASQPLSLRPEACRPAAGGAVHTRGLDFACDIYIWAPLAGTC GVLLLSLVITLYCNHKRGRKKLLYIFKQPFMRPVQTTQEEDGCSCR FPEEEEGGCELDYKDDDDKRRKRSGSGATNFSLLKQAGDVEENPG PNMALPVTALLLPLALLLHAARPDIQMTQTTSSLSASLGDRVTISCR ASQDISKYLNWYQQKPDGTVKLLIYHTSRLHSGVPSRFSGSGSGTD YSLTISNLEQEDIATYFCQQGNTLPYTFGGGTKLEITGGGGSGGGGS GGGGSEVKLQESGPGLVAPSQSLSVTCTVSGVSLPDYGVSWIRQPP RKGLEWLGVIWGSETTYYNSALKSRLTIIKDNSKSQVFLKMNSLQT DDTAIYYCAKHYYYGASYAMDYWGQGTSVTVSSAAAIEVEQKLIS EEDLLDNEKSNGTIIHVKGKHLCPSPLFPGPSKPFWVLVVVGGVLA CYSLLVTVAFIIFWVRSKRSRLLHSDYMNMTPRRPGPTRKHYQPYA PPRDFAAYRSRVKFSRSADAPAYQQGQNQLYNELNLGRREEYDVL DKRRGRDPEMGGKPRRKNPQEGLYNELQKDKMAEAYSEIGMKGE RRRGKGHDGLYQGLSTATKDTYDALHMQALPPR |
| SEQ ID NO: 49 FBB/Y01 pCAR | MGPGVLLLLLVATAWHGQGGDIQMTQTTSSLSASLGDRVTISCRA SQDISKYLNWYQQKPDGTVKLLIYHTSRLHSGVPSRFSGSGSGTDY SLTISNLEQEDIATYFCQQGNTLPYTFGGGTKLEITGGGGSGGGGSG GGGSEVKLQESGPGLVAPSQSLSVTCTVSGVSLPDYGVSWIRQPPR KGLEWLGVIWGSETTYYNSALKSRLTIIKDNSKSQVFLKMNSLQTD DTAIYYCAKHYYYGGSYAMDYWGQGTSVTVSSAAAPTTTPAPRPP TPAPTIASQPLSLRPEACRPAAGGAVHTRGLDFACDIYIWAPLAGTC GVLLLSLVITLYCNHKRGRKKLLYIFKQPFMRPVQTTQEEDGCSCR FPEEEEGGCELDYKDDDDKRRKRSGSGATNFSLLKQAGDVEENPG PNMALPVTALLLPLALLLHAARPDIQMTQTTSSLSASLGDRVTISCR ASQDISKYLNWYQQKPDGTVKLLIYHTSRLHSGVPSRFSGSGSGTD YSLTISNLEQEDIATYFCQQGNTLPYTFGGGTKLEITGGGGSGGGGS GGGGSEVKLQESGPGLVAPSQSLSVTCTVSGVSLPDYGVSWIRQPP RKGLEWLGVIWGSETTYYNSALKSRLTIIKDNSKSQVFLKMNSLQT DDTAIYYCAKHAYYGGSYAMDYWGQGTSVTVSSAAAIEVEQKLIS EEDLLDNEKSNGTIIHVKGKHLCPSPLFPGPSKPFWVLVVVGGVLA CYSLLVTVAFIIFWVRSKRSRLLHSDYMNMTPRRPGPTRKHYQPYA PPRDFAAYRSRVKFSRSADAPAYQQGQNQLYNELNLGRREEYDVL DKRRGRDPEMGGKPRRKNPQEGLYNELQKDKMAEAYSEIGMKGE RRRGKGHDGLYQGLSTATKDTYDALHMQALPPR |
| SEQ ID NO: 50 FBB/Y02 pCAR | MGPGVLLLLLVATAWHGQGGDIQMTQTTSSLSASLGDRVTISCRA SQDISKYLNWYQQKPDGTVKLLIYHTSRLHSGVPSRFSGSGSGTDY |

-continued

| 6. SEQUENCES | |
|---|---|
| ID | SEQ |
| | SLTISNLEQEDIATYFCQQGNTLPYTFGGGTKLEITGGGGSGGGGSG<br>GGGSEVKLQESGPGLVAPSQSLSVTCTVSGVSLPDYGVSWIRQPPR<br>KGLEWLGVIWGSETTYYNSALKSRLTIIKDNSKSQVFLKMNSLQTD<br>DTAIYYCAKHYYYGGSYAMDYWGQGTSVTVSSAAAPTTTPAPRPP<br>TPAPTIASQPLSLRPEACRPAAGGAVHTRGLDFACDIYIWAPLAGTC<br>GVLLLSLVITLYCNHKRGRKKLLYIFKQPFMRPVQTTQEEDGCSCR<br>FPEEEEGGCELDYKDDDDKRRKRSGSGATNFSLLKQAGDVEENPG<br>PNMALPVTALLLPLALLLHAARPDIQMTQTTSSLSASLGDRVTISCR<br>ASQDISKYLNWYQQKPDGTVKLLIYHTSRLHSGVPSRFSGSGSGTD<br>YSLTISNLEQEDIATYFCQQGNTLPYTFGGGTKLEITGGGGSGGGGS<br>GGGGSEVKLQESGPGLVAPSQSLSVTCTVSGVSLPDYGVSWIRQPP<br>RKGLEWLGVIWGSETTYYNSALKSRLTIIKDNSKSQVFLKMNSLQT<br>DDTAIYYCAKHYAYGGSYAMDYWGQGTSVTVSSAAAIEVEQKLIS<br>EEDLLDNEKSNGTIIHVKGKHLCPSPLFPGPSKPFWVLVVVGGVLA<br>CYSLLVTVAFIIFWVRSKRSRLLHSDYMNMTPRRPGPTRKHYQPYA<br>PPRDFAAYRSRVKFSRSADAPAYQQGQNQLYNELNLGRREEYDVL<br>DKRRGRDPEMGGKPRRKNPQEGLYNELQKDKMAEAYSEIGMKGE<br>RRRGKGHDGLYQGLSTATKDTYDALHMQALPPR |
| SEQ ID NO: 51<br>FBB/Y03 pCAR | MGPGVLLLLLVATAWHGQGGDIQMTQTTSSLSASLGDRVTISCRA<br>SQDISKYLNWYQQKPDGTVKLLIYHTSRLHSGVPSRFSGSGSGTDY<br>SLTISNLEQEDIATYFCQQGNTLPYTFGGGTKLEITGGGGSGGGGSG<br>GGGSEVKLQESGPGLVAPSQSLSVTCTVSGVSLPDYGVSWIRQPPR<br>KGLEWLGVIWGSETTYYNSALKSRLTIIKDNSKSQVFLKMNSLQTD<br>DTAIYYCAKHYYYGGSYAMDYWGQGTSVTVSSAAAPTTTPAPRPP<br>TPAPTIASQPLSLRPEACRPAAGGAVHTRGLDFACDIYIWAPLAGTC<br>GVLLLSLVITLYCNHKRGRKKLLYIFKQPFMRPVQTTQEEDGCSCR<br>FPEEEEGGCELDYKDDDDKRRKRSGSGATNFSLLKQAGDVEENPG<br>PNMALPVTALLLPLALLLHAARPDIQMTQTTSSLSASLGDRVTISCR<br>ASQDISKYLNWYQQKPDGTVKLLIYHTSRLHSGVPSRFSGSGSGTD<br>YSLTISNLEQEDIATYFCQQGNTLPYTFGGGTKLEITGGGGSGGGGS<br>GGGGSEVKLQESGPGLVAPSQSLSVTCTVSGVSLPDYGVSWIRQPP<br>RKGLEWLGVIWGSETTYYNSALKSRLTIIKDNSKSQVFLKMNSLQT<br>DDTAIYYCAKHYYAGGSYAMDYWGQGTSVTVSSAAAIEVEQKLIS<br>EEDLLDNEKSNGTIIHVKGKHLCPSPLFPGPSKPFWVLVVVGGVLA<br>CYSLLVTVAFIIFWVRSKRSRLLHSDYMNMTPRRPGPTRKHYQPYA<br>PPRDFAAYRSRVKFSRSADAPAYQQGQNQLYNELNLGRREEYDVL<br>DKRRGRDPEMGGKPRRKNPQEGLYNELQKDKMAEAYSEIGMKGE<br>RRRGKGHDGLYQGLSTATKDTYDALHMQALPPR |
| SEQ ID NO: 52<br>FBB/Y04 pCAR | MGPGVLLLLLVATAWHGQGGDIQMTQTTSSLSASLGDRVTISCRA<br>SQDISKYLNWYQQKPDGTVKLLIYHTSRLHSGVPSRFSGSGSGTDY<br>SLTISNLEQEDIATYFCQQGNTLPYTFGGGTKLEITGGGGSGGGGSG<br>GGGSEVKLQESGPGLVAPSQSLSVTCTVSGVSLPDYGVSWIRQPPR<br>KGLEWLGVIWGSETTYYNSALKSRLTIIKDNSKSQVFLKMNSLQTD<br>DTAIYYCAKHYYYGGSYAMDYWGQGTSVTVSSAAAPTTTPAPRPP<br>TPAPTIASQPLSLRPEACRPAAGGAVHTRGLDFACDIYIWAPLAGTC<br>GVLLLSLVITLYCNHKRGRKKLLYIFKQPFMRPVQTTQEEDGCSCR<br>FPEEEEGGCELDYKDDDDKRRKRSGSGATNFSLLKQAGDVEENPG<br>PNMALPVTALLLPLALLLHAARPDIQMTQTTSSLSASLGDRVTISCR<br>ASQDISKYLNWYQQKPDGTVKLLIYHTSRLHSGVPSRFSGSGSGTD<br>YSLTISNLEQEDIATYFCQQGNTLPYTFGGGTKLEITGGGGSGGGGS<br>GGGGSEVKLQESGPGLVAPSQSLSVTCTVSGVSLPDYGVSWIRQPP<br>RKGLEWLGVIWGSETTYYNSALKSRLTIIKDNSKSQVFLKMNSLQT<br>DDTAIYYCAKHYYYGGSAAMDYWGQGTSVTVSSAAAIEVEQKLIS<br>EEDLLDNEKSNGTIIHVKGKHLCPSPLFPGPSKPFWVLVVVGGVLA<br>CYSLLVTVAFIIFWVRSKRSRLLHSDYMNMTPRRPGPTRKHYQPYA<br>PPRDFAAYRSRVKFSRSADAPAYQQGQNQLYNELNLGRREEYDVL<br>DKRRGRDPEMGGKPRRKNPQEGLYNELQKDKMAEAYSEIGMKGE<br>RRRGKGHDGLYQGLSTATKDTYDALHMQALPPR |
| SEQ ID NO: 53<br>FBB/Y05 pCAR | MGPGVLLLLLVATAWHGQGGDIQMTQTTSSLSASLGDRVTISCRA<br>SQDISKYLNWYQQKPDGTVKLLIYHTSRLHSGVPSRFSGSGSGTDY<br>SLTISNLEQEDIATYFCQQGNTLPYTFGGGTKLEITGGGGSGGGGSG<br>GGGSEVKLQESGPGLVAPSQSLSVTCTVSGVSLPDYGVSWIRQPPR<br>KGLEWLGVIWGSETTYYNSALKSRLTIIKDNSKSQVFLKMNSLQTD<br>DTAIYYCAKHYYYGGSYAMDYWGQGTSVTVSSAAAPTTTPAPRPP<br>TPAPTIASQPLSLRPEACRPAAGGAVHTRGLDFACDIYIWAPLAGTC<br>GVLLLSLVITLYCNHKRGRKKLLYIFKQPFMRPVQTTQEEDGCSCR<br>FPEEEEGGCELDYKDDDDKRRKRSGSGATNFSLLKQAGDVEENPG<br>PNMALPVTALLLPLALLLHAARPDIQMTQTTSSLSASLGDRVTISCR<br>ASQDISKYLNWYQQKPDGTVKLLIYHTSRLHSGVPSRFSGSGSGTD<br>YSLTISNLEQEDIATYFCQQGNTLPYTFGGGTKLEITGGGGSGGGGS<br>GGGGSEVKLQESGPGLVAPSQSLSVTCTVSGVSLPDYGVSWIRQPP<br>RKGLEWLGVIWGSETTYYNSALKSRLTIIKDNSKSQVFLKMNSLQT |

-continued

6. SEQUENCES

| ID | SEQ |
|---|---|
| | DDTAIYYCAKHYYYGGSYAMDAWGQGTSVTVSSAAAIEVEQKLIS<br>EEDLLDNEKSNGTIIHVKGKHLCPSPLFPGPSKPFWVLVVVGGVLA<br>CYSLLVTVAFIIFWVRSKRSRLLHSDYMNMTPRRPGPTRKHYQPYA<br>PPRDFAAYRSRVKFSRSADAPAYQQGQNQLYNELNLGRREEYDVL<br>DKRRGRDPEMGGKPRRKNPQEGLYNELQKDKMAEAYSEIGMKGE<br>RRRGKGHDGLYQGLSTATKDTYDALHMQALPPR |
| SEQ ID NO: 54<br>1BB/F pCAR | MGPGVLLLLLVATAWHGQGGQIVLSQSPAILSASPGEKVTMTCRA<br>SSSLSFMHWYQQKPGSSPKPWIYATSNLASGVPARFSGSGSGTSYS<br>LTISRVEAEDAATYFCHQWSSNPLTFGAGTKVEIKRKGSTSGSGKP<br>GSGEGSTKGQVQLRQPGAELVKPGASVKMSCKASGYTFTSYNMH<br>WVKQTPGQGLEWIGAIYPGNGDTSYNQKFKGKATLTADKSSSTAY<br>MQLSSLTSEDSAVYYCARSHYGSNYVDYFDYWGQGTLVTVSTGA<br>AAPTTTPAPRPPTPAPTIASQPLSLRPEACRPAAGGAVHTRGLDFAC<br>DIYIWAPLAGTCGVLLLSLVITLYCNHKRGRKKLLYIFKQPFMRPV<br>QTTQEEDGCSCRFPEEEEGGCELDYKDDDDKRRKRSGSGATNFSLL<br>KQAGDVEENPGPNMALPVTALLLPLALLLHAARPDIQMTQTTSSLS<br>ASLGDRVTISCRASQDISKYLNWYQQKPDGTVKLLIYHTSRLHSGV<br>PSRFSGSGSGTDYSLTISNLEQEDIATYFCQQGNTLPYTFGGGTKLEI<br>TGGGGSGGGGSGGGGSEVKLQESGPGLVAPSQSLSVTCTVSGVSLP<br>DYGVSWIRQPPRKGLEWLGVIWGSETTYYNSALKSRLTIIKDNSKS<br>QVFLKMNSLQTDDTAIYYCAKHYYYGGSYAMDYWGQGTSVTVSS<br>AAAIEVEQKLISEEDLLDNEKSNGTIIHVKGKHLCPSPLFPGPSKPFW<br>VLVVVGGVLACYSLLVTVAFIIFWVRSKRSRLLHSDYMNMTPRRP<br>GPTRKHYQPYAPPRDFAAYRSRVKFSRSADAPAYQQGQNQLYNEL<br>NLGRREEYDVLDKRRGRDPEMGGKPRRKNPQEGLYNELQKDKMA<br>EAYSEIGMKGERRRGKGHDGLYQGLSTATKDTYDALHMQALPPR |
| SEQ ID NO: 55<br>RBB/F pCAR | MGPGVLLLLLVATAWHGQGDIQMTQTTSSLSASLGDRVTISCRAS<br>QDISNYLNWYQQKPDGTVKLLIYYTSILHSGVPSRFSGSGSGTDYSL<br>TISNLEQEDFATYFCQQGNTLPWTFGGGTKLEIKGSTSGSGKPGSGE<br>GSTKGEVQLVESGGGLVKPGGSLKLSCAASGFAFSIYDMSWVRQT<br>PEKRLEWVAYISSGGGTTYYPDTVKGRFTISRDNAKNTLYLQMSSL<br>KSEDTAMYYCARHSGYGSSYGVLFAYWGQGTLVTVSAAAAPTTT<br>PAPRPPTPAPTIASQPLSLRPEACRPAAGGAVHTRGLDFACDIYIWA<br>PLAGTCGVLLLSLVITLYCNHKRGRKKLLYIFKQPFMRPVQTTQEE<br>DGCSCRFPEEEEGGCELDYKDDDDKRRKRSGSGATNFSLLKQAGD<br>VEENPGPNMALPVTALLLPLALLLHAARPDIQMTQTTSSLSASLGD<br>RVTISCRASQDISKYLNWYQQKPDGTVKLLIYHTSRLHSGVPSRFSG<br>SGSGTDYSLTISNLEQEDIATYFCQQGNTLPYTFGGGTKLEITGGGG<br>SGGGGSGGGGSEVKLQESGPGLVAPSQSLSVTCTVSGVSLPDYGVS<br>WIRQPPRKGLEWLGVIWGSETTYYNSALKSRLTIIKDNSKSQVFLK<br>MNSLQTDDTAIYYCAKHYYYGGSYAMDYWGQGTSVTVSSAAAIE<br>VEQKLISEEDLLDNEKSNGTIIHVKGKHLCPSPLFPGPSKPFWVLVV<br>VGGVLACYSLLVTVAFIIFWVRSKRSRLLHSDYMNMTPRRPGPTRK<br>HYQPYAPPRDFAAYRSRVKFSRSADAPAYQQGQNQLYNELNLGRR<br>EEYDVLDKRRGRDPEMGGKPRRKNPQEGLYNELQKDKMAEAYSE<br>IGMKGERRRGKGHDGLYQGLSTATKDTYDALHMQALPPR |
| SEQ ID NO: 56<br>CAR of FBB/G01 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHYYYAGSYAMDYWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 57<br>CCR of FBB/G01,<br>FBB/G02, FBB/Y01,<br>FBB/Y02, FBB/Y03,<br>FBB/Y04, and<br>FBB/Y05 | MGPGVLLLLLVATAWHGQGGDIQMTQTTSSLSASLGDRVTISCRA<br>SQDISKYLNWYQQKPDGTVKLLIYHTSRLHSGVPSRFSGSGSGTDY<br>SLTISNLEQEDIATYFCQQGNTLPYTFGGGTKLEITGGGGSGGGGSG<br>GGGSEVKLQESGPGLVAPSQSLSVTCTVSGVSLPDYGVSWIRQPPR<br>KGLEWLGVIWGSETTYYNSALKSRLTIIKDNSKSQVFLKMNSLQTD<br>DTAIYYCAKHYYYGGSYAMDYWGQGTSVTVSSAAAPTTTPAPRPP<br>TPAPTIASQPLSLRPEACRPAAGGAVHTRGLDFACDIYIWAPLAGTC<br>GVLLLSLVITLYCNHKRGRKKLLYIFKQPFMRPVQTTQEEDGCSCR<br>FPEEEEGGCELDYKDDDDK |
| SEQ ID NO: 58<br>CAR of FBB/G02 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK |

-continued

6. SEQUENCES

| ID | SEQ |
|---|---|
| | GLEWLGVIWGSETTYYNSALKSRLTIIKDNSKSQVFLKMNSLQTDD<br>TAIYYCAKHYYYGASYAMDYWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 59<br>CAR of FBB/Y01 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHAYYGGSYAMDYWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 60<br>CAR of FBB/Y02 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHYAYGGSYAMDYWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 61<br>CAR of FBB/Y03 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHYYAGGSYAMDYWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 62<br>CAR of FBB/Y04 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHYYYGGSAAMDYWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 63<br>CAR of FBB/Y05 | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHYYYGGSYAMDAWGQGTSVTVSSAAAIEVEQKLISEE<br>DLLDNEKSNGTIIHVKGKHLCPSPLFPGPSKPFWVLVVVGGVLACY<br>SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 64<br>CAR of 1BB/F and<br>RBB/F | MALPVTALLLPLALLLHAARPDIQMTQTTSSLSASLGDRVTISCRAS<br>QDISKYLNWYQQKPDGTVKLLIYHTSRLHSGVPSRFSGSGSGTDYS<br>LTISNLEQEDIATYFCQQGNTLPYTFGGGTKLEITGGGGSGGGGSGG<br>GGSEVKLQESGPGLVAPSQSLSVTCTVSGVSLPDYGVSWIRQPPRK<br>GLEWLGVIWGSETTYYNSALKSRLTIIKDNSKSQVFLKMNSLQTDD<br>TAIYYCAKHYYYGGSYAMDYWGQGTSVTVSSAAAIEVEQKLISEE<br>DLLDNEKSNGTIIHVKGKHLCPSPLFPGPSKPFWVLVVVGGVLACY |

-continued

| 6. SEQUENCES | |
|---|---|
| ID | SEQ |
| | SLLVTVAFIIFWVRSKRSRLLHSDYMNMTPRRPGPTRKHYQPYAPP<br>RDFAAYRSRVKFSRSADAPAYQQGQNQLYNELNLGRREEYDVLD<br>KRRGRDPEMGGKPRRKNPQEGLYNELQKDKMAEAYSEIGMKGER<br>RRGKGHDGLYQGLSTATKDTYDALHMQALPPR |
| SEQ ID NO: 65<br>CCR of 1BB/F | MGPGVLLLLLVATAWHGQGGQIVLSQSPAILSASPGEKVTMTCRA<br>SSSLSFMHWYQQKPGSSPKPWIYATSNLASGVPARFSGSGSGTSYS<br>LTISRVEAEDAATYFCHQWSSNPLTFGAGTKVEIKRKGSTSGSGKP<br>GSGEGSTKGQVQLRQPGAELVKPGASVKMSCKASGYTFTSYNMH<br>WVKQTPGQGLEWIGAIYPGNGDTSYNQKFKGKATLTADKSSSTAY<br>MQLSSLTSEDSAVYYCARSHYGSNYVDYFDYWGQGTLVTVSTGA<br>AAPTTTPAPRPPTPAPTIASQPLSLRPEACRPAAGGAVHTRGLDFAC<br>DIYIWAPLAGTCGVLLLSLVITLYCNHKRGRKKLLYIFKQPFMRPV<br>QTTQEEDGCSCRFPEEEEGGCELDYKDDDDK |
| SEQ ID NO: 66<br>CCR of RBB/F | MGPGVLLLLLVATAWHGQGDIQMTQTTSSLSASLGDRVTISCRAS<br>QDISNYLNWYQQKPDGTVKLLIYYTSILHSGVPSRFSGSGSGTDYSL<br>TISNLEQEDFATYFCQQGNTLPWTFGGGTKLEIKGSTSGSGKPGSGE<br>GSTKGEVQLVESGGGLVKPGGSLKLSCAASGFAFSIYDMSWVRQT<br>PEKRLEWVAYISSGGGTTYYPDTVKGRFTISRDNAKNTLYLQMSSL<br>KSEDTAMYYCARHSGYGSSYGVLFAYWGQGTLVTVSAAAAPTTT<br>PAPRPPTPAPTIASQPLSLRPEACRPAAGGAVHTRGLDFACDIYIWA<br>PLAGTCGVLLLSLVITLYCNHKRGRKKLLYIFKQPFMRPVQTTQEE<br>DGCSCRFPEEEEGGCELDYKDDDDK |
| SEQ ID NO: 101<br>Nucleotide sequence<br>encoding for F-2 | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACTACTACTACGGCGG<br>AAGCTACGCTATGGACTACTGGGGCCAGGGAACCAGCGTGACC<br>GTGAGCAGCGCGGCCGCTATCGAGGTGGAGCAGAAGCTGATCA<br>GCGAGGAGGACCTGCTAGACAATGAGAAGAGCAATGGAACCAT<br>TATCCATGTGAAAGGGAAACACCTTTGTCCAAGTCCCCTATTTC<br>CCGGACCTTCTAAGCCCTTTTGGGTGCTGGTGGTGGTTGGTGGA<br>GTCCTGGCTTGCTATAGCTTGCTAGTAACAGTGGCCTTTATTATT<br>TTCTGGGTGAGGAGTAAGAGGAGCAGGCTCCTGCACAGTGACT<br>ACATGAACATGACTCCCCGCCGCCCCGGGCCCACCCGCAAGCAT<br>TACCAGCCCTATGCCCCACCACGCGACTTCGCAGCCTATCGCTC<br>CAGAGTGAAGTTCAGCAGGAGCGCAGACGCCCCCGCGTACCAG<br>CAGGGCCAGAACCAGCTCTATAACGAGCTCAATCTAGGACGAA<br>GAGAGGAGTACGATGTTTTGGACAAGAGACGTGGCCGGGACCC<br>TGAGATGGGGGGAAAGCCGAGAAGGAAGAACCCTCAGGAAGG<br>CCTGTACAATGAACTGCAGAAAGATAAGATGGCGGAGGCCTAC<br>AGTGAGATTGGGATGAAAGGCGAGCGCCGGAGGGGCAAGGGGC<br>ACGATGGCCTTTACCAGGGTCTCAGTACAGCCACCAAGGACACC<br>TACGACGCCCTTCACATGCAGGCCCTGCCCCCTCGCTAA |
| SEQ ID NO: 102<br>Nucleotide sequence<br>encoding for G01 | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA |

-continued

6. SEQUENCES

| ID | SEQ |
| --- | --- |
| | GCAAGTCCCAGGTGTTCCTGAAGATGAACAGCCTGCAGACCGAC<br>GACACCGCCATCTACTACTGCGCCAAGCACTACTACTACGCCGG<br>AAGCTACGCTATGGACTACTGGGGCCAGGGAACCAGCGTGACC<br>GTGAGCAGCGCGGCCGCTATCGAGGTGGAGCAGAAGCTGATCA<br>GCGAGGAGGACCTGCTAGACAATGAGAAGAGCAATGGAACCAT<br>TATCCATGTGAAAGGGAAACACCTTTGTCCAAGTCCCCTATTTC<br>CCGGACCTTCTAAGCCCTTTTGGGTGCTGGTGGTGGTTGGTGGA<br>GTCCTGGCTTGCTATAGCTTGCTAGTAACAGTGGCCTTTATTATT<br>TTCTGGGTGAGGAGTAAGAGGAGCAGGCTCCTGCACAGTGACT<br>ACATGAACATGACTCCCCGCCGCCCCGGGCCCACCCGCAAGCAT<br>TACCAGCCCTATGCCCCACCACGCGACTTCGCAGCCTATCGCTC<br>CAGAGTGAAGTTCAGCAGGAGCGCAGACGCCCCCGCGTACCAG<br>CAGGGCCAGAACCAGCTCTATAACGAGCTCAATCTAGGACGAA<br>GAGAGGAGTACGATGTTTTGGACAAGAGACGTGGCCGGGACCC<br>TGAGATGGGGGGAAAGCCGAGAAGGAAGAACCCTCAGGAAGG<br>CCTGTACAATGAACTGCAGAAAGATAAGATGGCGGAGGCCTAC<br>AGTGAGATTGGGATGAAAGGCGAGCGCCGGAGGGGCAAGGGGC<br>ACGATGGCCTTTACCAGGGTCTCAGTACAGCCACCAAGGACACC<br>TACGACGCCCTTCACATGCAGGCCCTGCCCCCTCGCTAA |
| SEQ ID NO: 103<br>Nucleotide sequence<br>encoding for G02 | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACTACTACTACGGCGC<br>CAGCTACGCTATGGACTACTGGGGCCAGGGAACCAGCGTGACC<br>GTGAGCAGCGCGGCCGCTATCGAGGTGGAGCAGAAGCTGATCA<br>GCGAGGAGGACCTGCTAGACAATGAGAAGAGCAATGGAACCAT<br>TATCCATGTGAAAGGGAAACACCTTTGTCCAAGTCCCCTATTTC<br>CCGGACCTTCTAAGCCCTTTTGGGTGCTGGTGGTGGTTGGTGGA<br>GTCCTGGCTTGCTATAGCTTGCTAGTAACAGTGGCCTTTATTATT<br>TTCTGGGTGAGGAGTAAGAGGAGCAGGCTCCTGCACAGTGACT<br>ACATGAACATGACTCCCCGCCGCCCCGGGCCCACCCGCAAGCAT<br>TACCAGCCCTATGCCCCACCACGCGACTTCGCAGCCTATCGCTC<br>CAGAGTGAAGTTCAGCAGGAGCGCAGACGCCCCCGCGTACCAG<br>CAGGGCCAGAACCAGCTCTATAACGAGCTCAATCTAGGACGAA<br>GAGAGGAGTACGATGTTTTGGACAAGAGACGTGGCCGGGACCC<br>TGAGATGGGGGGAAAGCCGAGAAGGAAGAACCCTCAGGAAGG<br>CCTGTACAATGAACTGCAGAAAGATAAGATGGCGGAGGCCTAC<br>AGTGAGATTGGGATGAAAGGCGAGCGCCGGAGGGGCAAGGGGC<br>ACGATGGCCTTTACCAGGGTCTCAGTACAGCCACCAAGGACACC<br>TACGACGCCCTTCACATGCAGGCCCTGCCCCCTCGCTAA |
| SEQ ID NO: 104<br>Nucleotide sequence<br>encoding for Y01 | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACGCCTACTACGGCGG<br>AAGCTACGCTATGGACTACTGGGGCCAGGGAACCAGCGTGACC<br>GTGAGCAGCGCGGCCGCTATCGAGGTGGAGCAGAAGCTGATCA<br>GCGAGGAGGACCTGCTAGACAATGAGAAGAGCAATGGAACCAT |

-continued

| 6. SEQUENCES | |
|---|---|
| ID | SEQ |
| | TATCCATGTGAAAGGGAAACACCTTTGTCCAAGTCCCCTATTTC CCGGACCTTCTAAGCCCTTTTGGGTGCTGGTGGTGGTTGGTGGA GTCCTGGCTTGCTATAGCTTGCTAGTAACAGTGGCCTTTATTATT TTCTGGGTGAGGAGTAAGAGGAGCAGGCTCCTGCACAGTGACT ACATGAACATGACTCCCCGCCGCCCCGGGCCCACCCGCAAGCAT TACCAGCCCTATGCCCCACCACGCGACTTCGCAGCCTATCGCTC CAGAGTGAAGTTCAGCAGGAGCGCAGACGCCCCCGCGTACCAG CAGGGCCAGAACCAGCTCTATAACGAGCTCAATCTAGGACGAA GAGAGGAGTACGATGTTTTGGACAAGAGACGTGGCCGGGACCC TGAGATGGGGGGAAAGCCGAGAAGGAAGAACCCTCAGGAAGG CCTGTACAATGAACTGCAGAAAGATAAGATGGCGGAGGCCTAC AGTGAGATTGGGATGAAAGGCGAGCGCCGGAGGGGCAAGGGGC ACGATGGCCTTTACCAGGGTCTCAGTACAGCCACCAAGGACACC TACGACGCCCTTCACATGCAGGCCCTGCCCCCTCGCTAA |
| SEQ ID NO: 105 Nucleotide sequence encoding for Y02 | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACGCCTACGGCGG AAGCTACGCTATGGACTACTGGGGCCAGGGAACCAGCGTGACC GTGAGCAGCGCGGCCGCTATCGAGGTGGAGCAGAAGCTGATCA GCGAGGAGGACCTGCTAGACAATGAGAAGAGCAATGGAACCAT TATCCATGTGAAAGGGAAACACCTTTGTCCAAGTCCCCTATTTC CCGGACCTTCTAAGCCCTTTTGGGTGCTGGTGGTGGTTGGTGGA GTCCTGGCTTGCTATAGCTTGCTAGTAACAGTGGCCTTTATTATT TTCTGGGTGAGGAGTAAGAGGAGCAGGCTCCTGCACAGTGACT ACATGAACATGACTCCCCGCCGCCCCGGGCCCACCCGCAAGCAT TACCAGCCCTATGCCCCACCACGCGACTTCGCAGCCTATCGCTC CAGAGTGAAGTTCAGCAGGAGCGCAGACGCCCCCGCGTACCAG CAGGGCCAGAACCAGCTCTATAACGAGCTCAATCTAGGACGAA GAGAGGAGTACGATGTTTTGGACAAGAGACGTGGCCGGGACCC TGAGATGGGGGGAAAGCCGAGAAGGAAGAACCCTCAGGAAGG CCTGTACAATGAACTGCAGAAAGATAAGATGGCGGAGGCCTAC AGTGAGATTGGGATGAAAGGCGAGCGCCGGAGGGGCAAGGGGC ACGATGGCCTTTACCAGGGTCTCAGTACAGCCACCAAGGACACC TACGACGCCCTTCACATGCAGGCCCTGCCCCCTCGCTAA |
| SEQ ID NO: 106 Nucleotide sequence encoding for Y03 | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACTACGCCGGCGG AAGCTACGCTATGGACTACTGGGGCCAGGGAACCAGCGTGACC GTGAGCAGCGCGGCCGCTATCGAGGTGGAGCAGAAGCTGATCA GCGAGGAGGACCTGCTAGACAATGAGAAGAGCAATGGAACCAT TATCCATGTGAAAGGGAAACACCTTTGTCCAAGTCCCCTATTTC CCGGACCTTCTAAGCCCTTTTGGGTGCTGGTGGTGGTTGGTGGA GTCCTGGCTTGCTATAGCTTGCTAGTAACAGTGGCCTTTATTATT TTCTGGGTGAGGAGTAAGAGGAGCAGGCTCCTGCACAGTGACT ACATGAACATGACTCCCCGCCGCCCCGGGCCCACCCGCAAGCAT |

-continued

6. SEQUENCES

| ID | SEQ |
|---|---|
| | TACCAGCCCTATGCCCCACCACGCGACTTCGCAGCCTATCGCTC CAGAGTGAAGTTCAGCAGGAGCGCAGACGCCCCCGCGTACCAG CAGGGCCAGAACCAGCTCTATAACGAGCTCAATCTAGGACGAA GAGAGGAGTACGATGTTTTGGACAAGAGACGTGGCCGGGACCC TGAGATGGGGGGAAAGCCGAGAAGGAAGAACCCTCAGGAAGG CCTGTACAATGAACTGCAGAAAGATAAGATGGCGGAGGCCTAC AGTGAGATTGGGATGAAAGGCGAGCGCCGGAGGGGCAAGGGGC ACGATGGCCTTTACCAGGGTCTCAGTACAGCCACCAAGGACACC TACGACGCCCTTCACATGCAGGCCCTGCCCCCTCGCTAA |
| SEQ ID NO: 107 Nucleotide sequence encoding for Y04 | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACTACTACGGCGG AAGCGCCGCTATGGACTACTGGGGCCAGGGAACCAGCGTGACC GTGAGCAGCGCGGCCGCTATCGAGGTGGAGCAGAAGCTGATCA GCGAGGAGGACCTGCTAGACAATGAGAAGAGCAATGGAACCAT TATCCATGTGAAAGGGAAACACCTTTGTCCAAGTCCCCTATTTC CCGGACCTTCTAAGCCCTTTTGGGTGCTGGTGGTGGTTGGTGGA GTCCTGGCTTGCTATAGCTTGCTAGTAACAGTGGCCTTTATTATT TTCTGGGTGAGGAGTAAGAGGAGCAGGCTCCTGCACAGTGACT ACATGAACATGACTCCCCGCCGCCCCGGGCCCACCCGCAAGCAT TACCAGCCCTATGCCCCACCACGCGACTTCGCAGCCTATCGCTC CAGAGTGAAGTTCAGCAGGAGCGCAGACGCCCCCGCGTACCAG CAGGGCCAGAACCAGCTCTATAACGAGCTCAATCTAGGACGAA GAGAGGAGTACGATGTTTTGGACAAGAGACGTGGCCGGGACCC TGAGATGGGGGGAAAGCCGAGAAGGAAGAACCCTCAGGAAGG CCTGTACAATGAACTGCAGAAAGATAAGATGGCGGAGGCCTAC AGTGAGATTGGGATGAAAGGCGAGCGCCGGAGGGGCAAGGGGC ACGATGGCCTTTACCAGGGTCTCAGTACAGCCACCAAGGACACC TACGACGCCCTTCACATGCAGGCCCTGCCCCCTCGCTAA |
| SEQ ID NO: 108 Nucleotide sequence encoding for Y05 | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACTACTACGGCGG AAGCTACGCTATGGACGCCTGGGGCCAGGGAACCAGCGTGACC GTGAGCAGCGCGGCCGCTATCGAGGTGGAGCAGAAGCTGATCA GCGAGGAGGACCTGCTAGACAATGAGAAGAGCAATGGAACCAT TATCCATGTGAAAGGGAAACACCTTTGTCCAAGTCCCCTATTTC CCGGACCTTCTAAGCCCTTTTGGGTGCTGGTGGTGGTTGGTGGA GTCCTGGCTTGCTATAGCTTGCTAGTAACAGTGGCCTTTATTATT TTCTGGGTGAGGAGTAAGAGGAGCAGGCTCCTGCACAGTGACT ACATGAACATGACTCCCCGCCGCCCCGGGCCCACCCGCAAGCAT TACCAGCCCTATGCCCCACCACGCGACTTCGCAGCCTATCGCTC CAGAGTGAAGTTCAGCAGGAGCGCAGACGCCCCCGCGTACCAG CAGGGCCAGAACCAGCTCTATAACGAGCTCAATCTAGGACGAA GAGAGGAGTACGATGTTTTGGACAAGAGACGTGGCCGGGACCC TGAGATGGGGGGAAAGCCGAGAAGGAAGAACCCTCAGGAAGG |

-continued

6. SEQUENCES

| ID | SEQ |
|---|---|
| | CCTGTACAATGAACTGCAGAAAGATAAGATGGCGGAGGCCTAC<br>AGTGAGATTGGGATGAAAGGCGAGCGCCGGAGGGGCAAGGGGC<br>ACGATGGCCTTTACCAGGGTCTCAGTACAGCCACCAAGGACACC<br>TACGACGCCCTTCACATGCAGGCCCTGCCCCCTCGCTAA |
| SEQ ID NO: 109<br>Nucleotide sequence<br>encoding for FBB/G01 | ATGGGCCCAGGAGTTCTGCTGCTCCTGCTGGTGGCCACAGCTTG<br>GCATGGTCAGGGAGGTGACATCCAGATGACACAGACAACATCC<br>TCCCTCTCCGCTTCCCTCGGAGACAGGGTCACAATTTCCTGCAG<br>GGCTTCCCAGGACATTTCCAAGTACCTCAACTGGTACCAGCAGA<br>AGCCTGACGGAACAGTCAAGCTCCTCATTTACCACACATCCAGG<br>CTCCACTCCGGAGTCCCTTCCAGGTTCTCCGGATCCGGATCCGG<br>AACAGACTACTCCCTCACAATTTCCAACCTCGAGCAGGAGGACA<br>TTGCTACATACTTCTGCCAGCAGGGAAACACACTCCCTTACACA<br>TTCGGAGGAGGAACAAAGCTCGAGATTACAGGAGGTGGCGGTT<br>CCGGTGGTGGAGGCTCCGGTGGTGGTGGATCTGAGGTCAAGCTC<br>CAGGAGTCCGGACCTGGACTTGTCGCTCCTTCTCAGTCTCTCTCC<br>GTCACATGCACAGTCTCCGGAGTCTCCCTCCCTGATTATGGAGT<br>CTCCTGGATTAGGCAACCTCCTAGGAAAGGACTCGAATGGCTCG<br>GAGTCATTTGGGGATCCGAAACAACATATTATAATTCCGCTCTC<br>AAATCCAGGCTCACAATTATTAAAGATAATTCCAAATCCCAAGT<br>CTTTCTCAAGATGAACTCCCTCCAGACAGACGACACAGCTATTT<br>ACTACTGCGCTAAGCACTACTACTACGGGGGATCTTACGCTATG<br>GACTACTGGGGACAGGGAACATCCGTCACAGTCTCTTCCGCTGC<br>TGCTCCCACCACCACACCCGCTCCCAGACCCCCTACCCCTGCCC<br>CCACCATCGCCAGCCAGCCCCTGAGCCTGAGACCCGAGGCCTGC<br>AGACCTGCCGCCGGCGGAGCCGTGCACACCAGAGGCCTGGACT<br>TCGCCTGCGACATCTACATCTGGGCTCCCCTGGCCGGCACCTGC<br>GGCGTGCTGCTGCTGAGCCTGGTGATCACCCTGTACTGCAACCA<br>CAAGAGAGGCAGAAAGAAGCTGCTGTACATCTTCAAGCAGCCC<br>TTCATGAGACCCGTGCAGACCACCCAGGAGGAGGACGGCTGCA<br>GCTGCAGATTCCCCGAGGAGGAGGAGGGCGGCTGCGAGCTGGA<br>CTACAAAGACGATGACGACAAGCGGAGAAAGCGCAGCGGCTCC<br>GGCGCCACGAACTTCTCTCTGTTAAAGCAAGCAGGAGACGTGGA<br>AGAAAACCCCGGTCCCAACATGGCTCTGCCTGTGACAGCTCTGC<br>TGCTGCCTCTGGCTCTGCTGCTGCACGCCGCTAGACCCGACATC<br>CAGATGACCCAGACCACCAGCAGCCTGAGCGCCAGCCTGGGCG<br>ACAGAGTGACCATCAGCTGCAGAGCCAGCCAGGACATCAGCAA<br>GTACCTGAACTGGTACCAGCAGAAGCCCGACGGCACCGTGAAG<br>CTGCTGATCTACCACACCAGCAGACTGCACAGCGGCGTGCCCAG<br>CAGATTCAGCGGCAGCGGCAGCGGCACCGACTACAGCCTGACC<br>ATCAGCAACCTGGAGCAGGAGGACATCGCCACCTACTTCTGCCA<br>GCAGGGCAACACCCTGCCCTACACCTTCGGCGGAGGCACCAAG<br>CTGGAGATCACCGGCGGAGGAGGAAGCGGAGGAGGAGGCAGC<br>GGAGGAGGAGGCAGCGAGGTGAAGCTGCAGGAGAGCGGCCCC<br>GGCCTGGTGGCCCCCAGCCAGAGCCTGAGCGTGACCTGCACCGT<br>GAGCGGCGTGAGCCTGCCCGACTACGGCGTGAGCTGGATCAGA<br>CAGCCTCCCAGAAAGGGCCTGGAGTGGCTGGGCGTGATCTGGG<br>GCAGCGAGACCACCTACTACAACAGCGCCCTGAAGAGCAGACT<br>GACCATCATTAAGGACAACAGCAAGTCCCAGGTGTTCCTGAAGA<br>TGAACAGCCTGCAGACCGACGACACCGCCATCTACTACTGCGCC<br>AAGCACTACTACTACGCCGGAAGCTACGCTATGGACTACTGGGG<br>CCAGGGAACCAGCGTGACCGTGAGCAGCGCGGCCGCTATCGAG<br>GTGGAGCAGAAGCTGATCAGCGAGGAGGACCTGCTGGACAACG<br>AGAAGAGCAACGGCACCATCATCCACGTGAAGGGCAAGCACCT<br>GTGCCCCAGCCCCCTGTTCCCCGGCCCCAGCAAGCCCTTCTGGG<br>TGCTGGTGGTGGTGGGCGGCGTGCTGGCCTGCTACAGCCTGCTG<br>GTGACCGTGGCCTTCATCATCTTCTGGGTGCGGAGCAAGCGGAG<br>CCGGCTGCTGCACAGCGACTACATGAACATGACCCCCCGGCGGC<br>CTGGGCCCACCCGCAAGCATTACCAGCCCTATGCCCCACCACGC<br>GACTTCGCAGCCTATCGCTCCAGAGTGAAGTTCAGCAGGAGCGC<br>AGACGCCCCCGCGTACCAGCAGGGCCAGAACCAGCTCTATAAC<br>GAGCTCAATCTAGGACGAAGAGAGGAGTACGATGTTTTGGACA<br>AGAGACGTGGCCGGGACCCTGAGATGGGGGGAAAGCCGAGAAG<br>GAAGAACCCTCAGGAAGGCCTGTACAATGAACTGCAGAAAGAT<br>AAGATGGCGGAGGCCTACAGTGAGATTGGGATGAAAGGCGAGC<br>GCCGGAGGGGCAAGGGGCACGATGGCCTTTACCAGGGTCTCAG<br>TACAGCCACCAAGGACACCTACGACGCCCTTCACATGCAGGCCC<br>TGCCCCCTCGCTAA |
| SEQ ID NO: 110<br>Nucleotide sequence<br>encoding for FBB/G02 | ATGGGCCCAGGAGTTCTGCTGCTCCTGCTGGTGGCCACAGCTTG<br>GCATGGTCAGGGAGGTGACATCCAGATGACACAGACAACATCC<br>TCCCTCTCCGCTTCCCTCGGAGACAGGGTCACAATTTCCTGCAG<br>GGCTTCCCAGGACATTTCCAAGTACCTCAACTGGTACCAGCAGA<br>AGCCTGACGGAACAGTCAAGCTCCTCATTTACCACACATCCAGG<br>CTCCACTCCGGAGTCCCTTCCAGGTTCTCCGGATCCGGATCCGG |

-continued

6. SEQUENCES

| ID | SEQ |
| --- | --- |
| | AACAGACTACTCCCTCACAATTTCCAACCTCGAGCAGGAGGACA TTGCTACATACTTCTGCCAGCAGGGAAACACACTCCCTTACACA TTCGGAGGAGGAACAAAGCTCGAGATTACAGGAGGTGGCGGTT CCGGTGGTGGAGGCTCCGGTGGTGGTGGATCTGAGGTCAAGCTC CAGGAGTCCGGACCTGGACTTGTCGCTCCTTCTCAGTCTCTCTCC GTCACATGCACAGTCTCCGGAGTCTCCCTCCCTGATTATGGAGT CTCCTGGATTAGGCAACCTCCTAGGAAAGGACTCGAATGGCTCG GAGTCATTTGGGGATCCGAAACAACATATTATAATTCCGCTCTC AAATCCAGGCTCACAATTATTAAAGATAATTCCAAATCCCAAGT CTTTCTCAAGATGAACTCCCTCCAGACAGACGACACAGCTATTT ACTACTGCGCTAAGCACTACTACTACGGGGGATCTTACGCTATG GACTACTGGGGACAGGGAACATCCGTCACAGTCTCTTCCGCTGC TGCTCCCACCACCACACCCGCTCCCAGACCCCCTACCCCTGCCC CCACCATCGCCAGCCAGCCCCTGAGCCTGAGACCCGAGGCCTGC AGACCTGCCGCCGGCGGAGCCGTGCACACCAGAGGCCTGGACT TCGCCTGCGACATCTACATCTGGGCTCCCCTGGCCGGCACCTGC GGCGTGCTGCTGCTGAGCCTGGTGATCACCCTGTACTGCAACCA CAAGAGAGGCAGAAAGAAGCTGCTGTACATCTTCAAGCAGCCC TTCATGAGACCCGTGCAGACCACCCAGGAGGAGGACGGCTGCA GCTGCAGATTCCCCGAGGAGGAGGAGGGCGGCTGCGAGCTGGA CTACAAAGACGATGACGACAAGCGGAGAAAGCGCAGCGGCTCC GGCGCCACGAACTTCTCTCTGTTAAAGCAAGCAGGAGACGTGGA AGAAAACCCCGGTCCCAACATGGCTCTGCCTGTGACAGCTCTGC TGCTGCCTCTGGCTCTGCTGCTGCACGCCGCTAGACCCGACATC CAGATGACCCAGACCACCAGCAGCCTGAGCGCCAGCCTGGGCG ACAGAGTGACCATCAGCTGCAGAGCCAGCCAGGACATCAGCAA GTACCTGAACTGGTACCAGCAGAAGCCCGACGGCACCGTGAAG CTGCTGATCTACCACACCAGCAGACTGCACAGCGGCGTGCCCAG CAGATTCAGCGGCAGCGGCAGCGGCACCGACTACAGCCTGACC ATCAGCAACCTGGAGCAGGAGGACATCGCCACCTACTTCTGCCA GCAGGGCAACACCCTGCCCTACACCTTCGGCGGAGGCACCAAG CTGGAGATCACCGGCGGAGGAGGAAGCGGAGGAGGAGGCAGC GGAGGAGGAGGCAGCGAGGTGAAGCTGCAGGAGAGCGGCCCC GGCCTGGTGGCCCCCAGCCAGAGCCTGAGCGTGACCTGCACCGT GAGCGGCGTGAGCCTGCCCGACTACGGCGTGAGCTGGATCAGA CAGCCTCCCAGAAAGGGCCTGGAGTGGCTGGGCGTGATCTGGG GCAGCGAGACCACCTACTACAACAGCGCCCTGAAGAGCAGACT GACCATCATTAAGGACAACAGCAAGTCCCAGGTGTTCCTGAAGA TGAACAGCCTGCAGACCGACGACACCGCCATCTACTACTGCGCC AAGCACTACTACTACGGCGCCAGCTACGCTATGGACTACTGGGG CCAGGGAACCAGCGTGACCGTGAGCAGCGCGGCCGCTATCGAG GTGGAGCAGAAGCTGATCAGCGAGGAGGACCTGCTGGACAACG AGAAGAGCAACGGCACCATCATCCACGTGAAGGGCAAGCACCT GTGCCCCAGCCCCCTGTTCCCCGGCCCCAGCAAGCCCTTCTGGG TGCTGGTGGTGGTGGGCGGCGTGCTGGCCTGCTACAGCCTGCTG GTGACCGTGGCCTTCATCATCTTCTGGGTGCGGAGCAAGCGGAG CCGGCTGCTGCACAGCGACTACATGAACATGACCCCCCGGCGGC CTGGGCCCACCCGCAAGCATTACCAGCCCTATGCCCCACCACGC GACTTCGCAGCCTATCGCTCCAGAGTGAAGTTCAGCAGGAGCGC AGACGCCCCCGCGTACCAGCAGGGCCAGAACCAGCTCTATAAC GAGCTCAATCTAGGACGAAGAGAGGAGTACGATGTTTTGGACA AGAGACGTGGCCGGGACCCTGAGATGGGGGGAAAGCCGAGAAG GAAGAACCCTCAGGAAGGCCTGTACAATGAACTGCAGAAAGAT AAGATGGCGGAGGCCTACAGTGAGATTGGGATGAAAGGCGAGC GCCGGAGGGGCAAGGGGCACGATGGCCTTTACCAGGGTCTCAG TACAGCCACCAAGGACACCTACGACGCCCTTCACATGCAGGCCC TGCCCCCTCGCTAA |
| SEQ ID NO: 111 Nucleotide sequence encoding for FBB/Y01 | ATGGGCCCAGGAGTTCTGCTGCTCCTGCTGGTGGCCACAGCTTG GCATGGTCAGGGAGGTGACATCCAGATGACACAGACAACATCC TCCCTCTCCGCTTCCCTCGGAGACAGGGTCACAATTTCCTGCAG GGCTTCCCAGGACATTTCCAAGTACCTCAACTGGTACCAGCAGA AGCCTGACGGAACAGTCAAGCTCCTCATTTACCACACATCCAGG CTCCACTCCGGAGTCCCTTCCAGGTTCTCCGGATCCGGATCCGG AACAGACTACTCCCTCACAATTTCCAACCTCGAGCAGGAGGACA TTGCTACATACTTCTGCCAGCAGGGAAACACACTCCCTTACACA TTCGGAGGAGGAACAAAGCTCGAGATTACAGGAGGTGGCGGTT CCGGTGGTGGAGGCTCCGGTGGTGGTGGATCTGAGGTCAAGCTC CAGGAGTCCGGACCTGGACTTGTCGCTCCTTCTCAGTCTCTCTCC GTCACATGCACAGTCTCCGGAGTCTCCCTCCCTGATTATGGAGT CTCCTGGATTAGGCAACCTCCTAGGAAAGGACTCGAATGGCTCG GAGTCATTTGGGGATCCGAAACAACATATTATAATTCCGCTCTC AAATCCAGGCTCACAATTATTAAAGATAATTCCAAATCCCAAGT CTTTCTCAAGATGAACTCCCTCCAGACAGACGACACAGCTATTT ACTACTGCGCTAAGCACTACTACTACGGGGGATCTTACGCTATG |

-continued

6. SEQUENCES

| ID | SEQ |
|---|---|
| | GACTACTGGGGACAGGGAACATCCGTCACAGTCTCTTCCGCTGC<br>TGCTCCCACCACCACACCCGCTCCCAGACCCCCTACCCCTGCCC<br>CCACCATCGCCAGCCAGCCCCTGAGCCTGAGACCCGAGGCCTGC<br>AGACCTGCCGCCGGCGGAGCCGTGCACACCAGAGGCCTGGACT<br>TCGCCTGCGACATCTACATCTGGGCTCCCCTGGCCGGCACCTGC<br>GGCGTGCTGCTGCTGAGCCTGGTGATCACCCTGTACTGCAACCA<br>CAAGAGAGGCAGAAAGAAGCTGCTGTACATCTTCAAGCAGCCC<br>TTCATGAGACCCGTGCAGACCACCCAGGAGGAGGACGGCTGCA<br>GCTGCAGATTCCCCGAGGAGGAGGAGGGCGGCTGCGAGCTGGA<br>CTACAAAGACGATGACGACAAGCGGAGAAAGCGCAGCGGCTCC<br>GGCGCCACGAACTTCTCTCTGTTAAAGCAAGCAGGAGACGTGGA<br>AGAAAACCCCGGTCCCAACATGGCTCTGCCTGTGACAGCTCTGC<br>TGCTGCCTCTGGCTCTGCTGCTGCACGCCGCTAGACCCGACATC<br>CAGATGACCCAGACCACCAGCAGCCTGAGCGCCAGCCTGGGCG<br>ACAGAGTGACCATCAGCTGCAGAGCCAGCCAGGACATCAGCAA<br>GTACCTGAACTGGTACCAGCAGAAGCCCGACGGCACCGTGAAG<br>CTGCTGATCTACCACACCAGCAGACTGCACAGCGGCGTGCCCAG<br>CAGATTCAGCGGCAGCGGCAGCGGCACCGACTACAGCCTGACC<br>ATCAGCAACCTGGAGCAGGAGGACATCGCCACCTACTTCTGCCA<br>GCAGGGCAACACCCTGCCCTACACCTTCGGCGGAGGCACCAAG<br>CTGGAGATCACCGGCGGAGGAGGAAGCGGAGGAGGAGGCAGC<br>GGAGGAGGAGGCAGCGAGGTGAAGCTGCAGGAGAGCGGCCCC<br>GGCCTGGTGGCCCCCAGCCAGAGCCTGAGCGTGACCTGCACCGT<br>GAGCGGCGTGAGCCTGCCCGACTACGGCGTGAGCTGGATCAGA<br>CAGCCTCCCAGAAAGGGCCTGGAGTGGCTGGGCGTGATCTGGG<br>GCAGCGAGACCACCTACTACAACAGCGCCCTGAAGAGCAGACT<br>GACCATCATTAAGGACAACAGCAAGTCCCAGGTGTTCCTGAAGA<br>TGAACAGCCTGCAGACCGACGACACCGCCATCTACTACTGCGCC<br>AAGCACGCCTACTACGGCGGAAGCTACGCTATGGACTACTGGG<br>GCCAGGGAACCAGCGTGACCGTGAGCAGCGCGGCCGCTATCGA<br>GGTGGAGCAGAAGCTGATCAGCGAGGAGGACCTGCTAGACAAT<br>GAGAAGAGCAATGGAACCATTATCCATGTGAAAGGGAAACACC<br>TTTGTCCAAGTCCCCTATTTCCCGGACCTTCTAAGCCCTTTTGGG<br>TGCTGGTGGTGGTTGGTGGAGTCCTGGCTTGCTATAGCTTGCTA<br>GTAACAGTGGCCTTTATTATTTTCTGGGTGAGGAGTAAGAGGAG<br>CAGGCTCCTGCACAGTGACTACATGAACATGACTCCCCGCCGCC<br>CCGGGCCCACCCGCAAGCATTACCAGCCCTATGCCCCACCACGC<br>GACTTCGCAGCCTATCGCTCCAGAGTGAAGTTCAGCAGGAGCGC<br>AGACGCCCCCGCGTACCAGCAGGGCCAGAACCAGCTCTATAAC<br>GAGCTCAATCTAGGACGAAGAGAGGAGTACGATGTTTTGGACA<br>AGAGACGTGGCCGGGACCCTGAGATGGGGGGAAAGCCGAGAAG<br>GAAGAACCCTCAGGAAGGCCTGTACAATGAACTGCAGAAAGAT<br>AAGATGGCGGAGGCCTACAGTGAGATTGGGATGAAAGGCGAGC<br>GCCGGAGGGGCAAGGGGCACGATGGCCTTTACCAGGGTCTCAG<br>TACAGCCACCAAGGACACCTACGACGCCCTTCACATGCAGGCCC<br>TGCCCCCTCGCTAA |
| SEQ ID NO: 112<br>Nucleotide sequence<br>encoding for FBB/Y02 | ATGGGCCCAGGAGTTCTGCTGCTCCTGCTGGTGGCCACAGCTTG<br>GCATGGTCAGGGAGGTGACATCCAGATGACACAGACAACATCC<br>TCCCTCTCCGCTTCCCTCGGAGACAGGGTCACAATTTCCTGCAG<br>GGCTTCCCAGGACATTTCCAAGTACCTCAACTGGTACCAGCAGA<br>AGCCTGACGGAACAGTCAAGCTCCTCATTTACCACACATCCAGG<br>CTCCACTCCGGAGTCCCTTCCAGGTTCTCCGGATCCGGATCCGG<br>AACAGACTACTCCCTCACAATTTCCAACCTCGAGCAGGAGGACA<br>TTGCTACATACTTCTGCCAGCAGGGAAACACACTCCCTTACACA<br>TTCGGAGGAGGAACAAAGCTCGAGATTACAGGAGGTGGCGGTT<br>CCGGTGGTGGAGGCTCCGGTGGTGGTGGATCTGAGGTCAAGCTC<br>CAGGAGTCCGGACCTGGACTTGTCGCTCCTTCTCAGTCTCTCTCC<br>GTCACATGCACAGTCTCCGGAGTCTCCCTCCCTGATTATGGAGT<br>CTCCTGGATTAGGCAACCTCCTAGGAAAGGACTCGAATGGCTCG<br>GAGTCATTTGGGGATCCGAAACAACATATTATAATTCCGCTCTC<br>AAATCCAGGCTCACAATTATTAAAGATAATTCCAAATCCCAAGT<br>CTTTCTCAAGATGAACTCCCTCCAGACAGACGACACAGCTATTT<br>ACTACTGCGCTAAGCACTACTACTACGGGGGATCTTACGCTATG<br>GACTACTGGGGACAGGGAACATCCGTCACAGTCTCTTCCGCTGC<br>TGCTCCCACCACCACACCCGCTCCCAGACCCCCTACCCCTGCCC<br>CCACCATCGCCAGCCAGCCCCTGAGCCTGAGACCCGAGGCCTGC<br>AGACCTGCCGCCGGCGGAGCCGTGCACACCAGAGGCCTGGACT<br>TCGCCTGCGACATCTACATCTGGGCTCCCCTGGCCGGCACCTGC<br>GGCGTGCTGCTGCTGAGCCTGGTGATCACCCTGTACTGCAACCA<br>CAAGAGAGGCAGAAAGAAGCTGCTGTACATCTTCAAGCAGCCC<br>TTCATGAGACCCGTGCAGACCACCCAGGAGGAGGACGGCTGCA<br>GCTGCAGATTCCCCGAGGAGGAGGAGGGCGGCTGCGAGCTGGA<br>CTACAAAGACGATGACGACAAGCGGAGAAAGCGCAGCGGCTCC<br>GGCGCCACGAACTTCTCTCTGTTAAAGCAAGCAGGAGACGTGGA |

-continued

| 6. SEQUENCES | |
|---|---|
| ID | SEQ |
| | AGAAAACCCCGGTCCCAACATGGCTCTGCCTGTGACAGCTCTGC<br>TGCTGCCTCTGGCTCTGCTGCTGCACGCCGCTAGACCCGACATC<br>CAGATGACCCAGACCACCAGCAGCCTGAGCGCCAGCCTGGGCG<br>ACAGAGTGACCATCAGCTGCAGAGCCAGCCAGGACATCAGCAA<br>GTACCTGAACTGGTACCAGCAGAAGCCCGACGGCACCGTGAAG<br>CTGCTGATCTACCACACCAGCAGACTGCACAGCGGCGTGCCCAG<br>CAGATTCAGCGGCAGCGGCAGCGGCACCGACTACAGCCTGACC<br>ATCAGCAACCTGGAGCAGGAGGACATCGCCACCTACTTCTGCCA<br>GCAGGGCAACACCCTGCCCTACACCTTCGGCGGAGGCACCAAG<br>CTGGAGATCACCGGCGGAGGAGGAAGCGGAGGAGGAGGCAGC<br>GGAGGAGGAGGCAGCGAGGTGAAGCTGCAGGAGAGCGGCCCC<br>GGCCTGGTGGCCCCCAGCCAGAGCCTGAGCGTGACCTGCACCGT<br>GAGCGGCGTGAGCCTGCCCGACTACGGCGTGAGCTGGATCAGA<br>CAGCCTCCCAGAAAGGGCCTGGAGTGGCTGGGCGTGATCTGGG<br>GCAGCGAGACCACCTACTACAACAGCGCCCTGAAGAGCAGACT<br>GACCATCATTAAGGACAACAGCAAGTCCCAGGTGTTCCTGAAGA<br>TGAACAGCCTGCAGACCGACGACACCGCCATCTACTACTGCGCC<br>AAGCACTACGCCTACGGCGGAAGCTACGCTATGGACTACTGGG<br>GCCAGGGAACCAGCGTGACCGTGAGCAGCGCGGCCGCTATCGA<br>GGTGGAGCAGAAGCTGATCAGCGAGGAGGACCTGCTGGACAAC<br>GAGAAGAGCAACGGCACCATCATCCACGTGAAGGGCAAGCACC<br>TGTGCCCCAGCCCCCTGTTCCCCGGCCCCAGCAAGCCCTTCTGG<br>GTGCTGGTGGTGGTGGGCGGCGTGCTGGCCTGCTACAGCCTGCT<br>GGTGACCGTGGCCTTCATCATCTTCTGGGTGCGGAGCAAGCGGA<br>GCCGGCTGCTGCACAGCGACTACATGAACATGACCCCCCGGCGG<br>CCTGGGCCCACCCGCAAGCATTACCAGCCCTATGCCCCACCACG<br>CGACTTCGCAGCCTATCGCTCCAGAGTGAAGTTCAGCAGGAGCG<br>CAGACGCCCCCGCGTACCAGCAGGGCCAGAACCAGCTCTATAA<br>CGAGCTCAATCTAGGACGAAGAGAGGAGTACGATGTTTTGGAC<br>AAGAGACGTGGCCGGGACCCTGAGATGGGGGGAAAGCCGAGAA<br>GGAAGAACCCTCAGGAAGGCCTGTACAATGAACTGCAGAAAGA<br>TAAGATGGCGGAGGCCTACAGTGAGATTGGGATGAAAGGCGAG<br>CGCCGGAGGGGCAAGGGGCACGATGGCCTTTACCAGGGTCTCA<br>GTACAGCCACCAAGGACACCTACGACGCCCTTCACATGCAGGCC<br>CTGCCCCCTCGCTAA |
| SEQ ID NO: 113<br>Nucleotide sequence<br>encoding for FBB/Y03 | ATGGGCCCAGGAGTTCTGCTGCTCCTGCTGGTGGCCACAGCTTG<br>GCATGGTCAGGGAGGTGACATCCAGATGACACAGACAACATCC<br>TCCCTCTCCGCTTCCCTCGGAGACAGGGTCACAATTTCCTGCAG<br>GGCTTCCCAGGACATTTCCAAGTACCTCAACTGGTACCAGCAGA<br>AGCCTGACGGAACAGTCAAGCTCCTCATTTACCACACATCCAGG<br>CTCCACTCCGGAGTCCCTTCCAGGTTCTCCGGATCCGGATCCGG<br>AACAGACTACTCCCTCACAATTTCCAACCTCGAGCAGGAGGACA<br>TTGCTACATACTTCTGCCAGCAGGGAAACACACTCCCTTACACA<br>TTCGGAGGAGGAACAAAGCTCGAGATTACAGGAGGTGGCGGTT<br>CCGGTGGTGGAGGCTCCGGTGGTGGTGGATCTGAGGTCAAGCTC<br>CAGGAGTCCGGACCTGGACTTGTCGCTCCTTCTCAGTCTCTCTCC<br>GTCACATGCACAGTCTCCGGAGTCTCCCTCCCTGATTATGGAGT<br>CTCCTGGATTAGGCAACCTCCTAGGAAAGGACTCGAATGGCTCG<br>GAGTCATTTGGGGATCCGAAACAACATATTATAATTCCGCTCTC<br>AAATCCAGGCTCACAATTATTAAAGATAATTCCAAATCCCAAGT<br>CTTTCTCAAGATGAACTCCCTCCAGACAGACGACACAGCTATTT<br>ACTACTGCGCTAAGCACTACTACTACGGGGGATCTTACGCTATG<br>GACTACTGGGGACAGGGAACATCCGTCACAGTCTCTTCCGCTGC<br>TGCTCCCACCACCACACCCGCTCCCAGACCCCCTACCCCTGCCC<br>CCACCATCGCCAGCCAGCCCCTGAGCCTGAGACCCGAGGCCTGC<br>AGACCTGCCGCCGGCGGAGCCGTGCACACCAGAGGCCTGGACT<br>TCGCCTGCGACATCTACATCTGGGCTCCCCTGGCCGGCACCTGC<br>GGCGTGCTGCTGCTGAGCCTGGTGATCACCCTGTACTGCAACCA<br>CAAGAGAGGCAGAAAGAAGCTGCTGTACATCTTCAAGCAGCCC<br>TTCATGAGACCCGTGCAGACCACCCAGGAGGAGGACGGCTGCA<br>GCTGCAGATTCCCCGAGGAGGAGGAGGGCGGCTGCGAGCTGGA<br>CTACAAAGACGATGACGACAAGCGGAGAAAGCGCAGCGGCTCC<br>GGCGCCACGAACTTCTCTCTGTTAAAGCAAGCAGGAGACGTGGA<br>AGAAAACCCCGGTCCCAACATGGCTCTGCCTGTGACAGCTCTGC<br>TGCTGCCTCTGGCTCTGCTGCTGCACGCCGCTAGACCCGACATC<br>CAGATGACCCAGACCACCAGCAGCCTGAGCGCCAGCCTGGGCG<br>ACAGAGTGACCATCAGCTGCAGAGCCAGCCAGGACATCAGCAA<br>GTACCTGAACTGGTACCAGCAGAAGCCCGACGGCACCGTGAAG<br>CTGCTGATCTACCACACCAGCAGACTGCACAGCGGCGTGCCCAG<br>CAGATTCAGCGGCAGCGGCAGCGGCACCGACTACAGCCTGACC<br>ATCAGCAACCTGGAGCAGGAGGACATCGCCACCTACTTCTGCCA<br>GCAGGGCAACACCCTGCCCTACACCTTCGGCGGAGGCACCAAG<br>CTGGAGATCACCGGCGGAGGAGGAAGCGGAGGAGGAGGCAGC<br>GGAGGAGGAGGCAGCGAGGTGAAGCTGCAGGAGAGCGGCCCC |

-continued

6. SEQUENCES

| ID | SEQ |
|---|---|
| | GGCCTGGTGGCCCCCAGCCAGAGCCTGAGCGTGACCTGCACCGT<br>GAGCGGCGTGAGCCTGCCCGACTACGGCGTGAGCTGGATCAGA<br>CAGCCTCCCAGAAAGGGCCTGGAGTGGCTGGGCGTGATCTGGG<br>GCAGCGAGACCACCTACTACAACAGCGCCCTGAAGAGCAGACT<br>GACCATCATTAAGGACAACAGCAAGTCCCAGGTGTTCCTGAAGA<br>TGAACAGCCTGCAGACCGACGACACCGCCATCTACTACTGCGCC<br>AAGCACTACTACGCCGGCGGAAGCTACGCTATGGACTACTGGG<br>GCCAGGGAACCAGCGTGACCGTGAGCAGCGCGGCCGCTATCGA<br>GGTGGAGCAGAAGCTGATCAGCGAGGAGGACCTGCTGGACAAC<br>GAGAAGAGCAACGGCACCATCATCCACGTGAAGGGCAAGCACC<br>TGTGCCCCAGCCCCCTGTTCCCCGGCCCCAGCAAGCCCTTCTGG<br>GTGCTGGTGGTGGTGGGCGGCGTGCTGGCCTGCTACAGCCTGCT<br>GGTGACCGTGGCCTTCATCATCTTCTGGGTGCGGAGCAAGCGGA<br>GCCGGCTGCTGCACAGCGACTACATGAACATGACCCCCCGGCGG<br>CCTGGGCCCACCCGCAAGCATTACCAGCCCTATGCCCCACCACG<br>CGACTTCGCAGCCTATCGCTCCAGAGTGAAGTTCAGCAGGAGCG<br>CAGACGCCCCCGCGTACCAGCAGGGCCAGAACCAGCTCTATAA<br>CGAGCTCAATCTAGGACGAAGAGAGGAGTACGATGTTTTGGAC<br>AAGAGACGTGGCCGGGACCCTGAGATGGGGGGAAAGCCGAGAA<br>GGAAGAACCCTCAGGAAGGCCTGTACAATGAACTGCAGAAAGA<br>TAAGATGGCGGAGGCCTACAGTGAGATTGGGATGAAAGGCGAG<br>CGCCGGAGGGGCAAGGGGCACGATGGCCTTTACCAGGGTCTCA<br>GTACAGCCACCAAGGACACCTACGACGCCCTTCACATGCAGGCC<br>CTGCCCCCTCGCTAA |
| SEQ ID NO: 114<br>Nucleotide sequence<br>encoding for FBB/Y04 | ATGGGCCCAGGAGTTCTGCTGCTCCTGCTGGTGGCCACAGCTTG<br>GCATGGTCAGGGAGGTGACATCCAGATGACACAGACAACATCC<br>TCCCTCTCCGCTTCCCTCGGAGACAGGGTCACAATTTCCTGCAG<br>GGCTTCCCAGGACATTTCCAAGTACCTCAACTGGTACCAGCAGA<br>AGCCTGACGGAACAGTCAAGCTCCTCATTTACCACACATCCAGG<br>CTCCACTCCGGAGTCCCTTCCAGGTTCTCCGGATCCGGATCCGG<br>AACAGACTACTCCCTCACAATTTCCAACCTCGAGCAGGAGGACA<br>TTGCTACATACTTCTGCCAGCAGGGAAACACACTCCCTTACACA<br>TTCGGAGGAGGAACAAAGCTCGAGATTACAGGAGGTGGCGGTT<br>CCGGTGGTGGAGGCTCCGGTGGTGGTGGATCTGAGGTCAAGCTC<br>CAGGAGTCCGGACCTGGACTTGTCGCTCCTTCTCAGTCTCTCTCC<br>GTCACATGCACAGTCTCCGGAGTCTCCCTCCCTGATTATGGAGT<br>CTCCTGGATTAGGCAACCTCCTAGGAAAGGACTCGAATGGCTCG<br>GAGTCATTTGGGGATCCGAAACAACATATTATAATTCCGCTCTC<br>AAATCCAGGCTCACAATTATTAAAGATAATTCCAAATCCCAAGT<br>CTTTCTCAAGATGAACTCCCTCCAGACAGACGACACAGCTATTT<br>ACTACTGCGCTAAGCACTACTACTACGGGGGATCTTACGCTATG<br>GACTACTGGGGACAGGGAACATCCGTCACAGTCTCTTCCGCTGC<br>TGCTCCCACCACCACACCCGCTCCCAGACCCCCTACCCCTGCCC<br>CCACCATCGCCAGCCAGCCCCTGAGCCTGAGACCCGAGGCCTGC<br>AGACCTGCCGCCGGCGGAGCCGTGCACACCAGAGGCCTGGACT<br>TCGCCTGCGACATCTACATCTGGGCTCCCCTGGCCGGCACCTGC<br>GGCGTGCTGCTGCTGAGCCTGGTGATCACCCTGTACTGCAACCA<br>CAAGAGAGGCAGAAAGAAGCTGCTGTACATCTTCAAGCAGCCC<br>TTCATGAGACCCGTGCAGACCACCCAGGAGGAGGACGGCTGCA<br>GCTGCAGATTCCCCGAGGAGGAGGAGGGCGGCTGCGAGCTGGA<br>CTACAAAGACGATGACGACAAGCGGAGAAAGCGCAGCGGCTCC<br>GGCGCCACGAACTTCTCTCTGTTAAAGCAAGCAGGAGACGTGGA<br>AGAAAACCCCGGTCCCAACATGGCTCTGCCTGTGACAGCTCTGC<br>TGCTGCCTCTGGCTCTGCTGCTGCACGCCGCTAGACCCGACATC<br>CAGATGACCCAGACCACCAGCAGCCTGAGCGCCAGCCTGGGCG<br>ACAGAGTGACCATCAGCTGCAGAGCCAGCCAGGACATCAGCAA<br>GTACCTGAACTGGTACCAGCAGAAGCCCGACGGCACCGTGAAG<br>CTGCTGATCTACCACACCAGCAGACTGCACAGCGGCGTGCCCAG<br>CAGATTCAGCGGCAGCGGCAGCGGCACCGACTACAGCCTGACC<br>ATCAGCAACCTGGAGCAGGAGGACATCGCCACCTACTTCTGCCA<br>GCAGGGCAACACCCTGCCCTACACCTTCGGCGGAGGCACCAAG<br>CTGGAGATCACCGGCGGAGGAGGAAGCGGAGGAGGAGGCAGC<br>GGAGGAGGAGGCAGCGAGGTGAAGCTGCAGGAGAGCGGCCCC<br>GGCCTGGTGGCCCCCAGCCAGAGCCTGAGCGTGACCTGCACCGT<br>GAGCGGCGTGAGCCTGCCCGACTACGGCGTGAGCTGGATCAGA<br>CAGCCTCCCAGAAAGGGCCTGGAGTGGCTGGGCGTGATCTGGG<br>GCAGCGAGACCACCTACTACAACAGCGCCCTGAAGAGCAGACT<br>GACCATCATTAAGGACAACAGCAAGTCCCAGGTGTTCCTGAAGA<br>TGAACAGCCTGCAGACCGACGACACCGCCATCTACTACTGCGCC<br>AAGCACTACTACTACGGCGGAAGCGCCGCTATGGACTACTGGG<br>GCCAGGGAACCAGCGTGACCGTGAGCAGCGCGGCCGCTATCGA<br>GGTGGAGCAGAAGCTGATCAGCGAGGAGGACCTGCTGGACAAC<br>GAGAAGAGCAACGGCACCATCATCCACGTGAAGGGCAAGCACC<br>TGTGCCCCAGCCCCCTGTTCCCCGGCCCCAGCAAGCCCTTCTGG |

-continued

6. SEQUENCES

| ID | SEQ |
|---|---|
| | GTGCTGGTGGTGGTGGGCGGCGTGCTGGCCTGCTACAGCCTGCT<br>GGTGACCGTGGCCTTCATCATCTTCTGGGTGCGGAGCAAGCGGA<br>GCCGGCTGCTGCACAGCGACTACATGAACATGACCCCCCGGCGG<br>CCTGGGCCCACCCGCAAGCATTACCAGCCCTATGCCCCACCACG<br>CGACTTCGCAGCCTATCGCTCCAGAGTGAAGTTCAGCAGGAGCG<br>CAGACGCCCCCGCGTACCAGCAGGGCCAGAACCAGCTCTATAA<br>CGAGCTCAATCTAGGACGAAGAGAGGAGTACGATGTTTTGGAC<br>AAGAGACGTGGCCGGGACCCTGAGATGGGGGGAAAGCCGAGAA<br>GGAAGAACCCTCAGGAAGGCCTGTACAATGAACTGCAGAAAGA<br>TAAGATGGCGGAGGCCTACAGTGAGATTGGGATGAAAGGCGAG<br>CGCCGGAGGGGCAAGGGGCACGATGGCCTTTACCAGGGTCTCA<br>GTACAGCCACCAAGGACACCTACGACGCCCTTCACATGCAGGCC<br>CTGCCCCCTCGCTAA |
| SEQ ID NO: 115<br>Nucleotide sequence<br>encoding for FBB/Y05 | ATGGGCCCAGGAGTTCTGCTGCTCCTGCTGGTGGCCACAGCTTG<br>GCATGGTCAGGGAGGTGACATCCAGATGACACAGACAACATCC<br>TCCCTCTCCGCTTCCCTCGGAGACAGGGTCACAATTTCCTGCAG<br>GGCTTCCCAGGACATTTCCAAGTACCTCAACTGGTACCAGCAGA<br>AGCCTGACGGAACAGTCAAGCTCCTCATTTACCACACATCCAGG<br>CTCCACTCCGGAGTCCCTTCCAGGTTCTCCGGATCCGGATCCGG<br>AACAGACTACTCCCTCACAATTTCCAACCTCGAGCAGGAGGACA<br>TTGCTACATACTTCTGCCAGCAGGGAAACACACTCCCTTACACA<br>TTCGGAGGAGGAACAAAGCTCGAGATTACAGGAGGTGGCGGTT<br>CCGGTGGTGGAGGCTCCGGTGGTGGTGGATCTGAGGTCAAGCTC<br>CAGGAGTCCGGACCTGGACTTGTCGCTCCTTCTCAGTCTCTCTCC<br>GTCACATGCACAGTCTCCGGAGTCTCCCTCCCTGATTATGGAGT<br>CTCCTGGATTAGGCAACCTCCTAGGAAAGGACTCGAATGGCTCG<br>GAGTCATTTGGGGATCCGAAACAACATATTATAATTCCGCTCTC<br>AAATCCAGGCTCACAATTATTAAAGATAATTCCAAATCCCAAGT<br>CTTTCTCAAGATGAACTCCCTCCAGACAGACGACACAGCTATTT<br>ACTACTGCGCTAAGCACTACTACTACGGGGGATCTTACGCTATG<br>GACTACTGGGGACAGGGAACATCCGTCACAGTCTCTTCCGCTGC<br>TGCTCCCACCACCACACCCGCTCCCAGACCCCCTACCCCTGCCC<br>CCACCATCGCCAGCCAGCCCCTGAGCCTGAGACCCGAGGCCTGC<br>AGACCTGCCGCCGGCGGAGCCGTGCACACCAGAGGCCTGGACT<br>TCGCCTGCGACATCTACATCTGGGCTCCCCTGGCCGGCACCTGC<br>GGCGTGCTGCTGCTGAGCCTGGTGATCACCCTGTACTGCAACCA<br>CAAGAGAGGCAGAAAGAAGCTGCTGTACATCTTCAAGCAGCCC<br>TTCATGAGACCCGTGCAGACCACCCAGGAGGAGGACGGCTGCA<br>GCTGCAGATTCCCCGAGGAGGAGGAGGGCGGCTGCGAGCTGGA<br>CTACAAAGACGATGACGACAAGCGGAGAAAGCGCAGCGGCTCC<br>GGCGCCACGAACTTCTCTCTGTTAAAGCAAGCAGGAGACGTGGA<br>AGAAAACCCCGGTCCCAACATGGCTCTGCCTGTGACAGCTCTGC<br>TGCTGCCTCTGGCTCTGCTGCTGCACGCCGCTAGACCCGACATC<br>CAGATGACCCAGACCACCAGCAGCCTGAGCGCCAGCCTGGGCG<br>ACAGAGTGACCATCAGCTGCAGAGCCAGCCAGGACATCAGCAA<br>GTACCTGAACTGGTACCAGCAGAAGCCCGACGGCACCGTGAAG<br>CTGCTGATCTACCACACCAGCAGACTGCACAGCGGCGTGCCCAG<br>CAGATTCAGCGGCAGCGGCAGCGGCACCGACTACAGCCTGACC<br>ATCAGCAACCTGGAGCAGGAGGACATCGCCACCTACTTCTGCCA<br>GCAGGGCAACACCCTGCCCTACACCTTCGGCGGAGGCACCAAG<br>CTGGAGATCACCGGCGGAGGAGGAAGCGGAGGAGGAGGCAGC<br>GGAGGAGGAGGCAGCGAGGTGAAGCTGCAGGAGAGCGGCCCC<br>GGCCTGGTGGCCCCCAGCCAGAGCCTGAGCGTGACCTGCACCGT<br>GAGCGGCGTGAGCCTGCCCGACTACGGCGTGAGCTGGATCAGA<br>CAGCCTCCCAGAAAGGGCCTGGAGTGGCTGGGCGTGATCTGGG<br>GCAGCGAGACCACCTACTACAACAGCGCCCTGAAGAGCAGACT<br>GACCATCATTAAGGACAACAGCAAGTCCCAGGTGTTCCTGAAGA<br>TGAACAGCCTGCAGACCGACGACACCGCCATCTACTACTGCGCC<br>AAGCACTACTACTACGGCGGAAGCTACGCTATGGACGCCTGGG<br>GCCAGGGAACCAGCGTGACCGTGAGCAGCGCGGCCGCTATCGA<br>GGTGGAGCAGAAGCTGATCAGCGAGGAGGACCTGCTGGACAAC<br>GAGAAGAGCAACGGCACCATCATCCACGTGAAGGGCAAGCACC<br>TGTGCCCCAGCCCCCTGTTCCCCGGCCCCAGCAAGCCCTTCTGG<br>GTGCTGGTGGTGGTGGGCGGCGTGCTGGCCTGCTACAGCCTGCT<br>GGTGACCGTGGCCTTCATCATCTTCTGGGTGCGGAGCAAGCGGA<br>GCCGGCTGCTGCACAGCGACTACATGAACATGACCCCCCGGCGG<br>CCTGGGCCCACCCGCAAGCATTACCAGCCCTATGCCCCACCACG<br>CGACTTCGCAGCCTATCGCTCCAGAGTGAAGTTCAGCAGGAGCG<br>CAGACGCCCCCGCGTACCAGCAGGGCCAGAACCAGCTCTATAA<br>CGAGCTCAATCTAGGACGAAGAGAGGAGTACGATGTTTTGGAC<br>AAGAGACGTGGCCGGGACCCTGAGATGGGGGGAAAGCCGAGAA<br>GGAAGAACCCTCAGGAAGGCCTGTACAATGAACTGCAGAAAGA<br>TAAGATGGCGGAGGCCTACAGTGAGATTGGGATGAAAGGCGAG<br>CGCCGGAGGGGCAAGGGGCACGATGGCCTTTACCAGGGTCTCA |

-continued

6. SEQUENCES

| ID | SEQ |
|---|---|
| | GTACAGCCACCAAGGACACCTACGACGCCCTTCACATGCAGGCC<br>CTGCCCCCTCGCTAA |
| SEQ ID NO: 116<br>Nucleotide sequence<br>encoding for 1BB/F | ATGGGACCTGGCGTGCTGCTGCTGCTGCTGGTGGCCACCGCTTG<br>GCATGGACAGGGAGGACAGATCGTGCTGAGCCAGAGCCCTGCC<br>ATCCTGAGCGCCAGCCCTGGCGAGAAGGTGACCATGACCTGCA<br>GAGCCAGCTCCAGCCTGAGCTTCATGCACTGGTACCAGCAGAAG<br>CCCGGCAGCAGCCCTAAGCCCTGGATCTACGCCACCAGCAACCT<br>GGCCAGCGGCGTGCCCGCCAGATTCAGCGGCAGCGGCAGCGGC<br>ACCAGCTACAGCCTGACCATCAGCAGAGTGGAGGCCGAGGACG<br>CCGCCACCTACTTCTGCCACCAGTGGAGCAGCAACCCCCTGACC<br>TTCGGCGCCGGCACCAAGGTGGAGATCAAGAGAAAGGGCAGCA<br>CCAGCGGAAGCGGCAAGCCTGGAAGCGGAGAGGGCAGCACCAA<br>GGGACAGGTGCAGCTGAGACAGCCTGGCGCCGAGCTGGTGAAG<br>CCCGGCGCCAGCGTGAAGATGAGCTGCAAGGCCAGCGGCTACA<br>CCTTCACCAGCTACAACATGCACTGGGTGAAGCAGACCCCTGGC<br>CAGGGCCTGGAGTGGATCGGCGCCATCTATCCCGGCAACGGCG<br>ACACCAGCTACAACCAGAAGTTCAAGGGCAAGGCCACCCTGAC<br>CGCCGACAAGAGCAGCAGCACCGCCTACATGCAGCTGAGCAGC<br>CTGACCAGCGAGGACAGCGCCGTGTACTACTGCGCCAGAAGCC<br>ACTACGGCAGCAACTACGTGGACTACTTCGACTACTGGGGCCAG<br>GGCACCCTGGTGACCGTGAGCACCGGCGCGGCCGCCCCCACCAC<br>CACACCCGCTCCCAGACCCCCTACCCCTGCCCCCACCATCGCCA<br>GCCAGCCCCTGAGCCTGAGACCCGAGGCCTGCAGACCTGCCGCC<br>GGCGGAGCCGTGCACACCAGAGGCCTGGACTTCGCCTGCGACAT<br>CTACATCTGGGCTCCCCTGGCCGGCACCTGCGGCGTGCTGCTGC<br>TGAGCCTGGTGATCACCCTGTACTGCAACCACAAGAGAGGCAG<br>AAAGAAGCTGCTGTACATCTTCAAGCAGCCCTTCATGAGACCCG<br>TGCAGACCACCCAGGAGGAGGACGGCTGCAGCTGCAGATTCCC<br>CGAGGAGGAGGAGGGCGGCTGCGAGCTGGACTACAAAGACGAT<br>GACGACAAGAGAAGAAAGAGAAGCGGCAGCGGCGCCACGAAC<br>TTCTCTCTGTTAAAGCAAGCAGGAGACGTGGAAGAAAACCCCG<br>GTCCCAACATGGCTCTGCCTGTGACAGCTCTGCTGCTGCCTCTGG<br>CTCTGCTGCTGCACGCCGCTAGACCCGACATCCAGATGACCCAG<br>ACCACCAGCAGCCTGAGCGCCAGCCTGGGCGACAGAGTGACCA<br>TCAGCTGCAGAGCCAGCCAGGACATCAGCAAGTACCTGAACTG<br>GTACCAGCAGAAGCCCGACGGCACCGTGAAGCTGCTGATCTACC<br>ACACCAGCAGACTGCACAGCGGCGTGCCCAGCAGATTCAGCGG<br>CAGCGGCAGCGGCACCGACTACAGCCTGACCATCAGCAACCTG<br>GAGCAGGAGGACATCGCCACCTACTTCTGCCAGCAGGGCAACA<br>CCCTGCCCTACACCTTCGGCGGAGGCACCAAGCTGGAGATCACC<br>GGCGGAGGAGGAAGCGGAGGAGGAGGCAGCGGAGGAGGAGGC<br>AGCGAGGTGAAGCTGCAGGAGAGCGGCCCCGGCCTGGTGGCCC<br>CCAGCCAGAGCCTGAGCGTGACCTGCACCGTGAGCGGCGTGAG<br>CCTGCCCGACTACGGCGTGAGCTGGATCAGACAGCCTCCCAGAA<br>AGGGCCTGGAGTGGCTGGGCGTGATCTGGGGCAGCGAGACCAC<br>CTACTACAACAGCGCCCTGAAGAGCAGACTGACCATCATTAAGG<br>ACAACAGCAAGTCCCAGGTGTTCCTGAAGATGAACAGCCTGCA<br>GACCGACGACACCGCCATCTACTACTGCGCCAAGCACTACTACT<br>ACGGCGGAAGCTACGCTATGGACTACTGGGGCCAGGGAACCAG<br>CGTGACCGTGAGCAGCGCGGCCGCTATCGAGGTGGAGCAGAAG<br>CTGATCAGCGAGGAGGACCTGCTAGACAATGAGAAGAGCAATG<br>GAACCATTATCCATGTGAAAGGGAAACACCTTTGTCCAAGTCCC<br>CTATTTCCCGGACCTTCTAAGCCCTTTTGGGTGCTGGTGGTGGTT<br>GGTGGAGTCCTGGCTTGCTATAGCTTGCTAGTAACAGTGGCCTT<br>TATTATTTTCTGGGTGAGGAGTAAGAGGAGCAGGCTCCTGCACA<br>GTGACTACATGAACATGACTCCCCGCCGCCCCGGGCCCACCCGC<br>AAGCATTACCAGCCCTATGCCCCACCACGCGACTTCGCAGCCTA<br>TCGCTCCAGAGTGAAGTTCAGCAGGAGCGCAGACGCCCCCGCGT<br>ACCAGCAGGGCCAGAACCAGCTCTATAACGAGCTCAATCTAGG<br>ACGAAGAGAGGAGTACGATGTTTTGGACAAGAGACGTGGCCGG<br>GACCCTGAGATGGGGGGAAAGCCGAGAAGGAAGAACCCTCAGG<br>AAGGCCTGTACAATGAACTGCAGAAAGATAAGATGGCGGAGGC<br>CTACAGTGAGATTGGGATGAAAGGCGAGCGCCGGAGGGGCAAG<br>GGGCACGATGGCCTTTACCAGGGTCTCAGTACAGCCACCAAGGA<br>CACCTACGACGCCCTTCACATGCAGGCCCTGCCCCCTCGCTAA |
| SEQ ID NO: 117<br>Nucleotide sequence<br>encoding for RBB/F | ATGGGCCCTGGAGTGCTGCTGCTCCTGCTGGTGGCCACAGCTTG<br>GCACGGCCAGGGAGATATCCAGATGACCCAGACTACATCCTCCC<br>TGTCTGCCTCTCTGGGAGACAGAGTCACCATTAGTTGCAGGGCA<br>AGTCAGGACATTAGCAATTATTTAAACTGGTATCAGCAGAAACC<br>AGATGGAACTGTTAAACTCCTGATCTACTACACATCAATATTAC<br>ACTCAGGAGTCCCATCAAGGTTCAGTGGCAGTGGGTCTGGAACA<br>GATTATTCTCTCACCATTAGCAACCTGGAGCAAGAAGATTTTGC<br>CACTTACTTTTGCCAACAGGGTAATACGCTTCCGTGGACGTTCG |

-continued

6. SEQUENCES

| ID | SEQ |
|---|---|
| | GTGGAGGCACCAAGCTGGAAATCAAAGGCAGCACCAGCGGAAG<br>CGGCAAGCCTGGAAGCGGAGAGGGCAGCACCAAGGGAGAAGT<br>GCAGCTGGTGGAGTCTGGGGGAGGCTTAGTGAAGCCTGGAGGG<br>TCCCTGAAACTCTCCTGTGCAGCCTCTGGATTCGCTTTCAGTATC<br>TATGACATGTCTTGGGTTCGCCAGACTCCGGAGAAGAGGCTGGA<br>GTGGGTCGCATACATTAGTAGTGGTGGTGGTACCACCTACTATC<br>CAGACACTGTGAAGGGCCGATTCACCATCTCCAGAGACAATGCC<br>AAGAACACCCTGTACCTGCAAATGAGCAGTCTGAAGTCTGAGG<br>ACACAGCCATGTATTACTGTGCAAGACATAGTGGCTACGGTAGT<br>AGCTACGGGGTTTTGTTTGCTTACTGGGGCCAAGGGACTCTGGT<br>CACTGTCTCTGCCGCGGCCGCCCCCACCACCACACCCGCTCCCA<br>GACCCCCTACCCCTGCCCCCACCATCGCCAGCCAGCCCCTGAGC<br>CTGAGACCCGAGGCCTGCAGACCTGCCGCCGGCGGAGCCGTGC<br>ACACCAGAGGCCTGGACTTCGCCTGCGACATCTACATCTGGGCT<br>CCCCTGGCCGGCACCTGCGGCGTGCTGCTGCTGAGCCTGGTGAT<br>CACCCTGTACTGCAACCACAAGAGAGGCAGAAAGAAGCTGCTG<br>TACATCTTCAAGCAGCCCTTCATGAGACCCGTGCAGACCACCCA<br>GGAGGAGGACGGCTGCAGCTGCAGATTCCCCGAGGAGGAGGAG<br>GGCGGCTGCGAGCTGGACTACAAAGACGATGACGACAAGCGGA<br>GAAAGCGCAGCGGCTCCGGCGCCACGAACTTCTCTCTGTTAAAG<br>CAAGCAGGAGACGTGGAAGAAAACCCCGGTCCCAACATGGCTC<br>TGCCTGTGACAGCTCTGCTGCTGCCTCTGGCTCTGCTGCTGCACG<br>CCGCTAGACCCGACATCCAGATGACCCAGACCACCAGCAGCCTG<br>AGCGCCAGCCTGGGCGACAGAGTGACCATCAGCTGCAGAGCCA<br>GCCAGGACATCAGCAAGTACCTGAACTGGTACCAGCAGAAGCC<br>CGACGGCACCGTGAAGCTGCTGATCTACCACACCAGCAGACTGC<br>ACAGCGGCGTGCCCAGCAGATTCAGCGGCAGCGGCAGCGGCAC<br>CGACTACAGCCTGACCATCAGCAACCTGGAGCAGGAGGACATC<br>GCCACCTACTTCTGCCAGCAGGGCAACACCCTGCCCTACACCTT<br>CGGCGGAGGCACCAAGCTGGAGATCACCGGCGGAGGAGGAAGC<br>GGAGGAGGAGGCAGCGGAGGAGGAGGCAGCGAGGTGAAGCTG<br>CAGGAGAGCGGCCCCGGCCTGGTGGCCCCCAGCCAGAGCCTGA<br>GCGTGACCTGCACCGTGAGCGGCGTGAGCCTGCCCGACTACGGC<br>GTGAGCTGGATCAGACAGCCTCCCAGAAAGGGCCTGGAGTGGC<br>TGGGCGTGATCTGGGGCAGCGAGACCACCTACTACAACAGCGC<br>CCTGAAGAGCAGACTGACCATCATTAAGGACAACAGCAAGTCC<br>CAGGTGTTCCTGAAGATGAACAGCCTGCAGACCGACGACACCG<br>CCATCTACTACTGCGCCAAGCACTACTACTACGGCGGAAGCTAC<br>GCTATGGACTACTGGGGCCAGGGAACCAGCGTGACCGTGAGCA<br>GCGCGGCCGCTATCGAGGTGGAGCAGAAGCTGATCAGCGAGGA<br>GGACCTGCTAGACAATGAGAAGAGCAATGGAACCATTATCCAT<br>GTGAAAGGGAAACACCTTTGTCCAAGTCCCCTATTTCCCGGACC<br>TTCTAAGCCCTTTTGGGTGCTGGTGGTGGTTGGTGGAGTCCTGGC<br>TTGCTATAGCTTGCTAGTAACAGTGGCCTTTATTATTTTCTGGGT<br>GAGGAGTAAGAGGAGCAGGCTCCTGCACAGTGACTACATGAAC<br>ATGACTCCCCGCCGCCCCGGGCCCACCCGCAAGCATTACCAGCC<br>CTATGCCCCACCACGCGACTTCGCAGCCTATCGCTCCAGAGTGA<br>AGTTCAGCAGGAGCGCAGACGCCCCCGCGTACCAGCAGGGCCA<br>GAACCAGCTCTATAACGAGCTCAATCTAGGACGAAGAGAGGAG<br>TACGATGTTTTGGACAAGAGACGTGGCCGGGACCCTGAGATGG<br>GGGGAAAGCCGAGAAGGAAGAACCCTCAGGAAGGCCTGTACAA<br>TGAACTGCAGAAAGATAAGATGGCGGAGGCCTACAGTGAGATT<br>GGGATGAAAGGCGAGCGCCGGAGGGGCAAGGGGCACGATGGC<br>CTTTACCAGGGTCTCAGTACAGCCACCAAGGACACCTACGACGC<br>CCTTCACATGCAGGCCCTGCCCCCTCGCTAA |
| SEQ ID NO: 118<br>Nucleotide sequence<br>encoding for FMC63<br>scFv used in CARs<br>and pCARs | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACTACTACTACGGCGG<br>AAGCTACGCTATGGACTACTGGGGCCAGGGAACCAGCGTGACC<br>GTGAGCAGCG |

-continued

6. SEQUENCES

| ID | SEQ |
|---|---|
| SEQ ID NO: 119<br>Nucleotide sequence encoding for FMC63 scFv containing $V_H$ CDR3 G01 mutation used in CARs and pCARs | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACTACTACTACGCCGG<br>AAGCTACGCTATGGACTACTGGGGCCAGGGAACCAGCGTGACC<br>GTGAGCAGC |
| SEQ ID NO: 120<br>Nucleotide sequence encoding for FMC63 scFv containing $V_H$ CDR3 G02 mutation used in CARs and pCARs | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACTACTACTACGGCGC<br>CAGCTACGCTATGGACTACTGGGGCCAGGGAACCAGCGTGACC<br>GTGAGCAGC |
| SEQ ID NO: 121<br>Nucleotide sequence encoding for FMC63 scFv containing $V_H$ CDR3 Y01 mutation used in CARs and pCARs | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC<br>AACAGCGCCCTGAAGAGCAGACTGACCATCATTAAGGACAACA<br>GCAAGTCCCAGGTGTTCCTGAAGATGAACAGCCTGCAGACCGAC<br>GACACCGCCATCTACTACTGCGCCAAGCACGCCTACTACGGCGG<br>AAGCTACGCTATGGACTACTGGGGCCAGGGAACCAGCGTGACC<br>GTGAGCAGC |
| SEQ ID NO: 122<br>Nucleotide sequence encoding for FMC63 scFv containing $V_H$ CDR3 Y02 mutation used in CARs and pCARs | ATGGCTCTGCCTGTGACAGCTCTGCTGCTGCCTCTGGCTCTGCTG<br>CTGCACGCCGCTAGACCCGACATCCAGATGACCCAGACCACCAG<br>CAGCCTGAGCGCCAGCCTGGGCGACAGAGTGACCATCAGCTGC<br>AGAGCCAGCCAGGACATCAGCAAGTACCTGAACTGGTACCAGC<br>AGAAGCCCGACGGCACCGTGAAGCTGCTGATCTACCACACCAG<br>CAGACTGCACAGCGGCGTGCCCAGCAGATTCAGCGGCAGCGGC<br>AGCGGCACCGACTACAGCCTGACCATCAGCAACCTGGAGCAGG<br>AGGACATCGCCACCTACTTCTGCCAGCAGGGCAACACCCTGCCC<br>TACACCTTCGGCGGAGGCACCAAGCTGGAGATCACCGGCGGAG<br>GAGGAAGCGGAGGAGGAGGCAGCGGAGGAGGAGGCAGCGAGG<br>TGAAGCTGCAGGAGAGCGGCCCCGGCCTGGTGGCCCCCAGCCA<br>GAGCCTGAGCGTGACCTGCACCGTGAGCGGCGTGAGCCTGCCCG<br>ACTACGGCGTGAGCTGGATCAGACAGCCTCCCAGAAAGGGCCT<br>GGAGTGGCTGGGCGTGATCTGGGGCAGCGAGACCACCTACTAC |

-continued

6. SEQUENCES

| ID | SEQ |
|---|---|
| | AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACGCCTACGGCGG AAGCTACGCTATGGACTACTGGGGCCAGGGAACCAGCGTGACC GTGAGCAGC |
| SEQ ID NO: 123 Nucleotide sequence encoding for FMC63 scFv containing $V_H$ CDR3 Y03 mutation used in CARs and pCARs | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACTACGCCGGCGG AAGCTACGCTATGGACTACTGGGGCCAGGGAACCAGCGTGACC GTGAGCAGC |
| SEQ ID NO: 124 Nucleotide sequence encoding for FMC63 scFv containing $V_H$ CDR3 Y04 mutation used in CARs and pCARs | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACTACTACGGCGG AAGCGCCGCTATGGACTACTGGGGCCAGGGAACCAGCGTGACC GTGAGCAGC |
| SEQ ID NO: 125 Nucleotide sequence encoding for FMC63 scFv containing $V_H$ CDR3 Y05 mutation used in CARs and pCARs | ATGGCTCTGCCTGTGACAGCTCTGCTGCTGCCTCTGGCTCTGCTG CTGCACGCCGCTAGACCCGACATCCAGATGACCCAGACCACCAG CAGCCTGAGCGCCAGCCTGGGCGACAGAGTGACCATCAGCTGC AGAGCCAGCCAGGACATCAGCAAGTACCTGAACTGGTACCAGC AGAAGCCCGACGGCACCGTGAAGCTGCTGATCTACCACACCAG CAGACTGCACAGCGGCGTGCCCAGCAGATTCAGCGGCAGCGGC AGCGGCACCGACTACAGCCTGACCATCAGCAACCTGGAGCAGG AGGACATCGCCACCTACTTCTGCCAGCAGGGCAACACCCTGCCC TACACCTTCGGCGGAGGCACCAAGCTGGAGATCACCGGCGGAG GAGGAAGCGGAGGAGGAGGCAGCGGAGGAGGAGGCAGCGAGG TGAAGCTGCAGGAGAGCGGCCCCGGCCTGGTGGCCCCCAGCCA GAGCCTGAGCGTGACCTGCACCGTGAGCGGCGTGAGCCTGCCCG ACTACGGCGTGAGCTGGATCAGACAGCCTCCCAGAAAGGGCCT GGAGTGGCTGGGCGTGATCTGGGGCAGCGAGACCACCTACTAC AACAGCGCCCTGAAGAGCAGACTGACCATCATTAAGGACAACA GCAAGTCCCAGGTGTTCCTGAAGATGAACAGCCTGCAGACCGAC GACACCGCCATCTACTACTGCGCCAAGCACTACTACTACGGCGG AAGCTACGCTATGGACGCCTGGGGCCAGGGAACCAGCGTGACC GTGAGCAGC |
| SEQ ID NO: 126 Nucleotide sequence encoding for 1F5 scFv | ATGGGACCTGGCGTGCTGCTGCTGCTGCTGGTGGCCACCGCTTG GCATGGACAGGGAGGACAGATCGTGCTGAGCCAGAGCCCTGCC ATCCTGAGCGCCAGCCCTGGCGAGAAGGTGACCATGACCTGCA GAGCCAGCTCCAGCCTGAGCTTCATGCACTGGTACCAGCAGAAG CCCGGCAGCAGCCCTAAGCCCTGGATCTACGCCACCAGCAACCT GGCCAGCGGCGTGCCCGCCAGATTCAGCGGCAGCGGCAGCGGC ACCAGCTACAGCCTGACCATCAGCAGAGTGGAGGCCGAGGACG CCGCCACCTACTTCTGCCACCAGTGGAGCAGCAACCCCCTGACC TTCGGCGCCGGCACCAAGGTGGAGATCAAGAGAAAGGGCAGCA |

-continued

6. SEQUENCES

| ID | SEQ |
|---|---|
| | CCAGCGGAAGCGGCAAGCCTGGAAGCGGAGAGGGCAGCACCAA GGGACAGGTGCAGCTGAGACAGCCTGGCGCCGAGCTGGTGAAG CCCGGCGCCAGCGTGAAGATGAGCTGCAAGGCCAGCGGCTACA CCTTCACCAGCTACAACATGCACTGGGTGAAGCAGACCCCTGGC CAGGGCCTGGAGTGGATCGGCGCCATCTATCCCGGCAACGGCG ACACCAGCTACAACCAGAAGTTCAAGGGCAAGGCCACCCTGAC CGCCGACAAGAGCAGCAGCACCGCCTACATGCAGCTGAGCAGC CTGACCAGCGAGGACAGCGCCGTGTACTACTGCGCCAGAAGCC ACTACGGCAGCAACTACGTGGACTACTTCGACTACTGGGGCCAG GGCACCCTGGTGACCGTGAGCACCGGC |
| SEQ ID NO: 127 Nucleotide sequence encoding for RFB4 scFv | ATGGGACCTGGCGTGCTGCTGCTGCTGCTGGTGGCCACCGCTTG GCATGGACAGGGAGGAGATATCCAGATGACCCAGACTACATCC TCCCTGTCTGCCTCTCTGGGAGACAGAGTCACCATTAGTTGCAG GGCAAGTCAGGACATTAGCAATTATTTAAACTGGTATCAGCAGA AACCAGATGGAACTGTTAAACTCCTGATCTACTACACATCAATA TTACACTCAGGAGTCCCATCAAGGTTCAGTGGCAGTGGGTCTGG AACAGATTATTCTCTCACCATTAGCAACCTGGAGCAAGAAGATT TTGCCACTTACTTTTGCCAACAGGGTAATACGCTTCCGTGGACGT TCGGTGGAGGCACCAAGCTGGAAATCAAAGGCAGCACCAGCGG AAGCGGCAAGCCTGGAAGCGGAGAGGGCAGCACCAAGGGAGA AGTGCAGCTGGTGGAGTCTGGGGGAGGCTTAGTGAAGCCTGGA GGGTCCCTGAAACTCTCCTGTGCAGCCTCTGGATTCGCTTTCAGT ATCTATGACATGTCTTGGGTTCGCCAGACTCCGGAGAAGAGGCT GGAGTGGGTCGCATACATTAGTAGTGGTGGTGGTACCACCTACT ATCCAGACACTGTGAAGGGCCGATTCACCATCTCCAGAGACAAT GCCAAGAACACCCTGTACCTGCAAATGAGCAGTCTGAAGTCTGA GGACACAGCCATGTATTACTGTGCAAGACATAGTGGCTACGGTA GTAGCTACGGGGTTTTGTTTGCTTACTGGGGCCAAGGGACTCTG GTCACTGTCTCTGCA |
| SEQ ID NO: 128 Nucleotide sequence encoding for FBB (FMC63 scFv-4-1BB CCR) | ATGGGCCCAGGAGTTCTGCTGCTCCTGCTGGTGGCCACAGCTTG GCATGGTCAGGGAGGTGACATCCAGATGACACAGACAACATCC TCCCTCTCCGCTTCCCTCGGAGACAGGGTCACAATTTCCTGCAG GGCTTCCCAGGACATTTCCAAGTACCTCAACTGGTACCAGCAGA AGCCTGACGGAACAGTCAAGCTCCTCATTTACCACACATCCAGG CTCCACTCCGGAGTCCCTTCCAGGTTCTCCGGATCCGGATCCGG AACAGACTACTCCCTCACAATTTCCAACCTCGAGCAGGAGGACA TTGCTACATACTTCTGCCAGCAGGGAAACACACTCCCTTACACA TTCGGAGGAGGAACAAAGCTCGAGATTACAGGAGGTGGCGGTT CCGGTGGTGGAGGCTCCGGTGGTGGTGGATCTGAGGTCAAGCTC CAGGAGTCCGGACCTGGACTTGTCGCTCCTTCTCAGTCTCTCTCC GTCACATGCACAGTCTCCGGAGTCTCCCTCCCTGATTATGGAGT CTCCTGGATTAGGCAACCTCCTAGGAAAGGACTCGAATGGCTCG GAGTCATTTGGGGATCCGAAACAACATATTATAATTCCGCTCTC AAATCCAGGCTCACAATTATTAAAGATAATTCCAAATCCCAAGT CTTTCTCAAGATGAACTCCCTCCAGACAGACGACACAGCTATTT ACTACTGCGCTAAGCACTACTACTACGGGGGATCTTACGCTATG GACTACTGGGGACAGGGAACATCCGTCACAGTCTCTTCCGCTGC TGCTCCCACCACCACACCCGCTCCCAGACCCCCTACCCCTGCCC CCACCATCGCCAGCCAGCCCCTGAGCCTGAGACCCGAGGCCTGC AGACCTGCCGCCGGCGGAGCCGTGCACACCAGAGGCCTGGACT TCGCCTGCGACATCTACATCTGGGCTCCCCTGGCCGGCACCTGC GGCGTGCTGCTGCTGAGCCTGGTGATCACCCTGTACTGCAACCA CAAGAGAGGCAGAAAGAAGCTGCTGTACATCTTCAAGCAGCCC TTCATGAGACCCGTGCAGACCACCCAGGAGGAGGACGGCTGCA GCTGCAGATTCCCCGAGGAGGAGGAGGGCGGCTGCGAGCTG |
| SEQ ID NO: 129 Nucleotide sequence encoding for 1BB (1F5 scFv-4-1BBCCR) | ATGGGACCTGGCGTGCTGCTGCTGCTGCTGGTGGCCACCGCTTG GCATGGACAGGGAGGACAGATCGTGCTGAGCCAGAGCCCTGCC ATCCTGAGCGCCAGCCCTGGCGAGAAGGTGACCATGACCTGCA GAGCCAGCTCCAGCCTGAGCTTCATGCACTGGTACCAGCAGAAG CCCGGCAGCAGCCCTAAGCCCTGGATCTACGCCACCAGCAACCT GGCCAGCGGCGTGCCCGCCAGATTCAGCGGCAGCGGCAGCGGC ACCAGCTACAGCCTGACCATCAGCAGAGTGGAGGCCGAGGACG CCGCCACCTACTTCTGCCACCAGTGGAGCAGCAACCCCCTGACC TTCGGCGCCGGCACCAAGGTGGAGATCAAGAGAAAGGGCAGCA CCAGCGGAAGCGGCAAGCCTGGAAGCGGAGAGGGCAGCACCAA GGGACAGGTGCAGCTGAGACAGCCTGGCGCCGAGCTGGTGAAG CCCGGCGCCAGCGTGAAGATGAGCTGCAAGGCCAGCGGCTACA CCTTCACCAGCTACAACATGCACTGGGTGAAGCAGACCCCTGGC CAGGGCCTGGAGTGGATCGGCGCCATCTATCCCGGCAACGGCG ACACCAGCTACAACCAGAAGTTCAAGGGCAAGGCCACCCTGAC CGCCGACAAGAGCAGCAGCACCGCCTACATGCAGCTGAGCAGC CTGACCAGCGAGGACAGCGCCGTGTACTACTGCGCCAGAAGCC |

-continued

| 6. SEQUENCES | |
|---|---|
| ID | SEQ |
| | ACTACGGCAGCAACTACGTGGACTACTTCGACTACTGGGGCCAG<br>GGCACCCTGGTGACCGTGAGCACCGGCGCGGCCGCCCCCACCAC<br>CACACCCGCTCCCAGACCCCCTACCCCTGCCCCCACCATCGCCA<br>GCCAGCCCCTGAGCCTGAGACCCGAGGCCTGCAGACCTGCCGCC<br>GGCGGAGCCGTGCACACCAGAGGCCTGGACTTCGCCTGCGACAT<br>CTACATCTGGGCTCCCCTGGCCGGCACCTGCGGCGTGCTGCTGC<br>TGAGCCTGGTGATCACCCTGTACTGCAACCACAAGAGAGGCAG<br>AAAGAAGCTGCTGTACATCTTCAAGCAGCCCTTCATGAGACCCG<br>TGCAGACCACCCAGGAGGAGGACGGCTGCAGCTGCAGATTCCC<br>CGAGGAGGAGGAGGGCGGCTGCGAGCTG |
| SEQ ID NO: 130<br>Nucleotide sequence<br>encoding for RBB<br>(RFB4 scFv-4-1BB<br>CCR) | ATGGGCCCTGGAGTGCTGCTGCTCCTGCTGGTGGCCACAGCTTG<br>GCACGGCCAGGGAGATATCCAGATGACCCAGACTACATCCTCCC<br>TGTCTGCCTCTCTGGGAGACAGAGTCACCATTAGTTGCAGGGCA<br>AGTCAGGACATTAGCAATTATTTAAACTGGTATCAGCAGAAACC<br>AGATGGAACTGTTAAACTCCTGATCTACTACACATCAATATTAC<br>ACTCAGGAGTCCCATCAAGGTTCAGTGGCAGTGGGTCTGGAACA<br>GATTATTCTCTCACCATTAGCAACCTGGAGCAAGAAGATTTTGC<br>CACTTACTTTTGCCAACAGGGTAATACGCTTCCGTGGACGTTCG<br>GTGGAGGCACCAAGCTGGAAATCAAAGGCAGCACCAGCGGAAG<br>CGGCAAGCCTGGAAGCGGAGAGGGCAGCACCAAGGGAGAAGT<br>GCAGCTGGTGGAGTCTGGGGGAGGCTTAGTGAAGCCTGGAGGG<br>TCCCTGAAACTCTCCTGTGCAGCCTCTGGATTCGCTTTCAGTATC<br>TATGACATGTCTTGGGTTCGCCAGACTCCGGAGAAGAGGCTGGA<br>GTGGGTCGCATACATTAGTAGTGGTGGTGGTACCACCTACTATC<br>CAGACACTGTGAAGGGCCGATTCACCATCTCCAGAGACAATGCC<br>AAGAACACCCTGTACCTGCAAATGAGCAGTCTGAAGTCTGAGG<br>ACACAGCCATGTATTACTGTGCAAGACATAGTGGCTACGGTAGT<br>AGCTACGGGGTTTTGTTTGCTTACTGGGGCCAAGGGACTCTGGT<br>CACTGTCTCTGCCGCGGCCGCCCCCACCACCACACCCGCTCCCA<br>GACCCCCTACCCCTGCCCCCACCATCGCCAGCCAGCCCCTGAGC<br>CTGAGACCCGAGGCCTGCAGACCTGCCGCCGGCGGAGCCGTGC<br>ACACCAGAGGCCTGGACTTCGCCTGCGACATCTACATCTGGGCT<br>CCCCTGGCCGGCACCTGCGGCGTGCTGCTGCTGAGCCTGGTGAT<br>CACCCTGTACTGCAACCACAAGAGAGGCAGAAAGAAGCTGCTG<br>TACATCTTCAAGCAGCCCTTCATGAGACCCGTGCAGACCACCCA<br>GGAGGAGGACGGCTGCAGCTGCAGATTCCCCGAGGAGGAGGAG<br>GGCGGCTGCGAGCTG |

7. EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

The invention claimed is:

1. An immuno-responsive cell expressing:

(i) a $2^{nd}$ generation chimeric antigen receptor (CAR) comprising a) a signaling region;

b) a first co-stimulatory signaling region;

c) a first transmembrane domain; and d) a first binding element that specifically interacts with a first epitope on a CD19 target antigen, wherein said first binding element comprises:

CDR1 $V_H$ comprising the sequence of SEQ ID NO: 10,

CDR2 $V_H$ comprising the sequence of SEQ ID NO: 11,

CDR3 $V_H$ comprising one of the sequences selected from SEQ ID NOs: 20-26,

CDR1 $V_L$ comprising the sequence of SEQ ID NO: 13,

CDR2 $V_L$ comprising the sequence of SEQ ID NO: 14, and

CDR3 $V_L$ comprising the sequence of SEQ ID NO: 15; and (ii) a chimeric co-stimulatory receptor (CCR) comprising e) a second co-stimulatory signaling region, wherein the second co-stimulatory signaling region is different from the first co-stimulatory signaling region;

f) a second transmembrane domain; and g) a second binding element that specifically interacts with a second epitope on a second target antigen, wherein the second target antigen is CD19 or another B cell lineage-specific target antigen.

2. The immuno-responsive cell of claim 1, wherein said first binding element comprises:

(i) $V_H$ comprising a variant of the sequence of SEQ ID NO: 16, wherein the variant has a G to A or Y to A single-amino acid mutation in CDR3 $V_H$ region of SEQ ID NO: 16 to comprise one of the sequences selected from SEQ ID NOs: 20-26, and $V_L$ comprising the sequence of SEQ ID NO: 17; or (ii) a single-chain variable fragment (scFv) comprising a variant of one of the sequences selected from SEQ ID NOs: 18-19, wherein the variant has a G to A or Y to A single amino-acid mutation in CDR3 $V_H$ region to comprise one of the sequences selected from SEQ ID NOs: 20-26.

3. The immuno-responsive cell of claim 1, wherein said second target antigen comprising said second epitope is a B cell lineage-specific antigen selected from the group consisting of CD19, CD20, CD22, CD23, CD79a and CD79b.

4. The immuno-responsive cell of claim 1, wherein said second binding element comprises:

CDR1 $V_H$ comprising the sequence of SEQ ID NO: 10,

CDR2 $V_H$ comprising the sequence of SEQ ID NO: 11,

CDR3 $V_H$ comprising the sequence of SEQ ID NO: 12,

CDR1 $V_L$ comprising the sequence of SEQ ID NO: 13,

CDR2 $V_L$ comprising the sequence of SEQ ID NO: 14, and

CDR3 $V_L$ comprising the sequence of SEQ ID NO: 15.

5. The immuno-responsive cell of claim 4, wherein said second binding element comprises (i) the $V_H$ region having the sequence of SEQ ID NO: 16 and $V_L$ region having the sequence of SEQ ID NO: 17 or (ii) the single-chain variable fragment (scFv) having the sequence of SEQ ID NO: 18 or 19.

6. The immuno-responsive cell of claim 1, wherein said second binding element comprises:

CDR1 $V_H$ comprising the sequence of SEQ ID NO: 27,

CDR2 $V_H$ comprising the sequence of SEQ ID NO: 28,

CDR3 $V_H$ comprising the sequence of SEQ ID NO: 29,

CDR1 $V_L$ comprising the sequence of SEQ ID NO: 30,

CDR2 $V_L$ comprising the sequence of SEQ ID NO: 31, and

CDR3 $V_L$ comprising the sequence of SEQ ID NO: 32.

7. The immuno-responsive cell of claim 6, wherein said second binding element comprises (i) the $V_H$ region with the sequence of SEQ ID NO: 33 and $V_L$ region with the sequence of SEQ ID NO: 34 or (ii) the single-chain variable fragment (scFv) having the sequence of SEQ ID NO: 35 or 36.

8. The immuno-responsive cell of claim 1, wherein said second binding element comprises:

CDR1 $V_H$ comprising the sequence of SEQ ID NO: 37,
CDR2 $V_H$ comprising the sequence of SEQ ID NO: 38,
CDR3 $V_H$ comprising the sequence of SEQ ID NO: 39,
CDR1 $V_L$ comprising the sequence of SEQ ID NO: 40,
CDR2 $V_L$ comprising the sequence of SEQ ID NO: 41, and
CDR3 $V_L$ comprising the sequence of SEQ ID NO: 42.

9. The immuno-responsive cell of claim 8, wherein said second binding element comprises (i) the $V_H$ region with the sequence of SEQ ID NO: 43 and Vi region with the sequence of SEQ ID NO: 44 or (ii) the single-chain variable fragment (scFv) having the sequence of SEQ ID NO: 45 or 46.

10. The immuno-responsive cell of claim 1, wherein the $2^{nd}$ generation CAR comprises the sequence of SEQ ID NO: 56, 58, 59, 60, 61, 62, or 63 and the CCR comprises the sequence of SEQ ID NO: 57.

11. The immuno-responsive cell of claim 1, wherein the $2^{nd}$ generation CAR comprises the sequence of SEQ ID NO: 63 and the CCR comprises the sequence of SEQ ID NO: 65 or 66.

12. The immuno-responsive cell of claim 1, wherein said immuno-responsive cell is an αβ T cell, γδ T cell, or a Natural Killer (NK) cell.

13. A polynucleotide or set of polynucleotides comprising:

(i) a first nucleic acid encoding a $2^{nd}$ generation chimeric antigen receptor (CAR) comprising
a) a signaling region;
b) a first co-stimulatory signaling region;
c) a first transmembrane domain; and
d) a first binding element that specifically interacts with a first epitope on a CD19 target antigen, wherein said first binding element comprises:
CDR1 $V_H$ comprising the sequence of SEO ID NO: 10,
CDR2 $V_H$ comprising the sequence of SEQ ID NO: 11,
CDR3 $V_H$ comprising one of the sequences selected from SEO ID NOs: 20-26,
CDR1 $V_L$ comprising the sequence of SEQ ID NO: 13,
CDR2 $V_L$ comprising the sequence of SEQ ID NO: 14, and
CDR3 $V_L$ comprising the sequence of SEQ ID NO: 15; and (i) a second nucleic acid encoding a chimeric co-stimulatory receptor (CCR) comprising
e) a second co-stimulatory signaling region, wherein the second co-stimulatory signaling region is different from the first co-stimulatory signaling region;
f) a second transmembrane domain, and
g) a second binding element that specifically interacts with a second epitope on a second target antigen, wherein the second target antigen is CD19 or another B cell lineage specific target antigen.

14. A method of preparing a modified immuno-responsive cell, said method comprising transfecting or transducing said polynucleotide or set of polynucleotides of claim 13 into an immuno-responsive cell.

15. A method for directing a T cell-mediated immune response to a target cell in a patient in need thereof, said method comprising administering to the patient the immuno-responsive cell of claim 1, wherein the target cell expresses CD19.

16. A method of treating cancer, said method comprising administering to the patient an effective amount of the immuno-responsive cell of claim 1, wherein the patient's cancer expresses CD19.

* * * * *